US011046658B2

(12) United States Patent
Douty et al.

(10) Patent No.: US 11,046,658 B2
(45) Date of Patent: Jun. 29, 2021

(54) AMINOPYRAZINE DERIVATIVES AS PI3K-γ INHIBITORS

(71) Applicant: Incyte Corporation, Wilmington, DE (US)

(72) Inventors: Brent Douty, Fallowfield, PA (US); Yanran Ai, West Chester, PA (US); David M. Burns, Plymouth Meeting, PA (US); Andrew P. Combs, Kennett Square, PA (US); Nikoo Falahatpisheh, Wilmington, DE (US); Daniel Levy, Philadelphia, PA (US); Padmaja Polam, Kennett Square, PA (US); Lixin Shao, Wilmington, DE (US); Stacey Shepard, Wilmington, DE (US); Artem Shvartsbart, Kennett Square, PA (US); Eddy W. Yue, Landenberg, PA (US); Andrew W. Buesking, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/458,530

(22) Filed: Jul. 1, 2019

(65) Prior Publication Data

US 2020/0002295 A1 Jan. 2, 2020

Related U.S. Application Data

(60) Provisional application No. 62/693,234, filed on Jul. 2, 2018, provisional application No. 62/693,145, filed on Jul. 2, 2018, provisional application No. 62/693,196, filed on Jul. 2, 2018, provisional application No. 62/693,247, filed on Jul. 2, 2018.

(51) Int. Cl.

| C07D 241/20 | (2006.01) |
|---|---|
| C07D 401/04 | (2006.01) |
| C07D 401/14 | (2006.01) |
| C07D 403/04 | (2006.01) |
| C07D 403/06 | (2006.01) |
| C07D 403/12 | (2006.01) |
| C07D 403/14 | (2006.01) |
| C07D 405/12 | (2006.01) |
| C07D 413/04 | (2006.01) |
| C07D 417/04 | (2006.01) |
| C07D 471/04 | (2006.01) |
| C07D 471/06 | (2006.01) |
| C07D 487/04 | (2006.01) |

(52) U.S. Cl.

CPC ......... C07D 241/20 (2013.01); C07D 401/04 (2013.01); C07D 401/14 (2013.01); C07D 403/04 (2013.01); C07D 403/06 (2013.01); C07D 403/12 (2013.01); C07D 403/14 (2013.01); C07D 405/12 (2013.01); C07D 413/04 (2013.01); C07D 417/04 (2013.01); C07D 471/04 (2013.01); C07D 471/06 (2013.01); C07D 487/04 (2013.01)

(58) Field of Classification Search

CPC ......................... C07D 241/10; A61K 31/4965
USPC ....................................... 544/336; 514/252.1
See application file for complete search history.

(56) References Cited

U.S. PATENT DOCUMENTS

| 4,705,853 A | 11/1987 | Cale |
|---|---|---|
| 4,861,884 A | 8/1989 | Treybig |
| 4,921,860 A | 5/1990 | Cliffe |
| 4,971,909 A | 11/1990 | Kaneoya et al. |
| 5,025,096 A | 6/1991 | Chiu et al. |
| 5,155,117 A | 10/1992 | Reitz |
| 5,232,945 A | 8/1993 | Hulin |
| 5,252,737 A | 10/1993 | Stern et al. |
| 5,315,043 A | 5/1994 | Fernandez et al. |
| 5,393,860 A | 2/1995 | Kvakovszky et al. |
| 5,430,123 A | 7/1995 | Kvakovszky et al. |

(Continued)

FOREIGN PATENT DOCUMENTS

| AR | 86653 | 1/2014 |
|---|---|---|
| CA | 2464604 | 10/2004 |

(Continued)

OTHER PUBLICATIONS

Atzrodt et al. Angew. Chem. Int. Ed. 2007, 46, 7744-7765.*

(Continued)

*Primary Examiner* — Paul V Ward
(74) *Attorney, Agent, or Firm* — Fish & Richardson P.C.

(57) ABSTRACT

This application relates to compounds of Formula (I):

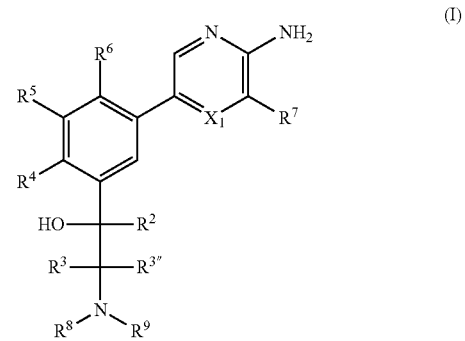

or pharmaceutically acceptable salts thereof, which are inhibitors of PI3K-γ which are useful for the treatment of disorders such as autoimmune diseases, cancer, cardiovascular diseases, and neurodegenerative diseases.

23 Claims, No Drawings

(56) References Cited

U.S. PATENT DOCUMENTS

| | | |
|---|---|---|
| 5,436,134 A | 7/1995 | Haugland et al. |
| 5,459,266 A | 10/1995 | Kvakovszky et al. |
| 5,521,056 A | 5/1996 | Buchanan et al. |
| 5,521,184 A | 5/1996 | Zimmerman |
| 5,534,416 A | 7/1996 | Millard et al. |
| 5,545,535 A | 8/1996 | Ruth et al. |
| 5,602,156 A | 2/1997 | Kohn et al. |
| 5,621,027 A | 4/1997 | Roschger et al. |
| 5,656,449 A | 8/1997 | Yue |
| 5,672,592 A | 9/1997 | Jackson et al. |
| 5,677,459 A | 10/1997 | McDonald et al. |
| 5,705,512 A | 1/1998 | McDonald et al. |
| 5,716,971 A | 2/1998 | Shiraishi et al. |
| 5,723,477 A | 3/1998 | McDonald et al. |
| 5,756,508 A | 5/1998 | Thompson et al. |
| 5,811,442 A | 9/1998 | Bencherif et al. |
| 5,863,903 A | 1/1999 | Lundgren et al. |
| 5,869,487 A | 2/1999 | Coburn et al. |
| 5,880,137 A | 3/1999 | Miller et al. |
| 5,883,106 A | 3/1999 | Stevens et al. |
| 5,929,075 A | 7/1999 | Heeres et al. |
| 6,172,084 B1 | 1/2001 | Cuny et al. |
| 6,197,798 B1 | 3/2001 | Fink et al. |
| 6,207,679 B1 | 3/2001 | Cuny et al. |
| 6,274,598 B1 | 8/2001 | Ellis et al. |
| 6,559,167 B1 | 5/2003 | Garst et al. |
| 7,745,437 B2 | 6/2010 | Ren et al. |
| 7,872,031 B2 | 1/2011 | Lauffer et al. |
| 8,232,406 B2 | 7/2012 | Lauffer et al. |
| 8,410,112 B2 | 4/2013 | Charrier et al. |
| 8,741,931 B2 | 6/2014 | Jimenez et al. |
| 8,841,308 B2 | 9/2014 | Charrier et al. |
| 8,841,337 B2 | 9/2014 | Charrier et al. |
| 8,841,450 B2 | 9/2014 | Charrier et al. |
| 8,846,917 B2 | 9/2014 | Charrier et al. |
| 8,846,918 B2 | 9/2014 | Charrier et al. |
| 8,962,623 B2 | 2/2015 | Shetty et al. |
| 8,969,356 B2 | 3/2015 | Charrier et al. |
| 9,035,053 B2 | 5/2015 | Charrier et al. |
| 9,096,584 B2 | 8/2015 | Charrier et al. |
| 9,365,557 B2 | 6/2016 | Charrier et al. |
| 9,701,674 B2 | 7/2017 | Charrier et al. |
| 10,669,262 B2 | 6/2020 | Shepard et al. |
| 2002/0103141 A1 | 8/2002 | McKearn et al. |
| 2002/0115678 A1 | 8/2002 | Ellis et al. |
| 2002/0169072 A1 | 11/2002 | Nakayama et al. |
| 2003/0008828 A1 | 1/2003 | Priestley et al. |
| 2003/0027798 A1 | 2/2003 | Druzgala et al. |
| 2003/0225142 A1 | 12/2003 | Crooks et al. |
| 2004/0082641 A1 | 4/2004 | Rytved et al. |
| 2004/0106621 A1 | 6/2004 | Wu et al. |
| 2004/0127519 A1 | 7/2004 | Reinhard et al. |
| 2004/0127719 A1 | 7/2004 | Yang et al. |
| 2004/0158065 A1 | 8/2004 | Berth et al. |
| 2004/0229873 A1 | 11/2004 | Harbige et al. |
| 2005/0048312 A1 | 3/2005 | Herron et al. |
| 2005/0069551 A1 | 3/2005 | Shoji et al. |
| 2005/0234046 A1 | 10/2005 | Zhao et al. |
| 2005/0234389 A1 | 10/2005 | Bouwstra et al. |
| 2005/0239826 A1 | 10/2005 | Stenkamp et al. |
| 2005/0282825 A1 | 12/2005 | Malamas et al. |
| 2005/0282826 A1 | 12/2005 | Malamas et al. |
| 2006/0205736 A1 | 9/2006 | Noble et al. |
| 2006/0270686 A1 | 11/2006 | Kelly et al. |
| 2007/0010573 A1 | 1/2007 | Kong et al. |
| 2007/0015752 A1 | 1/2007 | Hangauer |
| 2007/0039644 A1 | 2/2007 | Lee et al. |
| 2007/0060613 A1 | 3/2007 | Kim |
| 2007/0066619 A1 | 3/2007 | Hamilton et al. |
| 2007/0143936 A1 | 6/2007 | Lagrange |
| 2007/0190358 A1 | 8/2007 | Byun et al. |
| 2008/0009527 A1 | 1/2008 | Dumas et al. |
| 2008/0103074 A1 | 5/2008 | Stokes et al. |
| 2008/0184495 A1 | 8/2008 | Brun et al. |
| 2008/0255389 A1 | 10/2008 | Coggan et al. |
| 2008/0280891 A1 | 11/2008 | Kelly et al. |
| 2008/0281075 A1 | 11/2008 | Harwood et al. |
| 2008/0293739 A1 | 11/2008 | Trede |
| 2008/0300419 A1 | 12/2008 | Chen et al. |
| 2009/0011991 A1 | 1/2009 | Shoji et al. |
| 2009/0048280 A1 | 2/2009 | Burgoon, Jr. et al. |
| 2009/0093479 A1 | 4/2009 | Kelly et al. |
| 2009/0124602 A1 | 5/2009 | Maltais et al. |
| 2009/0124805 A1 | 5/2009 | Alleyne |
| 2009/0149653 A1 | 6/2009 | Cheng et al. |
| 2009/0163463 A1 | 6/2009 | Bruce et al. |
| 2009/0272946 A1 | 11/2009 | Lu |
| 2010/0036172 A1 | 2/2010 | Hung et al. |
| 2010/0056576 A1 | 3/2010 | Burger et al. |
| 2010/0099825 A1 | 4/2010 | Schmitz et al. |
| 2010/0160669 A1 | 6/2010 | Liu et al. |
| 2010/0184986 A1 | 7/2010 | Carter et al. |
| 2010/0273764 A1 | 10/2010 | Andrews et al. |
| 2011/0049497 A1 | 3/2011 | Ise |
| 2011/0082165 A1 | 4/2011 | Ellsworth et al. |
| 2011/0124663 A1 | 5/2011 | Conn et al. |
| 2011/0277841 A1 | 11/2011 | Chi et al. |
| 2011/0306707 A1 | 12/2011 | Benton et al. |
| 2012/0122708 A1 | 5/2012 | Castells et al. |
| 2012/0129888 A1 | 5/2012 | Castells et al. |
| 2012/0142930 A1 | 6/2012 | Castells et al. |
| 2012/0289481 A1 | 11/2012 | O'Neil et al. |
| 2013/0004859 A1 | 1/2013 | Yu et al. |
| 2013/0035323 A1 | 2/2013 | Amberg et al. |
| 2013/0056716 A1 | 3/2013 | Cheng et al. |
| 2013/0066029 A1 | 3/2013 | Radlauer et al. |
| 2013/0115311 A1 | 5/2013 | Charrier et al. |
| 2013/0115312 A1 | 5/2013 | Charrier et al. |
| 2013/0115313 A1 | 5/2013 | Charrier et al. |
| 2013/0115314 A1 | 5/2013 | Charrier et al. |
| 2013/0158031 A1 | 6/2013 | Cai et al. |
| 2013/0158067 A1 | 6/2013 | Woller et al. |
| 2013/0224121 A1 | 8/2013 | Fukui et al. |
| 2013/0261106 A1 | 10/2013 | Carry et al. |
| 2013/0267521 A1 | 10/2013 | Castro et al. |
| 2014/0088117 A1 | 3/2014 | Burch et al. |
| 2014/0117318 A1 | 5/2014 | Choi et al. |
| 2014/0148484 A1 | 5/2014 | Schnapp et al. |
| 2014/0171525 A1 | 6/2014 | Yu et al. |
| 2014/0178815 A1 | 6/2014 | Jung et al. |
| 2014/0200227 A1 | 7/2014 | Xue et al. |
| 2014/0275070 A1 | 9/2014 | Grembecka et al. |
| 2014/0275167 A1 | 9/2014 | Hartman |
| 2014/0288067 A1 | 9/2014 | Chesworth et al. |
| 2015/0057300 A1 | 2/2015 | Tafesse et al. |
| 2015/0137096 A1 | 5/2015 | Xia et al. |
| 2015/0141434 A1 | 5/2015 | Park |
| 2015/0171349 A1 | 6/2015 | Ma et al. |
| 2015/0197513 A1 | 7/2015 | Wrasidlo et al. |
| 2015/0249222 A1 | 9/2015 | Szigethy et al. |
| 2015/0306227 A1 | 10/2015 | Cruise et al. |
| 2015/0322076 A1 | 11/2015 | Chen et al. |
| 2015/0359797 A1 | 12/2015 | Helleday et al. |
| 2016/0122302 A1 | 5/2016 | Silverman et al. |
| 2016/0176857 A1 | 6/2016 | Ly |
| 2016/0200731 A1 | 7/2016 | Mickle et al. |
| 2016/0246152 A1 | 8/2016 | Igawa et al. |
| 2016/0311809 A1 | 10/2016 | Charrier et al. |
| 2016/0340311 A1 | 11/2016 | Biswas et al. |
| 2016/0359122 A1 | 12/2016 | Boudreault et al. |
| 2017/0092880 A1 | 3/2017 | Boudreault et al. |
| 2017/0101394 A1 | 4/2017 | Zhang |
| 2017/0101395 A1 | 4/2017 | Zhang |
| 2017/0101403 A1 | 4/2017 | Zhang |
| 2017/0186964 A1 | 6/2017 | Cho et al. |
| 2017/0186975 A1 | 6/2017 | Kim et al. |
| 2017/0275278 A1 | 9/2017 | Silverman et al. |
| 2017/0294597 A1 | 10/2017 | Tsai et al. |
| 2017/0305861 A1 | 10/2017 | Kim et al. |
| 2018/0086709 A1 | 3/2018 | Choi et al. |
| 2018/0173922 A1 | 6/2018 | Ghavanini et al. |
| 2019/0276435 A1 | 9/2019 | Shepard et al. |

(56) References Cited

U.S. PATENT DOCUMENTS

| | | | |
|---|---|---|---|
| 2020/0002295 | A1 | 1/2020 | Douty et al. |
| 2020/0339542 | A1 | 10/2020 | Shepard et al. |

FOREIGN PATENT DOCUMENTS

| | | |
|---|---|---|
| CN | 1374306 | 10/2002 |
| CN | 101058577 | 10/2007 |
| CN | 101513584 | 8/2009 |
| CN | 101591332 | 12/2009 |
| CN | 101712809 | 5/2010 |
| CN | 101781200 | 7/2010 |
| CN | 102125875 | 7/2011 |
| CN | 102260218 | 11/2011 |
| CN | 102850328 | 1/2013 |
| CN | 103087050 | 5/2013 |
| CN | 103193702 | 7/2013 |
| CN | 103524372 | 1/2014 |
| CN | 103588771 | 2/2014 |
| CN | 103664878 | 3/2014 |
| CN | 103694236 | 4/2014 |
| CN | 103804312 | 5/2014 |
| CN | 103848838 | 6/2014 |
| CN | 103923085 | 7/2014 |
| CN | 104004026 | 8/2014 |
| CN | 104557863 | 4/2015 |
| CN | 104744348 | 7/2015 |
| CN | 104926788 | 9/2015 |
| CN | 104927742 | 9/2015 |
| CN | 105175202 | 12/2015 |
| CN | 105315199 | 2/2016 |
| CN | 106831735 | 6/2017 |
| CN | 106905299 | 6/2017 |
| DE | 3628223 | 2/1987 |
| DE | 19509353 | 10/1995 |
| DE | 19718742 | 11/1998 |
| DE | 102009055828 | 7/2010 |
| DE | 102010054892 | 6/2012 |
| DE | 102012006896 | 10/2013 |
| EP | 0553009 | 7/1993 |
| EP | 0695743 | 2/1996 |
| EP | 0808838 | 11/1997 |
| EP | 0827135 | 3/1998 |
| EP | 0879814 | 11/1998 |
| EP | 0930302 | 7/1999 |
| EP | 1837330 | 9/2007 |
| EP | 2524918 | 11/2012 |
| EP | 3051604 | 8/2016 |
| EP | 3128041 | 2/2017 |
| ES | 2379919 | 5/2012 |
| GB | 2290489 | 1/1996 |
| IN | 110DEL2012 | 5/2015 |
| IT | 2006MI0895 | 8/2006 |
| IT | MI20110208 | 8/2012 |
| JP | 05058997 | 3/1993 |
| JP | 06001776 | 1/1994 |
| JP | H06256327 | 9/1994 |
| JP | H06340642 | 12/1994 |
| JP | 07082249 | 3/1995 |
| JP | H08175994 | 7/1996 |
| JP | H08337583 | 12/1996 |
| JP | H10188264 | 7/1998 |
| JP | H10324687 | 12/1998 |
| JP | H11292883 | 10/1999 |
| JP | 2000073094 | 3/2000 |
| JP | 2000076640 | 3/2000 |
| JP | 2000076642 | 3/2000 |
| JP | 2000076643 | 3/2000 |
| JP | 2001072660 | 3/2001 |
| JP | 2001089460 | 4/2001 |
| JP | 2001247548 | 9/2001 |
| JP | 2002338837 | 11/2002 |
| JP | 2003012645 | 1/2003 |
| JP | 2003040809 | 2/2003 |
| JP | 2003212706 | 7/2003 |
| JP | 2003292408 | 10/2003 |
| JP | 3502629 | 3/2004 |
| JP | 2004067540 | 3/2004 |
| JP | 2004123617 | 4/2004 |
| JP | 2004143061 | 5/2004 |
| JP | 2004143163 | 5/2004 |
| JP | 2004196670 | 7/2004 |
| JP | 2005029500 | 2/2005 |
| JP | 2005126586 | 5/2005 |
| JP | 2006041020 | 2/2006 |
| JP | 2007039388 | 2/2007 |
| JP | 2007145819 | 6/2007 |
| JP | 2007161674 | 6/2007 |
| JP | 2009001742 | 1/2009 |
| JP | 2009007342 | 1/2009 |
| JP | 2009023986 | 2/2009 |
| JP | 2010143829 | 7/2010 |
| JP | 2012036125 | 2/2012 |
| JP | 2013129651 | 7/2013 |
| JP | 2013129653 | 7/2013 |
| JP | 2014001205 | 1/2014 |
| JP | 2014015447 | 1/2014 |
| JP | 2014037382 | 2/2014 |
| JP | 2014078381 | 5/2014 |
| JP | 2014078382 | 5/2014 |
| JP | 2014111559 | 6/2014 |
| JP | 2014198841 | 10/2014 |
| JP | 2014198843 | 10/2014 |
| JP | 2014198844 | 10/2014 |
| JP | 2015003895 | 1/2015 |
| JP | 2015017236 | 1/2015 |
| JP | 2015043445 | 3/2015 |
| JP | 2015122247 | 7/2015 |
| JP | 2015125845 | 7/2015 |
| JP | 2015141806 | 8/2015 |
| JP | 2015193569 | 11/2015 |
| JP | 2016124730 | 7/2016 |
| JP | 2017019789 | 1/2017 |
| KR | 20100001274 | 1/2010 |
| KR | 20120063028 | 6/2012 |
| KR | 20130122361 | 11/2013 |
| KR | 20160126792 | 11/2016 |
| KR | 20170036233 | 4/2017 |
| KR | 20170093273 | 8/2017 |
| TW | I388566 | 3/2013 |
| WO | WO 98/29114 | 7/1988 |
| WO | WO 91/17979 | 11/1991 |
| WO | WO 94/22853 | 10/1994 |
| WO | WO 94/24213 | 10/1994 |
| WO | WO 94/25425 | 11/1994 |
| WO | WO 95/07695 | 3/1995 |
| WO | WO 95/08327 | 3/1995 |
| WO | WO 95/24391 | 9/1995 |
| WO | WO 95/29155 | 11/1995 |
| WO | WO 95/34564 | 12/1995 |
| WO | WO 96/11910 | 4/1996 |
| WO | WO 96/11911 | 4/1996 |
| WO | WO 96/13499 | 5/1996 |
| WO | WO 96/15123 | 5/1996 |
| WO | WO 96/18394 | 6/1996 |
| WO | WO 96/21651 | 7/1996 |
| WO | WO 96/37486 | 11/1996 |
| WO | WO 97/01538 | 1/1997 |
| WO | WO 97/11943 | 4/1997 |
| WO | WO 97/12864 | 4/1997 |
| WO | WO 97/16187 | 5/1997 |
| WO | WO 97/16192 | 5/1997 |
| WO | WO 97/21702 | 6/1997 |
| WO | WO 97/26258 | 7/1997 |
| WO | WO 97/33872 | 9/1997 |
| WO | WO 97/43267 | 11/1997 |
| WO | WO 98/05642 | 2/1998 |
| WO | WO 98/07702 | 2/1998 |
| WO | WO 98/13361 | 4/1998 |
| WO | WO 98/14436 | 4/1998 |
| WO | WO 98/17274 | 4/1998 |
| WO | WO 98/18326 | 5/1998 |
| WO | WO 98/27098 | 6/1998 |
| WO | WO 98/35961 | 8/1998 |
| WO | WO 98/55480 | 12/1998 |

(56) References Cited

FOREIGN PATENT DOCUMENTS

| | | |
|---|---|---|
| WO | WO 99/01453 | 1/1999 |
| WO | WO 99/02503 | 1/1999 |
| WO | WO 99/15169 | 4/1999 |
| WO | WO 99/27930 | 6/1999 |
| WO | WO 99/32110 | 7/1999 |
| WO | WO 99/32117 | 7/1999 |
| WO | WO 99/32455 | 7/1999 |
| WO | WO 99/33810 | 7/1999 |
| WO | WO 99/38829 | 8/1999 |
| WO | WO 99/55313 | 11/1999 |
| WO | WO 99/57113 | 11/1999 |
| WO | WO 99/63984 | 12/1999 |
| WO | WO 99/64407 | 12/1999 |
| WO | WO 00/05201 | 2/2000 |
| WO | WO 00/009495 | 2/2000 |
| WO | WO 00/09498 | 2/2000 |
| WO | WO 00/15615 | 3/2000 |
| WO | WO 00/25139 | 5/2000 |
| WO | WO 00/34230 | 6/2000 |
| WO | WO 00/34277 | 6/2000 |
| WO | WO 00/39094 | 7/2000 |
| WO | WO 00/43405 | 7/2000 |
| WO | WO 00/053595 | 9/2000 |
| WO | WO 01/04076 | 1/2001 |
| WO | WO 01/07407 | 2/2001 |
| WO | WO 01/014402 | 3/2001 |
| WO | WO 01/16122 | 3/2001 |
| WO | WO 01/32658 | 5/2001 |
| WO | WO 01/36415 | 5/2001 |
| WO | WO 01/40188 | 6/2001 |
| WO | WO 01/064655 | 9/2001 |
| WO | WO 01/81328 | 11/2001 |
| WO | WO 01/87853 | 11/2001 |
| WO | WO 02/000196 | 1/2002 |
| WO | WO 02/00648 | 1/2002 |
| WO | WO 02/06271 | 1/2002 |
| WO | WO 02/08199 | 1/2002 |
| WO | WO 02/09759 | 2/2002 |
| WO | WO 02/20501 | 3/2002 |
| WO | WO 02/24689 | 3/2002 |
| WO | WO 02/038628 | 5/2002 |
| WO | WO 02/042272 | 5/2002 |
| WO | WO 02/042306 | 5/2002 |
| WO | WO 02/046162 | 6/2002 |
| WO | WO 02/060877 | 8/2002 |
| WO | WO 02/069712 | 9/2002 |
| WO | WO 02/070514 | 9/2002 |
| WO | WO 02/072543 | 9/2002 |
| WO | WO 02/076395 | 10/2002 |
| WO | WO 02/079143 | 10/2002 |
| WO | WO 02/089738 | 11/2002 |
| WO | WO 03/004475 | 1/2003 |
| WO | WO 03/024441 | 3/2003 |
| WO | WO 03/024967 | 3/2003 |
| WO | WO 03/028684 | 4/2003 |
| WO | WO 03/034824 | 5/2003 |
| WO | WO 03/037347 | 5/2003 |
| WO | WO 03/040257 | 5/2003 |
| WO | WO 03/044015 | 5/2003 |
| WO | WO 03/053441 | 7/2003 |
| WO | WO 03/059348 | 7/2003 |
| WO | WO 03/059886 | 7/2003 |
| WO | WO 03/062201 | 7/2003 |
| WO | WO 03/062215 | 7/2003 |
| WO | WO 2003/057205 | 7/2003 |
| WO | WO 03/072548 | 9/2003 |
| WO | WO 03/074148 | 9/2003 |
| WO | WO 03/092889 | 11/2003 |
| WO | WO 2003/093258 | 11/2003 |
| WO | WO 2003/097644 | 11/2003 |
| WO | WO 03/099771 | 12/2003 |
| WO | WO 03/104220 | 12/2003 |
| WO | WO 2004/002948 | 1/2004 |
| WO | WO 2004/005281 | 1/2004 |
| WO | WO 2004/012726 | 2/2004 |
| WO | WO 2004/016600 | 2/2004 |
| WO | WO 2004/017920 | 3/2004 |
| WO | WO 2004/019863 | 3/2004 |
| WO | WO 2004/020413 | 3/2004 |
| WO | WO 2004/033444 | 4/2004 |
| WO | WO 2004/043443 | 5/2004 |
| WO | WO 2004/043956 | 5/2004 |
| WO | WO 2004/046120 | 6/2004 |
| WO | WO 2004/047840 | 6/2004 |
| WO | WO 2004/052890 | 6/2004 |
| WO | WO 04/056786 | 7/2004 |
| WO | WO 2004/054505 | 7/2004 |
| WO | WO 2004/055006 | 7/2004 |
| WO | WO 2004/055015 | 7/2004 |
| WO | WO 2004/056786 | 7/2004 |
| WO | WO 2004/058778 | 7/2004 |
| WO | WO 2004/064755 | 8/2004 |
| WO | WO 2004/065388 | 8/2004 |
| WO | WO 2004/069160 | 8/2004 |
| WO | WO 2004/069805 | 8/2004 |
| WO | WO 2004/069808 | 8/2004 |
| WO | WO 04/080980 | 9/2004 |
| WO | WO 2004/080980 | 9/2004 |
| WO | WO 2004/089910 | 10/2004 |
| WO | WO 2004/094372 | 11/2004 |
| WO | WO 2004/094405 | 11/2004 |
| WO | WO 2004/094406 | 11/2004 |
| WO | WO 2004/094416 | 11/2004 |
| WO | WO 2004/100943 | 11/2004 |
| WO | WO 2004/104052 | 12/2004 |
| WO | WO 2004/108673 | 12/2004 |
| WO | WO 2004/108686 | 12/2004 |
| WO | WO 2004/113258 | 12/2004 |
| WO | WO 2004/113277 | 12/2004 |
| WO | WO 2005/000309 | 1/2005 |
| WO | WO 2005/005382 | 1/2005 |
| WO | WO 2005/012298 | 2/2005 |
| WO | WO 05/028444 | 3/2005 |
| WO | WO 2005/025623 | 3/2005 |
| WO | WO 2005/026166 | 3/2005 |
| WO | WO 2005/028444 | 3/2005 |
| WO | WO 2005/030766 | 4/2005 |
| WO | WO 2005/047215 | 5/2005 |
| WO | WO 2005/049619 | 6/2005 |
| WO | WO 2005/054232 | 6/2005 |
| WO | WO 2005/058876 | 6/2005 |
| WO | WO 2005/066162 | 7/2005 |
| WO | WO 2005/074940 | 8/2005 |
| WO | WO 2005/075452 | 8/2005 |
| WO | WO 2005/079802 | 9/2005 |
| WO | WO 2005/092836 | 10/2005 |
| WO | WO 2005/099688 | 10/2005 |
| WO | WO 2005/105790 | 11/2005 |
| WO | WO 2005/115994 | 12/2005 |
| WO | WO 2006/002823 | 1/2006 |
| WO | WO 2006/010546 | 2/2006 |
| WO | WO 2006/038606 | 4/2006 |
| WO | WO 2006/047772 | 5/2006 |
| WO | WO 2006/051704 | 5/2006 |
| WO | WO 2006/051937 | 5/2006 |
| WO | WO 2006/055187 | 5/2006 |
| WO | WO 2006/055725 | 5/2006 |
| WO | WO 2006/056399 | 6/2006 |
| WO | WO 2006/056854 | 6/2006 |
| WO | WO 2006/060762 | 6/2006 |
| WO | WO 2006/069287 | 6/2006 |
| WO | WO 2006/070195 | 7/2006 |
| WO | WO 2006/080884 | 8/2006 |
| WO | WO 2006/082001 | 8/2006 |
| WO | WO 2006/084773 | 8/2006 |
| WO | WO 2006/088836 | 8/2006 |
| WO | WO 2006/103254 | 10/2006 |
| WO | WO 2006/114401 | 11/2006 |
| WO | WO 2006/124874 | 11/2006 |
| WO | WO 2006/128563 | 12/2006 |
| WO | WO 2006/138166 | 12/2006 |
| WO | WO 2007/000250 | 1/2007 |
| WO | WO 2007/006380 | 1/2007 |
| WO | WO 2007/009083 | 1/2007 |

(56) References Cited

FOREIGN PATENT DOCUMENTS

| | | |
|---|---|---|
| WO | WO 2007/009389 | 1/2007 |
| WO | WO 2007/011721 | 1/2007 |
| WO | WO 2007/016674 | 2/2007 |
| WO | WO 2007/025169 | 3/2007 |
| WO | WO 2007/031828 | 3/2007 |
| WO | WO 2007/033781 | 3/2007 |
| WO | WO 2007/038459 | 4/2007 |
| WO | WO 2007/044779 | 4/2007 |
| WO | WO 2007/049098 | 5/2007 |
| WO | WO 2007/051981 | 5/2007 |
| WO | WO 2007/055183 | 5/2007 |
| WO | WO 2007/063935 | 6/2007 |
| WO | WO 2007/064914 | 6/2007 |
| WO | WO 2007/073855 | 7/2007 |
| WO | WO 2007/077048 | 7/2007 |
| WO | WO 2007/077057 | 7/2007 |
| WO | WO 2007/077435 | 7/2007 |
| WO | WO 2007/085718 | 8/2007 |
| WO | WO 2007/091110 | 8/2007 |
| WO | WO 2007/101531 | 9/2007 |
| WO | WO 2007/107543 | 9/2007 |
| WO | WO 2007/109238 | 9/2007 |
| WO | WO 2007/111904 | 10/2007 |
| WO | WO 2007/112347 | 10/2007 |
| WO | WO 2007/113258 | 10/2007 |
| WO | WO 2007/120655 | 10/2007 |
| WO | WO 2007/120718 | 10/2007 |
| WO | WO 2007/124849 | 11/2007 |
| WO | WO 2007/125061 | 11/2007 |
| WO | WO 2007/129664 | 11/2007 |
| WO | WO 2007/137790 | 12/2007 |
| WO | WO 2007/147874 | 12/2007 |
| WO | WO 2008/002676 | 1/2008 |
| WO | WO 2008/004942 | 1/2008 |
| WO | WO 2008/005937 | 1/2008 |
| WO | WO 2008/006663 | 1/2008 |
| WO | WO 2008/007900 | 1/2008 |
| WO | WO 2008/008453 | 1/2008 |
| WO | WO 2008/016968 | 2/2008 |
| WO | WO 2008/025820 | 3/2008 |
| WO | WO 2008/034600 | 3/2008 |
| WO | WO 2008/038010 | 4/2008 |
| WO | WO 2008/038955 | 4/2008 |
| WO | WO 2008/043533 | 4/2008 |
| WO | WO 2008/044713 | 4/2008 |
| WO | WO 2008/046527 | 4/2008 |
| WO | WO 2008/052733 | 5/2008 |
| WO | WO 2008/054117 | 5/2008 |
| WO | WO 2008/070908 | 6/2008 |
| WO | WO 2008/071937 | 6/2008 |
| WO | WO 2008/073480 | 6/2008 |
| WO | WO 2008/073933 | 6/2008 |
| WO | WO 2008/074997 | 6/2008 |
| WO | WO 2008/077625 | 7/2008 |
| WO | WO 2008/080504 | 7/2008 |
| WO | WO 2008/094992 | 8/2008 |
| WO | WO 2008/095785 | 8/2008 |
| WO | WO 2008/100620 | 8/2008 |
| WO | WO 2008/116665 | 10/2008 |
| WO | WO 2008/116671 | 10/2008 |
| WO | WO 2008/124092 | 10/2008 |
| WO | WO 2008/127727 | 10/2008 |
| WO | WO 2008/127728 | 10/2008 |
| WO | WO 2008/132091 | 11/2008 |
| WO | WO 2008/137128 | 11/2008 |
| WO | WO 2008/143440 | 11/2008 |
| WO | WO 2008/145335 | 12/2008 |
| WO | WO 2008/147154 | 12/2008 |
| WO | WO 2008/150899 | 12/2008 |
| WO | WO 2008/151211 | 12/2008 |
| WO | WO 2009/002970 | 12/2008 |
| WO | WO 2009/007390 | 1/2009 |
| WO | WO 2009/013348 | 1/2009 |
| WO | WO 2009/014637 | 1/2009 |
| WO | WO 2009/051705 | 4/2009 |
| WO | WO 2009/054941 | 4/2009 |
| WO | WO 2009/057978 | 5/2009 |
| WO | WO 2009/071701 | 6/2009 |
| WO | WO 2009/073246 | 6/2009 |
| WO | WO 2009/086731 | 7/2009 |
| WO | WO 2009/087305 | 7/2009 |
| WO | WO 2009/088103 | 7/2009 |
| WO | WO 2009/092590 | 7/2009 |
| WO | WO 2009/093082 | 7/2009 |
| WO | WO 2009/100130 | 8/2009 |
| WO | WO 2009/102588 | 8/2009 |
| WO | WO 2009/105717 | 8/2009 |
| WO | WO 2009/109539 | 9/2009 |
| WO | WO 2009/112461 | 9/2009 |
| WO | WO 2009/112826 | 9/2009 |
| WO | WO 2009/112839 | 9/2009 |
| WO | WO 2009/114173 | 9/2009 |
| WO | WO 2009/115517 | 9/2009 |
| WO | WO 2009/120872 | 10/2009 |
| WO | WO 2009/123241 | 10/2009 |
| WO | WO 2009/135590 | 11/2009 |
| WO | WO 2009/141532 | 11/2009 |
| WO | WO 2009/144961 | 12/2009 |
| WO | WO 2009/147190 | 12/2009 |
| WO | WO 2009/148052 | 12/2009 |
| WO | WO 2009/158257 | 12/2009 |
| WO | WO 2009/158467 | 12/2009 |
| WO | WO 2009144394 | 12/2009 |
| WO | WO 2010/000198 | 1/2010 |
| WO | WO 2010/019930 | 2/2010 |
| WO | WO 2010/027583 | 3/2010 |
| WO | WO 2010/028151 | 3/2010 |
| WO | WO 2010/029082 | 3/2010 |
| WO | WO 2010/029300 | 3/2010 |
| WO | WO 2010/033168 | 3/2010 |
| WO | WO 2010/034500 | 4/2010 |
| WO | WO 2010/042500 | 4/2010 |
| WO | WO 2010/042799 | 4/2010 |
| WO | WO 2010/043784 | 4/2010 |
| WO | WO 2010/047712 | 4/2010 |
| WO | WO 2010/048131 | 4/2010 |
| WO | WO 2010/054398 | 5/2010 |
| WO | WO 2010/056992 | 5/2010 |
| WO | WO 2010/065333 | 6/2010 |
| WO | WO 2010/071837 | 6/2010 |
| WO | WO 2010/080488 | 7/2010 |
| WO | WO 2010/091384 | 8/2010 |
| WO | WO 2010/100475 | 9/2010 |
| WO | WO 2010/111573 | 9/2010 |
| WO | WO 2010/137302 | 12/2010 |
| WO | WO 2010/138901 | 12/2010 |
| WO | WO 2010/148351 | 12/2010 |
| WO | WO 2010/149819 | 12/2010 |
| WO | WO 2010/150204 | 12/2010 |
| WO | WO 2011/000992 | 1/2011 |
| WO | WO 2011/002991 | 1/2011 |
| WO | WO 2011/005786 | 1/2011 |
| WO | WO 2011/005793 | 1/2011 |
| WO | WO 2011/005842 | 1/2011 |
| WO | WO 2011/006074 | 1/2011 |
| WO | WO 2011/013681 | 2/2011 |
| WO | WO 2011/027289 | 3/2011 |
| WO | WO 2011/028638 | 3/2011 |
| WO | WO 2011/032034 | 3/2011 |
| WO | WO 2011/032277 | 3/2011 |
| WO | WO 2011/035855 | 3/2011 |
| WO | WO 2011/036461 | 3/2011 |
| WO | WO 2011/049150 | 4/2011 |
| WO | WO 2011/050323 | 4/2011 |
| WO | WO 2011/071109 | 6/2011 |
| WO | WO 2011/071860 | 6/2011 |
| WO | WO 2011/072064 | 6/2011 |
| WO | WO 2011/072791 | 6/2011 |
| WO | WO 2011/081937 | 7/2011 |
| WO | WO 2011/081945 | 7/2011 |
| WO | WO 2011/082488 | 7/2011 |
| WO | WO 2011/083304 | 7/2011 |
| WO | WO 2011/086531 | 7/2011 |
| WO | WO 2011/092140 | 8/2011 |

(56) References Cited

FOREIGN PATENT DOCUMENTS

| | | |
|---|---|---|
| WO | WO 2011/095196 | 8/2011 |
| WO | WO 2011/115940 | 9/2011 |
| WO | WO 2011/124580 | 10/2011 |
| WO | WO 2011/129936 | 10/2011 |
| WO | WO 2011/141642 | 11/2011 |
| WO | WO 2011/143365 | 11/2011 |
| WO | WO 2011/143422 | 11/2011 |
| WO | WO 2011/147038 | 12/2011 |
| WO | WO 2011/161612 | 12/2011 |
| WO | WO 2012/003189 | 1/2012 |
| WO | WO 2012/003912 | 1/2012 |
| WO | WO 2012/007869 | 1/2012 |
| WO | WO 2012/007877 | 1/2012 |
| WO | WO 2012/009227 | 1/2012 |
| WO | WO 2012/032065 | 3/2012 |
| WO | WO 2012/036278 | 3/2012 |
| WO | WO 2012/069852 | 5/2012 |
| WO | WO 2012/072620 | 6/2012 |
| WO | WO 2012/074869 | 6/2012 |
| WO | WO 2012/108879 | 8/2012 |
| WO | WO 2012/108881 | 8/2012 |
| WO | WO 2012/112956 | 8/2012 |
| WO | WO 2012/116137 | 8/2012 |
| WO | WO 2012/136111 | 10/2012 |
| WO | WO 2012/138938 | 10/2012 |
| WO | WO 2012/141487 | 10/2012 |
| WO | WO 2012/151355 | 11/2012 |
| WO | WO 2012/162334 | 11/2012 |
| WO | WO 2012/163489 | 12/2012 |
| WO | WO 2012/177639 | 12/2012 |
| WO | WO 2012/178123 | 12/2012 |
| WO | WO 2012/178125 | 12/2012 |
| WO | WO 2013/007707 | 1/2013 |
| WO | WO 2013/021276 | 2/2013 |
| WO | WO 2013/024003 | 2/2013 |
| WO | WO 2013/024005 | 2/2013 |
| WO | WO 2013/024169 | 2/2013 |
| WO | WO 2013/025805 | 2/2013 |
| WO | WO 2013/042137 | 3/2013 |
| WO | WO 2013/043764 | 3/2013 |
| WO | WO 2013/043765 | 3/2013 |
| WO | WO 2013/043767 | 3/2013 |
| WO | WO 2013/043797 | 3/2013 |
| WO | WO 2013/043799 | 3/2013 |
| WO | WO 2013/043825 | 3/2013 |
| WO | WO 2013/043846 | 3/2013 |
| WO | WO 2013/043874 | 3/2013 |
| WO | WO 2013/043912 | 3/2013 |
| WO | WO 2013/049726 | 4/2013 |
| WO | WO 2013/052391 | 4/2013 |
| WO | WO 2013/054764 | 4/2013 |
| WO | WO 2013/059194 | 4/2013 |
| WO | WO 2013/063204 | 5/2013 |
| WO | WO 2013/063549 | 5/2013 |
| WO | WO 2013/069242 | 5/2013 |
| WO | WO 2013/072758 | 5/2013 |
| WO | WO 2013/076092 | 5/2013 |
| WO | WO 2013/088315 | 6/2013 |
| WO | WO 2013/092936 | 6/2013 |
| WO | WO 2013/092939 | 6/2013 |
| WO | WO 2013/096226 | 6/2013 |
| WO | WO 2013/099867 | 7/2013 |
| WO | WO 2013/102826 | 7/2013 |
| WO | WO 2013/115280 | 8/2013 |
| WO | WO 2013/117649 | 8/2013 |
| WO | WO 2013/134079 | 9/2013 |
| WO | WO 2013/148227 | 10/2013 |
| WO | WO 2013/152727 | 10/2013 |
| WO | WO 2013/161929 | 10/2013 |
| WO | WO 2013/162061 | 10/2013 |
| WO | WO 2013/164769 | 11/2013 |
| WO | WO 2013/171729 | 11/2013 |
| WO | WO 2013/179049 | 12/2013 |
| WO | WO 2013/184794 | 12/2013 |
| WO | WO 2013/189848 | 12/2013 |
| WO | WO 2014/007395 | 1/2014 |
| WO | WO 2014/011768 | 1/2014 |
| WO | WO 2014/018741 | 1/2014 |
| WO | WO 2014/033631 | 3/2014 |
| WO | WO 2014/039714 | 3/2014 |
| WO | WO 2014/057078 | 4/2014 |
| WO | WO 2014/065073 | 5/2014 |
| WO | WO 2014/065209 | 5/2014 |
| WO | WO 2014/065236 | 5/2014 |
| WO | WO 2014/077285 | 5/2014 |
| WO | WO 2014/090147 | 6/2014 |
| WO | WO 2014/098831 | 6/2014 |
| WO | WO 2014/099834 | 6/2014 |
| WO | WO 2014/099836 | 6/2014 |
| WO | WO 2014/101295 | 7/2014 |
| WO | WO 2014/104387 | 7/2014 |
| WO | WO 2014/110297 | 7/2014 |
| WO | WO 2014/117718 | 8/2014 |
| WO | WO 2014/128591 | 8/2014 |
| WO | WO 2014/130582 | 8/2014 |
| WO | WO 2014/135617 | 9/2014 |
| WO | WO 2014/147021 | 9/2014 |
| WO | WO 2014/152588 | 9/2014 |
| WO | WO 2014/157994 | 10/2014 |
| WO | WO 2014/160185 | 10/2014 |
| WO | WO 2014/167084 | 10/2014 |
| WO | WO 2014/170873 | 10/2014 |
| WO | WO 2014/184343 | 11/2014 |
| WO | WO 2014/186450 | 11/2014 |
| WO | WO 2014/192902 | 12/2014 |
| WO | WO 2014/200882 | 12/2014 |
| WO | WO 2014/209034 | 12/2014 |
| WO | WO 2015/004029 | 1/2015 |
| WO | WO 2015/014900 | 2/2015 |
| WO | WO 2015/015993 | 2/2015 |
| WO | WO 2015/023664 | 2/2015 |
| WO | WO 2015/025172 | 2/2015 |
| WO | WO 2015/025962 | 2/2015 |
| WO | WO 2015/031561 | 3/2015 |
| WO | WO 2015/049034 | 4/2015 |
| WO | WO 2015/051071 | 4/2015 |
| WO | WO 2015/066188 | 5/2015 |
| WO | WO 2015/066697 | 5/2015 |
| WO | WO 2015/080904 | 6/2015 |
| WO | WO 2015/084842 | 6/2015 |
| WO | WO 2015/089634 | 6/2015 |
| WO | WO 2015/089809 | 6/2015 |
| WO | WO 2015/092009 | 6/2015 |
| WO | WO 2015/094118 | 6/2015 |
| WO | WO 2015/095256 | 6/2015 |
| WO | WO 2015/095701 | 6/2015 |
| WO | WO 2015/103317 | 7/2015 |
| WO | WO 2015/109109 | 7/2015 |
| WO | WO 2015/139621 | 9/2015 |
| WO | WO 2015/140133 | 9/2015 |
| WO | WO 2015/142903 | 9/2015 |
| WO | WO 2015/143185 | 9/2015 |
| WO | WO 2015/158689 | 10/2015 |
| WO | WO 2015/158690 | 10/2015 |
| WO | WO 2015/158692 | 10/2015 |
| WO | WO 2015/160636 | 10/2015 |
| WO | WO 2015/179563 | 11/2015 |
| WO | WO 2015/184983 | 12/2015 |
| WO | WO 2015/193219 | 12/2015 |
| WO | WO 2015/198045 | 12/2015 |
| WO | WO 2015/198046 | 12/2015 |
| WO | WO 2016/006511 | 1/2016 |
| WO | WO 2016/006512 | 1/2016 |
| WO | WO 2016/008381 | 1/2016 |
| WO | WO 2016/012958 | 1/2016 |
| WO | WO 2016/012965 | 1/2016 |
| WO | WO 2016/020864 | 2/2016 |
| WO | WO 2016/022464 | 2/2016 |
| WO | WO 2016/024745 | 2/2016 |
| WO | WO 2016/040305 | 3/2016 |
| WO | WO 2016/044171 | 3/2016 |
| WO | WO 2016/049524 | 3/2016 |
| WO | WO 2016/049565 | 3/2016 |
| WO | WO 2016/054406 | 4/2016 |

(56) References Cited

FOREIGN PATENT DOCUMENTS

| | | |
|---|---|---|
| WO | WO 2016/055786 | 4/2016 |
| WO | WO 2016/055790 | 4/2016 |
| WO | WO 2016/073470 | 5/2016 |
| WO | WO 2016/074757 | 5/2016 |
| WO | WO 2016/088354 | 6/2016 |
| WO | WO 2016/095581 | 6/2016 |
| WO | WO 2016/097918 | 6/2016 |
| WO | WO 2016/116517 | 7/2016 |
| WO | WO 2016/125560 | 8/2016 |
| WO | WO 2016/140973 | 9/2016 |
| WO | WO 2016/144702 | 9/2016 |
| WO | WO 2016/160833 | 10/2016 |
| WO | WO 2016/161145 | 10/2016 |
| WO | WO 2016/162785 | 10/2016 |
| WO | WO 2016/173557 | 11/2016 |
| WO | WO 2016/177845 | 11/2016 |
| WO | WO 2016/178110 | 11/2016 |
| WO | WO 2016/181772 | 11/2016 |
| WO | WO 2017/011279 | 1/2017 |
| WO | WO 2017/052187 | 3/2017 |
| WO | WO 2017/058728 | 4/2017 |
| WO | WO 2017/058807 | 4/2017 |
| WO | WO 2017/059357 | 4/2017 |
| WO | WO 2017/059434 | 4/2017 |
| WO | WO 2017/061581 | 4/2017 |
| WO | WO 2017/070003 | 4/2017 |
| WO | WO 2017/079641 | 5/2017 |
| WO | WO 2017/087695 | 5/2017 |
| WO | WO 2017/097216 | 6/2017 |
| WO | WO 2017/100644 | 6/2017 |
| WO | WO 2017/106818 | 6/2017 |
| WO | WO 2017/118734 | 7/2017 |
| WO | WO 2017/127637 | 7/2017 |
| WO | WO 2017/130828 | 8/2017 |
| WO | WO 2017/170765 | 10/2017 |
| WO | WO 2017/185034 | 10/2017 |
| WO | WO 2017/189569 | 11/2017 |
| WO | WO 2017/192961 | 11/2017 |
| WO | WO 2017/197046 | 11/2017 |
| WO | WO 2017/223414 | 12/2017 |
| WO | WO 2018/006795 | 1/2018 |
| WO | WO 2018/033019 | 2/2018 |
| WO | WO 2018/037058 | 3/2018 |
| WO | WO 2018/042362 | 3/2018 |
| WO | WO 2018/056643 | 3/2018 |
| WO | WO 2018/056644 | 3/2018 |

OTHER PUBLICATIONS

Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Blunt et al. Leukemia Research Reports 4 (2015) 60-63.*
Golub et al., Science, 286, 531-537, 1999.Golub et al., Science, 286, 531-537, 1999.*
Cohen et al., Current Opinion in Chemical Biology, 3,459-465, 1999.*
RD 371041, Mar. 10, 1995, KR.
Barber et al., "PI3Kgamma inhibition blocks glomerulonephritis and extends lifespan in a mouse model of systemic lupus," Nat. Medicine, 2005, 11(9):933-935.
Bennani et al., "A short route to a moshe'rs acid precursor via catalytic asymmetric dihydroxylation (AD)," Tetrahedron: Asymmetry, 1994, 5(8):1473-1476.
Berge et al., "Pharmaceutical Salts," Journal of Pharmaceutical Science, 1977, 66:1-19.
Berod et al., "PI3Kγ deficiency delays the onset of experimental autoimmune encephalomyelitis and ameliorates its clinical outcome," Euro. J. Immunol., Mar. 2011, 41(3):833-844.

Blom et al., "Optimizing Preparative LC-MS Configurations and Methods for Parallel Synthesis Purification," J. Comb. Chem., Jul. 39, 2003, 5(5):670-683.
Blom et al., "Preparative LC-MS Purification: Improved Compound Specific Method Optimization," J Comb Chem., Sep. 11, 2004, 6(6):874-883.
Blom et al., "Two-Pump at Column Dilution Configuration for Preparative LC-MS," J. Comb. Chem., Jul.-Aug. 2002, 4(4):295-301.
Brock et al., "Roles of Gβγ in membrane recruitment and activation of p110γ/p101 phosphoinositide 3-kinase γ," J. Cell Biol., 2003, 160(1):89-99.
Camps et al., "Blockade of PI3Kγ suppresses joint inflammation and damage in mouse models of rheumatoid arthritis," Nat. Medicine, 2005, 11(9):936-943.
Cantley et al., "The Phosphoinositide 3-Kinase Pathway," Science, 2002, 296(5573):1655-1657.
Carter et al., "Prioritization of driver mutations in pancreatic cancer using cancer-specific high-throughput annotation of somatic mutations (CHASM)," Cancer Biol. Ther., 2010, 10(6):582-587.
Cheung et al., "Mild and phosphine-free iron-catalyzed cross-coupling of nonactivated secondary alkyl halides with alkynyl Grignard reagents," Org. Lett., May 2, 2014, 16(9):2566-2569.
Choudhury-Mukherjee et al., "Design, Synthesis, and Evaluation of Analogues of 3,3,3-Trifluoro-2-Hydroxy-2-Phenyl-Propionamide as Orally Available General Anesthetics," J. Med. Chem., 2003, 46(12):2494-2501.
Cohen et al., "Physicians' Desk Reference," Arch. Intern. Med., Jul. 8, 1996, 516 (6 pages).
Comerford et al., "PI3Kγ Drives Priming and Survival of Autoreactive CD4+ T Cells during Experimental Autoimmune Encephalomyelitis," PLOS one, 2012, 7(9):e45095.
Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," J. Pharmacol. Exp. Ther. 2009, 328(3):758-765.
Doukas et al., "Phosphoinositide 3-kinase γ/δ inhibition limits infarct size after myocardial ischemia/reperfusion injury," Proc. Natl. Acad. Sci. USA, 2006, 103(52):19866-19871.
El Khoury et al., "Ccr2 deficiency impairs microglial accumulation and accelerates progression of Alzheimer-like disease," Nat. Med., 2007, 13(4):432-438.
Ellman et al., "N-tert-Butanesulfinyl Imines: Versatile Intermediates for the Asymmetric Synthesis of Amines," Acc. Chem. Res., 2002, 35(11):984-995.
Falasca et al., "Targeting p110gamma in gastrointestinal cancers: attack on multiple fronts," Frontiers in Physiology, 2014, 5(391):1-10.
Gennaro, "Remington's Pharmaceutical Sciences," Mack Publishing Company, Easton, Pa., 1985, 17th ed., p. 1418.
Giri et al., "Mechanism of amyloid peptide induced CCR5 expression in monocytes and its inhibition by iRNA for Egr-1," Am. J. Physiol. Cell Physiol., 2005, 289:C264-C276.
Gonzalez-Garcia et al., "Phosphatidylinositol 3-Kinase γ Inhibition Ameliorates Inflammation and Tumor Growth in a Model of Colitis-Associated Cancer," Gastroenterology, 2010, 138:1374-1384.
Hanahan et al., "Hallmarks of Cancer: The Next Generation," Cell, 2011, 144:646-674.
Hayer et al., "PI3Kγ regulates cartilage damage in chronic inflammatory arthritis," FASEB Journal, 2009, 23:4288-4298.
International Search Report and Written Opinion in International Application No. PCT/US2019/021186, dated Nov. 25, 2019, 12 pages.
International Search Report and Written Opinion in International Application No. PCT/US2019/040147, dated Sep. 13, 2019, 13 pages.
Jimenez et al.,"The p85 Regulatory Subunit Controls Sequential Activation of Phosphoinositide 3-Kinase by Tyr Kinases and Ras," J. Biol. Chem., 2002, 277(44):41556-41562.
Kaneda et al., "Abstract 3650: PI3-kinase gamma controls the macrophage M1-M2 switch, thereby promoting tumor immunosuppression and progression," Cancer Res., 2014, 74:(Suppl. 19: Abstract 3650).

(56) References Cited

OTHER PUBLICATIONS

Kendell and McKenzie, "B-Bromopropionic Acid," Org. Synth. Co., 1941, 1:131.
Kerekes et al., "Aurora Kinase Inhibitors Based on the Imidazo[1,2-a]pymzine Core: Fluorine and Deuterium Incorporation Improve Oral Absorption and Exposure," J. Med. Chem., 2011, 54(1):201-210.
Khoury et al., "Ccr2 deficiency impairs microglial accumulation and accelerates progression of Alzheimer-like disease," Nat. Med., 2007, 13(4):432-438.
Kolb et al., "Catalytic Asymmetric Dihydroxylation," Chem Rev., 1994, 94(8):2483-2547.
Laffargue et al., "Phosphoinositide 3-Kinase γ Is an Essential Amplifier of Mast Cell Function," Immunity, 2002, 16:441-451.
Lebel et al., "Highly Chemoselective Rhodium-Catalyzed Methylenation of Fluorine-Containing Ketones," Organic Letters, 2002, 4(10):1671-1674.
Li al., "PI3Kγ inhibition alleviates symptoms and increases axon number in experimental autoimmune encephalomyelitis mice," Neuroscience, 2013, 253:89-99.
Lupia et al., "Ablation of Phosphoinositide 3-Kinase-Reduces the Severity of Acute Pancreatitis," Am. J. Pathology, 2004, 165(6):2003-2011.
Luzung et al., "Rhenium-Catalyzed Coupling of Propargyl Alcohols and Allyl Silanes," J. Am. Chem. Soc., 2003, 125(51):15760-15761.
Manning et al., "An innovative and efficient synthesis of stable isotope labelled. 1-methyl-5-(4,4,5,5-tetramethyl-1,3,2-dioxaborolan-2-yl)-1H-pyrazole via [$^{13}C_4 {}^2H_3$]N-methylpyrazole," Journal of Labelled Compounds and Radiopharmaceuticals, Nov. 2012, 55(13):467-469.
Martin et al., "PI3Kγ Mediates Kaposi's Sarcoma Associated Herpesvirus vGPCR-Induced Sarcomagenesis," Cancer Cell, 2011, 19(6):805-813.
Marvel and Tuley, "Glutaric Acid," Org Synth Coll., 1941, 1:289.
Moreno-Dorado et al., "Enantioselective synthesis of alylmethoxyacetic acid derivatives," Tetrahedron: Asymmetry, Feb. 21, 2003, 14(4):503-510.
Passos et al., "Involvement of phosphoinositide 3-kinase γ in the neuro-inflammatory response and cognitive impairments induced by b-amyloid 1-40 peptide in mice," Brain Behav. Immun., 2010, 24:493-501.
Pinho et al., "Phosphoinositide-3 kinases critically regulate the recruitment and survival of eosinophils in vivo: importance for the resolution of allergic inflammation," Journal of Leukocyte Biology, 2005, 77:800-810.
Prete et al., "Defective dendritic cell migration and activation of adaptive immunity in PI3Kc-deficient mice," The EMBO Journal, 2004, 23:3505-3515.

Randis et al., "Role of PI3Kδ and PI3Kγ in inflammatory arthritis and tissue localization of neutrophils," Eur. J. Immunol, 2008, 38(5):1215-1224.
Read, "B-Hydroxypropianic Acid," Org Synth Coll., 1941, 1:321.
Remington's Pharmaceutical Sciences, 17th ed., Mack Publishing Company Easton, Pa., 1985, Chapter 76, 18 pages.
Robak et al., "Synthesis and Applications of tert-Butanesulfinamide," Chem. Rev., 2010, 110(6):3600-3740.
Rodrigues et al., "Absence of PI3Kγ leads to increased leukocyte apoptosis and diminished severity of experimental autoimmune encephalomyelitis," J. Neuroimmunol. 2010, 222:90-94.
Ruckle et al., "PI3Kγ inhibition: towards an 'aspirin of the 21st century'?" Nat. Rev. Drug Discovery, 2006, 5:903-918.
Saito et al, "Direct Dehydroxylative Coupling Reaction of Alcohols with Organosilanes through Si-X Bond Activation by Halogen Bonding," Org. Lett., 2015, 17(12):3000-3003.
Schmid et al., "Receptor tyrosine kinases and TLR/IL1Rs unexpectedly activate myeloid cell PI3Kγ, a single convergent point promoting tumor inflammation and progression," Cancer Cell, 2011, 19(6):715-727.
Schmidt et al., "Abstract 411: PI3 Kinase gamma control of Arginase-1 expression promotes tumor immunosuppression," Cancer Res. 2012, 72:(Suppl. 1: Abstract 411).
Sharpless et al., "The osmium-catalyzed asymmetric dihydroxylation: a new ligand class and a process improvement," J. Org. Chem., May 1, 1992, 57(10):2768-2771.
Sigmaaldrich.com, "L-α-Phosphatidyl-D-myo-inositol 4,5-diphosphate, dioctanoyl," CAS 204858-53-7, Retrieved on Jul. 6, 2020, 3 pages.
Subramanjam et al., "Targeting Nonclassical Oncogenes for Therapy in T-ALL," Cancer Cell, 2012, 21:459-472.
Thomas et al., "Airway inflammation: chemokine-induced neutrophilia and the class I phosphoinositide 3-kinases," Eur. J Immunol., 2005, 35:1283-1291.
Vanhaesebroeck et al., "Signalling by PI3K isoforms: insights from gene-targeted mice," Trends Biochem. Sci., 2005, 30(4):194-204.
Vecchione et al., Protection from angiotensin II-mediated vasculotoxic and hypertensive response in mice lacking PI3Ky, J Exp. Med., 2005, 201(8):1217-1228.
Winterfeldt, "Applications of Diisobutylaluminium Hydride (DIBAH) and Triisobutylaluminium (TIBA) as Reducing Agents in Organic Synthesis," Synthesis, 1975, 10:617-630.
Xu et al., "Design, synthesis and biological evaluation of deuterated nintedanib for improving pharmacokinetic properties," J Label Compd Radiopharm., Jun. 15, 2015, 58(7):308-312.
Yang et al., "Kumada-Corriu Reactions of Alkyl Halides with Alkynyl Nucleophiles," Org. Lett., 2004, 6(9):1461-1463.
Hulikal, "Deuterium Labeled Compounds in Drug Discovery Process," Bioorganics and Applied Marerials Pvt Ltd., 2010, Abstract L15 (Abstract Only).
International Preliminary Report on Patentability in International Application No. PCT/US2019/021186, dated Sep. 8, 2020, 7 pages.
International Preliminary Report on Patentability in International Application No. PCT/US2019/040147, dated Jan. 14, 2021, 8 pages.

* cited by examiner

AMINOPYRAZINE DERIVATIVES AS PI3K-γ INHIBITORS

TECHNICAL FIELD

The present invention provides derivatives of aminopyrazine compounds that modulate the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

Expression of PI3Kγ is mainly restricted to hematopoietic system, although it can be also detected at lower level in endothelium, heart and brain. PI3Kγ knockout or kinase dead knock in mice are normal and fertile and do not present any overt adverse phenotypes. Analysis at the cellular level indicates that PI3Kγ is required for GPCR ligand-induced PtdINs (3,4,5)P3 production, chemotaxis and respiratory burst in neutrophils. PI3Kγ-null macrophages and dendritic cell exhibit reduced migration towards various chemoattractants. T-cells deficient in PI3Kγ show impaired cytokine production in response to anti-CD3 or Con A stimulation. PI3Kγ working downstream of adenosine A3A receptor is critical for sustained degranulation of mast cells induced by FCεRI cross-linking with IgE. PI3Kγ is also essential for survival of eosinophils (Ruckle et al., Nat. Rev. Drug Discovery, 2006, 5, 903-918)

Given its unique expression pattern and cellular functions, the potential role of PI3Kγ in various autoimmune and inflammatory disease models has been investigated with genetic and pharmacological tools. In asthma and allergy models, PI3Kγ$^{-/-}$ mice or mice treated with PI3Kγ inhibitor showed a defective capacity to mount contact hypersensitivity and delayed-type hypersensitivity reactions. In these models, PI3Kγ was shown to be important for recruitment of neutrophils and eosinopohils to airways and degranulation of mast cells (see e.g. Laffargue et al., Immunity, 2002, 16, 441-451; Prete et al., The EMBO Journal, 2004, 23, 3505-3515; Pinho et al., L. Leukocyte Biology, 2005, 77, 800-810; Thomas et al., Eur. J. Immunol. 2005, 35, 1283-1291; Doukas et al., J. Pharmacol. Exp Ther. 2009, 328, 758-765).

In two different acute pancreatitis models, genetic ablation of PI3Kγ significantly reduced the extent of acinar cell injury/necrosis and neutrophil infiltration without any impact on secretive function of isolated pancreatic acini (Lupia et al., Am. J Pathology, 2004, 165, 2003-2011). PI3Kγ$^{-/-}$ mice were largely protected in four different models of rheumatoid arthritis (CIA, α-CII-IA, K/BxN serum transfer and TNF transgenic) and PI3Kγ inhibition suppressed the progression of joint inflammation and damage in the CIA and α-CII-IA models (see e.g., Camps et al., Nat. Medicine, 2005, 11, 939-943; Randis et al., Eur. J. Immunol, 2008, 38, 1215-1224; Hayer et al., FASB J, 2009, 4288-4298). In the MRL-lpr mouse model of human systemic lupus erythematous, inhibition of PI3Kγ reduced glomerulonephritis and prolonged life span (Barber et al., Nat. Medicine, 2005, 9, 933-935).

There is evidence suggesting that chronic inflammation due to infiltration by myeloid-derived cells is a key component in the progression of neurodegeneration diseases, such as Alzheimer's disease (AD) (Giri et al., Am. J. Physiol. Cell Physiol., 2005, 289, C264-C276; E I Khoury et al., Nat. Med., 2007, 13, 432-438). In line with this suggestion, PI3Kγ inhibition was shown to attenuate Aβ(1-40)-induced accumulation of activated astrocytes and microglia in the hippocampus and prevent the peptide-induced cognitive deficits and synaptic dysfunction in a mouse model of AD (Passos et al., Brain Behav. Immun. 2010, 24, 493-501). PI3Kγ deficiency or inhibition also was shown to delay onset and alleviate symptoms in experimental autoimmune encephalomyelitis in mice, a mouse model of human multiple sclerosis, which is another form of neurodegeneration disease (see e.g., Rodrigues et al., J. Neuroimmunol. 2010, 222, 90-94; Berod et al., Euro. J. Immunol. 2011, 41, 833-844; Comerford et al., PLOS one, 2012, 7, e45095; Li et al., Neuroscience, 2013, 253, 89-99).

Chronic inflammation has been formally recognized as one of the hallmarks for many different types of cancers. Accordingly, selective anti-inflammatory drugs represent a novel class of anti-cancer therapies (Hanahan and Weinberg, Cell, 2011, 144, 646-674). Since PI3Kγ is reported to mediate various inflammatory processes, its role as an immune oncology target has also been investigated. A recent study reported that PI3Kγ deficiency suppressed tumor growth in the syngeneic models of lung cancer, pancreatic cancer and melanoma (LLC, PAN02 and B16). PI3Kγ deficiency or inhibition also inhibited tumor growth in a spontaneous breast cancer model (Schmid et al., Cancer Cell, 2011, 19, 715-727). A further study reported that PI3Kγ deficiency could ameliorate inflammation and tumor growth in mice having colitis-associated colon cancer, (Gonzalez-Garcia et al., Gastroenterology, 2010, 138, 1373-1384). Detailed mechanistic analysis indicates that tumor infiltration by CD11b$^+$ myeloid cells can cause protumorigenic inflammation at tumor sites and PI3Kγ in the myeloid cells is critical in mediating signaling of various chemoattractants in bring the cells to the tumor (Schmid et al., Cancer Cell, 2011, 19, 715-727). Other studies suggest that PI3Kγ is also required for differentiation of naïve myeloid cells into M2 macrophages at tumor sites. M2 macrophages promote tumor growth and progression by secreting immunosuppressive factors such arginase 1, which depletes the tumor microenvironment of arginine, thereby promoting T-cell death and NK cell inhibition (Schmidt et al., Cancer Res.

2012, 72 (Suppl 1: Abstract, 411; Kaneda et al., Cancer Res., 74 (Suppl 19: Abstract 3650)).

In addition to its potential role in promoting protumorigenic microenvironment, PI3Kγ may play a direct role in cancer cells. PI3Kγ is reported to be required for signaling from the Kaposi's sarcoma-associated herpevirus encoded vGPCR oncogene and tumor growth in a mouse model of sarcoma (Martin et al., Cancer Cell, 2011, 19, 805-813). PI3Kγ was also suggested to be required for growth of T-ALL (Subramanjam et al., Cancer Cell, 2012, 21, 459-472), PDAC and HCC cells (Falasca and Maffucci, Frontiers in Physiology, 2014, 5, 1-10). Moreover, in a survey of driver mutations in pancreatic cancer, PI3Kγ gene was found to contain second highest scoring predicted driven mutation (R839C) among the set of genes not previously identified as a driver in pancreatic cancer (Carter et al., Cancer Biol. Ther. 2010, 10, 582-587).

Finally, PI3Kγ deficiency also has been reported to offer protection to experimental animals in different cardiovascular disease models. For examples, lack of PI3Kγ would reduce angiotensin-evoked smooth muscle contraction and, therefore, protect mice from angiotensin-induced hypertension (Vecchione et al., J Exp. Med. 2005, 201, 1217-1228). In rigorous animal myocardial infarction models, PI3Kγ inhibition provided potent cardioprotection, reducing infarct development and preserving myocardial function (Doukas et al., Proc. Natl. Acad. Sci. USA, 2006, 103, 19866-19871).

For these reasons, there is a need to develop new PI3Kγ inhibitors that can be used for the treatment of diseases such as cancer, autoimmune disorders, and inflammatory and cardiac diseases. This application is directed to this need and others.

SUMMARY

The present invention relates to, inter alia, compounds of Formula (I):

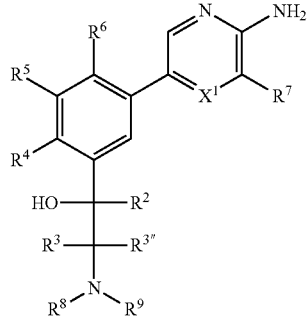

or a pharmaceutically acceptable salt thereof, wherein constituent members are defined herein.

The present invention further provides pharmaceutical compositions comprising a compound of Formula (I), or a pharmaceutically acceptable salt thereof, and a pharmaceutically acceptable carrier.

The present invention further provides methods of inhibiting an activity of PI3Kγ kinase comprising contacting the kinase with a compound of Formula (I), or a pharmaceutically acceptable salt thereof.

The present invention further provides methods of treating a disease or a disorder associated with abnormal PI3Kγ kinase expression or activity in a patient by administering to said patient a therapeutically effective amount of a compound of Formula (I), or a pharmaceutically acceptable salt thereof.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

DETAILED DESCRIPTION

Compound Subset (A)

The present application provides, inter alia, compounds of Formula (I):

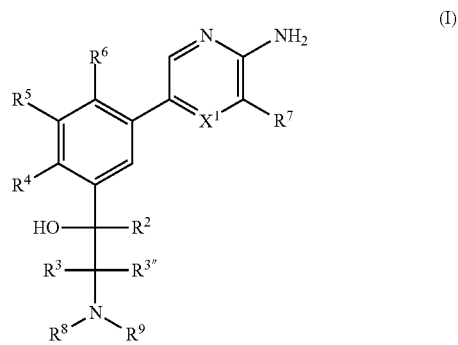

or a pharmaceutically acceptable salt thereof; wherein:

$X^1$ is N or $CR^1$;

$R^1$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH and $NH_2$;

$R^2$ is a $C_{1-6}$ haloalkyl, wherein each halogen is independently selected from F and Cl, wherein the haloalkyl is optionally substituted with $C(O)NR^aR^b$ or 1, 2, 3 or 4 independently selected $R^M$ substituents;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^3$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and $NH_2$;

$R^{3''}$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and $NH_2$;

or, alternatively, $R^3$ and $R^{3''}$ together form an oxo group;

$R^4$, $R^5$ and $R^6$ are each independently selected from H, D, halo, CN, OH, $NH_2$, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkylamino, di($C_{1-6}$ alkyl)amino, and $C(O)NR^aR^b$;

each $R^a$ and $R^b$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^a$ and $R^b$ are each optionally substituted with 1, 2, 3 or 4 independently selected $R^M$ substituents;

$R^7$ is selected from $C(O)R^{b7}$, $C(O)NR^{c7}R^{d7}$, $C(O)NR^{c7}(OR^{b7})$, $C(O)OR^{a7}$, $C(=NR^{e7})R^{b7}$, $C(=NOH)R^{b7}$, $C(=NCN)R^{b7}$, $C(=NR^{e7})NR^{c7}R^{d7}$, $S(O)R^{b7}$, $S(O)NR^{c7}R^{d7}$, $S(O)_2R^{b7}$, and $S(O)_2NR^{c7}R^{d7}$;

each $R^{a7}$, $R^{b7}$, $R^{c7}$, and $R^{d7}$ is independently selected from H, $C_{1-6}$ alkyl, $C_{2-6}$ alkenyl, $C_{2-6}$ alkynyl, $C_{3-12}$ cycloalkyl and 4-12 membered heterocycloalkyl, wherein the $C_{1-6}$ alkyl, $C_{2-6}$ alkenyl, $C_{2-6}$ alkynyl, $C_{3-12}$ cycloalkyl and 4-12 membered heterocycloalkyl of $R^{a7}$, $R^{b7}$, $R^{c7}$, and $R^{d7}$ are each optionally substituted with 1, 2, 3 or 4 independently selected $R^{7A}$ substituents;

or, $R^{c7}$ and $R^{d7}$, together with the N atom to which they are attached, form a 5- or 6-membered heteroaryl or a 4-14-membered heterocycloalkyl group, wherein the 5- or 6-membered heteroaryl or 4-14-membered heterocycloalkyl group is optionally substituted with 1, 2, 3 or 4 independently selected $R^{7A}$ substituents;

each $R^{e7}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-12}$ cycloalkyl, 5-14 membered heteroaryl, 4-12 membered heterocycloalkyl, $C_{6-14}$ aryl-$C_{1-6}$ alkyl-, $C_{3-12}$ cycloalkyl-$C_{1-6}$ alkyl-, (5-14 membered heteroaryl)-$C_{1-6}$ alkyl- and (4-12 membered heterocycloalkyl)-$C_{1-6}$ alkyl-;

$R^8$ and $R^9$ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b8}$, $C(O)NR^{c8}R^{d8}$, $C(O)OR^{a8}$, $C(=NR^{e8})R^{b8}$, $C(=NR^{e8})NR^{c8}R^{d8}$, $C(=NCN)NR^{c8}R^{d8}$, $C(=NOR^{a8})NR^{c8}$, $S(O)_2R^{b8}$, $S(O)(=NR^{c8})R^{d8}$, and $S(O)_2NR^{c8}R^{d8}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^8$ and $R^9$ are each optionally substituted with 1, 2, 3, or 4 independently selected $R^{8A}$ substituents;

or, $R^8$ and $R^9$, together with the N atom to which they are attached, form a 5- or 6-membered heteroaryl, or a 4-10 membered heterocycloalkyl group, wherein the 5- or 6-membered heteroaryl, or 4-10 membered heterocycloalkyl group is optionally substituted with 1, 2, 3, or 4 independently selected $R^{8A}$ substituents;

each $R^{7A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a71}$, $SR^{a71}$, $NHOR^{a71}$, $C(O)R^{b71}$, $C(O)NR^{c71}R^{d71}$, $C(O)NR^{c71}(OR^{b71})$, $C(O)OR^{a71}$, $OC(O)R^{b71}$, $OC(O)NR^{c71}R^{d71}$, $NR^{c71}R^{d71}$, $NR^{c71}NR^{c71}R^{d71}$, $NR^{c71}C(O)R^{b71}$, $NR^{c71}C(O)OR^{a71}$, $NR^{c71}C(O)NR^{c71}R^{d71}$, $C(=NR^{e71})R^{b71}$, $C(=NOH)R^{b71}$, $C(=NCN)R^{b71}$, $C(=NR^{e71})NR^{c71}R^{d71}$, $NR^{c71}C(=NR^{e71})NR^{c71}R^{d71}$, $NR^{c71}C(=NR^{e71})R^{b71}$, $NR^{c71}C(=NOH)NR^{c71}R^{d71}$, $NR^{c71}C(=NCN)NR^{c71}R^{d71}$, $NR^{c71}S(O)R^{b71}$, $NR^{c71}S(O)NR^{c71}R^{d71}$, $NR^{c71}S(O)_2R^{b71}$, $NR^{c71}S(O)_2NR^{c71}R^{d71}$, $S(O)R^{b71}$, $S(O)NR^{c71}R^{d71}$, $S(O)_2R^{b71}$, $S(O)_2NR^{c71}R^{d71}$, $OS(O)(=NR^{e71})R^{b71}$, $OS(O)_2R^{b71}$, $SF_5$, $P(O)R^{f71}R^{g71}$, $OP(O)(OR^{h71})(OR^{i71})$, $P(O)(OR^{h71})(OR^{i71})$ and $BR^{j71}R^{k71}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl and 4-10 membered heterocycloalkyl, of $R^{7A}$ are each optionally substituted with 1, 2, 3 or 4 independently selected $R^{7B}$ substituents;

each $R^{a71}$, $R^{b71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a71}$, $R^{b71}$, $R^{c71}$, and $R^{d71}$ are each optionally substituted with 1, 2, 3 or 4 independently selected $R^{7B}$ substituents;

or, any $R^{c71}$ and $R^{d71}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{7B}$ substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f71}$ and $R^{g71}$ is independently selected H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h71}$ and $R^{i71}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j71}$ and $R^{k71}$ is independently selected from OH, $C_{1-6}$ alkoxy, and $C_{1-6}$ haloalkoxy;

or any $R^{j71}$ and $R^{k71}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, OR$^{a72}$, SR$^{a72}$, NHOR$^{a72}$, C(O)R$^{b72}$, C(O)NR$^{c72}$R$^{d72}$, C(O)NR$^{72}$(OR$^{b72}$), C(O)OR$^{a72}$, OC(O)R$^{b72}$, OC(O)NR$^{c72}$R$^{d72}$, NR$^{c72}$R$^{d72}$, NR$^{c72}$NR$^{c72}$R$^{d72}$, NR$^{c72}$C(O)R$^{b72}$, NR$^{c72}$C(O)OR$^{a72}$, NR$^{c72}$C(O)NR$^{c72}$R$^{d72}$, C(=NR$^{e72}$)R$^{b72}$, C(=NOH)R$^{b72}$, C(=NCN)R$^{b72}$, C(=NR$^{e72}$)NR$^{c72}$R$^{d72}$, NR$^{c72}$C(=NR$^{e72}$)NR$^{c72}$R$^{d72}$, NR$^{c72}$C(=NR$^{e72}$)R$^{b72}$, NR$^{c72}$C(=NOH)NR$^{c72}$R$^{d72}$, NR$^{c72}$C(=NCN)NR$^{c72}$R$^{d72}$, NR$^{c72}$S(O)R$^{b72}$, NR$^{c72}$S(O)NR$^{c72}$R$^{d72}$, NR$^{c72}$S(O)$_2$R$^{b72}$, NR$^{c72}$S(O)$_2$NR$^{c72}$R$^{d72}$, S(O)R$^{b72}$, S(O)NR$^{c72}$R$^{d72}$, S(O)$_2$R$^{b72}$, S(O)$_2$NR$^{c72}$R$^{d72}$, OS(O)(=NR$^{e72}$)R$^{b72}$, OS(O)$_2$R$^{b72}$, SF$_5$, P(O)R$^{f72}$R$^{g72}$, OP(O)(OR$^{h72}$)(OR$^{i72}$), P(O)(OR$^{h72}$)(OR$^{i72}$), and BR$^{j72}$R$^{k72}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl- of R$^{7B}$ are each optionally substituted with 1, 2, 3 or 4 independently selected R$^{7C}$ substituents;

each R$^{a72}$, R$^{b72}$, R$^{c72}$, and R$^{d72}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl- of R$^{a72}$, R$^{b72}$, R$^{c72}$, and R$^{d72}$ are each optionally substituted with 1, 2, 3 or 4 independently selected R$^{7C}$ substituents;

or, any R$^{c72}$ and R$^{d72}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected R$^{7C}$ substituents;

each R$^{e72}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl-;

each R$^{f72}$ and R$^{g72}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl-;

each R$^{h72}$ and R$^{i72}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl-;

each R$^{j72}$ and R$^{k72}$ is independently selected from OH, C$_{1-6}$ alkoxy, and C$_{1-6}$ haloalkoxy;

or any R$^{j72}$ and R$^{k72}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{7C}$ is independently selected from D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a73}$, SR$^{a73}$, NHOR$^{a73}$, C(O)R$^{b73}$, C(O)NR$^{c73}$R$^{d73}$, C(O)NR$^{c73}$(OR$^{b73}$), C(O)OR$^{a73}$, OC(O)R$^{b73}$, OC(O)NR$^{c73}$R$^{d73}$, NR$^{c73}$R$^{d73}$, NR$^{c73}$NR$^{c73}$R$^{d73}$, NR$^{c73}$C(O)R$^{b73}$, NR$^{c73}$C(O)OR$^{a73}$, NR$^{c73}$C(O)NR$^{c73}$R$^{d73}$, C(=NR$^{e73}$)R$^{b73}$, C(=NOH)R$^{b73}$, C(=NCN)R$^{b73}$, C(=NR$^{e73}$)NR$^{c73}$R$^{d73}$, NR$^{c73}$C(=NR$^{e73}$)NR$^{c73}$R$^{d73}$, NR$^{c73}$C(=NR$^{e73}$)R$^{b73}$, NR$^{c73}$C(=NOH)NR$^{c73}$R$^{d73}$, NR$^{c73}$C(=NCN)NR$^{c73}$R$^{d73}$, NR$^{c73}$S(O)R$^{b73}$, NR$^{c73}$S(O)NR$^{c73}$R$^{d73}$, NR$^{c73}$S(O)$_2$R$^{b73}$, NR$^{c73}$S(O)$_2$NR$^{c73}$R$^{d73}$, S(O)R$^{b73}$, S(O)NR$^{c73}$R$^{d73}$, S(O)$_2$R$^{b73}$, S(O)$_2$NR$^{c73}$R$^{d73}$, OS(O)(=NR$^{e73}$)R$^{b73}$, OS(O)$_2$R$^{b73}$, SF$_5$, P(O)R$^{f73}$R$^{g73}$, OP(O)(OR$^{h73}$)(OR$^{i73}$), P(O)(OR$^{h73}$)(OR$^{i73}$), and BR$^{j73}$R$^{k73}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl- of R$^{7C}$ are each optionally substituted with 1, 2, 3 or 4 independently selected R$^{7D}$ substituents;

each R$^{a73}$, R$^{b73}$, R$^{c73}$, and R$^{d73}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl- of R$^{a73}$, R$^{b73}$, R$^{c73}$, and R$^{d73}$ are each optionally substituted with 1, 2, 3 or 4 independently selected R$^{7D}$ substituents;

or, any R$^{c73}$ and R$^{d73}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected R$^{7D}$ substituents;

each R$^{e73}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl-;

each R$^{f73}$ and R$^{g73}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl-;

each R$^{h73}$ and R$^{i73}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl-;

each R$^{j73}$ and R$^{k73}$ is independently selected from OH, C$_{1-6}$ alkoxy, and C$_{1-6}$ haloalkoxy;

or any R$^{j73}$ and R$^{k73}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7D}$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl- and (4-7 membered heterocycloalkyl)-$C_{1-6}$ alkyl;

each $R^{a8}$, $R^{b8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a8}$, $R^{b8}$, $R^{c8}$, and $R^{d8}$ are each optionally substituted with 1, 2, 3 or 4 independently selected $R^{8A}$ substituents;

or, any $R^{c8}$ and $R^{d8}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{8A}$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{8A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a81}$, $SR^{a81}$, $NHOR^{a81}$, $C(O)R^{b81}$, $C(O)NR^{c81}R^{d81}$, $C(O)NR^{c81}(OR^{b81})$, $C(O)OR^{a81}$, $OC(O)R^{b81}$, $OC(O)NR^{c81}R^{d81}$, $NR^{c81}R^{d81}$, $NR^{c81}NR^{c81}R^{d81}$, $NR^{c81}C(O)R^{b81}$, $NR^{c81}C(O)OR^{a81}$, $NR^{c81}C(O)NR^{c81}R^{d81}$, $C(=NR^{e81})R^{b81}$, $C(=NOH)R^{b81}$, $C(=NCN)R^{b81}$, $C(=NR^{e81})NR^{c81}R^{d81}$, $NR^{c81}C(=NR^{e81})NR^{c81}R^{d81}$, $NR^{c81}C(=NR^{e81})R^{b81}$, $NR^{c81}C(=NOH)NR^{c81}R^{d81}$, $NR^{c81}C(=NCN)NR^{c81}R^{d81}$, $NR^{c81}S(O)R^{b81}$, $NR^{c81}S(O)NR^{c81}R^{d81}$, $NR^{c81}S(O)_2R^{b81}$, $NR^{c81}S(O)_2NR^{c81}R^{d81}$, $S(O)R^{b81}$, $S(O)NR^{c81}R^{d81}$, $S(O)_2R^{b81}$, $S(O)_2NR^{c81}R^{d81}$, $OS(O)(=NR^{e81})R^{b81}$, $OS(O)_2R^{b81}$, $SF_5$, $P(O)R^{f81}R^{g81}$, $OP(O)(OR^{h81})(OR^{i81})$, $P(O)(OR^{h81})(OR^{i81})$, and $BR^{j81}R^{k81}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{8A}$ are each optionally substituted with 1, 2, 3 or 4 independently selected $R^{8B}$ substituents;

each $R^{a81}$, $R^{b81}$, $R^{c81}$, and $R^{d81}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a81}$, $R^{b81}$, $R^{c81}$, and $R^{d81}$ are each optionally substituted with 1, 2, 3 or 4 independently selected $R^{8B}$ substituents;

or, any $R^{c81}$ and $R^{d81}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{8B}$ substituents;

each $R^{e81}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f81}$ and $R^{g81}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h81}$ and $R^{i81}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j81}$ and $R^{k81}$ is independently selected from OH, $C_{1-6}$ alkoxy, and $C_{1-6}$ haloalkoxy;

or any $R^{j81}$ and $R^{k81}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^{8B}$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl- and (4-7 membered heterocycloalkyl)-$C_{1-6}$ alkyl.

In some embodiments, either: (a) $R^3$ and $R^{3''}$ together form an oxo group; or (b) $R^8$ is $C(O)R^{b8}$ In some embodiments, $X^1$ is N.

In some embodiments, $X^1$ is $CR^1$.

In some embodiments, $R^1$ is selected from H, D, and $C_{1-6}$ alkyl.

In some embodiments, $R^1$ is selected from H, D, and methyl.

In some embodiments, $R^1$ is H.

In some embodiments, $R^2$ is a $C_{1-6}$ haloalkyl, wherein each halogen of the $C_{1-6}$ haloalkyl is independently selected from F and Cl.

In some embodiments, $R^2$ is a $C_{1-3}$ haloalkyl, wherein each halogen of the $C_{1-3}$ haloalkyl is independently selected from F and Cl.

In some embodiments, $R^2$ is selected from $CF_3$, $CCl_3$, $CF_2H$, $CCl_2H$, $CF_2R^M$, $CCl_2R^M$, $CFH_2$, $CClH_2$, $CFHR^M$, $CClHR^M$, $CF(R^M)_2$ and $CCl(R^M)_2$.

In some embodiments, $R^2$ is selected from $CF_3$, $CF_2H$, $CF_2R^M$, $CFH_2$, $CFHR^M$, and $CF(R^M)_2$.

In some embodiments, $R^M$ is selected from D, halo, $C_{1-3}$ alkyl, and $C_{1-3}$ haloalkyl.

In some embodiments, $R^M$ is selected from halo and $C_{1-3}$ haloalkyl.

In some embodiments, $R^2$ is $C_{1-6}$ haloalkyl, wherein each halogen is F.

In some embodiments, $R^2$ is $C_{1-6}$ haloalkyl, wherein each halogen is Cl.

In some embodiments, $R^2$ is selected from $CH_2F$, $CHF_2$, $CF_3$, and $CF_2CF_3$.

In some embodiments, $R^2$ is $CF_3$ or $CHF_2$.

In some embodiments, $R^2$ is $CF_3$.

In some embodiments, $R^2$ is $CH_2F$.

In some embodiments, $R^2$ is $CHF_2$.

In some embodiments, $R^2$ is $CF_2CF_3$.

In some embodiments, $R^3$ is selected from H, D, $C_{1-6}$ alkyl, $C_{2-6}$ alkenyl, $C_{2-6}$ alkynyl, and $NH_2$.

In some embodiments, $R^3$ selected from H, D, and $C_{1-6}$ alkyl.

In some embodiments, $R^3$ is H or D.

In some embodiments, $R^3$ is H.

In some embodiments, $R^{3''}$ is selected from H, D, $C_{1-6}$ alkyl, $C_{2-6}$ alkenyl, $C_{2-6}$ alkynyl, and $NH_2$.

In some embodiments, $R^{3''}$ is selected from H, D, and $C_{1-6}$ alkyl.

In some embodiments, $R^{3''}$ is H or D.

In some embodiments, $R^{3''}$ is H.

In some embodiments, $R^3$ and $R^{3''}$ together form an oxo group.

In some embodiments, $R^4$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.

In some embodiments, $R^4$ is selected from H, D, halo, CN, OH, $NH_2$, and $C_{1-6}$ alkyl.

In some embodiments, $R^4$ selected from H, D, and $C_{1-6}$ alkyl, wherein the $C_{1-6}$ alkyl is optionally substituted with 1, 2, or 3 deuterium atoms.

In some embodiments, $R^4$ is H.

In some embodiments, $R^4$ is D.

In some embodiments, $R^5$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.

In some embodiments, $R^5$ is selected from H, D, halo, CN, OH, $NH_2$, and $C_{1-6}$ alkyl.

In some embodiments, $R^5$ is selected from H, D, and $C_{1-6}$ alkyl, wherein the $C_{1-6}$ alkyl is optionally substituted with 1, 2, or 3 deuterium atoms.

In some embodiments, $R^5$ is H.

In some embodiments, $R^5$ is D.

In some embodiments, $R^3$ and $R^4$ are each H.

In some embodiments, $R^3$ and $R^5$ are each H.

In some embodiments, $R^4$ and $R^5$ are each H.

In some embodiments, $R^3$, $R^{3''}$, $R^4$, and $R^5$ are each H.

In some embodiments, $R^3$ and $R^{3''}$ together form an oxo group; and $R^4$ and $R^5$ are each H.

In some embodiments, $R^6$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.

In some embodiments, $R^6$ is selected from H, D, and $C_{1-6}$ alkyl, wherein the $C_{1-6}$ alkyl is optionally substituted with 1, 2, or 3 deuterium atoms.

In some embodiments, $R^6$ is selected from H, D, halo, CN, OH, $NH_2$, and $C_{1-6}$ alkyl.

In some embodiments, $R^6$ is $C_{1-6}$ alkyl.

In some embodiments, $R^6$ is methyl.

In some embodiments, $R^6$ is $CD_3$.

In some embodiments, $R^6$ is H.

In some embodiments, $R^6$ is D.

In some embodiments, $R^7$ is selected from $C(O)R^{b7}$, $C(O)NR^{c7}R^{d7}$, $C(O)NR^{c7}(OR^{b7})$, $C(O)OR^{a7}$, $C(=NR^{e71})R^{b7}$, $C(=NOH)R^{b7}$, $C(=NCN)R^{b7}$, $C(=NR^{e71})NR^{c7}R^{d7}$, $S(O)R^{b7}$, $S(O)NR^{c7}R^{d7}$, $S(O)_2R^b$, and $S(O)_2NR^{c7}R^{d7}$;

each $R^{a7}$, $R^{b7}$, $R^{c7}$, and $R^{d7}$ is independently selected from H, $C_{1-6}$ alkyl, $C_{2-6}$ alkenyl, $C_{2-6}$ alkynyl, $C_{3-10}$ cycloalkyl and 4-10 membered heterocycloalkyl, wherein the $C_{1-6}$ alkyl, $C_{2-6}$ alkenyl, $C_{2-6}$ alkynyl, $C_{3-10}$ cycloalkyl and 4-10 membered heterocycloalkyl of $R^{a7}$, $R^{b7}$, $R^{c7}$, and $R^{d7}$ are each optionally substituted with 1, 2, or 3 independently selected $R^{7A}$ substituents;

or, $R^{c7}$ and $R^{d7}$, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, or 3 independently selected $R^{7A}$ substituents; and each $R^{e7}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-.

In some embodiments, $R^7$ is $C(O)NR^{C7}R^{d7}$.

In some embodiments, $R^7$ is selected from H, $C_{1-6}$ alkyl, $C_{2-6}$ alkenyl, and $C_{2-6}$ alkynyl.

In some embodiments, $R^7$ is H.

In some embodiments, $R^{d7}$ is selected from H, $C_{1-6}$ alkyl, $C_{3-10}$ cycloalkyl, and 4-8 membered heterocycloalkyl, wherein the $C_{1-6}$ alkyl, $C_{3-10}$ cycloalkyl and 4-8 membered heterocycloalkyl of $R^{d7}$ are each optionally substituted with 1 or 2 independently selected $R^{7A}$ substituents.

In some embodiments, each $R^{7A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a71}$, and $SR^{a71}$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl are each optionally substituted by 1 or 2 independently selected $R^{7B}$ substituents.

In some embodiments, each $R^{7A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-8}$ cycloalkyl, 5-10 membered heteroaryl, 4-10 membered heterocycloalkyl, CN, $NO_2$, $OR^{a71}$, and $SR^{a71}$ In some embodiments, each $R^{7A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-8}$ cycloalkyl, 5-10 membered heteroaryl, 4-10 membered heterocycloalkyl, CN, $NO_2$, $OR^{a71}$, and $SR^{a71}$; and each $R^{a71}$ is independently selected from H, $C_{1-6}$ alkyl, $C_{1-6}$ haloalkyl, $C_{2-6}$ alkenyl, and $C_{2-6}$ alkynyl.

In some embodiments, each $R^{7A}$ is independently selected from halo, $C_{1-6}$ alkyl, $C_{1-6}$ haloalkyl, $C_{3-8}$ cycloalkyl, CN, and $OR^{a71}$.

In some embodiments, each $R^{7A}$ is independently selected from halo, $C_{1-6}$ alkyl, $C_{1-6}$ haloalkyl, $C_{3-8}$ cycloalkyl, CN, and $OR^{a71}$, wherein each $R^{a71}$ is independently selected from H and $C_{1-6}$ alkyl.

In some embodiments, each $R^{7B}$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $OR^{a72}$, wherein the $C_{1-6}$ alkyl is optionally substituted by 1 or 2 OH groups.

In some embodiments, each $R^{7B}$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $OR^{a72}$, wherein the $C_{1-6}$ alkyl is optionally substituted by 1 or 2 OH groups; and
each $OR^{a72}$ is independently selected from H and $C_{1-6}$ alkyl.

In some embodiments, $R^{d7}$ is selected from $C_{1-6}$alkyl, hydroxyl-$C_{1-6}$ alkyl, cyano-$C_{1-6}$ alkyl, monocyclic $C_{3-6}$ cycloalkyl, bicyclic $C_{5-8}$ cycloalkyl, monocyclic 4-6 membered heterocycloalkyl, and bicyclic 4-10 membered heterocycloalkyl wherein the $C_{1-6}$ alkyl, hydroxyl-$C_{1-6}$ alkyl, cyano-$C_{1-6}$ alkyl, monocyclic $C_{3-6}$ cycloalkyl, bicyclic $C_{5-8}$ cycloalkyl, and 4-6 membered heterocycloalkyl are each optionally substituted by 1 or 2 $R^{7A}$ substituents independently selected from halo, OH, CN, $C_{1-3}$ alkoxy, $C_{1-3}$ haloalkyl, 4-10 membered heterocycloalkyl, and $C_{3-10}$ cycloalkyl.

In some embodiments, $R^{d7}$ is selected from $C_{1-6}$ alkyl, hydroxyl-$C_{1-6}$ alkyl, cyano-$C_{1-6}$ alkyl, monocyclic $C_{3-6}$ cycloalkyl, bicyclic $C_{5-8}$ cycloalkyl, and 4-6 membered heterocycloalkyl, wherein the $C_{1-6}$ alkyl, hydroxyl-$C_{1-6}$ alkyl, cyano-$C_{1-6}$ alkyl, monocyclic $C_{3-6}$ cycloalkyl, bicyclic $C_{5-8}$ cycloalkyl, and 4-6 membered heterocycloalkyl are each optionally substituted by 1 or 2 $R^{7A}$ substituents independently selected from halo, OH, CN, $C_{1-3}$ alkoxy, and $C_{3-10}$ cycloalkyl.

In some embodiments, $R^{d7}$ is selected from ethyl, 2-cyanoethyl, 2,2,2-trifluoroethyl, 2-propyl, 1-(cyanomethyl)propyl, 2-methoxy-2-methylpropyl, 2-cyano-2,2-dimethylethyl, 2-hydroxy-2-methylprop-1-yl, 2-cyano-1-methylethyl, 2-hydroxy-1-methylethyl, 2-hydroxy-1,1-dimethylethyl, 1-cyanocycloprop-1-ylethyl, 1-cyanocyclobut-1-ylethyl, 4-hydroxycyclohexyl, 4-methoxycyclohexyl, 4-hydroxy-4-methylcyclohexyl, 4-hydroxy-4-(trifluoromethyl)cyclohexyl, 4-(1-hydroxy-1-methylethyl)cyclohexyl, 4,4-difluorocyclohexyl, 3-cyanobicyclo[1.1.1]pentan-1-yl, 4-cyanobicyclo[2.1.1]hexan-1-yl, 4-cyanobicyclo[2.2.2]octan-1-yl, tetrahydrofuran-3-yl, tetrahydropyran-3-yl, 7-oxabicyclo[2.2.1]heptan-2-yl, 2-(tetrahydrofuran-3-yl)ethyl, 3,3,3-trifluoro-2-hydroxypropyl and tetrahydropyran-4-yl.

In some embodiments, $R^{d7}$ is selected from ethyl, 2-cyanoethyl, 2,2,2-trifluoroethyl, 2-propyl, 1-(cyanomethyl)propyl, 2-methoxy-2-methylpropyl, 2-cyano-2,2-dimethylethyl, 2-hydroxy-2-methylprop-1-yl, 2-cyano-1-methylethyl, 2-hydroxy-1-methylethyl, 2-hydroxy-1,1-dimethylethyl, 1-cyanocycloprop-1-ylethyl, 1-cyanocyclobut-1-ylethyl, 4-hydroxycyclohexyl, 4-methoxycyclohexyl, 4-hydroxy-4-methylcyclohexyl, 4-hydroxy-4-(trifluoromethyl)cyclohexyl, 4-(1-hydroxy-1-methylethyl)cyclohexyl, 4,4-difluorocyclohexyl, 3-cyanobicyclo[1.1.1]pentan-1-yl, 4-cyanobicyclo[2.1.1]hexan-1-yl, 4-cyanobicyclo[2.2.2]octan-1-yl, tetrahydrofuran-3-yl, tetrahydropyran-3-yl, and tetrahydropyran-4-yl.

In some embodiments, $R^{c7}$ and $R^{d7}$, together with the N atom to which they are attached, form an azetidine ring, optionally substituted with 1, 2, or 3 independently selected $R^{7A}$ substituents.

In some embodiments, $R^{c7}$ and $R^{d7}$, together with the N atom to which they are attached, form an azetidine ring, optionally substituted with 1, 2, or 3 independently selected $R^{7A}$ substituents selected from methyl and methoxymethyl.

In some embodiments, $R^{c7}$ and $R^{d7}$, together with the N atom to which they are attached, form a group selected from 2-(methoxymethyl)azetidin-1-yl and 2,2-dimethylazetidin-1-yl.

In some embodiments, $R^{c7}$ and $R^{d7}$, together with the N atom to which they are attached, form a 2,3-dihydro-1H-pyrrolo[2,3-b]pyridin-1-yl group.

In some embodiments, $R^8$ is selected from H, $C_{1-6}$ alkyl, $C_{2-6}$ alkenyl, $C_{2-6}$ alkynyl, $C_{1-6}$ haloalkyl, and $C(O)R^{b8}$.

In some embodiments, $R^8$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, and $C(O)R^{b8}$.

In some embodiments, $R^8$ is selected from H, $C_{1-6}$ alkyl, $C_{2-6}$ alkenyl, $C_{2-6}$ alkynyl, $C_{1-6}$ haloalkyl, and $C_{3-10}$ cycloalkyl.

In some embodiments, $R^8$ is selected from H, $C_{1-6}$ alkyl, and $C(O)R^{b8}$.

In some embodiments, $R^8$ is H or $C_{1-6}$ alkyl.

In some embodiments, $R^8$ is H, methyl, ethyl, propyl or isopropyl.

In some embodiments, $R^8$ is H or $C(O)R^{b8}$.

In some embodiments, $R^8$ is H.

In some embodiments, $R^8$ is $C(O)R^{b8}$.

In some embodiments, $R^{b8}$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{b8}$ are each optionally substituted with 1, 2, 3 or 4 independently selected $R^{8A}$ substituents.

In some embodiments, $R^{b8}$ is selected from H, $C_{1-6}$ alkyl, and $C_{1-6}$ haloalkyl, wherein the $C_{1-6}$ alkyl of $R^{b8}$ is optionally substituted with 1 or 2 $R^{8A}$ substituents independently selected from D, halo, CN, $NO_2$, OH, and SH.

In some embodiments, $R^{b8}$ is selected from methyl, fluoromethyl, cyanomethyl, and hydroxypropyl.

In some embodiments, $R^{b8}$ is selected from H, D, and $C_{1-6}$ alkyl.

In some embodiments, $R^{b8}$ is selected from H, D, and methyl.

In some embodiments, $R^{b8}$ is H.

In some embodiments, $R^9$ is selected from H, $C_{1-6}$ alkyl, $C_{2-6}$ alkenyl, $C_{2-6}$ alkynyl, $C_{1-6}$ haloalkyl and $C_{3-10}$ cycloalkyl.

In some embodiments, $R^9$ is selected from H, $C_{1-6}$ alkyl, $C_{2-6}$ alkenyl, $C_{2-6}$ alkynyl, and $C_{1-6}$ haloalkyl.

In some embodiments, $R^9$ is H or $C_{1-6}$ alkyl.

In some embodiments, $R^9$ is selected from H, methyl, ethyl, propyl, and isopropyl.

In some embodiments, $R^9$ is H.

In some embodiments, $R^8$ and $R^9$ are each H.

In some embodiments:
$R^3$ is selected from H, D, $C_{1-6}$ alkyl, $C_{2-6}$ alkenyl, $C_{2-6}$ alkynyl, $C_{1-6}$ haloalkyl, and $NH_2$;
$R^{3''}$ is selected from H, D, $C_{1-6}$ alkyl, $C_{2-6}$ alkenyl, $C_{2-6}$ alkynyl, $C_{1-6}$ haloalkyl, and $NH_2$; and
$R^8$ is $C(O)R^{b8}$.

In some embodiments:
$R^3$ and $R^{3''}$ together form an oxo group; and
$R^8$ is selected from H, $C_{1-6}$ alkyl, $C_{2-6}$ alkenyl, $C_{2-6}$ alkynyl, $C_{1-6}$ haloalkyl, and $C_{3-7}$ cycloalkyl.

In some embodiments:
$X^1$ is N or CH;
$R^2$ is a $C_{1-6}$ haloalkyl, wherein each halogen of the $C_{1-6}$ haloalkyl is independently selected from F and Cl;

$R^3$ is selected from H, D, $C_{1-6}$ alkyl, $C_{2-6}$ alkenyl, $C_{2-6}$ alkynyl, $C_{1-6}$ haloalkyl, and $NH_2$;

$R^{3''}$ is selected from H, D, $C_{1-6}$ alkyl, $C_{2-6}$ alkenyl, $C_{2-6}$ alkynyl, $C_{1-6}$ haloalkyl, and $NH_2$;

or, alternatively, $R^3$ and $R^{3''}$ together form an oxo group;

$R^4$ is selected from H, D, halo, CN, OH, $NH_2$, and $C_{1-6}$ alkyl;

$R^5$ is selected from H, D, halo, CN, OH, $NH_2$, and $C_{1-6}$ alkyl;

$R^6$ is selected from H, D, halo, CN, OH, $NH_2$, and $C_{1-6}$ alkyl;

$R^7$ is $C(O)NR^{c7}R^{d7}$;

$R^{c7}$ and $R^{d7}$ are each independently selected H, $C_{1-6}$ alkyl, $C_{2-6}$ alkenyl, $C_{2-6}$ alkynyl, $C_{3-10}$ cycloalkyl, and 4-8 membered heterocycloalkyl, wherein the $C_{1-6}$ alkyl, $C_{2-6}$ alkenyl, $C_{2-6}$ alkynyl, $C_{3-10}$ cycloalkyl, and 4-8 membered heterocycloalkyl of $R^{c7}$ and $R^{d7}$ are each optionally substituted with 1 or 2 independently selected $R^{7A}$ substituents;

$R^8$ is selected from H, $C_{1-6}$ alkyl, $C_{2-6}$ alkenyl, $C_{2-6}$ alkynyl, $C_{1-6}$ haloalkyl, and $C(O)R^{b8}$;

$R^9$ is selected from H, $C_{1-6}$ alkyl, $C_{2-6}$ alkenyl, $C_{2-6}$ alkynyl, and $C_{1-6}$ haloalkyl;

each $R^{7A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-8}$ cycloalkyl, 5-10 membered heteroaryl, 4-10 membered heterocycloalkyl, CN, $NO_2$, $OR^{a71}$, and $SR^{a71}$;

each $R^{a71}$ is independently selected from H, $C_{1-6}$ alkyl, $C_{1-6}$ haloalkyl, $C_{2-6}$ alkenyl, and $C_{2-6}$ alkynyl;

$R^{b8}$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{b8}$ are each optionally substituted with 1, 2, 3 or 4 independently selected $R^{8A}$ substituents; and each $R^{8A}$ is independently selected from D, halo, CN, $NO_2$, OH, and SH.

In some embodiments:

$X^1$ is N or CH;

$R^2$ is a $C_{1-3}$ haloalkyl, wherein each halogen of the $C_{1-3}$ haloalkyl is independently selected from F and Cl;

$R^3$ is H;

$R^{3''}$ is H;

or, alternatively, $R^3$ and $R^{3''}$ together form an oxo group;

$R^4$ is selected from H and $C_{1-6}$ alkyl;

$R^5$ is selected from H and $C_{1-6}$ alkyl;

$R^6$ is selected from H and $C_{1-6}$ alkyl;

$R^7$ is $C(O)NR^{c7}R^{d7}$;

$R^{c7}$ is selected from H, $C_{1-6}$ alkyl, $C_{2-6}$ alkenyl, and $C_{2-6}$ alkynyl;

$R^{d7}$ is selected from H, $C_{1-6}$ alkyl, $C_{3-10}$ cycloalkyl, and 4-8 membered heterocycloalkyl, wherein the $C_{1-6}$ alkyl, $C_{3-10}$ cycloalkyl and 4-8 membered heterocycloalkyl of $R^{d7}$ are each optionally substituted with 1 or 2 independently selected $R^{7A}$ substituents;

$R^8$ is selected from H and $C(O)R^{b8}$;

$R^9$ is H;

each $R^{7A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-8}$ cycloalkyl, 5-10 membered heteroaryl, 4-10 membered heterocycloalkyl, CN, $NO_2$, $OR^{a71}$, and $SR^{a71}$;

each $R^{a71}$ is independently selected from H, $C_{1-6}$ alkyl, $C_{1-6}$ haloalkyl, $C_{2-6}$ alkenyl, and $C_{2-6}$ alkynyl;

$R^{b8}$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{b8}$ are each optionally substituted with 1, 2, 3 or 4 independently selected $R^A$ substituents; and each $R^{8A}$ is independently selected from D, halo, CN, $NO_2$, OH, and SH.

In some embodiments:

$X^1$ is N or CH;

$R^2$ is a $C_{1-3}$ haloalkyl, wherein each halogen of the $C_{1-3}$ haloalkyl is independently selected from F and Cl;

$R^3$ is H;

$R^{3''}$ is H;

or, alternatively, $R^3$ and $R^{3''}$ together form an oxo group;

$R^4$ is H;

$R^5$ is H;

$R^6$ is $C_{1-6}$ alkyl;

$R^7$ is $C(O)NR^{c7}R^{d7}$;

$R^{c7}$ is selected from H and $C_{1-6}$ alkyl;

$R^{d7}$ is selected from H, $C_{1-6}$ alkyl, $C_{3-10}$ cycloalkyl, and 4-8 membered heterocycloalkyl, wherein the $C_{1-6}$ alkyl, $C_{3-10}$ cycloalkyl and 4-8 membered heterocycloalkyl of $R^{d7}$ are each optionally substituted with 1 or 2 independently selected $R^{7A}$ substituents;

$R^8$ is selected from H and $C(O)R^{b8}$;

$R^9$ is H;

each $R^{7A}$ is independently selected from halo, $C_{1-6}$ alkyl, $C_{1-6}$ haloalkyl, $C_{3-8}$ cycloalkyl, CN, $OR^{a71}$;

each $R^{a71}$ is independently selected from H and $C_{1-6}$ alkyl; and $R^{b8}$ is selected from H, $C_{1-6}$ alkyl, $C_{1-6}$ haloalkyl, $C_{2-6}$ alkenyl, and $C_{2-6}$ alkynyl.

In some embodiments, the compound of Formula (I) is a compound of Formula (II):

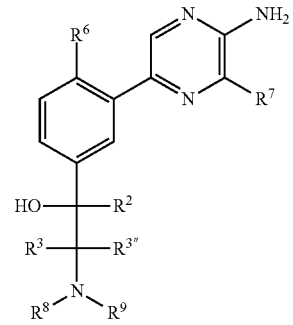

(II)

or a pharmaceutically acceptable salt thereof.

In some embodiments, the compound of Formula (I) is a compound of Formula (III):

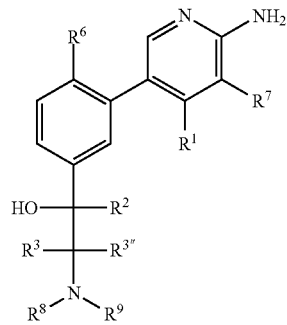

(III)

or a pharmaceutically acceptable salt thereof.

In some embodiments, the compound of Formula (I) is a compound of Formula (IV):

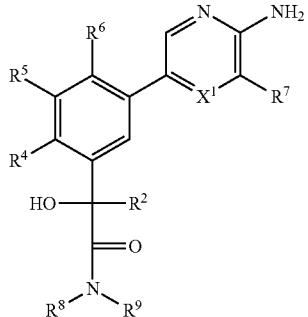

(IV)

or a pharmaceutically acceptable salt thereof.

In some embodiments, the compound of Formula (I) is a compound of Formula (IVa):

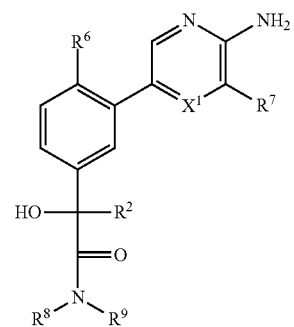

(IVa)

or a pharmaceutically acceptable salt thereof.

In some embodiments, the compound of Formula (I) is a compound of Formula (V):

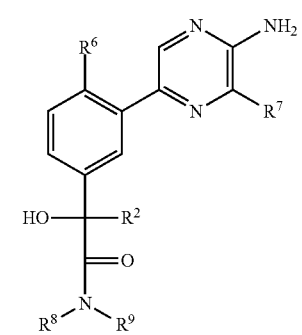

(V)

or a pharmaceutically acceptable salt thereof.

In some embodiments, the compound of Formula (I) is a compound of Formula (VI):

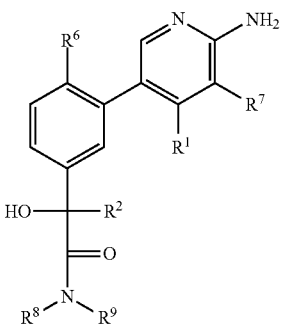

(VI)

or a pharmaceutically acceptable salt thereof.

In some embodiments, the compound of Formula (I) is a compound of Formula (VII):

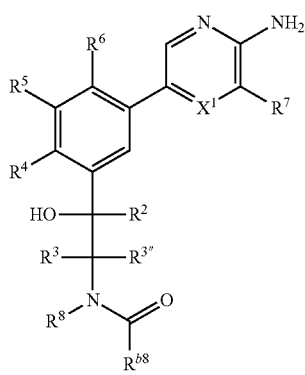

(VII)

or a pharmaceutically acceptable salt thereof.

In some embodiments, the compound of Formula (I) is a compound of Formula (VIIa):

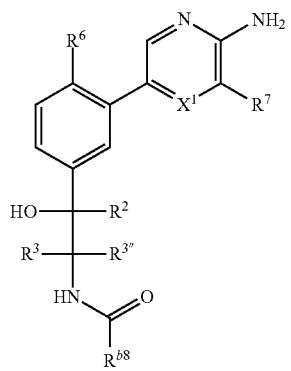

(VIIa)

or a pharmaceutically acceptable salt thereof.

In some embodiments, the compound of Formula (I) is a compound of Formula (VIII):

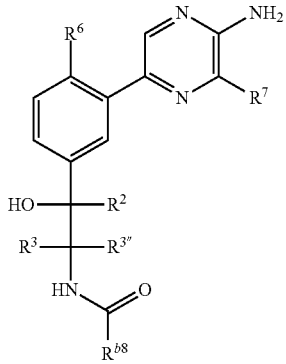

(VIII)

or a pharmaceutically acceptable salt thereof.

In some embodiments, the compound of Formula (I) is a compound of Formula (IX):

(IX)

or a pharmaceutically acceptable salt thereof.

In some embodiments, the compound is selected from:
3-amino-6-(5-(3-amino-1,1,1-trifluoro-2-hydroxy-3-oxopropan-2-yl)-2-methylphenyl)-N-(2-hydroxy-2-methylpropyl)pyrazine-2-carboxamide;
3-amino-6-(5-(3-amino-1,1,1-trifluoro-2-hydroxy-3-oxopropan-2-yl)-2-methylphenyl)-N-(tetrahydro-2H-pyran-4-yl)pyrazine-2-carboxamide;
3-amino-6-(5-(3-amino-1,1,1-trifluoro-2-hydroxy-3-oxopropan-2-yl)-2-methylphenyl)-N-((1r,4r)-4-hydroxycyclohexyl)pyrazine-2-carboxamide;
3-amino-6-(5-(3-amino-1,1,1-trifluoro-2-hydroxy-3-oxopropan-2-yl)-2-methylphenyl)-N-((1-cyanocyclopropyl)methyl)pyrazine-2-carboxamide;
3-amino-6-(5-(3-amino-1,1,1-trifluoro-2-hydroxy-3-oxopropan-2-yl)-2-methylphenyl)-N-isopropylpyrazine-2-carboxamide;
3-amino-6-(5-(3-amino-1,1,1-trifluoro-2-hydroxy-3-oxopropan-2-yl)-2-methylphenyl)-N-(4,4-difluorocyclohexyl)pyrazine-2-carboxamide;
3-amino-6-(5-(3-amino-1,1,1-trifluoro-2-hydroxy-3-oxopropan-2-yl)-2-methylphenyl)-N-ethylpyrazine-2-carboxamide;
3-amino-6-(5-(3-amino-1,1,1-trifluoro-2-hydroxy-3-oxopropan-2-yl)-2-methylphenyl)-N—((S)-1-cyanopropan-2-yl)pyrazine-2-carboxamide;
3-amino-6-(5-(3-amino-1,1,1-trifluoro-2-hydroxy-3-oxopropan-2-yl)-2-methylphenyl)-N—((R)-tetrahydro-2H-pyran-3-yl)pyrazine-2-carboxamide;
3-amino-6-(5-(3-amino-1,1,1-trifluoro-2-hydroxy-3-oxopropan-2-yl)-2-methylphenyl)-N—((S)-tetrahydro-2H-pyran-3-yl)pyrazine-2-carboxamide;
3-amino-6-(5-(3-amino-1,1,1-trifluoro-2-hydroxy-3-oxopropan-2-yl)-2-methylphenyl)-N—((S)-tetrahydrofuran-3-yl)pyrazine-2-carboxamide;
3-amino-6-(5-(3-amino-1,1,1-trifluoro-2-hydroxy-3-oxopropan-2-yl)-2-methylphenyl)-N—((S)-1-hydroxypropan-2-yl)pyrazine-2-carboxamide;
3-amino-6-(5-(3-amino-1,1,1-trifluoro-2-hydroxy-3-oxopropan-2-yl)-2-methylphenyl)-N-(1-hydroxy-2-methylpropan-2-yl)pyrazine-2-carboxamide;
3-amino-6-(5-(3-amino-1,1,1-trifluoro-2-hydroxy-3-oxopropan-2-yl)-2-methylphenyl)-N-(2-cyanoethyl)pyrazine-2-carboxamide;
3-amino-6-(5-(3-amino-1,1,1-trifluoro-2-hydroxy-3-oxopropan-2-yl)-2-methylphenyl)-N-(2-cyano-2-methylpropyl)pyrazine-2-carboxamide;
3-amino-6-(5-(3-amino-1,1,1-trifluoro-2-hydroxy-3-oxopropan-2-yl)-2-methylphenyl)-N-((1-cyanocyclobutyl)methyl)pyrazine-2-carboxamide;
3-amino-6-(5-(3-amino-1,1,1-trifluoro-2-hydroxy-3-oxopropan-2-yl)-2-methylphenyl)-N-((1r,4r)-4-hydroxy-4-methylcyclohexyl)pyrazine-2-carboxamide;
3-amino-6-(5-(3-amino-1,1,1-trifluoro-2-hydroxy-3-oxopropan-2-yl)-2-methylphenyl)-N-((1r,4r)-4-hydroxy-4-(trifluoromethyl)cyclohexyl)pyrazine-2-carboxamide;
3-amino-6-(5-(3-amino-1,1,1-trifluoro-2-hydroxy-3-oxopropan-2-yl)-2-methylphenyl)-N-((1r,4r)-4-(2-hydroxypropan-2-yl)cyclohexyl)pyrazine-2-carboxamide;
3-amino-6-(5-(3-amino-1,1,1-trifluoro-2-hydroxy-3-oxopropan-2-yl)-2-methylphenyl)-N—((S)-1-cyanobutan-2-yl)pyrazine-2-carboxamide;
3-amino-6-(5-(3-amino-1,1,1-trifluoro-2-hydroxy-3-oxopropan-2-yl)-2-methylphenyl)-N-(2-methoxy-2-methylpropyl)pyrazine-2-carboxamide;
3-amino-6-(5-(3-amino-1,1,1-trifluoro-2-hydroxy-3-oxopropan-2-yl)-2-methylphenyl)-N-((1r,4r)-4-methoxycyclohexyl)pyrazine-2-carboxamide;
3-amino-6-(5-(3-amino-1,1,1-trifluoro-2-hydroxy-3-oxopropan-2-yl)-2-methylphenyl)-N-(3-cyanobicyclo[1.1.1]pentan-1-yl)pyrazine-2-carboxamide;
3-amino-6-(5-(3-amino-1,1,1-trifluoro-2-hydroxy-3-oxopropan-2-yl)-2-methylphenyl)-N-(4-cyanobicyclo[2.1.1]hexan-1-yl)pyrazine-2-carboxamide;
3-amino-6-(5-(3-amino-1,1,1-trifluoro-2-hydroxy-3-oxopropan-2-yl)-2-methylphenyl)-N-(4-cyanobicyclo[2.2.2]octan-1-yl)pyrazine-2-carboxamide;
3-amino-6-(5-(1-amino-3,3-difluoro-2-hydroxy-1-oxopropan-2-yl)-2-methylphenyl)-N-methylpyrazine-2-carboxamide;
3-amino-6-(5-(1-amino-3,3-difluoro-2-hydroxy-1-oxopropan-2-yl)-2-methylphenyl)-N-ethylpyrazine-2-carboxamide;
3-amino-6-(5-(1-amino-3,3-difluoro-2-hydroxy-1-oxopropan-2-yl)-2-methylphenyl)-N-((1-cyanocyclopropyl)methyl)pyrazine-2-carboxamide;
3-amino-6-(5-(1-amino-3,3-difluoro-2-hydroxy-1-oxopropan-2-yl)-2-methylphenyl)-N-(4,4-difluorocyclohexyl)pyrazine-2-carboxamide;
3-amino-6-(5-(1-amino-3,3-difluoro-2-hydroxy-1-oxopropan-2-yl)-2-methylphenyl)-N-(2,2,2-trifluoroethyl)pyrazine-2-carboxamide;
3-amino-6-(5-(1-amino-3,3-difluoro-2-hydroxy-1-oxopropan-2-yl)-2-methylphenyl)-N-(1-hydroxy-2-methylpropan-2-yl)pyrazine-2-carboxamide;

3-amino-6-(5-(1-amino-3,3-difluoro-2-hydroxy-1-oxopropan-2-yl)-2-methylphenyl)-N-(tetrahydro-2H-pyran-4-yl)pyrazine-2-carboxamide;

6-(5-(3-acetamido-1,1,1-trifluoro-2-hydroxypropan-2-yl)-2-methylphenyl)-3-amino-N-isopropylpyrazine-2-carboxamide;

3-amino-N-isopropyl-6-(2-methyl-5-(1,1,1-trifluoro-3-(2-fluoroacetamido)-2-hydroxypropan-2-yl)phenyl)pyrazine-2-carboxamide;

3-amino-N-isopropyl-6-(2-methyl-5-(1,1,1-trifluoro-2-hydroxy-3-(2-hydroxy-2-methylpropanamido)propan-2-yl)phenyl)pyrazine-2-carboxamide; and 3-amino-6-(5-(3-(2-cyanoacetamido)-1,1,1-trifluoro-2-hydroxypropan-2-yl)-2-methylphenyl)-N-isopropylpyrazine-2-carboxamide;

or a pharmaceutically acceptable salt thereof.

In some embodiments, the compound is selected from:

2-(3-(5-amino-6-((R)-2-(methoxymethyl)azetidine-1-carbonyl)pyrazin-2-yl)-4-methylphenyl)-3,3,3-trifluoro-2-hydroxypropanamide;

2-(3-(5-amino-6-(2,2-dimethylazetidine-1-carbonyl)pyrazin-2-yl)-4-methylphenyl)-3,3,3-trifluoro-2-hydroxypropanamide;

2-(3-(5-amino-6-(2,3-dihydro-1H-pyrrolo[2,3-b]pyridine-1-carbonyl)pyrazin-2-yl)-4-methylphenyl)-3,3,3-trifluoro-2-hydroxypropanamide;

3-amino-6-(5-(3-amino-1,1,1-trifluoro-2-hydroxy-3-oxopropan-2-yl)-2-methylphenyl)-N-(7-oxabicyclo[2.2.1]heptan-2-yl)pyrazine-2-carboxamide;

3-amino-6-(5-(1-amino-3,3-difluoro-2-hydroxy-1-oxopropan-2-yl)-2-methylphenyl)-N-(2-(tetrahydrofuran-3-yl)ethyl)pyrazine-2-carboxamide; and 3-amino-6-(5-(3-amino-1,1,1-trifluoro-2-hydroxy-3-oxopropan-2-yl)-2-methylphenyl)-N-(3,3,3-trifluoro-2-hydroxypropyl)pyrazine-2-carboxamide;

or a pharmaceutically acceptable salt thereof.

Compound Subset (B)

The present application provides, inter alia, compounds of Formula (I):

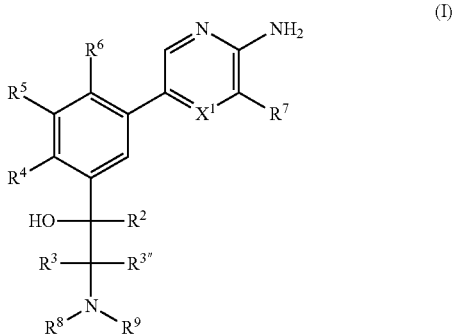

or a pharmaceutically acceptable salt thereof; wherein:

$X^1$ is N or $CR^1$;

$R^1$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH and $NH_2$;

$R^2$ is a $C_{1-6}$ haloalkyl, wherein each halogen is independently selected from F and Cl, wherein the haloalkyl is optionally substituted with $C(O)NR^aR^b$ or 1, 2, 3 or 4 independently selected $R^M$ substituents;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^3$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and $NH_2$;

$R^{3''}$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and $NH_2$;

or, alternatively, $R^3$ and $R^{3''}$ together form an oxo group;

$R^4$, $R^5$ and $R^6$ are each independently selected from H, D, halo, CN, OH, $NH_2$, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkylamino, di($C_{1-6}$ alkyl)amino, and $C(O)NR^aR^b$;

each $R^a$ and $R^b$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, 5 phenyl-$C_{1-6}$ alkyl-, $C_{3-7}$ cycloalkyl-$C_{1-6}$ alkyl-, (5-6 membered heteroaryl)-$C_{1-6}$s alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^a$ and $R^b$ are each optionally substituted with 1, 2, 3 or 4 independently selected $R^M$ substituents;

$R^7$ is selected from $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl and $C_{2-6}$ alkynyl are each optionally substituted with 1, 2, 3 or 4 independently selected $R^{7A}$ substituents;

$R^8$ and $R^9$ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b8}$, $C(O)NR^{c8}R^{d8}$, $C(O)OR^{a8}$, $C(=NR^{e8})R^{b8}$, $C(=NR^{e8})NR^{c8}R^{d8}$, $C(=NCN)NR^{c8}R^{d8}$, $C(=NOR^{a8})NR^{c8}$, $S(O)_2R^{b8}$, $S(O)(=NR^{c8})R^{d8}$, and $S(O)_2NR^{c8}R^{d8}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^8$ and $R^9$ are each optionally substituted with 1, 2, 3, or 4 independently selected $R^{8A}$ substituents;

or, $R^8$ and $R^9$, together with the N atom to which they are attached, form a 5- or 6-membered heteroaryl, or a 4-10 membered heterocycloalkyl group, wherein the 5- or 6-membered heteroaryl, or 4-10 membered heterocycloalkyl group is optionally substituted with 1, 2, 3, or 4 independently selected $R^{8A}$ substituents;

each $R^{7A}$ is independently selected from D, halo, $C_{1-6}$ alkyl, $C_{1-6}$ haloalkyl, $C_{2-6}$ alkenyl, $C_{2-6}$ alkynyl, $C_{6-14}$ aryl, $C_{3-12}$ cycloalkyl, 5-14 membered heteroaryl, 4-12 membered heterocycloalkyl, $C_{6-14}$ aryl-$C_{1-6}$ alkyl-, $C_{3-12}$ cycloalkyl-$C_{1-6}$ alkyl-, (5-14 membered heteroaryl)-$C_{1-6}$ alkyl-, (4-12 membered heterocycloalkyl)-$C_{1-6}$ alkyl-, CN, $NO_2$, $OR^{a71}$, $SR^{a71}$, $NHOR^{a71}$, $C(O)R^{b71}$, $C(O)NR^{c71}R^{d71}$, $C(O)NR^{c71}(OR^{b71})$, $C(O)OR^{a71}$, $OC(O)R^{b71}$, $OC(O)NR^{c71}R^{d71}$, $NR^{c71}R^{d71}$, $NR^{c71}NR^{c71}R^{d71}$, $NR^{c71}C(O)R^{b71}$, $NR^{c71}C(O)OR^{a}71$, $NR^{c71}C(O)NR^{c71}R^{d71}$, $C(=NR^{e71})R^{b71}$, $C(=NOH)R^{b71}$, $C(=NCN)R^{b71}$, $C(=NR^{e71})NR^{c71}R^{d71}$, $NR^{c71}C(=NR^{e71})NR^{c71}R^{d71}$, $NR^{c71}C(=NR^{e71})R^{b71}$, $NR^{c71}C(=NOH)NR^{c71}R^{d71}$, $NR^{c71}C(=NCN)NR^{c71}R^{d71}$, $NR^{c71}S(O)R^{b71}$, $NR^{c71}S(O)NR^{c71}R^{d71}$, $NR^{c71}S(O)_2R^{b71}$, $NR^{c71}S(O)_2NR^{c71}R^{d71}$, $S(O)R^{b71}$, $S(O)NR^{c71}R^{d71}$, $S(O)_2R^{b71}$, $S(O)_2NR^{c71}R^{d71}$, $OS(O)(=NR^{e71})R^{b71}$, $OS(O)_2R^{b71}$, $SF_5$, $P(O)R^{f71}R^{g71}$, $OP(O)(OR^{h71})(OR^{i71})$, $P(O)(OR^{h71})(OR^{i71})$, and $BR^{j71}R^{k71}$, wherein the $C_{1-6}$ alkyl, $C_{2-6}$ alkenyl, $C_{2-6}$ alkynyl, $C_{6-14}$ aryl, $C_{3-12}$ cycloalkyl, 5-14 membered heteroaryl 4-12 membered heterocycloalkyl, $C_{6-14}$ aryl-$C_{1-6}$ alkyl-, $C_{3-12}$ cycloalkyl-$C_{1-6}$ alkyl-, (5-14 membered heteroaryl)-$C_{1-6}$ alkyl-, and (4-12 membered heterocycloalkyl)-$C_{1-6}$ alkyl-, of $R^{7A}$ are each optionally substituted with 1, 2, 3 or 4 independently selected $R^{7B}$ substituents;

each $R^{a71}$, $R^{b71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-12}$ cycloalkyl, 5-14 membered heteroaryl, 4-12 membered heterocycloalkyl, $C_{6-14}$ aryl-$C_{1-6}$ alkyl-, $C_{3-12}$ cycloalkyl-$C_{1-6}$ alkyl-, (5-14 membered heteroaryl)-$C_{1-6}$ alkyl- and (4-12 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-12}$ cycloalkyl, 5-14 membered heteroaryl, 4-12 membered heterocycloalkyl, $C_{6-14}$ aryl-$C_{1-6}$ alkyl-, $C_{3-12}$ cycloalkyl-$C_{1-6}$ alkyl-, (5-14 membered heteroaryl)-$C_{1-6}$ alkyl- and (4-12 membered heterocycloalkyl)-$C_{1-6}$ alkyl- of $R^{a71}$, $R^{b71}$, $R^{c71}$, and $R^{d71}$ are each optionally substituted with 1, 2, 3 or 4 independently selected $R^{7B}$ substituents;

or, any $R^{c71}$ and $R^{d71}$ attached to the same N atom, together with the N atom to which they are attached, form a 5-10-membered heteroaryl or a 4-10-membered heterocycloalkyl group, wherein the 5-10-membered heteroaryl or 4-10-membered heterocycloalkyl group is optionally substituted with 1, 2, 3 or 4 independently selected $R^{7B}$ substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-12}$ cycloalkyl, 5-14 membered heteroaryl, 4-12 membered heterocycloalkyl, $C_{6-14}$ aryl-$C_{1-6}$ alkyl-, $C_{3-12}$ cycloalkyl-$C_{1-6}$ alkyl-, (5-14 membered heteroaryl)-$C_{1-6}$ alkyl- and (4-12 membered heterocycloalkyl)-$C_{1-6}$ alkyl-;

each $R^{f71}$ and $R^{g71}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-12}$ cycloalkyl, 5-14 membered heteroaryl, 4-12 membered heterocycloalkyl, $C_{6-14}$ aryl-$C_{1-6}$ alkyl-, $C_{3-12}$ cycloalkyl-$C_{1-6}$ alkyl-, (5-14 membered heteroaryl)-$C_{1-6}$ alkyl- and (4-12 membered heterocycloalkyl)-$C_{1-6}$ alkyl-;

each $R^{h71}$ and $R^{i71}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-12}$ cycloalkyl, 5-14 membered heteroaryl, 4-12 membered heterocycloalkyl, $C_{6-14}$ aryl-$C_{1-6}$ alkyl-, $C_{3-12}$ cycloalkyl-$C_{1-6}$ alkyl-, (5-14 membered heteroaryl)-$C_{1-6}$ alkyl- and (4-12 membered heterocycloalkyl)-$C_{1-6}$ alkyl-;

each $R^{j71}$ and $R^{k71}$ is independently selected from OH, $C_{1-6}$ alkoxy, and $C_{1-6}$ haloalkoxy;

or any $R^{j71}$ and $R^{k71}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a72}$, $SR^{a72}$, $NHOR^{a72}$, $C(O)R^{b72}$, $C(O)NR^{c72}R^{d72}$, $C(O)NR^{c72}(OR^{b72})$, $C(O)OR^{a72}$, $OC(O)R^{b72}$, $OC(O)NR^{c72}R^{d72}$, $NR^{c72}R^{d72}$, $NR^{72}NR^{c72}R^{d72}$, $NR^{c72}C(O)R^{b72}$, $NR^{c72}C(O)OR^{a72}$, $NR^{c72}C(O)NR^{c72}R^{d72}$, $C(=NR^{e72})R^{b72}$, $C(=NOH)R^{b72}$, $C(=NCN)R^{b72}$, $C(=NR^{e72})NR^{c72}R^{d72}$, $NR^{c72}C(=NR^{e72})NR^{c72}R^{d72}$, $NR^{c72}C(=NR^{e72})R^{b72}$, $NR^{c72}C(=NOH)NR^{c72}R^{d72}$ $NR^{c72}C(=NCN)NR^{c72}R^{d72}$ $NR^{c72}S(O)R^{b72}$ $NR^{c72}S(O)NR^{c72}R^{d72}$, $NR^{c72}S(O)_2R^{b72}$, $NR^{c72}S(O)_2NR^{c72}R^{d72}$, $S(O)R^{b72}$, $S(O)NR^{c72}R^{d72}$, $S(O)_2R^{b72}$ $S(O)_2NR^{c72}R^{d72}$, $OS(O)(=NR^{e72})R^{b72}$, $OS(O)_2R^{b72}$, $SF_5$, $P(O)R^{f72}R^{g72}$, $OP(O)(OR^{h72})(OR^{i72})$, $P(O)(OR^{h72})(OR^{i72})$, and $BR^{j72}R^{k72}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{7B}$ are each optionally substituted with 1, 2, 3 or 4 independently selected $R^{7C}$ substituents;

each $R^{a72}$, $R^{b72}$, $R^{c72}$, and $R^{d72}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a72}$, $R^{b72}$, $R^{c72}$, and $R^{d72}$ are each optionally substituted with 1, 2, 3 or 4 independently selected $R^{7C}$ substituents;

or, any $R^{c72}$ and $R^{d72}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{7C}$ substituents;

each $R^{e72}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f72}$ and $R^{g72}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h72}$ and $R^{i72}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j72}$ and $R^{k72}$ is independently selected from OH, $C_{1-6}$ alkoxy, and $C_{1-6}$ haloalkoxy;

or any $R^{j72}$ and $R^{k72}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7C}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a73}$, $SR^{a73}$, $NHOR^{a73}$, $C(O)R^{b73}$, $C(O)NR^{c73}R^{d73}$, $C(O)NR^{c73}(OR^{b73})$, $C(O)OR^{a73}$, $OC(O)R^{b73}$, $OC(O)NR^{c73}R^{d73}$, $NR^{c73}R^{d73}$, $NR^{c73}NR^{c73}R^{d73}$, $NR^{c73}C(O)R^{b73}$, $NR^{c73}C(O)OR^{a73}$, $NR^{c73}C(O)NR^{c73}R^{d73}$, $C(=NR^{e73})R^{b73}$, $C(=NOH)R^{b73}$, $C(=NCN)R^{b73}$, $C(=NR^{e73})NR^{c73}R^{d73}$, $NR^{c73}C(=NR^{e73})NR^{c73}R^{d73}$, $NR^{c73}C(=NR^{e73})R^{b73}$, $NR^{c73}C(=NOH)NR^{c73}R^{d73}$, $NR^{c73}C(=NCN)NR^{c73}R^{d73}$, $NR^{c73}S(O)R^{b73}$, $NR^{c73}S(O)NR^{c73}R^{d73}$, $NR^{c73}S(O)_2R^{b73}$, $NR^{c73}S(O)_2NR^{c73}R^{d73}$, $S(O)R^{b73}$, $S(O)NR^{c73}R^{d73}$, $S(O)_2R^{b73}$, $S(O)_2NR^{c73}R^{d73}$, $OS(O)(=NR^{e73})R^{b73}$, $OS(O)_2R^{b73}$, $SF_5$, $P(O)R^{f73}R^{g73}$, $OP(O)(OR^{h73})(OR^{i73})$, $P(O)(OR^{h73})(OR^{i73})$, and $BR^{j73}R^{k73}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{7C}$ are each optionally substituted with 1, 2, 3 or 4 independently selected $R^{7D}$ substituents;

each $R^{a73}$, $R^{b73}$, $R^{c73}$, and $R^{d73}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a73}$, $R^{b73}$, $R^{c73}$, and $R^{d73}$ are each optionally substituted with 1, 2, 3 or 4 independently selected $R^{7D}$ substituents;

or, any $R^{c73}$ and $R^{d73}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{7D}$ substituents;

each $R^{e73}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f73}$ and $R^{g73}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h73}$ and $R^{i73}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j73}$ and $R^{k73}$ is independently selected from OH, $C_{1-6}$ alkoxy, and $C_{1-6}$ haloalkoxy;

or any $R^{j73}$ and $R^{k73}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7D}$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl- and (4-7 membered heterocycloalkyl)-$C_{1-6}$ alkyl;

each $R^{a8}$, $R^{b8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a8}$, $R^{b8}$, $R^{c8}$, and $R^{d8}$ are each optionally substituted with 1, 2, 3 or 4 independently selected $R^{8A}$ substituents;

or, any $R^{c8}$ and $R^{d8}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{8A}$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{8A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a81}$, $SR^{a81}$, $NHOR^{a81}$, $C(O)R^{b81}$, $C(O)NR^{c81}R^{d81}$, $C(O)NR^{c81}(OR^{b81})$, $C(O)OR^{a81}$, $OC(O)R^{b81}$, $OC(O)NR^{c81}R^{d81}$, $NR^{c81}R^{d81}$, $NR^{c81}NR^{c81}R^{d81}$, $NR^{c81}C(O)R^{b81}$, $NR^{c81}C(O)OR^{a81}$, $NR^{c81}C(O)NR^{c81}R^{d81}$, $C(=NR^{e81})R^{b81}$, $C(=NOH)R^{b81}$, $C(=NCN)R^{b81}$, $C(=NR^{e81})NR^{c81}R^{d81}$, $NR^{c81}C(=NR^{e81})NR^{c81}R^{d81}$, $NR^{c81}C(=NR^{e81})R^{b81}$, $NR^{c81}C(=NOH)NR^{c81}R^{d81}$, $NR^{c81}C(=NCN)NR^{c81}R^{d81}$, $NR^{c81}S(O)R^{b81}$, $NR^{c81}S(O)NR^{c81}R^{d81}$, $NR^{c81}S(O)_2R^{b81}$, $NR^{c81}S(O)_2NR^{c81}R^{d81}$, $S(O)R^{b81}$, $S(O)NR^{c81}R^{d81}$, $S(O)_2R^{b81}$, $S(O)_2NR^{c81}R^{d81}$, $OS(O)(=NR^{e81})R^{b81}$, $OS(O)_2R^{b81}$, $SF_5$, $P(O)R^{f81}R^{g81}$, $OP(O)(OR^{h81})(OR^{i81})$, $P(O)(OR^{h81})(OR^{i81})$, and $BR^{j81}R^{k81}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-

$C_{1-6}$ alkyl- of $R^{8A}$ are each optionally substituted with 1, 2, 3 or 4 independently selected $R^{8B}$ substituents;

each $R^{a81}$, $R^{b81}$, $R^{c81}$, and $R^{d81}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a81}$, $R^{b81}$, $R^{c81}$, and $R^{d81}$ are each optionally substituted with 1, 2, 3 or 4 independently selected $R^{8B}$ substituents;

or, any $R^{c81}$ and $R^{d81}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{8B}$ substituents;

each $R^{e81}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f81}$ and $R^{g81}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h81}$ and $R^{i81}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j8i}$ and $R^{k81}$ is independently selected from OH, $C_{1-6}$ alkoxy, and $C_{1-6}$ haloalkoxy;

or any $R^{j81}$ and $R^{k81}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^{8B}$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl- and (4-7 membered heterocycloalkyl)-$C_{1-6}$ alkyl.

In some embodiments, either: (a) $R^3$ and $R^{3''}$ together form an oxo group; or (b) $R^8$ is $C(O)R^{b8}$.

In some embodiments, the present application provides a compound of Formula (X):

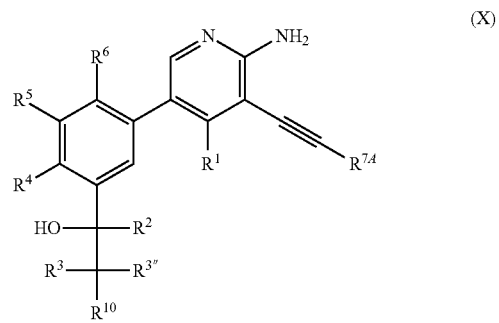

or a pharmaceutically acceptable salt thereof, wherein:

$R^1$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH and $NH_2$;

$R^2$ is a $C_{1-6}$ alkoxy, C haloalkyl, wherein each halogen is independently selected from F and Cl, wherein the haloalkyl is optionally substituted with $C(O)NR^aR^b$ or 1, 2, 3 or 4 independently selected $R^M$ substituents;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^3$, $R^{3''}$, and $R^{10}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a101}$, $SR^{a101}$, $NHOR^{a101}$, $C(O)R^{b101}$, $C(O)NR^{c101}R^{d101}$, $C(O)NR^{c101}(OR^{b101})$, $C(O)OR^{a101}$, $OC(O)R^{b101}$, $OC(O)NR^{c101}R^{d101}$, $NR^{c101}R^{d101}$, $NR^{c101}NR^{c101}R^{d101}$, $NR^{c101}C(O)R^{b101}$, $NR^{c101}C(O)OR^{a101}$, $NR^{c101}C(O)NR^{c101}R^{d101}$, $C(=NR^{e101})R^{b101}$, $C(=NOH)R^{b101}$, $C(=NCN)R^{b101}$, $C(=NR^{e101})NR^{c101}R^{d101}$, $NR^{c101}C(=NR^{e101})NR^{c101}R^{d101}$, $NR^{c101}C(=NR^{e101})R^{b101}$, $NR^{c101}C(=NOH)NR^{c101}R^{d101}$, $NR^{c101}C(=NCN)NR^{c101}R^{d101}$, $NR^{c101}S(O)R^{b101}$, $NR^{c101}S(O)NR^{c101}R^{d101}$, $NR^{c101}S(O)_2R^{b101}$, $NR^{c101}S(O)_2NR^{c101}R^{d101}$, $S(O)R^{b101}$, $S(O)NR^{c101}R^{d101}$, $S(O)_2R^{b101}$, $S(O)_2NR^{c101}R^{d101}$, $OS(O)(=NR^{e101})R^{b101}$, $OS(O)_2R^{b101}$, $SF_5$, $P(O)R^{f101}R^{g101}$, $OP(O)(OR^{h101})(OR^{i101})$, $P(O)(OR^{h101})(OR^{i101})$, and $BR^{j101}R^{k101}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^3$, $R^{3''}$, and $R^{10}$ are each optionally substituted with 1, 2, 3 or 4 independently selected $R^{10A}$ substituents, provided that none of $R^3$, $R^{3''}$, and $R^{10}$ is OH;

or, alternatively, any two of $R^3$, $R^{3''}$, and $R^{10}$ together form an oxo group;

$R^4$, $R^5$ and $R^6$ are each selected from H, D, halo, CN, OH, $NH_2$, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkylamino, di($C_{1-6}$ alkyl)amino, and $C(O)NR^aR^b$;

each $R^a$ and $R^b$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^a$ and $R^b$ are each optionally substituted with 1, 2, 3 or 4 independently selected $R^M$ substituents;

each $R^{a101}$, $R^{b101}$, $R^{c101}$, and $R^{d101}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a101}$, $R^{b101}$, $R^{c101}$, and $R^{d101}$ are each optionally substituted with 1, 2, 3 or 4 independently selected $R^{10A}$ substituents;

or, any $R^{c101}$ and $R^{d101}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{10A}$ substituents;

each $R^{e101}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f101}$ and $R^{g101}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h101}$ and $R^{i101}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j101}$ and $R^{k101}$ is independently selected from OH, $C_{1-6}$ alkoxy, and $C_{1-6}$ haloalkoxy;

or any $R^{j101}$ and $R^{k101}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{10A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a102}$, $SR^{a102}$, $NHOR^{a102}$, $C(O)R^{b102}$, $C(O)NR^{c102}R^{d102}$, $C(O)NR^{c102}(OR^{b102})$, $C(O)OR^{a102}$, $OC(O)R^{b102}$, $OC(O)NR^{c102}R^{d102}$, $NR^{c102}R^{d102}$, $NR^{c102}NR^{c102}R^{d102}$, $NR^{c102}C(O)R^{b102}$, $NR^{c102}C(O)OR^{a102}$, $NR^{c102}C(O)NR^{c102}R^{d102}$, $C(=NR^{e102})R^{b102}$, $C(=NOH)R^{b102}$, $C(=NCN)R^{b102}$, $C(=NR^{e102})NR^{c102}R^{d102}$, $NR^{c102}C(=NR^{e102})NR^{c102}R^{d102}$, $NR^{c102}C(=NR^{e102})R^{b102}$, $NR^{c102}C(=NOH)NR^{c102}R^{d102}$, $NR^{c102}C(=NCN)NR^{c102}R^{d102}$ $NR^{c102}S(O)R^{b102}$, $NR^{c102}S(O)NR^{c102}R^{d102}$ $NR^{c102}S(O)_2R^{b102}$ $NR^{c102}S(O)_2NR^{c102}R^{d02}$, $S(O)R^{b102}$, $S(O)NR^{c102}R^{d102}$, $S(O)_2R^{b102}$, $S(O)_2NR^{c102}R^{d102}$, $OS(O)(=NR^{e102})R^{b102}$, $OS(O)_2R^{b102}$, $SF_5$, $P(O)R^{f102}R^{g102}$, $OP(O)(OR^{h102})(OR^{i102})$, $P(O)(OR^{h102})(OR^{i102})$, and $BR^{j102}R^{k102}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10A}$ are each optionally substituted with 1, 2, 3 or 4 independently selected $R^{10B}$ substituents;

each $R^{a02}$, $R^{b102}$, $R^{c102}$, and $R^{d102}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a102}$, $R^{b102}$, $R^{c102}$, and $R^{d102}$ are each optionally substituted with 1, 2, 3 or 4 independently selected $R^{10B}$ substituents;

or, any $R^{c102}$ and $R^{d102}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected R10B substituents;

each $R^{e102}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f102}$ and $R^{g102}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h102}$ and $R^{i102}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl-;

each R$^{j102}$ and R$^{k102}$ is independently selected from OH, C$_{1-6}$ alkoxy, and C$_{1-6}$ haloalkoxy;

or any R$^{j102}$ and R$^{k102}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{10B}$ is independently selected from H, D, halo, CN, NO$_2$, SF$_5$, C$_{1-6}$ alkyl, C$_{1-6}$ alkoxy, C$_{1-6}$ haloalkyl, C$_{2-6}$ alkenyl, C$_{2-6}$ alkynyl, phenyl, C$_{3-7}$ cycloalkyl, 5-7 membered heteroaryl, 4-7 membered heterocycloalkyl, phenyl-C$_{1-6}$ alkyl-, C$_{3-7}$ cycloalkyl-C$_{1-6}$ alkyl-, (5-7 membered heteroaryl)-C$_{1-6}$ alkyl- and (4-7 membered heterocycloalkyl)-C$_{1-6}$ alkyl; and each R$^{7A}$ is independently selected from D, halo, C$_{1-6}$ alkyl, C$_{1-6}$ haloalkyl, C$_{2-6}$ alkenyl, C$_{2-6}$ alkynyl, C$_{6-14}$ aryl, C$_{3-12}$ cycloalkyl, 5-14 membered heteroaryl, 4-12 membered heterocycloalkyl, C$_{6-14}$ aryl-C$_{1-6}$ alkyl-, C$_{3-12}$ cycloalkyl-C$_{1-6}$ alkyl-, (5-14 membered heteroaryl)-C$_{1-6}$ alkyl-, (4-12 membered heterocycloalkyl)-C$_{1-6}$ alkyl-, CN, NO$_2$, OR$^{a71}$, SR$^{a71}$, NHOR$^{a71}$, C(O)R$^{b71}$, C(O)NR$^{c71}$R$^{d71}$, C(O)NR$^{c71}$(OR$^{b71}$), C(O)OR$^{a71}$, OC(O)R$^{b71}$, OC(O)NR$^{c71}$R$^{d71}$, NR$^{c71}$R$^{d71}$, NR$^{c71}$NR$^{c71}$R$^{d71}$, NR$^{c71}$C(O)R$^{b71}$, NR$^{c71}$C(O)OR$^{a71}$, NR$^{c71}$C(O)NR$^{c71}$R$^{d71}$, C(=NR$^{e71}$)R$^{b71}$, C(=NOH)R$^{b71}$, C(=NCN)R$^{b71}$, C(=NR$^{e71}$)NR$^{c71}$R$^{d71}$, NR$^{c71}$C(=NR$^{e71}$)NR$^{c71}$R$^{d71}$, NR$^{c71}$C(=NR$^{e71}$)R$^{b71}$, NR$^{c71}$C(=NOH)NR$^{c71}$R$^{d71}$, NR$^{c71}$C(=NCN)NR$^{c71}$R$^{d71}$, NR$^{c71}$S(O)R$^{b71}$, NR$^{c71}$S(O)NR$^{c71}$R$^{d71}$, NR$^{c71}$S(O)$_2$R$^{b71}$, NR$^{c71}$S(O)$_2$NR$^{c71}$R$^{d71}$, S(O)R$^{b71}$, S(O)NR$^{c71}$R$^{d71}$, S(O)$_2$R$^{b71}$, S(O)$_2$NR$^{c71}$R$^{d71}$, OS(O)(=NR$^{e71}$)R$^{b71}$, OS(O)$_2$R$^{b71}$, SF$_5$, P(O)R$^{f71}$R$^{g71}$, OP(O)(OR$^{h71}$)(OR$^{i71}$), P(O)(OR$^{h71}$)(OR$^{i71}$), and BR$^{j71}$R$^{k71}$, wherein the C$_{1-6}$ alkyl, C$_{2-6}$ alkenyl, C$_{2-6}$ alkynyl, C$_{6-14}$ aryl, C$_{3-12}$ cycloalkyl, 5-14 membered heteroaryl 4-12 membered heterocycloalkyl, C$_{6-14}$ aryl-C$_{1-6}$ alkyl-, C$_{3-12}$ cycloalkyl-C$_{1-6}$ alkyl-, (5-14 membered heteroaryl)-C$_{1-6}$ alkyl-, and (4-12 membered heterocycloalkyl)-C$_{1-6}$ alkyl-, of R$^{7A}$ are each optionally substituted with 1, 2, 3 or 4 independently selected R$^{7B}$ substituents;

each R$^{a71}$, R$^{b71}$, R$^{c71}$, and R$^{d71}$ is independently selected from H, C$_{1-6}$ alkyl, C$_{1-6}$ haloalkyl, C$_{2-6}$ alkenyl, C$_{2-6}$ alkynyl, C$_{6-14}$ aryl, C$_{3-12}$ cycloalkyl, 5-14 membered heteroaryl, 4-12 membered heterocycloalkyl, C$_{6-14}$ aryl-C$_{1-6}$ alkyl-, C$_{3-12}$ cycloalkyl-C$_{1-6}$ alkyl-, (5-14 membered heteroaryl)-C$_{1-6}$ alkyl- and (4-12 membered heterocycloalkyl)-C$_{1-6}$ alkyl-, wherein the C$_{1-6}$ alkyl, C$_{2-6}$ alkenyl, C$_{2-6}$ alkynyl, C$_{6-14}$ aryl, C$_{3-12}$ cycloalkyl, 5-14 membered heteroaryl, 4-12 membered heterocycloalkyl, C$_{6-14}$ aryl-C$_{1-6}$ alkyl-, C$_{3-12}$ cycloalkyl-C$_{1-6}$ alkyl-, (5-14 membered heteroaryl)-C$_{1-6}$ alkyl- and (4-12 membered heterocycloalkyl)-C$_{1-6}$ alkyl- of R$^{a71}$, R$^{b71}$, R$^{c71}$, and R$^{d71}$ are each optionally substituted with 1, 2, 3 or 4 independently selected R$^{7B}$ substituents;

or, any R$^{c71}$ and R$^{d71}$ attached to the same N atom, together with the N atom to which they are attached, form a 5-10-membered heteroaryl or a 4-10-membered heterocycloalkyl group, wherein the 5-10-membered heteroaryl or 4-10-membered heterocycloalkyl group is optionally substituted with 1, 2, 3 or 4 independently selected R$^{7B}$ substituents;

each R$^{e71}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-14}$ aryl, C$_{3-12}$ cycloalkyl, 5-14 membered heteroaryl, 4-12 membered heterocycloalkyl, C$_{6-14}$ aryl-C$_{1-6}$ alkyl-, C$_{3-12}$ cycloalkyl-C$_{1-6}$ alkyl-, (5-14 membered heteroaryl)-C$_{1-6}$ alkyl- and (4-12 membered heterocycloalkyl)-C$_{1-6}$ alkyl-;

each R$^{f71}$ and R$^{g71}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-14}$ aryl, C$_{3-12}$ cycloalkyl, 5-14 membered heteroaryl, 4-12 membered heterocycloalkyl, C$_{6-14}$ aryl-C$_{1-6}$ alkyl-, C$_{3-12}$ cycloalkyl-C$_{1-6}$ alkyl-, (5-14 membered heteroaryl)-C$_{1-6}$s alkyl- and (4-12 membered heterocycloalkyl)-C$_{1-6}$ alkyl-;

each R$^{h71}$ and R$^{i71}$ is independently selected from H, C$_{1-6}$ alkyl, C$_{1-6}$ haloalkyl, C$_{2-6}$ alkenyl, C$_{2-6}$ alkynyl, C$_{6-14}$ aryl, C$_{3-12}$ cycloalkyl, 5-14 membered heteroaryl, 4-12 membered heterocycloalkyl, C$_{6-14}$ aryl-C$_{1-6}$ alkyl-, C$_{3-12}$ cycloalkyl-C$_{1-6}$ alkyl-, (5-14 membered heteroaryl)-C$_{1-6}$ alkyl- and (4-12 membered heterocycloalkyl)-C$_{1-6}$ alkyl-;

each R$^{j71}$ and R$^{k71}$ is independently selected from OH, C$_{1-6}$ alkoxy, and C$_{1-6}$ haloalkoxy;

or any R$^{j71}$ and R$^{k}$71 attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{7B}$ is independently selected from D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a72}$, SR$^{a72}$, NHOR$^{a72}$, C(O)R$^{b72}$, C(O)NR$^{c72}$R$^{d72}$, C(O)NR$^{c72}$(OR$^{b72}$), C(O)OR$^{a72}$, OC(O)R$^{b72}$, OC(O)NR$^{c72}$R$^{d72}$, NR$^{c72}$R$^{d72}$, NR$^{72}$NR$^{c72}$R$^{d72}$, NR$^{c72}$C(O)R$^{b72}$, NR$^{c72}$C(O)OR$^{a72}$, NR$^{c72}$C(O)NR$^{c72}$R$^{d72}$, C(=NR$^{e72}$)R$^{b72}$, C(=NOH)R$^{b72}$, C(=NCN)R$^{b72}$, C(=NR$^{e72}$)NR$^{c72}$R$^{d72}$, NR$^{c72}$C(=NR$^{e72}$)NR$^{c72}$R$^{d72}$, NR$^{c72}$C(=NR$^{e72}$)R$^{b72}$, NR$^{c72}$C(=NOH)NR$^{c72}$R$^{d72}$, NR$^{c72}$C(=NCN)NR$^{c72}$R$^{d72}$, NR$^{c72}$S(O)R$^{b72}$ NR$^{c72}$S(O)NR$^{c72}$R$^{d72}$, NR$^{c72}$S(O)$_2$R$^{b72}$, NR$^{c72}$S(O)$_2$NR$^{c72}$R$^{d72}$, S(O)R$^{b72}$, S(O)NR$^{c72}$R$^{d72}$, S(O)$_2$R$^{b72}$ S(O)$_2$NR$^{c72}$R$^{d72}$, OS(O)(=NR$^{e72}$)R$^{b72}$, OS(O)$_2$R$^{b72}$, SF$_5$, P(O)R$^{f72}$R$^{g72}$, OP(O)(OR$^{h72}$)(OR$^{i72}$), P(O)(OR$^{h72}$)(OR$^{i72}$), and BR$^{j72}$R$^{k72}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl- of R$^{7B}$ are each optionally substituted with 1, 2, 3 or 4 independently selected R$^{7C}$ substituents;

each R$^{a72}$, R$^{b72}$, R$^{c72}$, and R$^{d72}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl- and (4-10 membered heterocycloalkyl)-C$_{1-6}$ alkyl- of R$^{a72}$, R$^{b72}$, R$^{c72}$, and R$^{d72}$ are each optionally substituted with 1, 2, 3 or 4 independently selected R$^{7C}$ substituents;

or, any R$^{c72}$ and R$^{d72}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected R$^{7C}$ substituents;

each R$^{e72}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f72}$ and $R^{g72}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h72}$ and $R^{i72}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j72}$ and $R^{k72}$ is independently selected from OH, $C_{1-6}$ alkoxy, and $C_{1-6}$ haloalkoxy;

or any $R^{j72}$ and $R^{k72}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7C}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a73}$, $SR^{a73}$, $NHOR^{a73}$, $C(O)R^{b73}$, $C(O)NR^{c73}R^{d73}$, $C(O)NR^{c73}(OR^{b73})$, $C(O)OR^{a73}$, $OC(O)R^{b73}$, $OC(O)NR^{c73}R^{d73}$, $NR^{c73}R^{d73}$, $NR^{c73}NR^{c73}R^{d73}$, $NR^{c73}C(O)R^{b73}$, $NR^{c73}C(O)OR^{a73}$, $NR^{c73}C(O)NR^{c73}R^{d73}$, $C(=NR^{e73})R^{b73}$, $C(=NOH)R^{b73}$, $C(=NCN)R^{b73}$, $C(=NR^{e73})NR^{c73}R^{d73}$, $NR^{c73}C(=NR^{e73})NR^{c73}R^{d73}$, $NR^{c73}C(=NR^{e73})R^{b73}$, $NR^{c73}C(=NOH)NR^{c73}R^{d73}$, $NR^{c73}C(=NCN)NR^{c73}R^{d73}$, $NR^{c73}S(O)R^{b73}$, $NR^{c73}S(O)NR^{c73}R^{d73}$, $NR^{c73}S(O)_2R^{b73}$, $NR^{c73}S(O)_2NR^{c73}R^{d73}$, $S(O)R^{b73}$, $S(O)NR^{c73}R^{d73}$, $S(O)_2R^{b73}$, $S(O)_2NR^{c73}R^{d73}$, $OS(O)(=NR^{e73})R^{b73}$, $OS(O)_2R^{b73}$, $SF_5$, $P(O)R^{f73}R^{g73}$, $OP(O)(OR^{h73})(OR^{i73})$, $P(O)(OR^{h73})(OR^{i73})$, and $BR^{j73}R^{k73}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{7C}$ are each optionally substituted with 1, 2, 3 or 4 independently selected $R^{7D}$ substituents;

each $R^{a73}$, $R^{b73}$, $R^{c73}$, and $R^{d73}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a73}$, $R^{b73}$, $R^{c73}$, and $R^{d73}$ are each optionally substituted with 1, 2, 3 or 4 independently selected $R^{7D}$ substituents;

or, any $R^{c73}$ and $R^{d73}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{7D}$ substituents;

each $R^{e73}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f73}$ and $R^{g73}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h73}$ and $R^{i73}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j73}$ and $R^{k73}$ is independently selected from OH, $C_{1-6}$ alkoxy, and $C_{1-6}$ haloalkoxy;

or any $R^{j73}$ and $R^{k73}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^{7D}$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl- and (4-7 membered heterocycloalkyl)-$C_{1-6}$ alkyl.

In some embodiments, $X^1$ is N.

In some embodiments, $X^1$ is $CR^1$.

In some embodiments, $R^1$ is selected from H, D, and $C_{1-6}$ alkyl.

In some embodiments, $R^1$ is selected from H, D, and methyl.

In some embodiments, $R^1$ is H.

In some embodiments, $R^2$ is a $C_{1-6}$ haloalkyl, wherein each halogen of the $C_{1-6}$ haloalkyl is independently selected from F and Cl.

In some embodiments, $R^2$ is a $C_{1-3}$ haloalkyl, wherein each halogen of the $C_{1-3}$ haloalkyl is independently selected from F and Cl.

In some embodiments, $R^2$ is selected from $CF_3$, $CCl_3$, $CF_2H$, $CCl_2H$, $CF_2R^M$, $CCl_2R^M$, $CFH_2$, $CClH_2$, $CFHR^M$, $CClHR^M$, $CF(R^M)_2$ and $CCl(R^M)_2$.

In some embodiments, $R^2$ is selected from $CF_3$, $CF_2H$, $CF_2R^M$, $CFH_2$, $CFHR^M$, and $CF(R^M)_2$.

In some embodiments, $R^M$ is selected from D, halo, $C_{1-3}$ alkyl, and $C_{1-3}$ haloalkyl.

In some embodiments, $R^M$ is selected from halo and $C_{1-3}$ haloalkyl.

In some embodiments, $R^2$ is $C_{1-6}$ haloalkyl, wherein each halogen is F.

In some embodiments, $R^2$ is $C_{1-6}$ haloalkyl, wherein each halogen is Cl.

In some embodiments, $R^2$ is selected from $CH_2F$, $CHF_2$, $CF_3$, and $CF_2CF_3$.

In some embodiments, $R^2$ is $CF_3$ or $CHF_2$.

In some embodiments, $R^2$ is $CF_3$.

In some embodiments, $R^2$ is $CH_2F$.
In some embodiments, $R^2$ is $CHF_2$.
In some embodiments, $R^2$ is $CF_2CF_3$.
In some embodiments, $R^3$ is selected from H, D, $C_{1-6}$ alkyl, $C_{2-6}$ alkenyl, $C_{2-6}$ alkynyl, and $NH_2$.
In some embodiments, $R^3$ selected from H, D, and $C_{1-6}$ alkyl.
In some embodiments, $R^3$ is H or D.
In some embodiments, $R^3$ is H.
In some embodiments, $R^{3''}$ is selected from H, D, $C_{1-6}$ alkyl, $C_{2-6}$ alkenyl, $C_{2-6}$ alkynyl, and $NH_2$.
In some embodiments, $R^{3''}$ is selected from H, D, and $C_{1-6}$ alkyl.
In some embodiments, $R^{3''}$ is H or D.
In some embodiments, $R^{3''}$ is H.
In some embodiments, $R^3$ and $R^{3''}$ together form an oxo group.
In some embodiments, $R^4$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.
In some embodiments, $R^4$ is selected from H, D, halo, CN, OH, $NH_2$, and $C_{1-6}$ alkyl.
In some embodiments, $R^4$ is selected from H, D, and $C_{1-6}$ alkyl, wherein the $C_{1-6}$ alkyl is optionally substituted with 1, 2, or 3 deuterium atoms.
In some embodiments, $R^4$ is H.
In some embodiments, $R^4$ is D.
In some embodiments, $R^5$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.
In some embodiments, $R^5$ is selected from H, D, halo, CN, OH, $NH_2$, and $C_{1-6}$ alkyl.
In some embodiments, $R^5$ is selected from H, D, and $C_{1-6}$ alkyl, wherein the $C_{1-6}$ alkyl is optionally substituted with 1, 2, or 3 deuterium atoms.
In some embodiments, $R^5$ is H.
In some embodiments, $R^5$ is D.
In some embodiments, $R^3$ and $R^4$ are each H.
In some embodiments, $R^3$ and $R^5$ are each H.
In some embodiments, $R^4$ and $R^5$ are each H.
In some embodiments, $R^3$, $R^{3''}$, $R^4$, and $R^5$ are each H.
In some embodiments, $R^3$ and $R^{3''}$ together form an oxo group; and $R^4$ and $R^5$ are each H.
In some embodiments, $R^6$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.
In some embodiments, $R^6$ is selected from H, D, and $C_{1-6}$ alkyl, wherein the $C_{1-6}$ alkyl is optionally substituted with 1, 2, or 3 deuterium atoms.
In some embodiments, $R^6$ is selected from H, D, halo, CN, OH, $NH_2$, and $C_{1-6}$ alkyl.
In some embodiments, $R^6$ is $C_{1-6}$ alkyl.
In some embodiments, $R^6$ is methyl.
In some embodiments, $R^6$ is $CD_3$.
In some embodiments, $R^6$ is H.
In some embodiments, $R^6$ is D.
In some embodiments, $R^7$ is selected from $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl and $C_{2-6}$ alkynyl are each optionally substituted with 1, 2, or 3 independently selected $R^{7A}$ substituents.

In some embodiments, $R^7$ is $C_{1-6}$ alkyl, which is optionally substituted by 1, 2, or 3 independently selected $R^{7A}$ groups.
In some embodiments, $R^7$ is $C_{1-6}$ alkyl.
In some embodiments, $R^7$ is propyl.
In some embodiments, $R^7$ is $C_{2-6}$ alkenyl, which is optionally substituted by 1, 2, or 3 independently selected $R^{7A}$ groups.
In some embodiments, $R^7$ is $C_{2-6}$ alkenyl.
In some embodiments, $R^7$ is propenyl or butenyl.
In some embodiments, $R^7$ is prop-1-enyl or but-1-enyl.
In some embodiments, $R^7$ is $C_{2-6}$ alkynyl, which is optionally substituted with 1, 2 or 3 independently selected $R^{7A}$ substituents.
In some embodiments, $R^7$ is ethynyl, propynyl, butynyl, or pentynyl, wherein the ethynyl is optionally substituted by $R^{7A}$, and the propynyl, butynyl, and pentynyl groups are each optionally substituted by 1, 2, or 3 independently selected $R^{7A}$ groups.
In some embodiments, $R^7$ is selected from ethynyl, prop-1-ynyl, but-1-ynyl, and pent-1-ynyl, wherein the ethynyl is substituted by $R^{7A}$, and the prop-1-ynyl, but-1-ynyl, and pent-1-ynyl are each optionally substituted by 1, 2, or 3 independently selected $R^{7A}$ groups.
In some embodiments, $R^7$ is selected from prop-1-ynyl, but-1-ynyl, and pent-1-ynyl, wherein the prop-1-ynyl, but-1-ynyl, and pent-1-ynyl are each optionally substituted by 1, 2, or 3 independently selected $R^{7A}$ groups.
In some embodiments, $R^7$ is ethynyl, wherein the ethynyl is optionally substituted by 1, 2, or 3 independently selected $R^{7A}$ groups.
In some embodiments, each $R^{7A}$ is independently selected from H, D, $C_{1-6}$ alkyl, $C_{1-6}$ haloalkyl, $C_{6-10}$ aryl, $C_{3-12}$ cycloalkyl, 5-10 membered heteroaryl, 4-12 membered heterocycloalkyl, wherein the $C_{1-6}$ alkyl, $C_{6-10}$ aryl, $C_{3-12}$ cycloalkyl, 5-10 membered heteroaryl, and 4-12 membered heterocycloalkyl, are each optionally substituted with 1, 2, 3, 4, or 5 independently selected $R^{7B}$ substituents.
In some embodiments, each $R^{7A}$ is independently selected from H, D, $C_{1-6}$ alkyl, $C_{1-6}$ haloalkyl, $C_{6-10}$ aryl, $C_{3-12}$ cycloalkyl, 5-10 membered heteroaryl, 4-12 membered heterocycloalkyl, $C_{6-10}$ aryl-$C_{1-6}$ alkyl-, $C_{3-12}$ cycloalkyl-$C_{1-6}$ alkyl-, (5-10 membered heteroaryl)-$C_{1-6}$ alkyl- and (4-12 membered heterocycloalkyl)-$C_{1-6}$ alkyl-, wherein the $C_{1-6}$ alkyl, $C_{6-10}$ aryl, $C_{3-12}$ cycloalkyl, 5-10 membered heteroaryl, 4-12 membered heterocycloalkyl, $C_{6-10}$ aryl-$C_{1-6}$ alkyl-, $C_{3-12}$ cycloalkyl-$C_{1-6}$ alkyl-, (5-10 membered heteroaryl)-$C_{1-6}$ alkyl- and (4-12 membered heterocycloalkyl)-$C_{1-6}$ alkyl- are each optionally substituted with 1, 2, 3, 4, or 5 independently selected $R^{7B}$ substituents, and wherein the connection of $C_{6-10}$ aryl-$C_{1-6}$ alkyl-, $C_{3-12}$ cycloalkyl-$C_{1-6}$ alkyl-, (5-10 membered heteroaryl)-$C_{1-6}$ alkyl- and (4-12 membered heterocycloalkyl)-$C_{1-6}$ alkyl-groups to $R^7$ (e.g., to an alkynyl group of $R^7$) may occur through the aforementioned ring or the $C_{1-6}$ alkyl group.
In some embodiments, each $R^{7A}$ is independently selected from D, halo, $C_{1-6}$ alkyl, $C_{6-10}$ aryl, $C_{3-10}$ cycloalkyl, 5-10 membered heteroaryl, 4-10 membered heterocycloalkyl, CN, $NO_2$, and $OR^{a71}$, wherein the $C_{1-6}$ alkyl, $C_{6-10}$ aryl, $C_{3-10}$ cycloalkyl, 5-10 membered heteroaryl, and 4-10 membered heterocycloalkyl of $R^{7A}$ are each optionally substituted by 1 or 2 independently selected $R^{7B}$ groups.
In some embodiments, each $R^{a71}$ is independently selected from H and $C_{1-6}$ alkyl.
In some embodiments, each $R^{7A}$ is independently selected from D, halo, $C_{1-6}$ alkyl, $C_{6-10}$ aryl, $C_{3-10}$ cycloalkyl, 5-10 membered heteroaryl, 4-10 membered heterocycloalkyl, CN, NO$_2$, and OR$^{a71}$, wherein the C$_{1-6}$ alkyl, C$_{6-10}$ aryl, C$_{3-10}$ cycloalkyl, 5-10 membered heteroaryl, and 4-10 membered heterocycloalkyl of R$^{7A}$ are each optionally substituted by 1 or 2 independently selected R$^{7B}$ groups; and
each R$^{a71}$ is independently selected from H and C$_{1-6}$ alkyl.

In some embodiments, each R$^{7A}$ is independently selected from C$_{1-6}$ alkyl, C$_{6-10}$ aryl, C$_{3-10}$ cycloalkyl, 5-10 membered heteroaryl, 4-10 membered heterocycloalkyl, and OR$^{a71}$, wherein the C$_{1-6}$ alkyl, C$_{6-10}$ aryl, C$_{3-10}$ cycloalkyl, 5-10 membered heteroaryl and 4-10 membered heterocycloalkyl of R$^{7A}$ are each optionally substituted by 1 or 2 independently selected R$^{7B}$ groups.

In some embodiments, each R$^{7A}$ is independently selected from methyl, cyclopropyl, pyrazolyl, imidazolyl, phenyl, pyridinyl, pyrimidinyl, pyrazinyl, imidazopyrazinyl, hydroxyl, and methoxy, wherein the cyclopropyl, pyrazolyl, imidazolyl, phenyl, pyridinyl, pyrimidinyl, pyrazinyl, imidazopyrazinyl of R$^{7A}$ are each optionally substituted by 1 or 2 independently selected R$^{7B}$ groups.

In some embodiments, each R$^{7B}$ is independently selected from halo, C$_{1-6}$ alkyl, CN, cyano-C$_{1-6}$ alkyl, and OR$^{a72}$.

In some embodiments, each R$^{a72}$ is independently selected from H and C$_{1-6}$ alkyl.

In some embodiments, each R$^{7B}$ is independently selected from halo, C$_{1-6}$ alkyl, CN, cyano-C$_{1-6}$ alkyl, and OR$^{a72}$; and
each R$^{a72}$ is independently selected from H and C$_{1-6}$ alkyl.

In some embodiments, each R$^{7A}$ is independently selected from C$_{1-6}$ alkyl, C$_{6-10}$ aryl, C$_{3-10}$ cycloalkyl, 5-10 membered heteroaryl, 4-10 membered heterocycloalkyl, and OR$^{a71}$, wherein the C$_{1-6}$ alkyl, C$_{6-10}$ aryl, C$_{3-10}$ cycloalkyl, 5-10 membered heteroaryl and 4-10 membered heterocycloalkyl of R$^{7A}$ are each optionally substituted by 1 or 2 independently selected R$^{7B}$ groups and
each R$^{7B}$ is independently selected from halo, C$_{1-6}$ alkyl, CN, cyano-C$_{1-6}$ alkyl, and OR$^{a72}$.

In some embodiments, each R$^{7A}$ is independently selected from methyl, cyclopropyl, pyrazolyl, imidazolyl, phenyl, pyridinyl, pyrimidinyl, pyrazinyl, imidazopyrazinyl, hydroxyl, and methoxy, wherein the cyclopropyl, pyrazolyl, imidazolyl, phenyl, pyridinyl, pyrimidinyl, pyrazinyl, imidazopyrazinyl of R$^{7A}$ are each optionally substituted by 1 or 2 independently selected R$^{7B}$ groups; and
each R$^{7B}$ is independently selected from methyl, cyano, cyanomethyl, and methoxy.

In some embodiments, R$^7$ is selected from C$_{1-6}$ haloalkyl.
In some embodiments, R$^7$ is trifluoromethyl.
In some embodiments, R$^8$ is selected from H, C$_{1-6}$ alkyl, C$_{2-6}$ alkenyl, C$_{2-6}$ alkynyl, C$_{1-6}$ haloalkyl, and C(O)R$^{b8}$.
In some embodiments, R$^8$ is selected from H, C$_{1-6}$ alkyl, C$_{2-6}$ alkenyl, C$_{2-6}$ alkynyl, C$_{1-6}$ haloalkyl, C$_{3-10}$ cycloalkyl, and C(O)R$^{b8}$.
In some embodiments, R$^8$ is selected from H, C$_{1-6}$ alkyl, C$_{2-6}$ alkenyl, C$_{2-6}$ alkynyl, C$_{1-6}$ haloalkyl, and C$_{3-10}$ cycloalkyl.
In some embodiments, R$^8$ is selected from H, C$_{1-6}$ alkyl, and C(O)R$^{b8}$.
In some embodiments, R$^8$ is H or C$_{1-6}$ alkyl.
In some embodiments, R$^8$ is H, methyl, ethyl, propyl or isopropyl.
In some embodiments, R$^8$ is H or C(O)R$^{b8}$.
In some embodiments, R$^8$ is H.
In some embodiments, R$^8$ is C(O)R$^{b8}$.
In some embodiments, R$^{b8}$ is selected from H, C$_{1-6}$ alkyl, C$_{1-6}$ haloalkyl, C$_{2-6}$ alkenyl, and C$_{2-6}$ alkynyl, wherein the C$_{1-6}$ alkyl, C$_{2-6}$ alkenyl, and C$_{2-6}$ alkynyl of R$^{b8}$ are each optionally substituted with 1, 2, 3 or 4 independently selected R$^{8A}$ substituents.

In some embodiments, R$^{b8}$ is selected from H, C$_{1-6}$ alkyl, and C$_{1-6}$ haloalkyl, wherein the C$_{1-6}$ alkyl of R$^{b8}$ is optionally substituted with 1 or 2 R$^{8A}$ substituents independently selected from D, halo, CN, NO$_2$, OH, and SH.

In some embodiments, R$^{b8}$ is selected from methyl, fluoromethyl, cyanomethyl, and hydroxypropyl.

In some embodiments, R$^{b8}$ is selected from H, D, and C$_{1-6}$ alkyl.

In some embodiments, R$^{b8}$ is selected from H, D, and methyl.

In some embodiments, R$^{b8}$ is H.

In some embodiments, R$^9$ is selected from H, C$_{1-6}$ alkyl, C$_{2-6}$ alkenyl, C$_{2-6}$ alkynyl, C$_{1-6}$ haloalkyl and C$_{3-10}$ cycloalkyl.

In some embodiments, R$^9$ is selected from H, C$_{1-6}$ alkyl, C$_{2-6}$ alkenyl, C$_{2-6}$ alkynyl, and C$_{1-6}$ haloalkyl.

In some embodiments, R$^9$ is H or C$_{1-6}$ alkyl.

In some embodiments, R$^9$ is selected from H, methyl, ethyl, propyl, and isopropyl.

In some embodiments, R$^9$ is H.

In some embodiments, R$^8$ and R$^9$ are each H.

In some embodiments:
R$^3$ is selected from H, D, C$_{1-6}$ alkyl, C$_{2-6}$ alkenyl, C$_{2-6}$ alkynyl, C$_{1-6}$ haloalkyl, and NH$_2$;
R$^{3"}$ is selected from H, D, C$_{1-6}$ alkyl, C$_{2-6}$ alkenyl, C$_{2-6}$ alkynyl, C$_{1-6}$ haloalkyl, and NH$_2$; and
R$^8$ is C(O)R$^{b8}$.

In some embodiments:
R$^3$ and R$^{3"}$ together form an oxo group; and
R$^8$ is selected from H, C$_{1-6}$ alkyl, C$_{2-6}$ alkenyl, C$_{2-6}$ alkynyl, C$_{1-6}$ haloalkyl, and C$_{3-7}$ cycloalkyl.

In some embodiments:
X$^1$ is N or CH;
R$^2$ is a C$_{1-6}$ haloalkyl, wherein each halogen of the C$_{1-6}$ haloalkyl is independently selected from F and Cl;
R$^3$ is selected from H, D, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, and NH$_2$;
R$^{3"}$ is selected from H, D, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, and NH$_2$;
or, alternatively, R$^3$ and R$^{3"}$ together form an oxo group;
R$^4$ is selected from H, D, halo, CN, OH, NH$_2$, and C$_{1-6}$ alkyl;
R$^5$ is selected from H, D, halo, CN, OH, NH$_2$, and C$_{1-6}$ alkyl;
R$^6$ is selected from H, D, halo, CN, OH, NH$_2$, and C$_{1-6}$ alkyl;
R$^7$ is selected from C$_{1-6}$ alkyl, C$_{1-6}$ haloalkyl, C$_{2-6}$ alkenyl, and C$_{2-6}$ alkynyl, wherein the C$_{1-6}$ alkyl, C$_{2-6}$ alkenyl and C$_{2-6}$ alkynyl are each optionally substituted with 1, 2, or 3 independently selected R$^{7A}$ substituents;
R$^8$ is selected from H, C$_{1-6}$ alkyl, C$_{2-6}$ alkenyl, C$_{2-6}$ alkynyl, C$_{1-6}$ haloalkyl, and C(O)R$^{b8}$;
R$^9$ is selected from H, C$_{1-6}$ alkyl, C$_{2-6}$ alkenyl, C$_{2-6}$ alkynyl, and C$_{1-6}$ haloalkyl;
each R$^{7A}$ is independently selected from D, halo, C$_{1-6}$ alkyl, C$_{6-10}$ aryl, C$_{3-10}$ cycloalkyl, 5-10 membered heteroaryl, 4-10 membered heterocycloalkyl, CN, NO$_2$, and OR$^{a71}$, wherein the C$_{1-6}$ alkyl, C$_{6-10}$ aryl, C$_{3-10}$ cycloalkyl, 5-10 membered heteroaryl, and 4-10 membered heterocycloalkyl of R$^{7A}$ are each optionally substituted by 1 or 2 independently selected R$^{7B}$ groups;
each R$^{a71}$ is independently selected from H and C$_{1-6}$ alkyl;
each R$^{7B}$ is independently selected from halo, C$_{1-6}$ alkyl, CN, cyano-C$_{1-6}$ alkyl, and OR$^{a72}$;

each $R^{a72}$ is independently selected from H and $C_{1-6}$ alkyl;

$R^{b8}$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{b8}$ are each optionally substituted with 1, 2, 3 or 4 independently selected $R^{84}$ substituents; and each $R^{84}$ is independently selected from D, halo, CN, $NO_2$, OH, and SH.

In some embodiments:

$X^1$ is N or CH;

$R^2$ is a $C_{1-3}$ haloalkyl, wherein each halogen of the $C_{1-3}$ haloalkyl is independently selected from F and Cl;

$R^3$ is H;

$R^{3''}$ is H;

or, alternatively, $R^3$ and $R^{3''}$ together form an oxo group;

$R^4$ is selected from H and $C_{1-6}$ alkyl;

$R^5$ is selected from H and $C_{1-6}$ alkyl;

$R^6$ is selected from H and $C_{1-6}$ alkyl;

$R^7$ is selected from $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with 1 or 2 independently selected $R^{7A}$ substituents;

each $R^{7A}$ is independently selected from D, halo, $C_{1-6}$ alkyl, $C_{6-10}$ aryl, $C_{3-10}$ cycloalkyl, 5-10 membered heteroaryl, 4-10 membered heterocycloalkyl, CN, $NO_2$, and $OR^{a71}$, wherein the $C_{1-6}$ alkyl, $C_{6-10}$ aryl, $C_{3-10}$ cycloalkyl, 5-10 membered heteroaryl, and 4-10 membered heterocycloalkyl of $R^{7A}$ are each optionally substituted by 1 or 2 independently selected $R^{7B}$ groups;

each $R^{a7}$ is independently selected from H and $C_{1-6}$ alkyl;

each $R^{7B}$ is independently selected from halo, $C_{1-6}$ alkyl, CN, cyano-$C_{1-6}$ alkyl, and $OR^{a72}$;

each $R^{a2}$ is independently selected from H and $C_{1-6}$ alkyl;

$R^8$ is selected from H and $C(O)R^{b8}$;

$R^9$ is H;

$R^{b8}$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{b8}$ are each optionally substituted with 1, 2, 3 or 4 independently selected $R^{84}$ substituents; and each $R^{84}$ is independently selected from D, halo, CN, $NO_2$, OH, and SH.

In some embodiments:

$X^1$ is N or CH;

$R^2$ is a $C_{1-3}$ haloalkyl, wherein each halogen of the $C_{1-3}$ haloalkyl is independently selected from F and Cl;

$R^3$ is H;

$R^{3''}$ is H;

or, alternatively, $R^3$ and $R^{3''}$ together form an oxo group;

$R^4$ is H;

$R^5$ is H;

$R^6$ is $C_{1-6}$ alkyl;

$R^7$ is selected from trifluoromethyl, propyl, propenyl, ethynyl, propynyl, butynyl, and pentynyl, wherein the ethynyl is optionally substituted by $R^{7A}$, and the propynyl, butynyl, and pentynyl groups are each optionally substituted by 1, 2, or 3 independently selected $R^{7A}$ groups;

each $R^{7A}$ is independently selected from $C_{1-6}$ alkyl, $C_{6-10}$ aryl, $C_{3-10}$ cycloalkyl, 5-10 membered heteroaryl, 4-10 membered heterocycloalkyl, and $OR^{a71}$, wherein the $C_{1-6}$ alkyl, $C_{6-10}$ aryl, $C_{3-10}$ cycloalkyl, 5-10 membered heteroaryl and 4-10 membered heterocycloalkyl of $R^{7A}$ are each optionally substituted by 1 or 2 independently selected $R^{7B}$ groups;

each $R^{7B}$ is independently selected from halo, $C_{1-6}$ alkyl, CN, cyano-$C_{1-6}$ alkyl, and $OR^{a72}$;

each $R^{a72}$ is independently selected from H and $C_{1-6}$ alkyl;

$R^8$ is selected from H and $C(O)R^{b8}$;

$R^9$ is H; and $R^{b8}$ is selected from H, $C_{1-6}$ alkyl, $C_{1-6}$ haloalkyl, $C_{2-6}$ alkenyl, and $C_{2-6}$ alkynyl.

In some embodiments:

$X^1$ is N or CH;

$R^2$ is a $C_{1-3}$ haloalkyl, wherein each halogen of the $C_{1-3}$ haloalkyl is independently selected from F and Cl;

$R^3$ is H;

$R^{3''}$ is H;

or, alternatively, $R^3$ and $R^{3''}$ together form an oxo group;

$R^4$ is H;

$R^5$ is H;

$R^6$ is $C_{1-6}$ alkyl;

$R^7$ is selected from trifluoromethyl, propyl, propenyl, ethynyl, propynyl, butynyl, and pentynyl, wherein the ethynyl is optionally substituted by $R^{7A}$, and the propynyl, butynyl, and pentynyl groups are each optionally substituted by 1, 2, or 3 independently selected $R^{7A}$ groups;

each $R^{7A}$ is independently selected from methyl, cyclopropyl, pyrazolyl, imidazolyl, phenyl, pyridinyl, pyrimidinyl, pyrazinyl, imidazopyrazinyl, hydroxyl, and methoxy, wherein the cyclopropyl, pyrazolyl, imidazolyl, phenyl, pyridinyl, pyrimidinyl, pyrazinyl, imidazopyrazinyl of $R^{7A}$ are each optionally substituted by 1 or 2 independently selected $R^{7B}$ groups;

each $R^{7B}$ is independently selected from methyl, cyano, cyanomethyl, and methoxy;

$R^8$ is selected from H and $C(O)R^{b8}$;

$R^9$ is H; and $R^{b8}$ is selected from H, $C_{1-6}$ alkyl, $C_{1-6}$ haloalkyl, $C_{2-6}$ alkenyl, and $C_{2-6}$ alkynyl.

In some embodiments, the compound of Formula (I) is a compound of Formula (II):

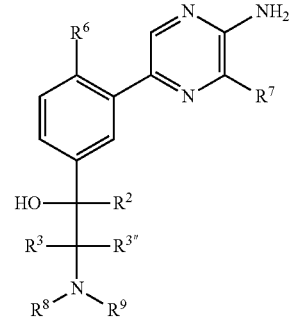

or a pharmaceutically acceptable salt thereof.

In some embodiments, the compound of Formula (I) is a compound of Formula (III):

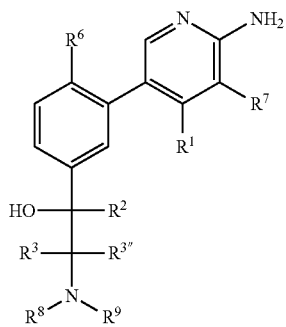

(III)

or a pharmaceutically acceptable salt thereof.

In some embodiments, the compound of Formula (I) is a compound of Formula (IV):

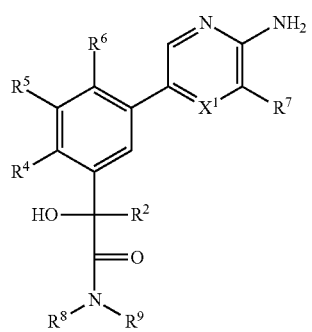

(IV)

or a pharmaceutically acceptable salt thereof.

In some embodiments, the compound of Formula (I) is a compound of Formula (IVa):

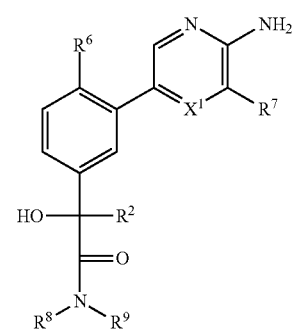

(IVa)

or a pharmaceutically acceptable salt thereof.

In some embodiments, the compound of Formula (I) is a compound of Formula (V):

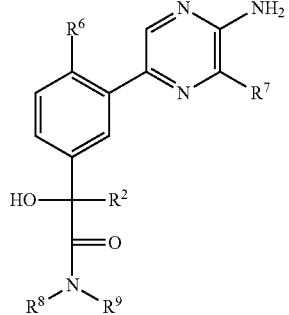

(V)

or a pharmaceutically acceptable salt thereof.

In some embodiments, the compound of Formula (I) is a compound of Formula (VI):

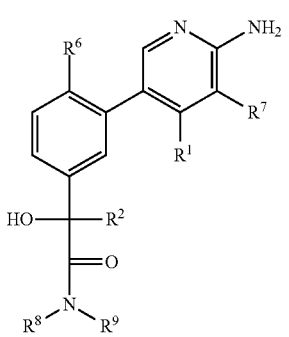

(VI)

or a pharmaceutically acceptable salt thereof.

In some embodiments, the compound of Formula (I) is a compound of Formula (VII):

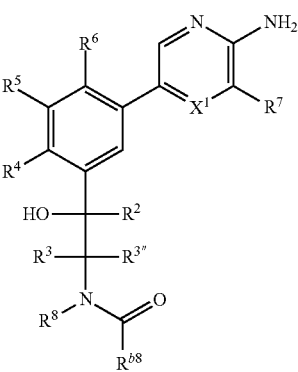

(VII)

or a pharmaceutically acceptable salt thereof.

In some embodiments, the compound of Formula (I) is a compound of Formula (VIIa):

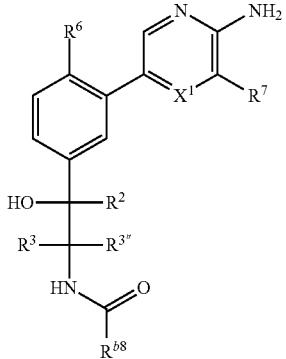

(VIIa)

or a pharmaceutically acceptable salt thereof.

In some embodiments, the compound of Formula (I) is a compound of Formula (VIII):

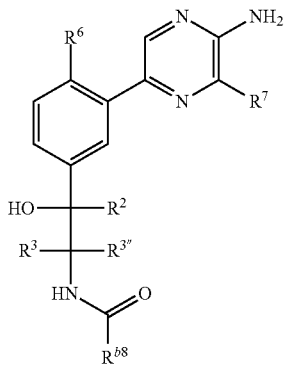

(VIII)

or a pharmaceutically acceptable salt thereof.

In some embodiments, the compound of Formula (I) is a compound of Formula (IX):

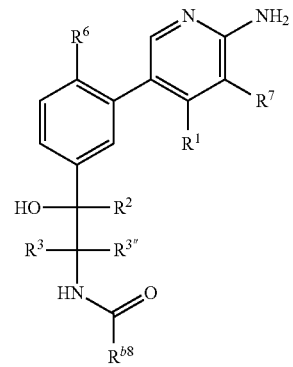

(IX)

or a pharmaceutically acceptable salt thereof.

In some embodiments, the compound is selected from:
2-(3-(5-amino-6-(prop-1-en-1-yl)pyrazin-2-yl)-4-methylphenyl)-3,3,3-trifluoro-2-hydroxypropanamide;
2-(3-(5-amino-6-propylpyrazin-2-yl)-4-methylphenyl)-3,3,3-trifluoro-2-hydroxypropanamide;
2-(3-(5-amino-6-(trifluoromethyl)pyrazin-2-yl)-4-methylphenyl)-3,3,3-trifluoro-2-hydroxypropanamide;
2-(3-(5-amino-6-(3-methoxyprop-1-ynyl)pyrazin-2-yl)-4-methylphenyl)-3,3,3-trifluoro-2-hydroxypropanamide trifluoroacetate;
2-(3-(5-amino-6-(cyclopropylethynyl)pyrazin-2-yl)-4-methylphenyl)-3,3,3-trifluoro-2-hydroxypropanamide;
2-(3-(5-amino-6-(3-methylbut-1-ynyl)pyrazin-2-yl)-4-methylphenyl)-3,3,3-trifluoro-2-hydroxypropanamide;
2-(3-(5-amino-6-(3-hydroxy-3-methylbut-1-ynyl)pyrazin-2-yl)-4-methylphenyl)-3,3,3-trifluoro-2-hydroxypropanamide;
2-(3-(5-amino-6-(4-hydroxypent-1-ynyl)pyrazin-2-yl)-4-methylphenyl)-3,3,3-trifluoro-2-hydroxypropanamide;
2-(3-(6-((1H-pyrazol-5-yl)ethynyl)-5-aminopyrazin-2-yl)-4-methylphenyl)-3,3,3-trifluoro-2-hydroxypropanamide;
2-(3-(5-amino-6-((1-methyl-1H-imidazol-5-yl)ethynyl)pyrazin-2-yl)-4-methylphenyl)-3,3,3-trifluoro-2-hydroxypropanamide;
2-(3-(5-amino-6-((1-methyl-1H-pyrazol-4-yl)ethynyl)pyrazin-2-yl)-4-methylphenyl)-3,3,3-trifluoro-2-hydroxypropanamide;
2-(3-(5-amino-6-(pyridin-2-ylethynyl)pyrazin-2-yl)-4-methylphenyl)-3,3,3-trifluoro-2-hydroxypropanamide;
2-(3-(5-amino-6-(pyrimidin-5-ylethynyl)pyrazin-2-yl)-4-methylphenyl)-3,3,3-trifluoro-2-hydroxypropanamide;
2-(3-(5-amino-6-(pyrazin-2-ylethynyl)pyrazin-2-yl)-4-methylphenyl)-3,3,3-trifluoro-2-hydroxypropanamide;
2-(3-(5-amino-6-((4-cyanophenyl)ethynyl)pyrazin-2-yl)-4-methylphenyl)-3,3,3-trifluoro-2-hydroxypropanamide;
2-(3-(5-amino-6-((4-(cyanomethyl)phenyl)ethynyl)pyrazin-2-yl)-4-methylphenyl)-3,3,3-trifluoro-2-hydroxypropanamide;
2-(3-(5-amino-6-((3,5-dimethoxyphenyl)ethynyl)pyrazin-2-yl)-4-methylphenyl)-3,3,3-trifluoro-2-hydroxypropanamide;
2-(3-(5-amino-6-((3-fluorophenyl)ethynyl)pyrazin-2-yl)-4-methylphenyl)-3,3,3-trifluoro-2-hydroxypropanamide;
2-(3-(5-amino-6-(3-hydroxy-3,4-dimethylpent-1-ynyl)pyrazin-2-yl)-4-methylphenyl)-3,3,3-trifluoro-2-hydroxypropanamide;
2-(3-(5-amino-6-((tetrahydro-2H-pyran-4-yl)ethynyl)pyrazin-2-yl)-4-methylphenyl)-3,3,3-trifluoro-2-hydroxypropanamide;
2-(3-(5-amino-6-((4-methyltetrahydro-2H-pyran-4-yl)ethynyl)pyrazin-2-yl)-4-methylphenyl)-3,3,3-trifluoro-2-hydroxypropanamide;
2-(3-(5-amino-6-((3-hydroxy-1-methyl-2-oxopyrrolidin-3-yl)ethynyl)pyrazin-2-yl)-4-methylphenyl)-3,3,3-trifluoro-2-hydroxypropanamide;
2-(3-(5-amino-6-((5-methylpyrazin-2-yl)ethynyl)pyrazin-2-yl)-4-methylphenyl)-3,3,3-trifluoro-2-hydroxypropanamide;
2-(3-(5-amino-6-((5-methoxypyrazin-2-yl)ethynyl)pyrazin-2-yl)-4-methylphenyl)-3,3,3-trifluoro-2-hydroxypropanamide; and
2-(3-(5-amino-6-(imidazo[1,2-a]pyrazin-6-ylethynyl)pyrazin-2-yl)-4-methylphenyl)-3,3,3-trifluoro-2-hydroxypropanamide or a pharmaceutically acceptable salt thereof.

Compound Subset (C)

The present application provides, inter alia, compounds of Formula (I):

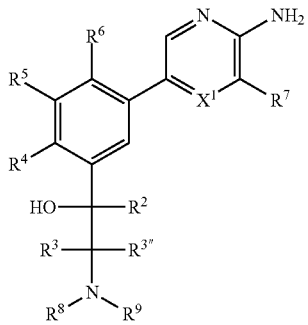

(I)

or a pharmaceutically acceptable salt thereof; wherein:

$X^1$ is N or $CR^1$;

$R^1$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH and $NH_2$;

$R^2$ is a $C_{1-6}$ haloalkyl, wherein each halogen is independently selected from F and Cl, wherein the haloalkyl is optionally substituted with $C(O)NR^aR^b$ or 1, 2, 3 or 4 independently selected $R^M$ substituents;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^3$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and $NH_2$;

$R^{3''}$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and $NH_2$;

or, alternatively, $R^3$ and $R^{3''}$ together form an oxo group;

$R^4$, $R^5$ and $R^6$ are each independently selected from H, D, halo, CN, OH, $NH_2$, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkylamino, di($C_{1-6}$ alkyl)amino, and $C(O)NR^aR^b$;

each $R^a$ and $R^b$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^a$ and $R^b$ are each optionally substituted with 1, 2, 3 or 4 independently selected $R^M$ substituents;

$R^7$ is selected from $C_{6-14}$ aryl, 5-14 membered heteroaryl and $C(O)NR^{c7}R^{c8}$, wherein the $C_{6-14}$ aryl and 5-14 membered heteroaryl are each optionally substituted with 1, 2, 3 or 4 independently selected $R^{74}$ substituents;

each $R^{c7}$ and $R^{d7}$ is independently selected from H, $C_{1-6}$ alkyl, $C_{2-6}$ alkenyl, $C_{2-6}$ alkynyl, $C_{6-14}$ aryl, $C_{3-12}$ cycloalkyl, 5-14 membered heteroaryl and 4-12 membered heterocycloalkyl, wherein the $C_{1-6}$ alkyl, $C_{2-6}$ alkenyl, $C_{2-6}$ alkynyl, $C_{6-14}$ aryl, $C_{3-12}$ cycloalkyl, 5-14 membered heteroaryl and 4-12 membered heterocycloalkyl of $R^{c7}$ and $R^{d7}$ are each optionally substituted with 1, 2, 3 or 4 independently selected $R^{74}$ substituents;

provided that at least one of $R^{c7}$ and $R^{d7}$ is $C_{6-14}$ aryl or 5-14 membered heteroaryl;

$R^8$ and $R^9$ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b8}$, $C(O)NR^{c8}R^{d8}$, $C(O)OR^{a8}$, $C(=NR^{e8})R^{b8}$, $C(=NR^{e8})NR^{c8}R^{d8}$, $C(=NCN)NR^{c8}R^{d8}$, $C(=NOR^{a8})NR^{c8}$, $S(O)_2R^{b8}$, $S(O)(=NR^{c8})R^{d8}$, and $S(O)_2NR^{c8}R^{d8}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^8$ and $R^9$ are each optionally substituted with 1, 2, 3, or 4 independently selected $R^{8A}$ substituents;

or, $R^8$ and $R^9$, together with the N atom to which they are attached, form a 5- or 6-membered heteroaryl, or a 4-10 membered heterocycloalkyl group, wherein the 5- or 6-membered heteroaryl, or 4-10 membered heterocycloalkyl group is optionally substituted with 1, 2, 3, or 4 independently selected $R^{8A}$ substituents;

each $R^{74}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a71}$, $SR^{a71}$, $NHOR^{a71}$, $C(O)R^{b71}$, $C(O)NR^{c71}R^{d71}$, $C(O)NR^{c71}(OR^{b71})$, $C(O)OR^{a71}$, $OC(O)R^{b71}$, $OC(O)NR^{c71}R^{d71}$, $NR^{c71}R^{d71}$, $NR^{c71}NR^{c71}R^{d71}$, $NR^{c71}C(O)R^{b71}$, $NR^{c71}C(O)OR^{a71}$, $NR^{c71}C(O)NR^{c71}R^{d71}$, $C(=NR^{e71})R^{b71}$, $C(=NOH)R^{b71}$, $C(=NCN)R^{b71}$, $C(=NR^{e71})NR^{c71}R^{d71}$, $NR^{c71}C(=NR^{e71})NR^{c71}R^{d71}$, $NR^{c71}C(=NR^{e71})R^{b71}$, $NR^{c71}C(=NOH)NR^{c71}R^{d71}$, $NR^{c71}C(=NCN)NR^{c71}R^{d71}$, $NR^{c71}S(O)R^{b71}$, $NR^{c71}S(O)NR^{c71}R^{d71}$, $NR^{c71}S(O)_2R^{b71}$, $NR^{c71}S(O)_2NR^{c71}R^{d71}$, $S(O)R^{b71}$, $S(O)NR^{c71}R^{d71}$, $S(O)_2R^{b71}$, $S(O)_2NR^{c71}R^{d71}$, $OS(O)(=NR^{e71})R^{b71}$, $OS(O)_2R^{b71}$, $SF_5$, $P(O)R^{f71}R^{g71}$, $OP(O)(OR^{h71})(OR^{i71})$, $P(O)(OR^{h71})(OR^{i71})$, and $BR^{j71}R^{k71}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl and 4-10 membered heterocycloalkyl, of $R^{74}$ are each optionally substituted with 1, 2, 3 or 4 independently selected $R^{7B}$ substituents;

each $R^{a71}$, $R^{b71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a71}$, $R^{b71}$, $R^{c71}$, and $R^{d71}$ are each optionally substituted with 1, 2, 3 or 4 independently selected $R^{7B}$ substituents;

or, any $R^{e71}$ and $R^{d71}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{7B}$ substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f71}$ and $R^{g71}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h71}$ and $R^{i71}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j71}$ and $R^{k71}$ is independently selected from OH, $C_{1-6}$ alkoxy, and $C_{1-6}$ haloalkoxy;

or any $R^{j71}$ and $R^{k71}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a72}$, $SR^{a72}$, $NHOR^{a72}$, $C(O)R^{b72}$, $C(O)NR^{c72}R^{d72}$, $C(O)NR^{c72}(OR^{b72})$, $C(O)OR^{a72}$, $OC(O)R^{b72}$, $OC(O)NR^{c72}R^{d72}$, $NR^{c72}R^{d72}$, $NR^{c72}NR^{c72}R^{d72}$, $NR^{c72}C(O)R^{b72}$, $NR^{c72}C(O)OR^{a72}$, $NR^{c72}C(O)NR^{c72}R^{d72}$, $C(=NR^{e72})R^{b72}$, $C(=NOH)R^{b72}$, $C(=NCN)R^{b72}$, $C(=NR^{e72})NR^{c72}R^{d72}$, $NR^{c72}C(=NR^{e72})NR^{c72}R^{d72}$, $NR^{c72}C(=NR^{e72})R^{b72}$, $NR^{c72}C(=NOH)NR^{c72}R^{d72}$, $NR^{c72}C(=NCN)NR^{c72}R^{d72}$, $NR^{c72}S(O)R^{b72}$, $NR^{c72}S(O)NR^{c72}R^{d72}$, $NR^{c72}S(O)_2R^{b72}$, $NR^{c72}S(O)_2NR^{c72}R^{d72}$, $S(O)R^{b72}$, $S(O)NR^{c72}R^{d72}$, $S(O)_2R^{b72}$, $S(O)_2NR^{c72}R^{d72}$, $OS(O)(=NR^{e72})R^{b72}$, $OS(O)_2R^{b72}$, $SF_5$, $P(O)R^{f72}R^{g72}$, $OP(O)(OR^{h72})(OR^{i72})$, $P(O)(OR^{h72})(OR^{i72})$, and $BR^{j72}R^{k72}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{7B}$ are each optionally substituted with 1, 2, 3 or 4 independently selected $R^{7C}$ substituents;

each $R^{a72}$, $R^{b72}$, $R^{c72}$, and $R^{d72}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a72}$, $R^{b72}$, $R^{c72}$, and $R^{d72}$ are each optionally substituted with 1, 2, 3 or 4 independently selected $R^{7C}$ substituents;

or, any $R^{c72}$ and $R^{d72}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{7C}$ substituents;

each $R^{e72}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f72}$ and $R^{g72}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h72}$ and $R^{i72}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j72}$ and $R^{k72}$ is independently selected from OH, $C_{1-6}$ alkoxy, and $C_{1-6}$ haloalkoxy;

or any $R^{j72}$ and $R^{k72}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7C}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a73}$, $SR^{a73}$, $NHOR^{a73}$, $C(O)R^{b73}$, $C(O)NR^{c73}R^{d73}$, $C(O)NR^{c73}(OR^{b73})$, $C(O)OR^{a73}$, $OC(O)R^{b73}$, $OC(O)NR^{c73}R^{d73}$, $NR^{c73}R^{d73}$, $NR^{c73}NR^{c73}R^{d73}$, $NR^{c73}C(O)R^{b73}$, $NR^{c73}C(O)OR^{a73}$, $NR^{c73}C(O)NR^{c73}R^{d73}$, $C(=NR^{e73})R^{b73}$, $C(=NOH)R^{b73}$, $C(=NCN)R^{b73}$, $C(=NR^{e73})NR^{c73}R^{d73}$, $NR^{c73}C(=NR^{e73})NR^{c73}R^{d73}$, $NR^{c73}C(=NR^{e73})R^{b73}$, $NR^{c73}C(=NOH)NR^{c73}R^{d73}$, $NR^{c73}C(=NCN)NR^{c73}R^{d73}$, $NR^{c73}S(O)R^{b73}$, $NR^{c73}S(O)NR^{c73}R^{d73}$, $NR^{c73}S(O)_2R^{b73}$, $NR^{c73}S(O)_2NR^{c73}R^{d73}$, $S(O)R^{b73}$, $S(O)NR^{c73}R^{d73}$, $S(O)_2R^{b73}$, $S(O)_2NR^{c73}R^{d73}$, $OS(O)(=NR^{e73})R^{b73}$, $OS(O)_2R^{b73}$, $SF_5$, $P(O)R^{f73}R^{g73}$, $OP(O)(OR^{h73})(OR^{i73})$, $P(O)(OR^{h73})(OR^{i73})$, and $BR^{j73}R^{k73}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{7C}$ are each optionally substituted with 1, 2, 3 or 4 independently selected $R^{7D}$ substituents;

each $R^{a73}$, $R^{b73}$, $R^{c73}$, and $R^{d73}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-

$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a73}$, $R^{b73}$, $R^{c73}$, and $R^{d73}$ are each optionally substituted with 1, 2, 3 or 4 independently selected $R^{7D}$ substituents;

or, any $R^{c73}$ and $R^{d73}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{7D}$ substituents;

each $R^{e73}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f73}$ and $R^{g73}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$alkyl- and (4-10 membered heterocycloalkyl)-$C_{1-6}$ alkyl-;

each $R^{h73}$ and $R^{i73}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j73}$ and $R^{k73}$ is independently selected from OH, $C_{1-6}$ alkoxy, and $C_{1-6}$ haloalkoxy;

or any $R^{j73}$ and $R^{k73}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7D}$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl- and (4-7 membered heterocycloalkyl)-$C_{1-6}$ alkyl;

each $R^{a8}$, $R^{b8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a8}$, $R^{b8}$, $R^{c8}$, and $R^{d8}$ are each optionally substituted with 1, 2, 3 or 4 independently selected $R^{8A}$ substituents;

or, any $R^{c8}$ and $R^{d8}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{8A}$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{8A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a81}$, $SR^{a81}$, $NHOR^{a81}$, $C(O)R^{b81}$, $C(O)NR^{c81}R^{d81}$, $C(O)NR^{81}(OR^{b81})$, $C(O)OR^{a81}$, $OC(O)R^{b81}$, $OC(O)NR^{c81}R^{d81}$, $NR^{c81}R^{d81}$, $NR^{c81}NR^{c81}R^{d81}$, $NR^{c81}C(O)R^{b81}$, $NR^{c81}C(O)OR^{a81}$, $NR^{c81}C(O)NR^{c81}R^{d81}$, $C(=NR^{e81})R^{b81}$, $C(=NOH)R^{b81}$, $C(=NCN)R^{b81}$, $C(=NR^{e81})NR^{c81}R^{d81}$, $NR^{c81}C(=NR^{e81})NR^{c81}R^{d81}$, $NR^{c81}C(=NR^{e81})R^{b81}$, $NR^{c81}C(=NOH)NR^{c81}R^{d81}$, $NR^{c81}C(=NCN)NR^{c81}R^{d81}$, $NR^{c81}S(O)R^{b81}$, $NR^{c81}S(O)NR^{c81}R^{d81}$, $NR^{c81}S(O)_2R^{b81}$, $NR^{c81}S(O)_2NR^{c81}R^{d81}$, $S(O)R^{b81}$, $S(O)NR^{c81}R^{d81}$, $S(O)_2R^{b81}$, $S(O)_2NR^{c81}R^{d81}$, $OS(O)(=NR^{e81})R^{b81}$, $OS(O)_2R^{b81}$, $SF_5$, $P(O)R1R^{g81}$, $OP(O)(OR^{h81})(OR^{i81})$, $P(O)(OR^{h81})(OR^{i81})$, and $BR^{j81}R^{k81}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{8A}$ are each optionally substituted with 1, 2, 3 or 4 independently selected $R^{8B}$ substituents;

each $R^{a81}$, $R^{b81}$, $R^{c81}$, and $R^{d81}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a81}$, $R^{b81}$, $R^{c81}$, and $R^{d81}$ are each optionally substituted with 1, 2, 3 or 4 independently selected $R^{8B}$ substituents;

or, any $R^{c81}$ and $R^{d81}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{8B}$ substituents;

each $R^{e81}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f81}$ and $R^{g81}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h81}$ and $R^{i81}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j81}$ and $R^{k81}$ is independently selected from OH, $C_{1-6}$ alkoxy, and $C_{1-6}$ haloalkoxy;

or any $R^{j81}$ and $R^{k81}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^{8B}$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl- and (4-7 membered heterocycloalkyl)-$C_{1-6}$ alkyl.

In some embodiments, either: (a) $R^3$ and $R^{3''}$ together form an oxo group; or (b) $R^8$ is $C(O)R^{b8}$.

In some embodiments, $X^1$ is N.
In some embodiments, $X^1$ is $CR^1$.
In some embodiments, $R^1$ is selected from H, D, and $C_{1-6}$ alkyl.
In some embodiments, $R^1$ is selected from H, D, and methyl.
In some embodiments, $R^1$ is H.
In some embodiments, $R^2$ is a $C_{1-6}$ haloalkyl, wherein each halogen of the $C_{1-6}$ haloalkyl is independently selected from F and Cl.
In some embodiments, $R^2$ is a $C_{1-3}$ haloalkyl, wherein each halogen of the $C_{1-3}$ haloalkyl is independently selected from F and Cl.
In some embodiments, $R^2$ is selected from $CF_3$, $CCl_3$, $CF_2H$, $CCl_2H$, $CF_2R^M$, $CCl_2R^M$, $CFH_2$, $CClH_2$, $CFHR^M$, $CClHR^M$, $CF(R^M)_2$ and $CCl(R^M)_2$.
In some embodiments, $R^2$ is selected from $CF_3$, $CF_2H$, $CF_2R^M$, $CFH_2$, $CFHR^M$, and $CF(R^M)_2$.
In some embodiments, $R^M$ is selected from D, halo, $C_{1-3}$ alkyl, and $C_{1-3}$ haloalkyl.
In some embodiments, $R^M$ is selected from halo and $C_{1-3}$ haloalkyl.
In some embodiments, $R^2$ is $C_{1-6}$ haloalkyl, wherein each halogen is F.
In some embodiments, $R^2$ is $C_{1-6}$ haloalkyl, wherein each halogen is Cl.
In some embodiments, $R^2$ is selected from $CH_2F$, $CHF_2$, $CF_3$, and $CF_2CF_3$.
In some embodiments, $R^2$ is $CF_3$ or $CHF_2$.
In some embodiments, $R^2$ is $CF_3$.
In some embodiments, $R^2$ is $CH_2F$.
In some embodiments, $R^2$ is $CHF_2$.
In some embodiments, $R^2$ is $CF_2CF_3$.
In some embodiments, $R^3$ is selected from H, D, $C_{1-6}$ alkyl, $C_{2-6}$ alkenyl, $C_{2-6}$ alkynyl, $C_{1-6}$ haloalkyl, and $NH_2$.
In some embodiments, $R^3$ selected from H, D, and $C_{1-6}$ alkyl.
In some embodiments, $R^3$ is H or D.
In some embodiments, $R^3$ is H.
In some embodiments, $R^{3''}$ is selected from H, D, $C_{1-6}$ alkyl, $C_{2-6}$ alkenyl, $C_{2-6}$ alkynyl, $C_{1-6}$ haloalkyl, and $NH_2$.

In some embodiments, $R^{3''}$ is selected from H, D, and $C_{1-6}$ alkyl.
In some embodiments, $R^{3''}$ is H or D.
In some embodiments, $R^{3''}$ is H.
In some embodiments, $R^3$ and $R^{3''}$ together form an oxo group.
In some embodiments, $R^4$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.
In some embodiments, $R^4$ is selected from H, D, halo, CN, OH, $NH_2$, and $C_{1-6}$ alkyl.
In some embodiments, $R^4$ is selected from H, D, and $C_{1-6}$ alkyl, wherein the $C_{1-6}$ alkyl is optionally substituted with 1, 2, or 3 deuterium atoms.
In some embodiments, $R^4$ is H.
In some embodiments, $R^4$ is D.
In some embodiments, $R^5$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.
In some embodiments, $R^5$ is selected from H, D, halo, CN, OH, $NH_2$, and $C_{1-6}$ alkyl.
In some embodiments, $R^5$ is selected from H, D, and $C_{1-6}$ alkyl, wherein the $C_{1-6}$ alkyl is optionally substituted with 1, 2, or 3 deuterium atoms.
In some embodiments, $R^5$ is H.
In some embodiments, $R^5$ is D.
In some embodiments, $R^3$ and $R^4$ are each H.
In some embodiments, $R^3$ and $R^5$ are each H.
In some embodiments, $R^4$ and $R^5$ are each H.
In some embodiments, $R^3$, $R^{3''}$, $R^4$, and $R^5$ are each H.
In some embodiments, $R^3$ and $R^{3''}$ together form an oxo group; and $R^4$ and $R^5$ are each H.
In some embodiments, $R^6$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.
In some embodiments, $R^6$ is selected from H, D, and $C_{1-6}$ alkyl, wherein the $C_{1-6}$ alkyl is optionally substituted with 1, 2, or 3 deuterium atoms.
In some embodiments, $R^6$ is selected from H, D, halo, CN, OH, $NH_2$, and $C_{1-6}$ alkyl.
In some embodiments, $R^6$ is $C_{1-6}$ alkyl.
In some embodiments, $R^6$ is methyl.
In some embodiments, $R^6$ is $CD_3$.
In some embodiments, $R^6$ is H.
In some embodiments, $R^6$ is D.
In some embodiments, $R^7$ is selected from phenyl, 5-10 membered heteroaryl, and $C(O)NR^{c7}R^{c8}$, wherein the phenyl and 5-10 membered heteroaryl of $R^7$ are each optionally substituted with 1 or 2 independently selected $R^{7A}$ substituents.
In some embodiments, $R^7$ is selected from phenyl, a monocyclic 5-6 membered heteroaryl, and $C(O)NR^{c7}R^{c8}$, wherein the phenyl and monocyclic 5-6 membered heteroaryl of $R^7$ are each optionally substituted with 1 or 2 independently selected $R^{7A}$ substituents.
In some embodiments, $R^7$ is selected from phenyl, pyrazolyl, oxazolyl, thiazolyl, triazolyl, pyridinyl, and pyrimidinyl, wherein the phenyl, pyrazolyl, oxazolyl, thiazolyl, triazolyl, pyridinyl, and pyrimidinyl, of $R^7$ are each optionally substituted with 1 or 2 independently selected $R^{7A}$ substituents.

In some embodiments, each $R^{7A}$ is independently selected from D, halo, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, $C(O)NR^{c71}R^{d71}$, and $BR^{j71}R^{k71}$, wherein the $C_{1-6}$ alkyl, $C_{2-6}$ alkenyl, $C_{2-6}$ alkynyl, $C_{3-10}$ cycloalkyl, and $C_{6-10}$ aryl of $R^{7A}$ are each optionally substituted with 1 or 2 independently selected $R^{7B}$ substituents.

In some embodiments, each $R^{7A}$ is independently selected from $C_{1-6}$ alkyl, $C_{1-6}$ haloalkyl, $C_{3-10}$ cycloalkyl, $C(O)NR^{c71}R^{d71}$, and $B(OH)_2$, wherein the $C_{1-6}$ alkyl and $C_{3-10}$ cycloalkyl of $R^{7A}$ are each optionally substituted with 1 or 2 independently selected $R^{7B}$ substituents.

In some embodiments, each $R^{7B}$ is independently selected from CN, OH, $C_{1-3}$ alkoxy, and $C_{3-6}$ cycloalkyl.

In some embodiments, each $R^{7A}$ is independently selected from $C_{1-6}$ alkyl, $C_{1-6}$ haloalkyl, $C_{3-10}$ cycloalkyl, $C(O)NR^{c71}R^{d71}$, and $B(OH)_2$, wherein the $C_{1-6}$ alkyl and $C_{3-10}$ cycloalkyl of $R^{7A}$ are each optionally substituted with 1 or 2 independently selected $R^{7B}$ substituents selected from CN, OH, $C_{1-3}$ alkoxy, and $C_{3-6}$ cycloalkyl.

In some embodiments, each $R^{c71}$ and $R^{d71}$ is independently selected from H and $C_{1-6}$ alkyl.

In some embodiments, each $R^{7A}$ is independently selected from $C_{1-6}$ alkyl, $C_{1-6}$ haloalkyl, $C_{3-10}$ cycloalkyl, $C(O)NR^{c71}R^{d71}$, and $B(OH)_2$, wherein the $C_{1-6}$ alkyl and $C_{3-10}$ cycloalkyl of $R^{7A}$ are each optionally substituted with 1 or 2 independently selected $R^{7B}$ substituents selected from CN, OH, $C_{1-3}$ alkoxy, and $C_{3-6}$ cycloalkyl; and each $R^{c71}$ and $R^{d71}$ is independently selected from H and $C_{1-6}$ alkyl.

In some embodiments, $R^7$ is selected from phenyl, 5-10 membered heteroaryl, and $C(O)NR^{c7}R^{c8}$, wherein the phenyl and 5-10 membered heteroaryl of $R^7$ are each optionally substituted with 1 or 2 independently selected $R^{7A}$ substituents; and each $R^{7A}$ is independently selected from D, halo, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, $C(O)NR^{c71}R^{d71}$, and $BR^{j71}R^{k71}$, wherein the $C_{1-6}$ alkyl, $C_{2-6}$ alkenyl, $C_{2-6}$ alkynyl, $C_{3-10}$ cycloalkyl, and $C_{6-10}$ aryl of $R^{7A}$ are each optionally substituted with 1 or 2 independently selected $R^{7B}$ substituents.

In some embodiments, $R^7$ is selected from phenyl, 5-10 membered heteroaryl, and $C(O)NR^{c7}R^{c8}$, wherein the phenyl and 5-10 membered heteroaryl of $R^7$ are each optionally substituted with 1 or 2 independently selected $R^{7A}$ substituents; and each $R^{7A}$ is independently selected from $C_{1-6}$ alkyl, $C_{1-6}$ haloalkyl, $C_{3-10}$ cycloalkyl, $C(O)NR^{c71}R^{d71}$, and $B(OH)_2$, wherein the $C_{1-6}$ alkyl and $C_{3-10}$ cycloalkyl of $R^{7A}$ are each optionally substituted with 1 or 2 independently selected $R^{7B}$ substituents selected from CN, OH, $C_{1-3}$ alkoxy, and $C_{3-6}$ cycloalkyl.

In some embodiments, $R^7$ is selected from phenyl, pyrazolyl, oxazolyl, thiazolyl, triazolyl, pyridinyl, and pyrimidinyl, wherein the phenyl, pyrazolyl, oxazolyl, thiazolyl, triazolyl, pyridinyl, and pyrimidinyl, of $R^7$ are each optionally substituted with 1 or 2 independently selected $R^{7A}$ substituents;

each $R^{7A}$ is independently selected from $C_{1-6}$ alkyl, $C_{1-6}$ haloalkyl, $C_{3-10}$ cycloalkyl, $C(O)NR^{c71}R^{d71}$, and $B(OH)_2$, wherein the $C_{1-6}$ alkyl and $C_{3-10}$ cycloalkyl of $R^{7A}$ are each optionally substituted with 1 or 2 independently selected $R^{7B}$ substituents selected from CN, OH, $C_{1-3}$ alkoxy, and $C_{3-6}$ cycloalkyl; and each $R^{c71}$ and $R^{d71}$ is independently selected from H and $C_{1-6}$ alkyl.

In some embodiments, $R^8$ is selected from H, $C_{1-6}$ alkyl, $C_{2-6}$ alkenyl, $C_{2-6}$ alkynyl, $C_{1-6}$ haloalkyl, and $C(O)R^{b8}$.

In some embodiments, $R^8$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, and $C(O)R^{b8}$.

In some embodiments, $R^8$ is selected from H, $C_{1-6}$ alkyl, $C_{2-6}$ alkenyl, $C_{2-6}$ alkynyl, $C_{1-6}$ haloalkyl, and $C_{3-10}$ cycloalkyl.

In some embodiments, $R^8$ is selected from H, $C_{1-6}$ alkyl, and $C(O)R^{b8}$.

In some embodiments, $R^8$ is H or $C_{1-6}$ alkyl.

In some embodiments, $R^8$ is H, methyl, ethyl, propyl or isopropyl.

In some embodiments, $R^8$ is H or $C(O)R^{b8}$.

In some embodiments, $R^8$ is H.

In some embodiments, $R^8$ is $C(O)R^{b8}$.

In some embodiments, $R^{b8}$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{b8}$ are each optionally substituted with 1, 2, 3 or 4 independently selected $R^{8A}$ substituents.

In some embodiments, $R^{b8}$ is selected from H, $C_{1-6}$ alkyl, and $C_{1-6}$ haloalkyl, wherein the $C_{1-6}$ alkyl of $R^{b8}$ is optionally substituted with 1 or 2 $R^{8A}$ substituents independently selected from D, halo, CN, $NO_2$, OH, and SH.

In some embodiments, $R^{b8}$ is selected from methyl, fluoromethyl, cyanomethyl, and hydroxypropyl.

In some embodiments, $R^{b8}$ is selected from H, D, and $C_{1-6}$ alkyl.

In some embodiments, $R^{b8}$ is selected from H, D, and methyl.

In some embodiments, $R^{b8}$ is H.

In some embodiments, $R^9$ is selected from H, $C_{1-6}$ alkyl, $C_{2-6}$ alkenyl, $C_{2-6}$ alkynyl, $C_{1-6}$ haloalkyl and $C_{3-10}$ cycloalkyl.

In some embodiments, $R^9$ is selected from H, $C_{1-6}$ alkyl, $C_{2-6}$ alkenyl, $C_{2-6}$ alkynyl, and $C_{1-6}$ haloalkyl.

In some embodiments, $R^9$ is H or $C_{1-6}$ alkyl.

In some embodiments, $R^9$ is selected from H, methyl, ethyl, propyl, and isopropyl.

In some embodiments, $R^9$ is H.

In some embodiments, $R^8$ and $R^9$ are each H.

In some embodiments:
$R^3$ is selected from H, D, $C_{1-6}$ alkyl, $C_{2-6}$ alkenyl, $C_{2-6}$ alkynyl, $C_{1-6}$ haloalkyl, and $NH_2$;
$R^{3''}$ is selected from H, D, $C_{1-6}$ alkyl, $C_{2-6}$ alkenyl, $C_{2-6}$ alkynyl, $C_{1-6}$ haloalkyl, and $NH_2$; and
$R^8$ is $C(O)R^{b8}$.

In some embodiments:
$R^3$ and $R^{3''}$ together form an oxo group; and
$R^8$ is selected from H, $C_{1-6}$ alkyl, $C_{2-6}$ alkenyl, $C_{2-6}$ alkynyl, $C_{1-6}$ haloalkyl, and $C_{3-7}$ cycloalkyl.

In some embodiments:
$X^1$ is N or CH;
$R^2$ is a $C_{1-6}$ haloalkyl, wherein each halogen of the $C_{1-6}$ haloalkyl is independently selected from F and Cl;
$R^3$ is selected from H, D, $C_{1-6}$ alkyl, $C_{2-6}$ alkenyl, $C_{2-6}$ alkynyl, $C_{1-6}$ haloalkyl, and $NH_2$;
$R^{3''}$ is selected from H, D, $C_{1-6}$ alkyl, $C_{2-6}$ alkenyl, $C_{2-6}$ alkynyl, $C_{1-6}$ haloalkyl, and $NH_2$;
or, alternatively, $R^3$ and $R^{3''}$ together form an oxo group;
$R^4$ is selected from H, D, halo, CN, OH, $NH_2$, and $C_{1-6}$ alkyl;
$R^5$ is selected from H, D, halo, CN, OH, $NH_2$, and $C_{1-6}$ alkyl;
$R^6$ is selected from H, D, halo, CN, OH, $NH_2$, and $C_{1-6}$ alkyl;

R[7] is selected from phenyl, 5-10 membered heteroaryl, and C(O)NR$^{c7}$R$^{c8}$, wherein the phenyl and 5-10 membered heteroaryl of R[7] are each optionally substituted with 1 or 2 independently selected R$^{7A}$ substituents;

each R$^{7A}$ is independently selected from D, halo, C$_{1-6}$ alkyl, C$_{1-6}$ haloalkyl, C$_{2-6}$ alkenyl, C$_{2-6}$ alkynyl, C$_{3-10}$ cycloalkyl, C$_{6-10}$ aryl, C(O)NR$^{c71}$R$^{d71}$, and BR$^{j71}$R$^{k71}$, wherein the C$_{1-6}$ alkyl, C$_{2-6}$ alkenyl, C$_{2-6}$ alkynyl, C$_{3-10}$ cycloalkyl, and C$_{6-10}$ aryl of R$^{7A}$ are each optionally substituted with 1 or 2 independently selected R$^{7B}$ substituents;

each R$^{7B}$ is independently selected from C$_{1-6}$ alkyl, C$_{1-6}$ haloalkyl, C$_{2-6}$ alkenyl, C$_{2-6}$ alkynyl, halo CN, OH, C$_{1-6}$ alkoxy, and C$_{3-6}$ cycloalkyl;

R[8] is selected from H, C$_{1-6}$ alkyl, C$_{2-6}$ alkenyl, C$_{2-6}$ alkynyl, C$_{1-6}$ haloalkyl, and C(O)R$^{b8}$;

R[9] is selected from H, C$_{1-6}$ alkyl, C$_{2-6}$ alkenyl, C$_{2-6}$ alkynyl, and C$_{1-6}$ haloalkyl;

R$^{b8}$ is selected from H, C$_{1-6}$ alkyl, C$_{1-6}$ haloalkyl, C$_{2-6}$ alkenyl, and C$_{2-6}$ alkynyl, wherein the C$_{1-6}$ alkyl, C$_{2-6}$ alkenyl, and C$_{2-6}$ alkynyl of R$^{b8}$ are each optionally substituted with 1, 2, 3 or 4 independently selected R$^{8A}$ substituents;

each R$^{8A}$ is independently selected from D, halo, CN, NO$_2$, OH, and SH;

each R$^{c71}$ and R$^{d71}$ is independently selected from H and C$_{1-6}$ alkyl; and each R$^{j71}$ and R$^{k71}$ is independently selected from H and C$_{1-6}$ alkyl.

In some embodiments:

X[1] is N or CH;

R[2] is a C$_{1-3}$ haloalkyl, wherein each halogen of the C$_{1-3}$ haloalkyl is independently selected from F and Cl;

R[3] is H;

R[3″] is H;

or, alternatively, R[3] and R[3″] together form an oxo group;

R[4] is selected from H and C$_{1-6}$ alkyl;

R[5] is selected from H and C$_{1-6}$ alkyl;

R[6] is selected from H and C$_{1-6}$ alkyl;

R[7] is selected from phenyl, 5-10 membered heteroaryl, and C(O)NR$^{c7}$R$^{c8}$, wherein the phenyl and 5-10 membered heteroaryl of R[7] are each optionally substituted with 1 or 2 independently selected R$^{7A}$ substituents;

each R$^{7A}$ is independently selected from C$_{1-6}$ alkyl, C$_{1-6}$ haloalkyl, C$_{3-10}$ cycloalkyl, C(O)NR$^{c71}$R$^{d71}$, and B(OH)$_2$, wherein the C$_{1-6}$ alkyl and C$_{3-10}$ cycloalkyl of R$^{7A}$ are each optionally substituted with 1 or 2 independently selected R$^{7B}$ substituents;

each R$^{7B}$ is independently selected from CN, OH, C$_{1-3}$ alkoxy, and C$_{3-6}$ cycloalkyl;

R[8] is selected from H and C(O)R$^{b8}$;

R[9] is H;

R$^{b8}$ is selected from H, C$_{1-6}$ alkyl, C$_{1-6}$ haloalkyl, C$_{2-6}$ alkenyl, and C$_{2-6}$ alkynyl, wherein the C$_{1-6}$ alkyl, C$_{2-6}$ alkenyl, and C$_{2-6}$ alkynyl of R$^{b8}$ are each optionally substituted with 1, 2, 3 or 4 independently selected R$^{8A}$ substituents;

each R$^{8A}$ is independently selected from D, halo, CN, NO$_2$, OH, and SH; and each R$^{c71}$ and R$^{d71}$ is independently selected from H and C$_{1-6}$ alkyl.

In some embodiments:

X[1] is N or CH;

R[2] is a C$_{1-3}$ haloalkyl, wherein each halogen of the C$_{1-3}$ haloalkyl is independently selected from F and Cl;

R[3] is H;

R[3″] is H;

or, alternatively, R[3] and R[3″] together form an oxo group;

R[4] is H;

R[5] is H;

R[6] is C$_{1-6}$ alkyl;

R[7] is selected from phenyl, pyrazolyl, oxazolyl, thiazolyl, triazolyl, pyridinyl, and pyrimidinyl, wherein the phenyl, pyrazolyl, oxazolyl, thiazolyl, triazolyl, pyridinyl, and pyrimidinyl, of R[7] are each optionally substituted with 1 or 2 independently selected R$^{7A}$ substituents;

each R$^{7A}$ is independently selected from C$_{1-6}$ alkyl, C$_{1-6}$ haloalkyl, C$_{3-10}$ cycloalkyl, C(O)NR$^{c71}$R$^{d71}$, and B(OH)$_2$, wherein the C$_{1-6}$ alkyl and C$_{3-10}$ cycloalkyl of R$^{7A}$ are each optionally substituted with 1 or 2 independently selected R$^{7B}$ substituents;

each R$^{7B}$ is independently selected from CN, OH, C$_{1-3}$ alkoxy, and C$_{3-6}$ cycloalkyl;

R[8] is selected from H and C(O)R$^{b8}$;

R[9] is H;

R$^{b8}$ is selected from H, C$_{1-6}$ alkyl, C$_{1-6}$ haloalkyl, C$_{2-6}$ alkenyl, and C$_{2-6}$ alkynyl; and each R$^{c71}$ and R$^{d71}$ is independently selected from H and C$_{1-6}$ alkyl.

In some embodiments, the compound of Formula (I) is a compound of Formula (II):

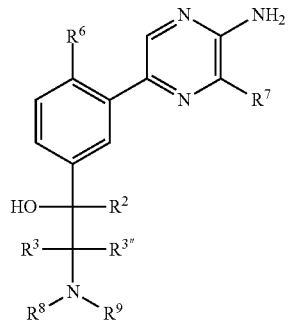

(II)

or a pharmaceutically acceptable salt thereof.

In some embodiments, the compound of Formula (I) is a compound of Formula (III):

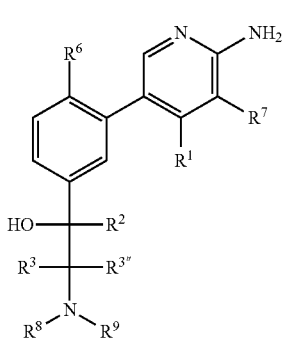

(III)

or a pharmaceutically acceptable salt thereof.

In some embodiments, the compound of Formula (I) is a compound of Formula (IV):

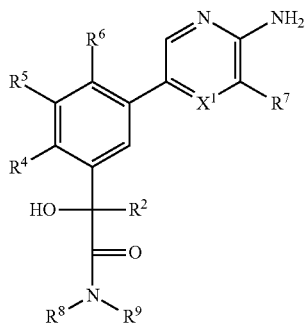

(IV)

or a pharmaceutically acceptable salt thereof.

In some embodiments, the compound of Formula (I) is a compound of Formula (IVa):

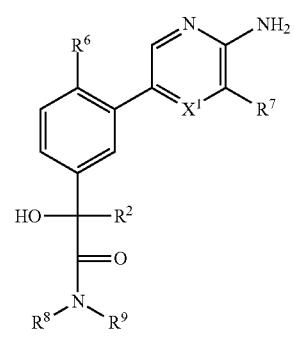

(IVa)

or a pharmaceutically acceptable salt thereof.

In some embodiments, the compound of Formula (I) is a compound of Formula (V):

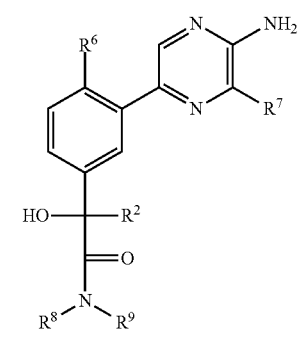

(V)

or a pharmaceutically acceptable salt thereof.

In some embodiments, the compound of Formula (I) is a compound of Formula (VI):

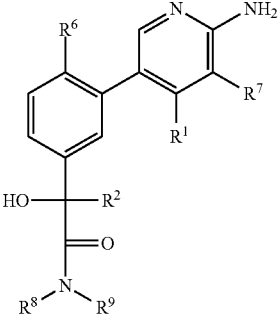

(VI)

or a pharmaceutically acceptable salt thereof.

In some embodiments, the compound of Formula (I) is a compound of Formula (VII):

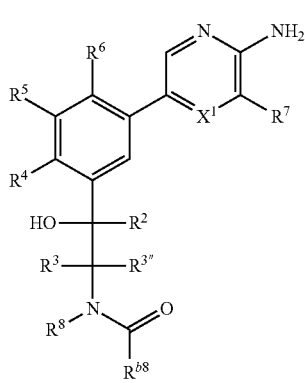

(VII)

or a pharmaceutically acceptable salt thereof.

In some embodiments, the compound of Formula (I) is a compound of Formula (VIIa):

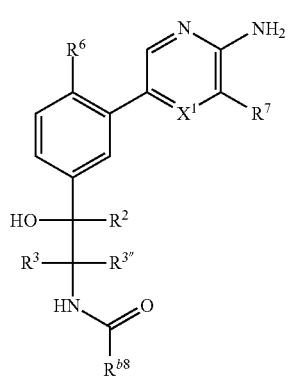

(VIIa)

or a pharmaceutically acceptable salt thereof.

In some embodiments, the compound of Formula (I) is a compound of Formula (VIII):

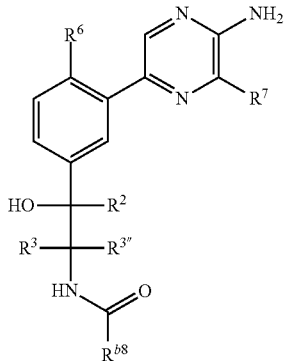

(VIII)

or a pharmaceutically acceptable salt thereof.

In some embodiments, the compound of Formula (I) is a compound of Formula (IX):

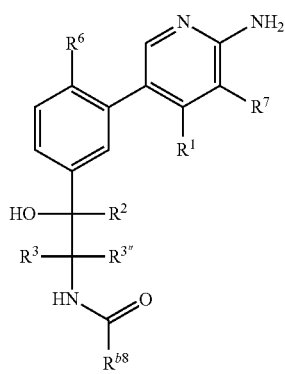

(IX)

or a pharmaceutically acceptable salt thereof.

In some embodiments, the compound is 2-(3-(5-amino-6-(1-methyl-1H-pyrazol-5-yl)pyrazin-2-yl)-4-methylphenyl)-3,3,3-trifluoro-2-hydroxypropanamide;
2-(3-(5-amino-6-(2-methyloxazol-5-yl)pyrazin-2-yl)-4-methylphenyl)-3,3,3-trifluoro-2-hydroxypropanamide;
2-(3-(5-amino-6-(1-methyl-1H-pyrazol-4-yl)pyrazin-2-yl)-4-methylphenyl)-3,3,3-trifluoro-2-hydroxypropanamide;
2-(3-(5-amino-6-(2-methylthiazol-5-yl)pyrazin-2-yl)-4-methylphenyl)-3,3,3-trifluoro-2-hydroxypropanamide;
2-(3-(5-amino-6-(2-methyl-2H-1,2,3-triazol-4-yl)pyrazin-2-yl)-4-methylphenyl)-3,3,3-trifluoro-2-hydroxypropanamide;
2-(3-(5-amino-6-(1-methyl-1H-1,2,3-triazol-5-yl)pyrazin-2-yl)-4-methylphenyl)-3,3,3-trifluoro-2-hydroxypropanamide;
2-(3-(5-amino-6-(1-(2,2,2-trifluoroethyl)-1H-pyrazol-4-yl)pyrazin-2-yl)-4-methylphenyl)-3,3,3-trifluoro-2-hydroxypropanamide;
2-(3-(5-amino-6-(1-(2-cyanopropan-2-yl)-1H-pyrazol-4-yl)pyrazin-2-yl)-4-methylphenyl)-3,3,3-trifluoro-2-hydroxypropanamide;
2-(3-(5-amino-6-(1-(tetrahydro-2H-pyran-4-yl)-1H-pyrazol-4-yl)pyrazin-2-yl)-4-methylphenyl)-3,3,3-trifluoro-2-hydroxypropanamide;
2-(3-(5-amino-6-(1-((1-cyanocyclopropyl)methyl)-1H-pyrazol-4-yl)pyrazin-2-yl)-4-methylphenyl)-3,3,3-trifluoro-2-hydroxypropanamide;
2-(3-(5-amino-6-(1-(2-methoxyethyl)-1H-pyrazol-4-yl)pyrazin-2-yl)-4-methylphenyl)-3,3,3-trifluoro-2-hydroxypropanamide;
5-(3-amino-6-(5-(3-amino-1,1,1-trifluoro-2-hydroxy-3-oxopropan-2-yl)-2-methylphenyl)pyrazin-2-yl)-N-methylpicolinamide;
2-(3-(5-amino-6-(pyrimidin-5-yl)pyrazin-2-yl)-4-methylphenyl)-3,3,3-trifluoro-2-hydroxypropanamide;
2-(3-(5-amino-6-(6-methylpyridin-3-yl)pyrazin-2-yl)-4-methylphenyl)-3,3,3-trifluoro-2-hydroxypropanamide;
2-(3-(5-amino-6-(6-(trifluoromethyl)pyridin-3-yl)pyrazin-2-yl)-4-methylphenyl)-3,3,3-trifluoro-2-hydroxypropanamide;
2-(3-(5-amino-6-(2-cyclopropylthiazol-5-yl)pyrazin-2-yl)-4-methylphenyl)-3,3,3-trifluoro-2-hydroxypropanamide;
2-(3-(5-amino-6-(2-(hydroxymethyl)pyridin-4-yl)pyrazin-2-yl)-4-methylphenyl)-3,3,3-trifluoro-2-hydroxypropanamide;
2-(3-(5-amino-6-(1-(cyclopropylmethyl)-1H-pyrazol-4-yl)pyrazin-2-yl)-4-methylphenyl)-3,3,3-trifluoro-2-hydroxypropanamide;
2-(3-(5-amino-6-(4-(cyanomethyl)phenyl)pyrazin-2-yl)-4-methylphenyl)-3,3,3-trifluoro-2-hydroxypropanamide;
2-(3-(5-amino-6-(4-(hydroxymethyl)phenyl)pyrazin-2-yl)-4-methylphenyl)-3,3,3-trifluoro-2-hydroxypropanamide;
4-(3-amino-6-(5-(3-amino-1,1,1-trifluoro-2-hydroxy-3-oxopropan-2-yl)-2-methylphenyl)pyrazin-2-yl)-N-methylbenzamide;
2-(3-(5-amino-6-(3-isopropylphenyl)pyrazin-2-yl)-4-methylphenyl)-3,3,3-trifluoro-2-hydroxypropanamide;
2-(3-(5-amino-6-(4-(2-hydroxypropan-2-yl)phenyl)pyrazin-2-yl)-4-methylphenyl)-3,3,3-trifluoro-2-hydroxypropanamide;
2-(3-(5-amino-6-(4-cyclopropylphenyl)pyrazin-2-yl)-4-methylphenyl)-3,3,3-trifluoro-2-hydroxypropanamide;
2-(3-(5-amino-6-(1H-pyrazol-1-yl)pyrazin-2-yl)-4-methylphenyl)-3,3,3-trifluoro-2-hydroxypropanamide;
2-(3-(5-amino-6-(1H-1,2,4-triazol-1-yl)pyrazin-2-yl)-4-methylphenyl)-3,3,3-trifluoro-2-hydroxy-N-methylpropanamide;
2-(3-(5-amino-6-(1H-1,2,4-triazol-1-yl)pyrazin-2-yl)-4-methylphenyl)-3,3,3-trifluoro-2-hydroxy-N,N-dimethylpropanamide;
2-(3-(5-amino-6-(1-methyl-1H-pyrazol-4-yl)pyrazin-2-yl)-4-methylphenyl)-3,3,3-trifluoro-2-hydroxy-N-methylpropanamide;
(4-(3-amino-6-(5-(3-amino-1,1,1-trifluoro-2-hydroxy-3-oxopropan-2-yl)-2-methylphenyl)pyrazin-2-yl)phenyl)boronic acid;
2-(3-(5-amino-6-(1-methyl-1H-pyrazol-5-yl)pyrazin-2-yl)-4-methylphenyl)-3,3-difluoro-2-hydroxypropanamide;
2-(3-(5-amino-6-(1-methyl-1H-pyrazol-5-yl)pyrazin-2-yl)-4-methylphenyl)-3,3-difluoro-2-hydroxypropanamide;
2-(3-(5-amino-6-(2-methyloxazol-5-yl)pyrazin-2-yl)-4-methylphenyl)-3,3-difluoro-2-hydroxypropanamide;
2-(3-(5-amino-6-(2-methyl-2H-1,2,3-triazol-4-yl)pyrazin-2-yl)-4-methylphenyl)-3,3-difluoro-2-hydroxypropanamide;
N-(2-(3-(5-amino-6-(2-cyclopropylthiazol-5-yl)pyrazin-2-yl)-4-methylphenyl)-3,3,3-trifluoro-2-hydroxypropyl)formamide;
N-(2-(3-(5-amino-6-(1H-pyrazol-4-yl)pyrazin-2-yl)-4-methylphenyl)-3,3,3-trifluoro-2-hydroxypropyl)formamide;
N-(2-(3-(5-amino-6-(1-(2,2,2-trifluoroethyl)-1H-pyrazol-4-yl)pyrazin-2-yl)-4-methylphenyl)-3,3,3-trifluoro-2-hydroxypropyl)acetamide;

N-(2-(3-(5-amino-6-(1H-pyrazol-4-yl)pyrazin-2-yl)-4-methylphenyl)-3,3,3-trifluoro-2-hydroxypropyl)acetamide; and 3-amino-6-(5-(3-amino-1,1,1-trifluoro-2-hydroxy-3-oxopropan-2-yl)-2-methylphenyl)-N-(1-methyl-1H-pyrazol-5-yl)pyrazine-2-carboxamide;

or a pharmaceutically acceptable salt thereof.

Compound Subset (D)

The present application provides, inter alia, compounds of Formula (I):

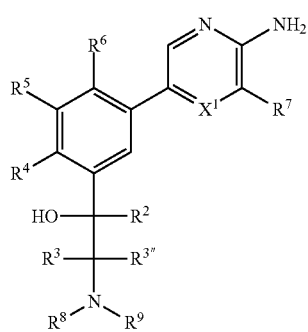

or a pharmaceutically acceptable salt thereof; wherein:

$X^1$ is N or $CR^1$;

$R^1$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH and $NH_2$;

$R^2$ is a $C_{1-6}$ haloalkyl, wherein each halogen is independently selected from F and Cl, wherein the haloalkyl is optionally substituted with $C(O)NR^aR^b$ or 1, 2, 3 or 4 independently selected $R^M$ substituents;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^3$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and $NH_2$;

$R^{3''}$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and $NH_2$;

or, alternatively, $R^3$ and $R^{3''}$ together form an oxo group;

$R^4$, $R^5$ and $R^6$ are each independently selected from H, D, halo, CN, OH, $NH_2$, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkylamino, di($C_{1-6}$ alkyl)amino, and $C(O)NR^aR^b$;

each $R^a$ and $R^b$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^a$ and $R^b$ are each optionally substituted with 1, 2, 3 or 4 independently selected $R^M$ substituents;

$R^7$ is selected from $C_{3-12}$ cycloalkyl and 4-12 membered heterocycloalkyl, wherein the $C_{3-12}$ cycloalkyl and 4-12 membered heterocycloalkyl are each optionally substituted with 1, 2, 3 or 4 independently selected $R^{7A}$ substituents;

$R^8$ and $R^9$ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b8}$, $C(O)NR^{c8}R^{d8}$, $C(O)OR^{a8}$, $C(=NR^{e8})R^{b8}$, $C(=NR^{e8})NR^{c8}R^{d8}$, $C(=NCN)NR^{c8}R^{d8}$, $C(=NOR^{a8})NR^{c8}$, $S(O)_2R^{b8}$, $S(O)(=NR^{c8})R^{d8}$, and $S(O)_2NR^{c8}R^{d8}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^8$ and $R^9$ are each optionally substituted with 1, 2, 3, or 4 independently selected $R^{8A}$ substituents;

or, $R^8$ and $R^9$, together with the N atom to which they are attached, form a 5- or 6-membered heteroaryl, or a 4-10 membered heterocycloalkyl group, wherein the 5- or 6-membered heteroaryl, or 4-10-membered heterocycloalkyl group is optionally substituted with 1, 2, 3, or 4 independently selected $R^{8A}$ substituents;

each $R^{7A}$ is independently selected from D, oxo, halo, $C_{1-6}$ alkyl, $C_{1-6}$ haloalkyl, $C_{2-6}$ alkenyl, $C_{2-6}$ alkynyl, $C_{6-10}$ aryl, $C_{3-12}$ cycloalkyl, 5-10 membered heteroaryl, 4-12 membered heterocycloalkyl, CN, $NO_2$, $OR^{a71}$, $SR^{a71}$, $NHOR^{a71}$, $C(O)R^{b71}$, $C(O)NR^{c71}R^{d71}$, $C(O)NR^{c71}(OR^{b71})$, $C(O)OR^{a71}$, $OC(O)R^{b71}$, $OC(O)NR^{c71}R^{d71}$, $NR^{c71}R^{d71}$, $NR^{c71}NR^{c71}R^{d71}$, $NR^{c71}C(O)R^{b71}$, $NR^{c71}C(O)OR^{a71}$, $NR^{c71}C(O)NR^{c71}R^{d71}$, $C(=NR^{e71})R^{b71}$, $C(=NOH)R^{b71}$, $C(=NCN)R^{b71}$, $C(=NR^{e71})NR^{c71}R^{d71}$, $NR^{c71}C(=NR^{e71})NR^{c71}R^{d71}$, $NR^{c71}C(=NR^{e71})R^{b71}$, $NR^{c71}C(=NOH)NR^{c71}R^{d71}$, $NR^{c71}C(=NCN)NR^{c71}R^{d71}$, $NR^{c71}S(O)R^{b71}$, $NR^{c71}S(O)NR^{c71}R^{d71}$, $NR^{c71}S(O)_2R^{b71}$, $NR^{c71}S(O)_2NR^{c71}R^{d71}$, $S(O)R^{b71}$, $S(O)NR^{c71}R^{d71}$, $S(O)_2R^{b71}$, $S(O)_2NR^{c71}R^{d71}$, $OS(O)(=NR^{e71})R^{b71}$, $OS(O)_2R^{b71}$, $SF_5$, $P(O)R^{f71}R^{g71}$, $OP(O)(OR^{h71})(OR^{i71})$, $P(O)(OR^{h71})(OR^{i71})$, and $BR^{j71}R^{k71}$, wherein the $C_{1-6}$ alkyl, $C_{2-6}$ alkenyl, $C_{2-6}$ alkynyl, $C_{6-10}$ aryl, $C_{3-12}$ cycloalkyl, 5-10 membered heteroaryl and 4-12 membered heterocycloalkyl, of $R^{7A}$ are each optionally substituted with 1, 2, 3 or 4 independently selected $R^{7B}$ substituents;

each $R^{a71}$, $R^{b71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a71}$, $R^{b71}$, $R^{c71}$, and $R^{d71}$ are each optionally substituted with 1, 2, 3 or 4 independently selected $R^{7B}$ substituents;

or, any $R^{c71}$ and $R^{d71}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{7B}$ substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f71}$ and $R^{g71}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h71}$ and $R^{i71}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j71}$ and $R^{k71}$ is independently selected from OH, $C_{1-6}$ alkoxy, and $C_{1-6}$ haloalkoxy;

or any $R^{j71}$ and $R^{k71}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a72}$, $SR^{a72}$, $NHOR^{a72}$, $C(O)R^{b72}$, $C(O)NR^{c72}R^{d72}$, $C(O)NR^{c72}(OR^{b72})$, $C(O)OR^{a72}$, $OC(O)R^{b72}$, $OC(O)NR^{c72}R^{d72}$, $NR^{c72}R^{d72}$, $NR^{c72}NR^{c72}R^{d72}$, $NR^{c72}C(O)R^{b72}$, $NR^{c72}C(O)OR^{a72}$, $NR^{c72}C(O)NR^{c72}R^{d72}$, $C(=NR^{e72})R^{b72}$, $C(=NOH)R^{b72}$, $C(=NCN)R^{b72}$, $C(=NR^{e72})NR^{c72}R^{d72}$, $NR^{c72}C(=NR^{e72})NR^{c72}R^{d72}$, $NR^{c72}C(=NR^{e72})R^{b72}$, $NR^{c72}C(=NOH)NR^{c72}R^{d72}$, $NR^{c72}C(=NCN)NR^{c72}R^{d72}$, $NR^{c72}S(O)R^{b72}$, $NR^{c72}S(O)NR^{c72}R^{d72}$, $NR^{c72}S(O)_2R^{b72}$, $NR^{c72}S(O)_2NR^{c72}R^{d72}$, $S(O)R^{b72}$, $S(O)NR^{c72}R^{d72}$, $S(O)_2R^{b72}$, $S(O)_2NR^{c72}R^{d72}$, $OS(O)(=NR^{e72})R^{b72}$, $OS(O)_2R^{b72}$, $SF_5$, $P(O)R^{f72}R^{g72}$, $OP(O)(OR^{h72})(OR^{i72})$, $P(O)(OR^{h72})(OR^{i72})$, and $BR^{j72}R^{k72}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{7B}$ are each optionally substituted with 1, 2, 3 or 4 independently selected $R^{7C}$ substituents;

each $R^{a72}$, $R^{b72}$, $R^{c72}$, and $R^{d72}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a72}$, $R^{b72}$, $R^{c72}$, and $R^{d72}$ are each optionally substituted with 1, 2, 3 or 4 independently selected $R^{7C}$ substituents;

or, any $R^{c72}$ and $R^{d72}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{7C}$ substituents;

each $R^{e72}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f72}$ and $R^{g72}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h72}$ and $R^{i72}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j72}$ and $R^{k72}$ is independently selected from OH, $C_{1-6}$ alkoxy, and $C_{1-6}$ haloalkoxy;

or any $R^{j72}$ and $R^{k72}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7C}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a73}$, $SR^{a73}$, $NHOR^{a73}$, $C(O)R^{b73}$, $C(O)NR^{c73}R^{d73}$, $C(O)NR^{c73}(OR^{b73})$, $C(O)OR^{a73}$, $OC(O)R^{b73}$, $OC(O)NR^{c73}R^{d73}$, $NR^{c73}R^{d73}$, $NR^{c73}NR^{c73}R^{d73}$, $NR^{c73}C(O)R^{b73}$, $NR^{c73}C(O)OR^{a73}$, $NR^{c73}C(O)NR^{c73}R^{d73}$, $C(=NR^{e73})R^{b73}$, $C(=NOH)R^{b73}$, $C(=NCN)R^{b73}$, $C(=NR^{e73})NR^{c73}R^{d73}$, $NR^{c73}C(=NR^{e73})NR^{c73}R^{d73}$, $NR^{c73}C(=NR^{e73})R^{b73}$, $NR^{c73}C(=NOH)NR^{c73}R^{d73}$, $NR^{c73}C(=NCN)NR^{c73}R^{d73}$, $NR^{c73}S(O)R^{b73}$, $NR^{c73}S(O)NR^{c73}R^{d73}$, $NR^{c73}S(O)_2R^{b73}$, $NR^{c73}S(O)_2NR^{c73}R^{d73}$, $S(O)R^{b73}$, $S(O)NR^{c73}R^{d73}$, $S(O)_2R^{b73}$, $S(O)_2NR^{c73}R^{d73}$, $OS(O)(=NR^{e73})R^{b73}$, $OS(O)_2R^{b73}$, $SF_5$, $P(O)R^{f73}R^{g73}$, $OP(O)(OR^{h73})(OR^{i73})$, $P(O)(OR^{h73})(OR^{i73})$, and $BR^{j73}R^{k73}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{7C}$ are each optionally substituted with 1, 2, 3 or 4 independently selected $R^{7D}$ substituents;

each $R^{a73}$, $R^{b73}$, $R^{c73}$, and $R^{d73}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a73}$, $R^{b73}$, $R^{c73}$, and $R^{d73}$ are each optionally substituted with 1, 2, 3 or 4 independently selected $R^{7D}$ substituents;

or, any $R^{c73}$ and $R^{d73}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{7D}$ substituents;

each $R^{e73}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f73}$ and $R^{g73}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$alkyl- and (4-10 membered heterocycloalkyl)-$C_{1-6}$ alkyl-;

each $R^{h73}$ and $R^{i73}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j73}$ and $R^{k73}$ is independently selected from OH, $C_{1-6}$ alkoxy, and $C_{1-6}$ haloalkoxy;

or any $R^{j73}$ and $R^{k73}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7D}$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl- and (4-7 membered heterocycloalkyl)-$C_{1-6}$ alkyl;

each $R^{a8}$, $R^{b8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a8}$, $R^{b8}$, $R^{c8}$, and $R^{d8}$ are each optionally substituted with 1, 2, 3 or 4 independently selected $R^{8A}$ substituents;

or, any $R^{c8}$ and $R^{d8}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{8A}$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{8A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a81}$, $SR^{a81}$, $NHOR^{a81}$, $C(O)R^{b81}$, $C(O)NR^{c81}R^{d81}$, $C(O)NR^{c81}(OR^{b81})$, $C(O)OR^{a81}$, $OC(O)R^{b81}$, $OC(O)NR^{c81}R^{d81}$, $NR^{c81}R^{d81}$, $NR^{c81}NR^{c81}R^{d81}$, $NR^{c81}C(O)R^{b81}$, $NR^{c81}C(O)OR^{a81}$, $NR^{c81}C(O)NR^{c81}R^{d81}$, $C(=NR^{e81})R^{b81}$, $C(=NOH)R^{b81}$, $C(=NCN)R^{b81}$, $C(=NR^{e81})NR^{c81}R^{d81}$, $NR^{c81}C(=NR^{e81})NR^{c81}R^{d81}$, $NR^{c81}C(=NR^{e81})R^{b81}$, $NR^{c81}C(=NOH)NR^{c81}R^{d81}$, $NR^{c81}C(=NCN)NR^{c81}R^{d81}$, $NR^{c81}S(O)R^{b81}$, $NR^{c81}S(O)NR^{c81}R^{d81}$, $NR^{c81}S(O)_2R^{b81}$, $NR^{c81}S(O)_2NR^{c81}R^{d81}$, $S(O)R^{b81}$, $S(O)NR^{c81}R^{d81}$, $S(O)_2R^{b81}$, $S(O)_2NR^{c81}R^{d81}$, $OS(O)(=NR^{e81})R^{b81}$, $OS(O)_2R^{b81}$, $SF_5$, $P(O)R^{f81}R^{g81}$, $OP(O)(OR^{h81})(OR^{i81})$, $P(O)(OR^{h81})(OR^{i81})$, and $BR^{j81}R^{k81}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{8A}$ are each optionally substituted with 1, 2, 3 or 4 independently selected $R^{8B}$ substituents;

each $R^{a81}$, $R^{b81}$, $R^{c81}$, and $R^{d81}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{a81}$, $R^{b81}$, $R^{c81}$, and $R^{d81}$ are each optionally substituted with 1, 2, 3 or 4 independently selected $R^{8B}$ substituents;

or, any $R^{c81}$ and $R^{d81}$ attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3 or 4 independently selected $R^{8B}$ substituents;

each $R^{e81}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{f81}$ and $R^{g81}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{h81}$ and $R^{i81}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

each $R^{j81}$ and $R^{k81}$ is independently selected from OH, $C_{1-6}$ alkoxy, and $C_{1-6}$ haloalkoxy;

or any $R^{j81}$ and $R^{k81}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^{8B}$ is independently selected from H, D, halo, CN, $NO_2$, $SF_5$, $C_{1-6}$ alkyl, $C_{1-6}$ alkoxy, $C_{1-6}$ haloalkyl, $C_{2-6}$ alkenyl, $C_{2-6}$ alkynyl, phenyl, $C_{3-7}$ cycloalkyl, 5-7 membered heteroaryl, 4-7 membered heterocycloalkyl, phenyl-$C_{1-6}$ alkyl-, $C_{3-7}$ cycloalkyl-$C_{1-6}$ alkyl-, (5-7 membered heteroaryl)-$C_{1-6}$ alkyl- and (4-7 membered heterocycloalkyl)-$C_{1-6}$ alkyl.

In some embodiments, either: (a) $R^3$ and $R^{3''}$ together form an oxo group; or (b) $R^8$ is $C(O)R^{b8}$.

In some embodiments, $X^1$ is N.

In some embodiments, $X^1$ is $CR^1$.

In some embodiments, $R^1$ is selected from H, D, and $C_{1-6}$ alkyl.

In some embodiments, $R^1$ is selected from H, D, and methyl.

In some embodiments, $R^1$ is H.

In some embodiments, $R^2$ is a $C_{1-6}$ haloalkyl, wherein each halogen of the $C_{1-6}$ haloalkyl is independently selected from F and Cl.

In some embodiments, $R^2$ is a $C_{1-3}$ haloalkyl, wherein each halogen of the $C_{1-3}$ haloalkyl is independently selected from F and Cl.

In some embodiments, $R^2$ is selected from $CF_3$, $CCl_3$, $CF_2H$, $CCl_2H$, $CF_2R^M$, $CCl_2R^M$, $CFH_2$, $CClH_2$, $CFHR^M$, $CClHR^M$, $CF(R^M)_2$ and $CCl(R^M)_2$.

In some embodiments, $R^2$ is selected from $CF_3$, $CF_2H$, $CF_2R^M$, $CFH_2$, $CFHR^M$, and $CF(R^M)_2$.

In some embodiments, $R^M$ is selected from D, halo, $C_{1-3}$ alkyl, and $C_{1-3}$ haloalkyl.

In some embodiments, $R^M$ is selected from halo and $C_{1-3}$ haloalkyl.

In some embodiments, $R^2$ is $C_{1-6}$ haloalkyl, wherein each halogen is F.

In some embodiments, $R^2$ is $C_{1-6}$ haloalkyl, wherein each halogen is Cl.

In some embodiments, $R^2$ is selected from $CH_2F$, $CHF_2$, $CF_3$, and $CF_2CF_3$.

In some embodiments, $R^2$ is $CF_3$ or $CHF_2$.

In some embodiments, $R^2$ is $CF_3$.

In some embodiments, $R^2$ is $CH_2F$.

In some embodiments, $R^2$ is $CHF_2$.

In some embodiments, $R^2$ is $CF_2CF_3$.

In some embodiments, $R^3$ is selected from H, D, $C_{1-6}$ alkyl, $C_{2-6}$ alkenyl, $C_{2-6}$ alkynyl, $C_{1-6}$ haloalkyl, and $NH_2$.

In some embodiments, $R^3$ selected from H, D, and $C_{1-6}$ alkyl.

In some embodiments, $R^3$ is H or D.

In some embodiments, $R^3$ is H.

In some embodiments, $R^{3''}$ is selected from H, D, $C_{1-6}$ alkyl, $C_{2-6}$ alkenyl, $C_{2-6}$ alkynyl, $C_{1-6}$ haloalkyl, and $NH_2$.

In some embodiments, $R^{3''}$ is selected from H, D, and $C_{1-6}$ alkyl.

In some embodiments, $R^{3''}$ is H or D.

In some embodiments, $R^{3''}$ is H.

In some embodiments, $R^3$ and $R^{3''}$ together form an oxo group.

In some embodiments, $R^4$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.

In some embodiments, $R^4$ is selected from H, D, halo, CN, OH, $NH_2$, and $C_{1-6}$ alkyl.

In some embodiments, $R^4$ is selected from H, D, and $C_{1-6}$ alkyl, wherein the $C_{1-6}$ alkyl is optionally substituted with 1, 2, or 3 deuterium atoms.

In some embodiments, $R^4$ is H.

In some embodiments, $R^4$ is D.

In some embodiments, $R^5$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.

In some embodiments, $R^5$ is selected from H, D, halo, CN, OH, $NH_2$, and $C_{1-6}$ alkyl.

In some embodiments, $R^5$ is selected from H, D, and $C_{1-6}$ alkyl, wherein the $C_{1-6}$ alkyl is optionally substituted with 1, 2, or 3 deuterium atoms.

In some embodiments, $R^5$ is H.

In some embodiments, $R^5$ is D.

In some embodiments, $R^3$ and $R^4$ are each H.

In some embodiments, $R^3$ and $R^5$ are each H.

In some embodiments, $R^4$ and $R^5$ are each H.

In some embodiments, $R^3$, $R^{3''}$, $R^4$, and $R^5$ are each H.

In some embodiments, $R^3$ and $R^{3''}$ together form an oxo group; and $R^4$ and $R^5$ are each H.

In some embodiments, $R^6$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with 1, 2, or 3 deuterium atoms.

In some embodiments, $R^6$ is selected from H, D, and $C_{1-6}$ alkyl, wherein the $C_{1-6}$ alkyl is optionally substituted with 1, 2, or 3 deuterium atoms.

In some embodiments, $R^6$ is selected from H, D, halo, CN, OH, $NH_2$, and $C_{1-6}$ alkyl.

In some embodiments, $R^6$ is $C_{1-6}$ alkyl.

In some embodiments, $R^6$ is methyl.

In some embodiments, $R^6$ is $CD_3$.

In some embodiments, $R^6$ is H.

In some embodiments, $R^6$ is D.

In some embodiments, $R^7$ is selected from $C_{3-6}$ cycloalkyl and 4-10 membered heterocycloalkyl, wherein the $C_{3-6}$ cycloalkyl and 4-10 membered heterocycloalkyl are each optionally substituted with 1, 2, or 3 independently selected $R^{7A}$ substituents.

In some embodiments, each $R^{7A}$ is independently selected from D, halo, oxo, $C_{1-6}$ alkyl, $C_{6-10}$ aryl, $C_{3-6}$ cycloalkyl, 5-10 membered heteroaryl, $C(O)R^{b71}$, $C(O)OR^{a71}$, and $S(O)_2R^{b71}$, wherein the $C_{1-6}$ alkyl, $C_{6-10}$ aryl, $C_{3-6}$ cycloalkyl, and 5-10 membered heteroaryl of $R^{7A}$ are each optionally substituted with 1 or 2 independently selected $R^{7B}$ substituents.

In some embodiments, each $R^{a71}$ and $R^{b71}$ is independently selected from $C_{1-6}$ alkyl, $C_{3-6}$ cycloalkyl, and 5-10 membered heteroaryl, wherein the $C_{1-6}$ alkyl, $C_{3-6}$ cycloalkyl, and 5-10 membered heteroaryl of $R^{a71}$ and $R^{b71}$ are each optionally substituted with 1 or 2 independently selected $R^{7B}$ substituents.

In some embodiments, each $R^{7B}$ substituent is independently selected from OH, CN, $C_{1-6}$ alkyl, $C_{1-6}$ alkoxy, and $C_{1-6}$ haloalkyl.

In some embodiments, $R^7$ is selected from $C_{3-6}$ cycloalkyl and 4-10 membered heterocycloalkyl, wherein the $C_{3-6}$ cycloalkyl and 4-10 membered heterocycloalkyl of $R^7$ are each optionally substituted with 1, 2 or 3 independently selected $R^{7A}$ substituents; and each $R^{7A}$ is independently selected from oxo, $C_{1-6}$ alkyl, phenyl, $C_{3-6}$ cycloalkyl, 5-10 membered heteroaryl, $C(O)R^{b71}$, $C(O)OR^{a71}$, and $S(O)_2R^{b71}$, wherein the $C_{1-6}$ alkyl, phenyl, $C_{3-6}$ cycloalkyl, and 5-10 membered heteroaryl of $R^{7A}$ are each optionally substituted with 1 or 2 independently selected $R^{7B}$ substituents.

In some embodiments, $R^7$ is selected from $C_{3-6}$ cycloalkyl and 4-10 membered heterocycloalkyl, wherein the $C_{3-6}$ cycloalkyl and 4-10 membered heterocycloalkyl of $R^7$ are each optionally substituted with 1, 2 or 3 independently selected $R^{7A}$ substituents; and each $R^{7A}$ is independently selected from oxo, $C_{1-6}$ alkyl, phenyl, $C_{3-6}$ cycloalkyl, 5-9 membered heteroaryl, $C(O)R^{b71}$, $C(O)OR^{a71}$, and $S(O)_2R^{b71}$, wherein the $C_{1-6}$ alkyl, phenyl, $C_{3-6}$ cycloalkyl, and 5-10 membered heteroaryl of $R^{7A}$ are each optionally substituted with 1 or 2 independently selected $R^{7B}$ substituents.

In some embodiments, $R^7$ is selected from $C_{3-6}$ cycloalkyl and 4-10 membered heterocycloalkyl, wherein the $C_{3-6}$ cycloalkyl and 4-10 membered heterocycloalkyl of $R^7$ are each optionally substituted with 1, 2 or 3 independently selected $R^{7A}$ substituents;

each $R^{7A}$ is independently selected from oxo, $C_{1-6}$ alkyl, phenyl, $C_{3-6}$ cycloalkyl, 5-10 membered heteroaryl, $C(O)R^{b71}$, $C(O)OR^{a71}$, and $S(O)_2R^{b71}$, wherein the $C_{1-6}$ alkyl, phenyl, $C_{3-6}$ cycloalkyl, and 5-10 membered heteroaryl of $R^{7A}$ are each optionally substituted with 1 or 2 independently selected $R^{7B}$ substituents; and each $R^{a71}$ and $R^{b71}$ is independently selected from $C_{1-6}$ alkyl, $C_{3-6}$ cycloalkyl, and 5-10 membered heteroaryl, wherein the $C_{1-6}$ alkyl, $C_{3-6}$ cycloalkyl, and 5-10 membered heteroaryl of $R^{a71}$ and $R^{b71}$ are each optionally substituted with 1 or 2 independently selected $R^{7B}$ substituents.

In some embodiments, $R^7$ is selected from azetidinyl, cyclobutyl, piperazinyl, and hexahydropyrrolo[1,2-a]pyrazinyl, wherein the azetidinyl, cyclobutyl, piperazinyl, and hexahydropyrrolo[1,2-a]pyrazinyl of $R^7$ are each optionally substituted with 1, 2, or 3 independently selected $R^{7A}$ substituents.

In some embodiments, $R^7$ is selected from azetidinyl, cyclobutyl, piperazinyl, and hexahydropyrrolo[1,2-a]pyrazinyl, wherein the azetidinyl, cyclobutyl, piperazinyl, and hexahydropyrrolo[1,2-a]pyrazinyl of $R^7$ are each optionally substituted with 1, 2, or 3 independently selected $R^{7A}$ substituents; and each $R^{7A}$ is independently selected from oxo, $C_{1-6}$ alkyl, phenyl, $C_{3-6}$ cycloalkyl, 5-10 membered heteroaryl, $C(O)R^{b71}$, $C(O)OR^{a71}$, and $S(O)_2R^{b71}$, wherein the $C_{1-6}$ alkyl, phenyl, $C_{3-6}$ cycloalkyl, and 5-10 membered heteroaryl, of $R^{7A}$ are each optionally substituted with 1 or 2 independently selected $R^{7B}$ substituents.

In some embodiments, $R^7$ is selected from azetidinyl, cyclobutyl, piperazinyl, and hexahydropyrrolo[1,2-a]pyrazinyl, wherein the azetidinyl, cyclobutyl, piperazinyl, and hexahydropyrrolo[1,2-a]pyrazinyl of $R^7$ are each optionally substituted with 1, 2, or 3 independently selected $R^{7A}$ substituents;

each $R^{7A}$ is independently selected from oxo, $C_{1-6}$ alkyl, phenyl, $C_{3-6}$ cycloalkyl, 5-10 membered heteroaryl, $C(O)R^{b71}$, $C(O)OR^{a71}$, and $S(O)_2R^{b71}$, wherein the $C_{1-6}$ alkyl, phenyl, $C_{3-6}$ cycloalkyl, and 5-10 membered heteroaryl of $R^{7A}$ are each optionally substituted with 1 or 2 independently selected $R^{7B}$ substituents; and each $R^{a71}$ and $R^{b71}$ is independently selected from $C_{1-6}$ alkyl, $C_{3-6}$ cycloalkyl, and 5-10 membered heteroaryl, wherein the $C_{1-6}$ alkyl, $C_{3-6}$ cycloalkyl, and 5-10 membered heteroaryl of $R^{a71}$ and $R^{b71}$ are each optionally substituted with 1 or 2 independently selected $R^{7B}$ substituents.

In some embodiments, $R^7$ is selected from azetidinyl, cyclobutyl, piperazinyl, and hexahydropyrrolo[1,2-a]pyrazinyl, wherein the azetidinyl, cyclobutyl, piperazinyl, and hexahydropyrrolo[1,2-a]pyrazinyl of $R^7$ are each optionally substituted with 1, 2, or 3 independently selected $R^{7A}$ substituents;

each $R^{7A}$ is independently selected from oxo, $C_{1-6}$ alkyl, phenyl, $C_{3-6}$ cycloalkyl, 5-10 membered heteroaryl, $C(O)R^{b71}$, $C(O)OR^{a71}$, and $S(O)_2R^{b71}$, wherein the $C_{1-6}$ alkyl, phenyl, $C_{3-6}$ cycloalkyl, and 5-10 membered heteroaryl, of $R^{7A}$ are each optionally substituted with 1 or 2 independently selected $R^{7B}$ substituents;

each $R^{a71}$ and $R^{b71}$ is independently selected from $C_{1-6}$ alkyl, $C_{3-6}$ cycloalkyl, 5-10 membered heteroaryl, wherein the $C_{1-6}$ alkyl, $C_{3-6}$ cycloalkyl, and 5-10 membered heteroaryl of $R^{a71}$ and $R^{b71}$ are each optionally substituted with 1 or 2 independently selected $R^{7B}$ substituents; and each $R^{7B}$ substituent is independently selected from OH, CN, $C_{1-6}$ alkyl, $C_{1-6}$ alkoxy and $C_{1-6}$ haloalkyl.

In some embodiments, $R^7$ is selected from azetidinyl, cyclobutyl, piperazinyl, and hexahydropyrrolo[1,2-a]pyrazinyl, wherein the azetidinyl, cyclobutyl, piperazinyl, and hexahydropyrrolo[1,2-a]pyrazinyl of $R^7$ are each optionally substituted with 1, 2, or 3 $R^{7A}$ substituents independently selected from (1-methyl-1H-pyrazol-4-yl)sulfonyl, ethylcarboxylate, oxo, cyclopropyl, butyl, acetyl, cyclopropanecarbonyl, phenyl, methylphenyl, dimethylphenyl, pyrindinyl, thiazolyl, trifluoromethylphenyl, cyanophenyl, hydroxyphenyl, hydroxymethyl, cyanoethyl, oxohexahydropyrrolo[1,2-a]pyrazine-2-yl, furan-2-carbonyl, cyanopyrazinyl, and ethoxyphenyl.

In some embodiments, $R^8$ is selected from H, $C_{1-6}$ alkyl, $C_{2-6}$ alkenyl, $C_{2-6}$ alkynyl, $C_{1-6}$ haloalkyl, and $C(O)R^{b8}$.

In some embodiments, $R^8$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, and $C(O)R^{b8}$.

In some embodiments, $R^8$ is selected from H, $C_{1-6}$ alkyl, $C_{2-6}$ alkenyl, $C_{2-6}$ alkynyl, $C_{1-6}$ haloalkyl, and $C_{3-10}$ cycloalkyl.

In some embodiments, $R^8$ is selected from H, $C_{1-6}$ alkyl, and $C(O)R^{b8}$.

In some embodiments, $R^8$ is H or $C_{1-6}$ alkyl.

In some embodiments, $R^8$ is H, methyl, ethyl, propyl or isopropyl.

In some embodiments, $R^8$ is H or $C(O)R^{b8}$.

In some embodiments, $R^8$ is H.

In some embodiments, $R^8$ is $C(O)R^{b8}$.

In some embodiments, $R^{b8}$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{b8}$ are each optionally substituted with 1, 2, 3 or 4 independently selected $R^{8A}$ substituents.

In some embodiments, $R^{b8}$ is selected from H, $C_{1-6}$ alkyl, and $C_{1-6}$ haloalkyl, wherein the $C_{1-6}$ alkyl of $R^{b8}$ is optionally substituted with 1 or 2 $R^{84}$ substituents independently selected from D, halo, CN, $NO_2$, OH, and SH.

In some embodiments, $R^{b8}$ is selected from methyl, fluoromethyl, cyanomethyl, and hydroxypropyl.

In some embodiments, $R^{b8}$ is selected from H, D, and $C_{1-6}$ alkyl.

In some embodiments, $R^{b8}$ is selected from H, D, and methyl.

In some embodiments, $R^{b8}$ is H.

In some embodiments, $R^9$ is selected from H, $C_{1-6}$ alkyl, $C_{2-6}$ alkenyl, $C_{2-6}$ alkynyl, $C_{1-6}$ haloalkyl and $C_{3-10}$ cycloalkyl.

In some embodiments, $R^9$ is selected from H, $C_{1-6}$ alkyl, $C_{2-6}$ alkenyl, $C_{2-6}$ alkynyl, and $C_{1-6}$ haloalkyl.

In some embodiments, $R^9$ is H or $C_{1-6}$ alkyl.

In some embodiments, $R^9$ is selected from H, methyl, ethyl, propyl, and isopropyl.

In some embodiments, $R^9$ is H.

In some embodiments, $R^8$ and $R^9$ are each H.

In some embodiments:
$R^3$ is selected from H, D, $C_{1-6}$ alkyl, $C_{2-6}$ alkenyl, $C_{2-6}$ alkynyl, $C_{1-6}$ haloalkyl, and $NH_2$;
$R^{3''}$ is selected from H, D, $C_{1-6}$ alkyl, $C_{2-6}$ alkenyl, $C_{2-6}$ alkynyl, $C_{1-6}$ haloalkyl, and $NH_2$; and
$R^8$ is $C(O)R^{b8}$.

In some embodiments:
$R^3$ and $R^{3''}$ together form an oxo group; and
$R^8$ is selected from H, $C_{1-6}$ alkyl, $C_{2-6}$ alkenyl, $C_{2-6}$ alkynyl, $C_{1-6}$ haloalkyl, and $C_{3-7}$ cycloalkyl.

In some embodiments:
$X^1$ is N or CH;
$R^2$ is a $C_{1-6}$ haloalkyl, wherein each halogen of the $C_{1-6}$ haloalkyl is independently selected from F and Cl;
$R^3$ is selected from H, D, $C_{1-6}$ alkyl, $C_{2-6}$ alkenyl, $C_{2-6}$ alkynyl, $C_{1-6}$ haloalkyl, and $NH_2$;
$R^{3''}$ is selected from H, D, $C_{1-6}$ alkyl, $C_{2-6}$ alkenyl, $C_{2-6}$ alkynyl, $C_{1-6}$ haloalkyl, and $NH_2$;
or, alternatively, $R^3$ and $R^{3''}$ together form an oxo group;
$R^4$ is selected from H, D, halo, CN, OH, $NH_2$, and $C_{1-6}$ alkyl;
$R^5$ is selected from H, D, halo, CN, OH, $NH_2$, and $C_{1-6}$ alkyl;
$R^6$ is selected from H, D, halo, CN, OH, $NH_2$, and $C_{1-6}$ alkyl;
$R^7$ is selected from $C_{3-6}$ cycloalkyl and 4-10 membered heterocycloalkyl, wherein the $C_{3-6}$ cycloalkyl and 4-10 membered heterocycloalkyl are each optionally substituted with 1, 2, or 3 independently selected $R^{7A}$ substituents;
each $R^{7A}$ is independently selected from oxo, $C_{1-6}$ alkyl, phenyl, $C_{3-6}$ cycloalkyl, 5-10 membered heteroaryl, $C(O)R^{b71}$, $C(O)OR^{a71}$, and $S(O)_2R^{b71}$, wherein the $C_{1-6}$ alkyl, phenyl, $C_{3-6}$ cycloalkyl, and 5-10 membered heteroaryl, of $R^{7A}$ are each optionally substituted with 1 or 2 independently selected $R^{7B}$ substituents;
each $R^{a71}$ and $R^{b71}$ is independently selected from $C_{1-6}$ alkyl, $C_{3-6}$ cycloalkyl, and 5-10 membered heteroaryl, wherein the $C_{1-6}$ alkyl, $C_{3-6}$ cycloalkyl, and 5-10 membered heteroaryl of $R^{a71}$ and $R^{b71}$ are each optionally substituted with 1 or 2 independently selected $R^{7B}$ substituents;
each $R^{7B}$ is independently selected from OH, CN, $C_{1-6}$ alkyl, $C_{1-6}$ alkoxy, and $C_{1-6}$ haloalkyl;
$R^8$ is selected from H, $C_{1-6}$ alkyl, $C_{2-6}$ alkenyl, $C_{2-6}$ alkynyl, $C_{1-6}$ haloalkyl, and $C(O)R^{b8}$;
$R^9$ is selected from H, $C_{1-6}$ alkyl, $C_{2-6}$ alkenyl, $C_{2-6}$ alkynyl, and $C_{1-6}$ haloalkyl;

$R^{b8}$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{b8}$ are each optionally substituted with 1, 2, 3 or 4 independently selected $R^{84}$ substituents; and
each $R^{84}$ is independently selected from D, halo, CN, $NO_2$, OH, and SH.

In some embodiments:
$X^1$ is N or CH;
$R^2$ is a $C_{1-3}$ haloalkyl, wherein each halogen of the $C_{1-6}$ haloalkyl is independently selected from F and Cl;
$R^3$ is H;
$R^{3''}$ is H;
or, alternatively, $R^3$ and $R^{3''}$ together form an oxo group;
$R^4$ is selected from H and $C_{1-6}$ alkyl;
$R^5$ is selected from H and $C_{1-6}$ alkyl;
$R^6$ is selected from H and $C_{1-6}$ alkyl;
$R^7$ is selected from $C_{3-6}$ cycloalkyl and 4-10 membered heterocycloalkyl, wherein the $C_{3-6}$ cycloalkyl and 4-10 membered heterocycloalkyl are each optionally substituted with 1, 2, or 3 $R^{7A}$ substituents independently selected from oxo, $C_{1-6}$ alkyl, phenyl, $C_{3-6}$ cycloalkyl, 5-10 membered heteroaryl, $C(O)R^{b71}$, $C(O)OR^{a71}$, and $S(O)_2R^{b71}$, wherein the $C_{1-6}$ alkyl, phenyl, $C_{3-6}$ cycloalkyl, and 5-10 membered heteroaryl of $R^{7A}$ are each optionally substituted with 1 or 2 independently selected $R^{7B}$ substituents;
each $R^{a71}$ and $R^{b71}$ is independently selected from $C_{1-6}$ alkyl, $C_{3-6}$ cycloalkyl, and 5-10 membered heteroaryl, wherein the $C_{1-6}$ alkyl, $C_{3-6}$ cycloalkyl, and 5-10 membered heteroaryl of $R^{a71}$ and $R^{b71}$ are each optionally substituted with 1 or 2 independently selected $R^{7B}$ substituents;
each $R^{7B}$ is independently selected from OH, CN, $C_{1-6}$ alkyl, $C_{1-6}$ alkoxy, and $C_{1-6}$ haloalkyl;
$R^8$ is selected from H and $C(O)R^{b8}$;
$R^9$ is H;
$R^{b8}$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{b8}$ are each optionally substituted with 1, 2, 3 or 4 independently selected $R^{84}$ substituents; and
each $R^{84}$ is independently selected from D, halo, CN, $NO_2$, OH, and SH.

In some embodiments:
$X^1$ is N or CH;
$R^2$ is a $C_{1-3}$ haloalkyl, wherein each halogen of the $C_{1-6}$ haloalkyl is independently selected from F and Cl;
$R^3$ is H;
$R^{3''}$ is H;
or, alternatively, $R^3$ and $R^{3''}$ together form an oxo group;
$R^4$ is H;
$R^5$ is H;
$R^6$ is $C_{1-6}$ alkyl;
$R^7$ is selected from azetidinyl, cyclobutyl, piperazinyl, and hexahydropyrrolo[1,2-a]pyrazinyl, wherein the azetidinyl, cyclobutyl, piperazinyl, and hexahydropyrrolo[1,2-a]pyrazinyl of $R^7$ are each optionally substituted with 1, 2 or 3 $R^{7A}$ substituents independently selected from (1-methyl-1H-pyrazol-4-yl)sulfonyl, ethylcarboxylate, oxo, cyclopropyl, butyl, acetyl, cyclopropanecarbonyl, phenyl, methylphenyl, dimethylphenyl, pyrindinyl, thiazolyl, trifluoromethylphenyl, cyanophenyl, hydroxyphenyl, hydroxymethyl, cyanoethyl, oxohexahydropyrrolo[1,2-a]pyrazine-2-yl, furan-2-carbonyl, cyanopyrazinyl, and ethoxyphenyl;
$R^8$ is selected from H and $C(O)R^{b8}$;
$R^9$ is H; and $R^{b8}$ is selected from H, $C_{1-6}$ alkyl, $C_{1-6}$ haloalkyl, $C_{2-6}$ alkenyl, and $C_{2-6}$ alkynyl.

In some embodiments, the compound of Formula (I) is a compound of Formula (II):

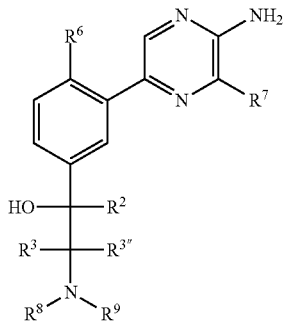

(II)

or a pharmaceutically acceptable salt thereof.

In some embodiments, the compound of Formula (I) is a compound of Formula (III):

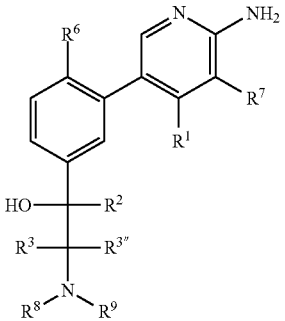

(III)

or a pharmaceutically acceptable salt thereof.

In some embodiments, the compound of Formula (I) is a compound of Formula (IV):

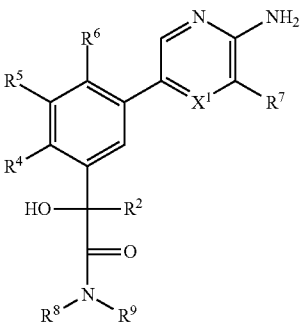

(IV)

or a pharmaceutically acceptable salt thereof.

In some embodiments, the compound of Formula (I) is a compound of Formula (IVa):

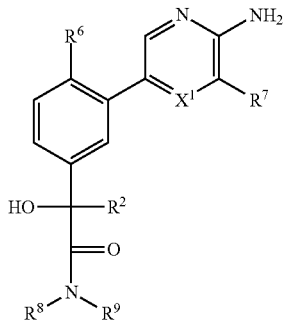

(IVa)

or a pharmaceutically acceptable salt thereof.

In some embodiments, the compound of Formula (I) is a compound of Formula (V):

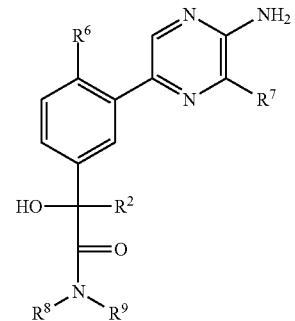

(V)

or a pharmaceutically acceptable salt thereof.

In some embodiments, the compound of Formula (I) is a compound of Formula (VI):

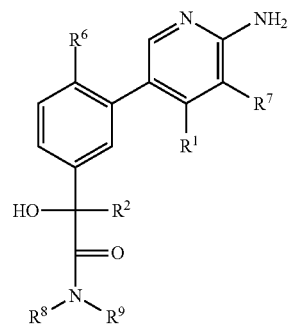

(VI)

or a pharmaceutically acceptable salt thereof.

In some embodiments, the compound of Formula (I) is a compound of Formula (VII):

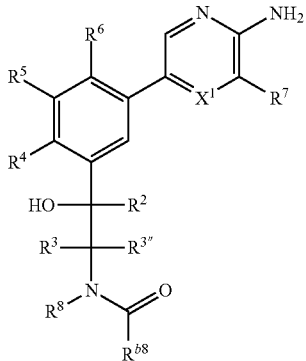

(VII)

or a pharmaceutically acceptable salt thereof.

In some embodiments, the compound of Formula (I) is a compound of Formula (VIIa):

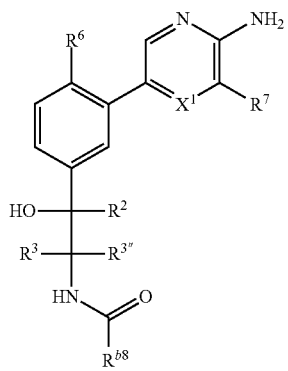

(VIIa)

or a pharmaceutically acceptable salt thereof.

In some embodiments, the compound of Formula (I) is a compound of Formula (VIII):

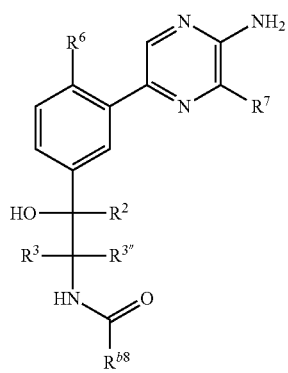

(VIII)

or a pharmaceutically acceptable salt thereof.

In some embodiments, the compound of Formula (I) is a compound of Formula (IX):

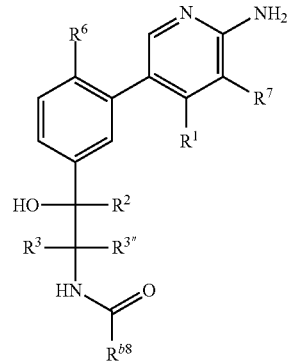

(IX)

or a pharmaceutically acceptable salt thereof.

In some embodiments, the compound is selected from:
2-(3-(5-amino-6-(prop-1-en-1-yl)pyrazin-2-yl)-4-methylphenyl)-3,3,3-trifluoro-2-hydroxypropanamide;
2-(3-(5-amino-6-propylpyrazin-2-yl)-4-methylphenyl)-3,3,3-trifluoro-2-hydroxypropanamide;
2-(3-(5-amino-6-(trifluoromethyl)pyrazin-2-yl)-4-methylphenyl)-3,3,3-trifluoro-2-hydroxypropanamide;
2-(3-(5-Amino-6-(1-((1-methyl-1H-pyrazol-4-yl)sulfonyl)azetidin-3-yl)pyrazin-2-yl)-4-methylphenyl)-3,3,3-trifluoro-2-hydroxypropanamide;
(cis) Ethyl 3-(3-amino-6-(5-(3-amino-1,1,1-trifluoro-2-hydroxy-3-oxopropan-2-yl)-2-methylphenyl)pyrazin-2-yl)cyclobutane-1-carboxylate;
(trans) Ethyl 3-(3-amino-6-(5-(3-amino-1,1,1-trifluoro-2-hydroxy-3-oxopropan-2-yl)-2-methylphenyl)pyrazin-2-yl)cyclobutane- 1-carboxylate;
2-(3-(5-amino-6-(4-cyclopropyl-3-oxopiperazin-1-yl)pyrazin-2-yl)-4-methylphenyl)-3,3,3-trifluoro-2-hydroxypropanamide;
2-(3-(5-amino-6-(4-tert-butyl-3-oxopiperazin-1-yl)pyrazin-2-yl)-4-methylphenyl)-3,3,3-trifluoro-2-hydroxypropanamide;
2-(3-(6-(4-acetylpiperazin-1-yl)-5-aminopyrazin-2-yl)-4-methylphenyl)-3,3,3-trifluoro-2-hydroxypropanamide;
(R)-2-(3-(5-amino-6-(4-(cyclopropanecarbonyl)piperazin-1-yl)pyrazin-2-yl)-4-methylphenyl)-3,3,3-trifluoro-2-hydroxypropanamide;
2-(3-(5-amino-6-(4-phenylpiperazin-1-yl)pyrazin-2-yl)-4-methylphenyl)-3,3,3-trifluoro-2-hydroxypropanamide;
2-(3-(5-amino-6-(4-(pyridin-2-yl)piperazin-1-yl)pyrazin-2-yl)-4-methylphenyl)-3,3,3-trifluoro-2-hydroxypropanamide;
2-(3-(5-amino-6-(4-o-tolylpiperazin-1-yl)pyrazin-2-yl)-4-methylphenyl)-3,3,3-trifluoro-2-hydroxypropanamide;
2-(3-(5-amino-6-(4-(2,5-dimethylphenyl)piperazin-1-yl)pyrazin-2-yl)-4-methylphenyl)-3,3,3-trifluoro-2-hydroxypropanamide;
2-(3-(5-amino-6-(4-(thiazol-5-yl)piperazin-1-yl)pyrazin-2-yl)-4-methylphenyl)-3,3,3-trifluoro-2-hydroxypropanamide;
2-(3-(5-amino-6-(4-(3-(trifluoromethyl)phenyl)piperazin-1-yl)pyrazin-2-yl)-4-methylphenyl)-3,3,3-trifluoro-2-hydroxypropanamide;
2-(3-(5-amino-6-(4-(2-cyanophenyl)piperazin-1-yl)pyrazin-2-yl)-4-methylphenyl)-3,3,3-trifluoro-2-hydroxypropanamide;
2-(3-(5-amino-6-(4-(4-cyanophenyl)piperazin-1-yl)pyrazin-2-yl)-4-methylphenyl)-3,3,3-trifluoro-2-hydroxypropanamide;

2-(3-(5-amino-6-((R)-3-(hydroxymethyl)-4-(4-hydroxyphenyl)-5-oxopiperazin-1-yl)pyrazin-2-yl)-4-methylphenyl)-3,3,3-trifluoro-2-hydroxypropanamide;

2-(3-(5-amino-6-(4-(2-cyanoethyl)piperazin-1-yl)pyrazin-2-yl)-4-methylphenyl)-3,3,3-trifluoro-2-hydroxypropanamide;

2-(3-(5-amino-6-(6-oxohexahydropyrrolo[1,2-a]pyrazin-2(1H)-yl)pyrazin-2-yl)-4-methylphenyl)-3,3,3-trifluoro-2-hydroxypropanamide;

2-(3-(5-amino-6-(4-(furan-2-carbonyl)piperazin-1-yl)pyrazin-2-yl)-4-methylphenyl)-3,3,3-trifluoro-2-hydroxypropanamide;

2-(3-(5-amino-6-(4-(3-cyanopyrazin-2-yl)piperazin-1-yl)pyrazin-2-yl)-4-methylphenyl)-3,3,3-trifluoro-2-hydroxypropanamide; and 2-(3-(5-amino-6-(4-(2-ethoxyphenyl)piperazin-1-yl)pyrazin-2-yl)-4-methylphenyl)-3,3,3-trifluoro-2-hydroxypropanamide;

or a pharmaceutically acceptable salt thereof.

In some embodiments, the compound is the (S)-enantiomer of one of the preceding compounds, or a pharmaceutically acceptable salt thereof. In some embodiments, the compound is the (R)-enantiomer of one of the preceding compounds, or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 14, or 6 to 10, carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$ haloalkoxy" refers to a group of formula —O-haloalkyl having n to m carbon atoms. Example haloalkoxy groups include OCF$_3$ and OCHF$_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include CF$_3$, C$_2$F$_5$, CHF$_2$, CH$_2$F, CCl$_3$, CHCl$_2$, C$_2$Cl$_5$ and the like.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonylamino" refers to a group of formula —NHC(O)O($C_{n-m}$ alkyl), wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "carbamyl" to a group of formula —C(O)NH$_2$.

As used herein, the term "carbonyl", employed alone or in combination with other terms, refers to a —C(O)— group.

As used herein, the term "cyano-$C_{1-3}$ alkyl" refers to a group of formula —($C_{1-6}$ alkylene)-CN.

As used herein, the term "HO—$C_{1-6}$ alkyl" refers to a group of formula —($C_{1-6}$ alkylene)-OH.

As used herein, the term "HO—$C_{1-3}$ alkyl" refers to a group of formula —($C_{1-3}$ alkylene)-OH.

As used herein, the term "$C_{1-6}$ alkoxy-$C_{1-6}$ alkyl" refers to a group of formula —($C_{1-6}$ alkylene)-O($C_{1-6}$ alkyl).

As used herein, the term "$C_{1-3}$ alkoxy-$C_{1-3}$ alkyl" refers to a group of formula —($C_{1-3}$ alkylene)-O($C_{1-3}$ alkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "aminocarbonyloxy" refers to a group of formula —OC(O)NH$_2$.

As used herein, the term "$C_{1-3}$ alkylcarbonyloxy" refers to a group of formula —OC(O)($C_{1-3}$ alkyl).

As used herein, the term "$C_{1-3}$ alkylaminocarbonyloxy" refers to a group of formula —OC(O)NH($C_{1-3}$ alkyl).

As used herein, the term "di($C_{1-3}$ alkyl)aminocarbonyloxy" refers to a group of formula —OC(O)N($C_{1-3}$ alkyl)$_2$, wherein the two alkyl groups each has, independently, 1 to 3 carbon atoms.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, or 12 ring-forming carbons (i.e., $C_{3-12}$). In some embodiments, the cycloalkyl is a $C_{3-12}$ monocyclic or bicyclic cycloalkyl. In some embodiments, the cycloalkyl is a $C_{3-10}$ monocyclic or bicyclic cycloalkyl. In some embodiments, the cycloalkyl is a $C_{3-12}$ monocyclic or bicyclic cycloalkyl which is optionally substituted by CH$_2$F, CHF$_2$, CF$_3$, and CF$_2$CF$_3$. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-12}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B, wherein any ring forming N is optionally an N-oxide group. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-14 membered monocyclic or bicyclic heteroaryl having 1, 2, 3, or 4 heteroatom ring members independently selected from N, O, S and B. In some embodiments, the heteroaryl is a 5-14 membered monocyclic or bicyclic heteroaryl having 1, 2, 3, or 4 heteroatom ring members independently selected from N, O, and S. In some embodiments, the heteroaryl is a 5-10 membered monocyclic or bicyclic heteroaryl having 1, 2, 3, or 4 heteroatom ring members independently selected from N, O, S and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S and B. In some embodiments, the heteroaryl is a 5-6 monocyclic heteroaryl ring having 1 or 2 heteroatom ring members independently selected from N, O or S. In some embodiments, the heteroaryl group contains 3 to 14, 3 to 10, 4 to 14, 4 to 10, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine, thieno[3,2-b]pyridine, imidazo[1,2-a]pyridine, 1,5-naphthyridine, 1H-pyrazolo[4,3-b]pyridine and the like.

A five-membered heteroaryl is a heteroaryl group having five ring-forming atoms wherein one or more (e.g., 1, 2, or 3) of the ring-forming atoms are independently selected from N, O, S or B. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine.

A six-membered heteroaryl is a heteroaryl group having six ring-forming atoms wherein one or more (e.g., 1, 2, or 3) of the ring-forming atoms are independently selected from N, O, S and B. Exemplary six-membered ring heteroaryls are pyridyl, pyrazinyl, pyrimidinyl, triazinyl and pyridazinyl.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S and B, and wherein the ring-forming carbon atoms and heteroatoms of the heterocycloalkyl group can be optionally substituted by one or more oxo or sulfido (e.g., C(O), S(O), C(S), or $S(O)_2$, etc.). Heterocycloalkyl groups include monocyclic and polycyclic (e.g., having 2 fused rings) systems. Included in heterocycloalkyl are monocyclic and polycyclic 3-12, 4-12, 3-10-, 4-10-, 3-7-, 4-7-, and 5-6-membered heterocycloalkyl groups. Heterocycloalkyl groups can also include spirocycles and bridged rings (e.g., a 5-10 membered bridged biheterocycloalkyl ring having one or more of the ring-forming carbon atoms replaced by a heteroatom independently selected from N, O, S and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 12 ring-forming atoms, 4 to 14 ring-forming atoms, 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members.

Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, 1,2,3,4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.1]octanyl, oxabicyclo[2.2.2]octanyl, azabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl, 2,3-dihydro-1H-pyrrolo[2,3-b]pyridin-1-yl and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

As used herein, the term "independently selected from" means that each occurrence of a variable or substituent, e.g., $R^M$ or $R^{7A}$, are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of σ-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

Compounds of Formula (I) can be prepared as shown in Scheme 1. Suitable starting materials 1-1, where $Y^1$ is a halogen (e.g., Cl, Br, or I) or pseudohalogen (e.g., OTf or OMs), can be converted to secondary alcohol 1-3 with silane 1-2 where $Z^1$ is a halogen (e.g., F or Br) under standard conditions (e.g., in the presence of TBAF or $PPh_3$ and DMPU). In some instances $Z^1$ can be H wherein a $CHF_2$ group ($R^2$) can be formed. Oxidation of secondary alcohol 1-3 under standard conditions (e.g., Swern oxidation or Dess-Martin periodinane) can give ketone 1-4. Ketone 1-4 can be converted to cyanohydrin 1-5 under standard conditions (e.g., in the presence of KCN, TMSCN, and 18-crown-6). Cyanohydrin 1-5 can be converted to aldehyde 1-6 upon reduction (e.g., DIBAL-H (for a review see Synthesis 1975, 10, 617-630)). Aldehyde 1-6 can be converted to amine 1-8 under standard reductive amination conditions with amine 1-7 and an appropriate reducing agent (e.g., sodium borohydride, sodium triacetoxyborohydride, or sodium cyanoborohydride). Alternatively, cyanohydrin 1-5 can be reduced directly to amine 1-8 (where $R^8$ and $R^9$ are hydrogen) under standard conditions (e.g., $LiAlH_4$ in $Et_2O$).

The $Y^1$ group of 1-8 can be converted to an appropriately substituted metal 1-9 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichlorobis(triphenylphosphine)palladium(II) or [1,1'-bis(diphenylphosphino)ferrocene]dichloropalladium(II) complex with dichloromethane, and a base, such as potassium acetate) and then coupled to 1-10 where $Y^7$ is a halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium (0) catalyst, such as tetrakis(triphenylphosphine)palladium (0) or [1,1'-bis(diphenylphosphino)ferrocene]dichloropalladium(II)) to give compounds of Formula (I).

Scheme 1.

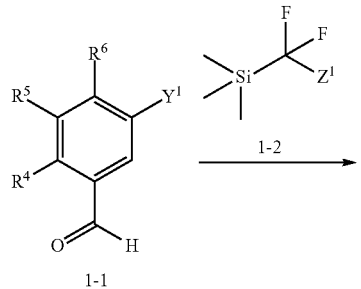

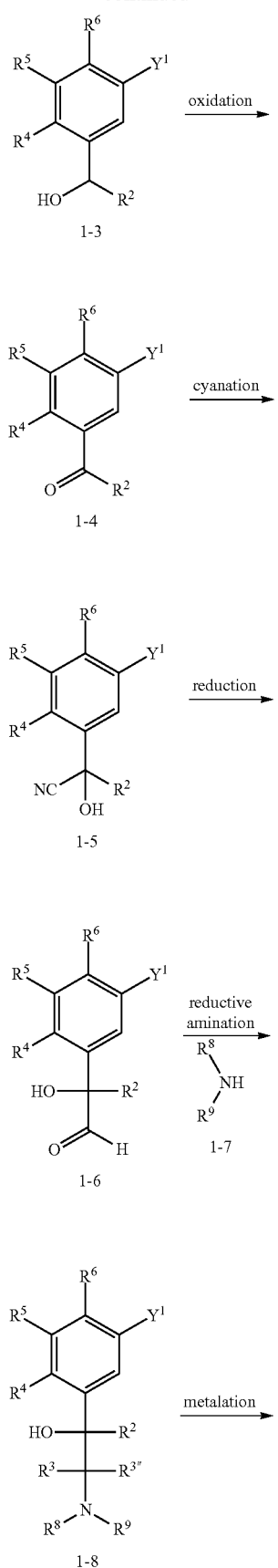

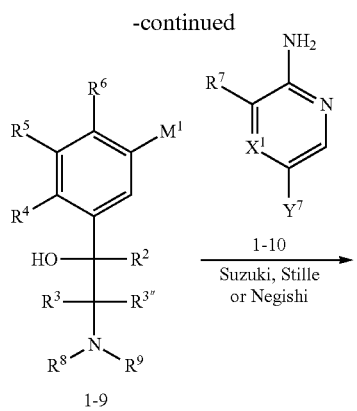

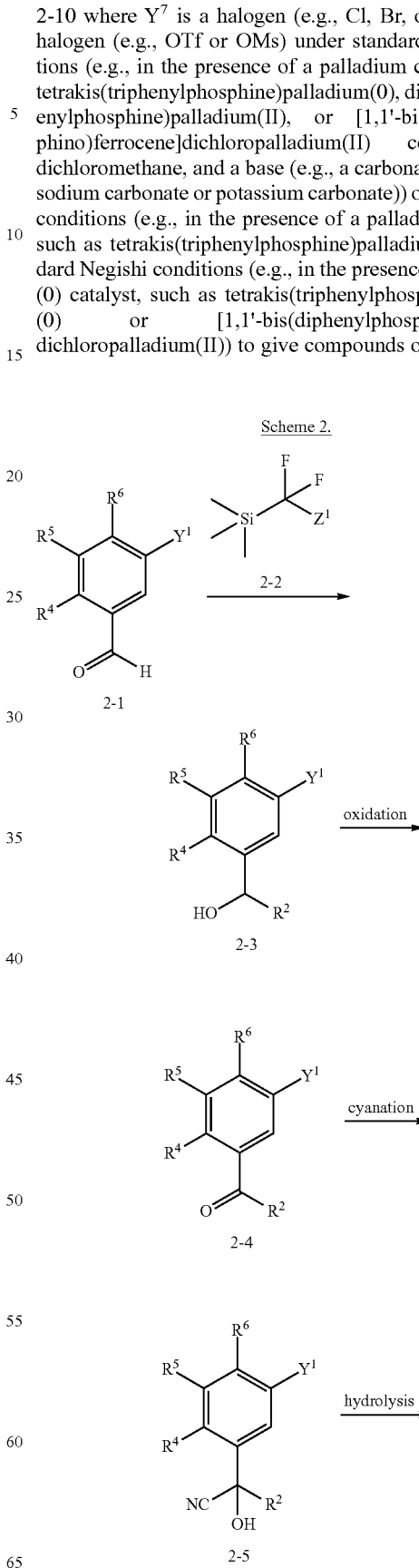

Scheme 2.

2-10 where $Y^7$ is a halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium (0) catalyst, such as tetrakis(triphenylphosphine)palladium (0) or [1,1'-bis(diphenylphosphino)ferrocene] dichloropalladium(II)) to give compounds of Formula (IV).

Compounds of Formula (IV) can be prepared as shown in Scheme 2. Suitable starting materials 2-1, where $Y^1$ is a halogen (e.g., Cl, Br, or I) or pseudohalogen (e.g., OTf or OMs), can be converted to secondary alcohol 2-3 with silane 2-2 where $Z^1$ is a halogen (e.g., F or Br) under standard conditions (e.g., in the presence of TBAF or PPh$_3$ and DMPU). In some instances $Z^1$ can be H wherein a CHF$_2$ group ($R^2$) can be formed. Oxidation of secondary alcohol 2-3 under standard conditions (e.g., Swern oxidation or Dess-Martin periodinane) can give ketone 2-4. Ketone 2-4 can be converted to cyanohydrin 2-5 under standard conditions (e.g., in the presence of KCN, TMSCN, and 18-crown-6). Cyanohydrin 2-5 can be converted to carboxylic acid 2-6 under standard acidic hydrolysis conditions (e.g., HCl or HBr in water (Org. Syn. Coll. Vol. 1 1941, 289 and 131)) or standard basic hydrolysis conditions (e.g., NaOH in water (*Org. Syn. Coll. Vol.* 1 1941, 321)). Carboxylic acid 2-6 can be coupled with amine 2-7 under standard amide formation conditions (e.g., in the presence of a coupling reagent, such as HATU, and amine, such as diisopropylethylamine or by conversion of acid 2-6 to the acid chloride (e.g., with oxalyl chloride) and condensing with amine 2-7) to give amide 2-8. Alternatively, cyanohydrin 2-5 can be hydrolysed directly to primary amide 2-8 (where $R^8$ and $R^9$ are hydrogen) with concentrated HCl and HCl gas (*J. Med. Chem.* 2003, 46, 2494-2501).

The yl group of 2-8 can be converted to an appropriately substituted metal 2-9 (e.g., $M^1$ is B(OH)$_2$, Bpin, BF$_3$K, Sn(Bu)$_3$, or Zn) under standard conditions (e.g., in the presence of a diboron reagent such as bis(pinacolato)diboron, a palladium catalyst, such as dichlorobis(triphenylphosphine)palladium(II) or [1,1'-bis(diphenylphosphino)ferrocene]dichloropalladium(II) complex with dichloromethane, and a base, such as potassium acetate) and then coupled to

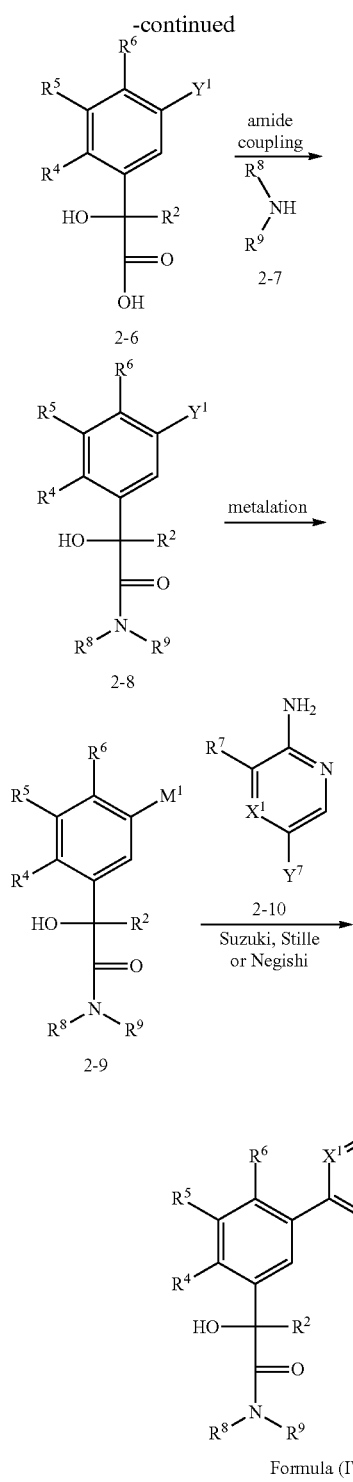

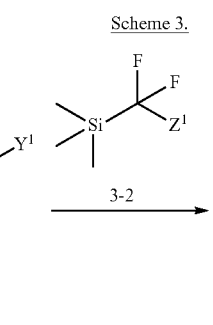

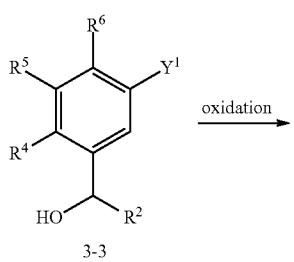

can be converted to cyanohydrin 3-5 under standard conditions (e.g., in the presence of KCN, TMSCN, and 18-crown-6). Cyanohydrin 3-5 can be converted to aldehyde 3-6 upon reduction (e.g., DIBAL-H (for a review see *Synthesis* 1975, 10, 617-630)). Aldehyde 3-6 can be converted to amine 3-8 under standard reductive amination conditions with amine 3-7 and an appropriate reducing agent (e.g., sodium borohydride, sodium triacetoxyborohydride, or sodium cyanoborohydride). Alternatively, cyanohydrin 3-5 can be reduced directly to amine 3-8 (where $R^8$ and $R^9$ are hydrogen) under standard conditions (e.g., $LiAlH_4$ in $Et_2O$).

The $Y^1$ group of 3-8 can be converted to an appropriately substituted metal 3-9 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichlorobis(triphenylphosphine)palladium(II) or [1,1'-bis(diphenylphosphino)ferrocene]dichloropalladium(II) complex with dichloromethane, and a base, such as potassium acetate) and then coupled to 3-10 where $Y^7$ is a halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium (0) catalyst, such as tetrakis(triphenylphosphine)palladium (0) or [1,1'-bis(diphenylphosphino)ferrocene] dichloropalladium(II)) to give 3-11. Amine 3-11 can be coupled with carboxylic acid 3-12 under standard amide formation conditions (e.g., in the presence of a coupling reagent, such as HATU, and amine, such as diisopropylethylamine) to give compounds of Formula (VII).

Scheme 3.

Compounds of Formula (VII) can be prepared as shown in Scheme 3. Suitable starting materials 3-1, where $Y^1$ is a halogen (e.g., Cl, Br, or I) or pseudohalogen (e.g., OTf or OMs), can be converted to secondary alcohol 3-3 with silane 3-2 where $Z^1$ is a halogen (e.g., F or Br) under standard conditions (e.g., in the presence of TBAF or $PPh_3$ and DMPU). In some instances $Z^1$ can be H wherein a $CHF_2$ group ($R^2$) can be formed. Oxidation of secondary alcohol 3-3 under standard conditions (e.g., Swern oxidation or Dess-Martin periodinane) can give ketone 3-4. Ketone 3-4

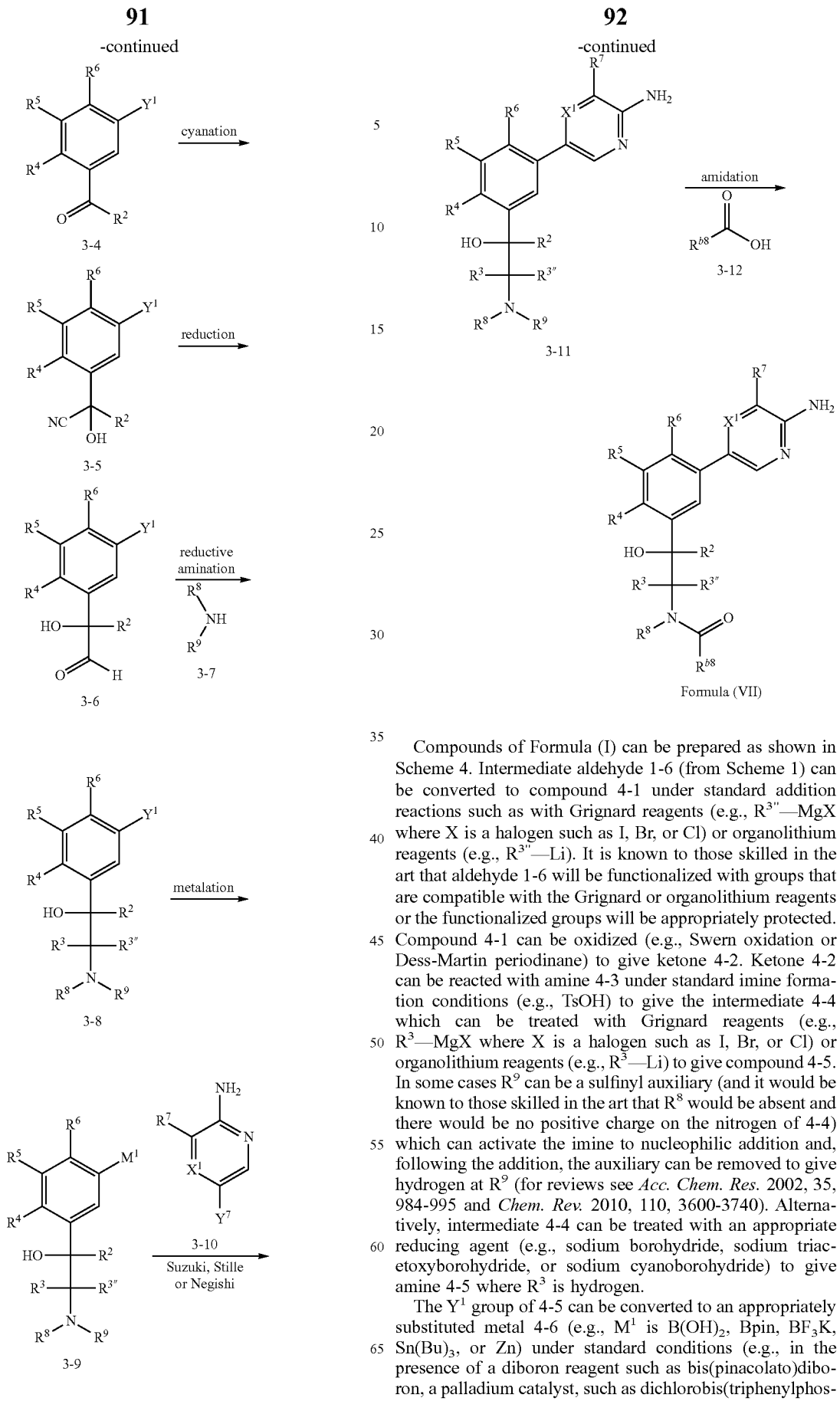

Compounds of Formula (I) can be prepared as shown in Scheme 4. Intermediate aldehyde 1-6 (from Scheme 1) can be converted to compound 4-1 under standard addition reactions such as with Grignard reagents (e.g., $R^{3''}$—MgX where X is a halogen such as I, Br, or Cl) or organolithium reagents (e.g., $R^{3''}$—Li). It is known to those skilled in the art that aldehyde 1-6 will be functionalized with groups that are compatible with the Grignard or organolithium reagents or the functionalized groups will be appropriately protected. Compound 4-1 can be oxidized (e.g., Swern oxidation or Dess-Martin periodinane) to give ketone 4-2. Ketone 4-2 can be reacted with amine 4-3 under standard imine formation conditions (e.g., TsOH) to give the intermediate 4-4 which can be treated with Grignard reagents (e.g., $R^3$—MgX where X is a halogen such as I, Br, or Cl) or organolithium reagents (e.g., $R^3$—Li) to give compound 4-5. In some cases $R^9$ can be a sulfinyl auxiliary (and it would be known to those skilled in the art that $R^8$ would be absent and there would be no positive charge on the nitrogen of 4-4) which can activate the imine to nucleophilic addition and, following the addition, the auxiliary can be removed to give hydrogen at $R^9$ (for reviews see *Acc. Chem. Res.* 2002, 35, 984-995 and *Chem. Rev.* 2010, 110, 3600-3740). Alternatively, intermediate 4-4 can be treated with an appropriate reducing agent (e.g., sodium borohydride, sodium triacetoxyborohydride, or sodium cyanoborohydride) to give amine 4-5 where $R^3$ is hydrogen.

The $Y^1$ group of 4-5 can be converted to an appropriately substituted metal 4-6 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichlorobis(triphenylphosphine)palladium(II) or [1,1'-bis(diphenylphosphino)ferrocene]dichloropalladium(II) complex with dichloromethane, and a base, such as potassium acetate) and then coupled to 4-7 where $Y^7$ is a halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium (0) catalyst, such as tetrakis(triphenylphosphine)palladium (0) or [1,1'-bis(diphenylphosphino)ferrocene] dichloropalladium(II)) to give compounds of Formula (I).

Scheme 4.

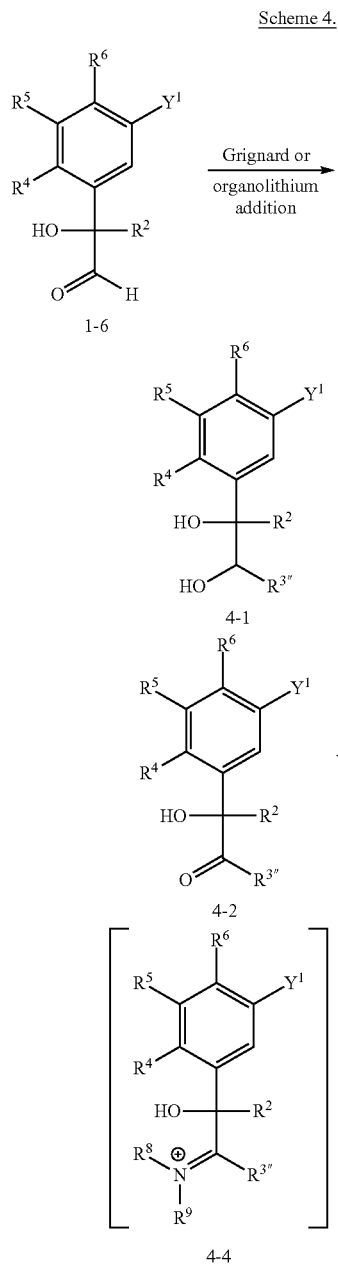

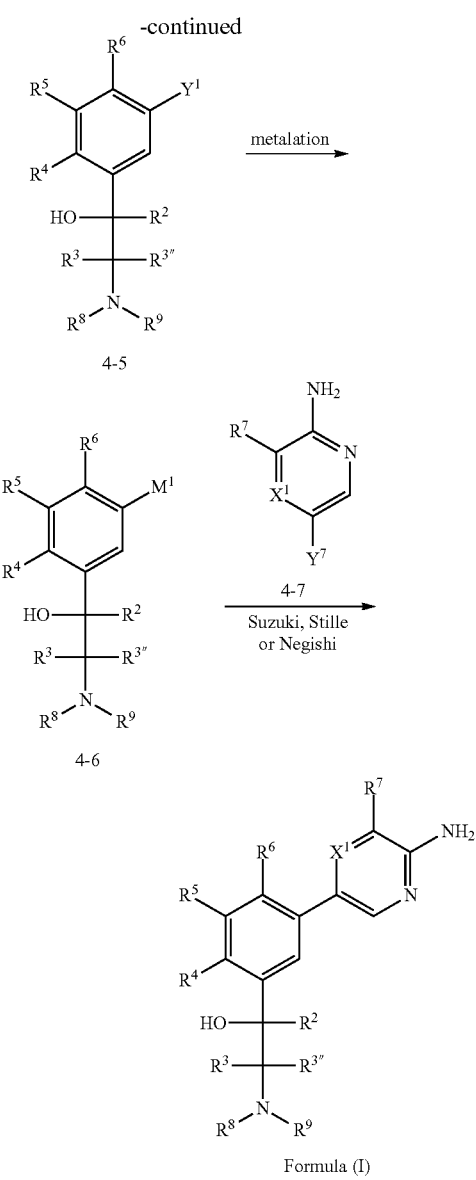

Compounds of Formula (IV) can be prepared as shown in Scheme 5. Suitable starting materials 5-1, where yl and $Y^8$ are independently a halogen (e.g., Cl, Br, or I) or pseudohalogen (e.g., OTf or OMs), can be converted to an appropriately substituted metal 5-2 (e.g., $M^2$ is $B(OH)_2$, Bpin, $BF_3K$, $Sn(Bu)_3$, or Zn) under standard conditions (e.g., in the presence of a diboron reagent such as bis(pinacolato) diboron, a palladium catalyst, such as [1,1'-bis(diphenylphosphino)ferrocene]dichloropalladium(II) complex with dichloromethane, and a base, such as potassium acetate) and then coupled to 5-3 where $Y^6$ is halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(O) or dichlorobis(triphenylphosphine)palladium(II), and a base (e.g., a carbonate base, such as sodium carbonate or potassium carbonate)) or standard Stille conditions (e.g., in the presence of a palladium(0) catalyst, such as tetrakis (triphenylphosphine)palladium(0)), or standard Negishi conditions (e.g., in the presence of a palladium(0) catalyst, such as tetrakis(triphenylphosphine)palladium(0) or [1,1'- bis(diphenylphosphino)ferrocene]dichloropalladium(II)) to give compound 5-4. Intermediate 5-4 can be converted to diol-containing intermediate 5-5 by exposure to reagents for dihydroxylation (e.g., AD-mix α or AD-mix β or osmium tetroxide and a re-oxidant such as N-methylmorpholine-N-oxide). Under standard conditions (e.g., in the presence of a transition metal catalyst, such as platinum on carbon, in the presence of an oxygen source, such as air), diol 5-5 can be oxidized to give α-hydroxy carboxylic acid 5-6. Coupling of acid 5-6 with amine 5-7 using standard amide coupling conditions (e.g., formation of the acid chloride with an appropriate reagent, such as oxalyl chloride, and in situ quenching with amine 5-7) can afford amide 5-8.

The $Y^1$ group of 5-8 can be converted to an appropriately substituted metal 5-9 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron; a base, such as potassium acetate; a palladium catalyst, such as tris(dibenzylideneacetone)dipalladium(0); and optionally a ligand, such as 2-dicyclohexylphosphino-2',4',6'-triisopropylbiphenyl) and then coupled to 5-10 where $Y^7$ is a halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compounds of Formula (IV).

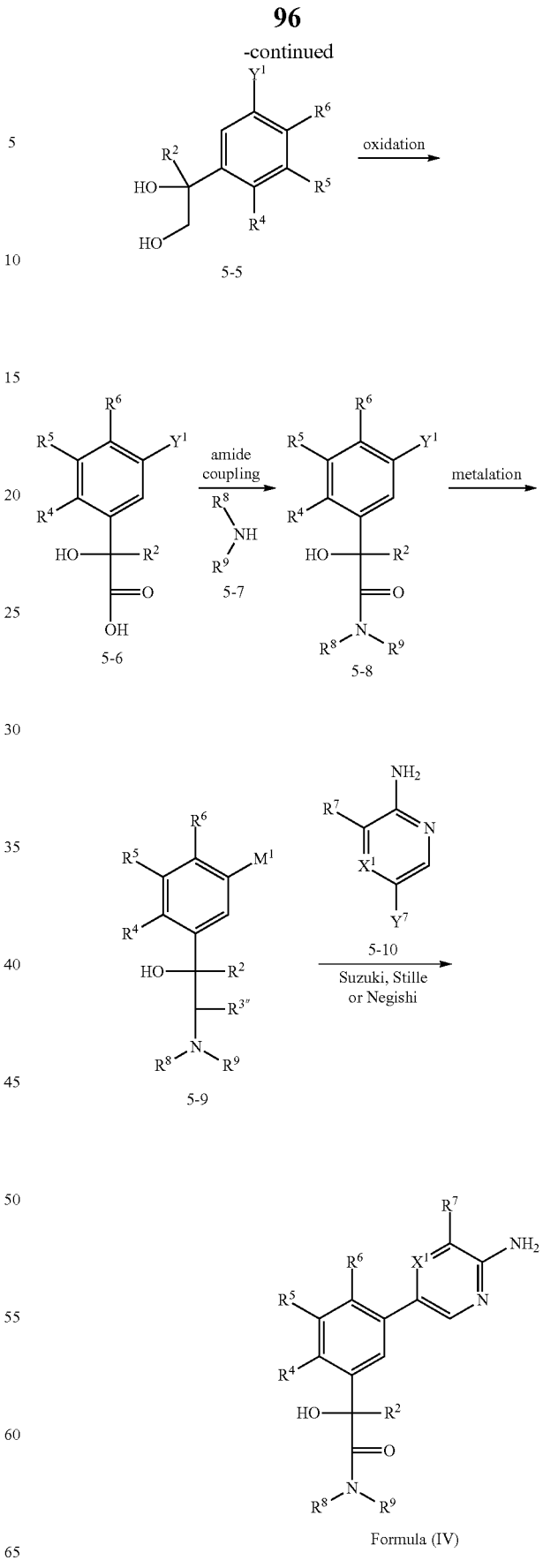

Compounds of Formula (I) can be prepared as shown in Scheme 6. Intermediate 1-9 (from Scheme 1) can be coupled to 6-1 where $Y^2$ and $Y^7$ are independently a halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compound 6-2. Compound 6-2 can be reacted with amines ($NHR^{c7}R^{d7}$) in the presence of CO gas along with an appropriate catalyst (e.g., [1,1'-bis(diphenylphosphino)ferrocene]dichloropalladium(II) complex with dichloromethane) to give 6-3 (compounds of Formula (I) where $R^7$ is $C(O)NR^{c7}R^{d7}$).

Compound 6-2 can also be reacted with alcohols ($R^{a7}OH$) in the presence of CO gas along with an appropriate catalyst (e.g., [1,1'-bis(diphenylphosphino)ferrocene]dichloropalladium(II) complex with dichloromethane) to give 6-4 (compounds of Formula (I) where $R^7$ is $C(O)OR^{a7}$).

Compound 6-4 can be converted to amides using standard amidation conditions (e.g., by reacting with amine $NHR^{c7}R^{d7}$ in the presence of $AlMe_3$) to give 6-5 (compounds of Formula (I) where $R^7$ is $C(O)NR^{c7}R^{d7}$). Or, compound 6-4 can be converted to amides under standard conditions for hydrolysis (e.g., LiOH), followed by coupling of the resulting acid with amine $NHR^{c7}R^{d7}$ using standard amide coupling conditions (e.g., in the presence of a coupling reagent such as HATU) to give 6-5 (compounds of Formula (I) where $R^7$ is $C(O)NR^{c7}R^{d7}$).

Alternatively, the $Y^2$ group of intermediate 6-2 (wherein $Y^2$ is Cl, Br or I) can be converted to a nitrile group via nucleophilic displacement with a cyanide source (e.g., heating in the presence of NaCN) or by coupling with a cyanide source under standard Negishi conditions (e.g., heating with $Zn(CN)_2$ in the presence of a palladium catalyst, such as tetrakis(triphenylphosphine)palladium(0) or [1,1'-bis(diphenylphosphino)ferrocene]dichloropalladium(II)) to afford cyano intermediate 6-6. Nitrile containing intermediate 6-6 can be converted to amides by hydrolysis (e.g., heating in the presence of aqueous acid or KOH in tBuOH) to give 6-5 (compounds of Formula (I) where $R^7$ is $C(O)NR^{c7}R^{d7}$).

Scheme 6.

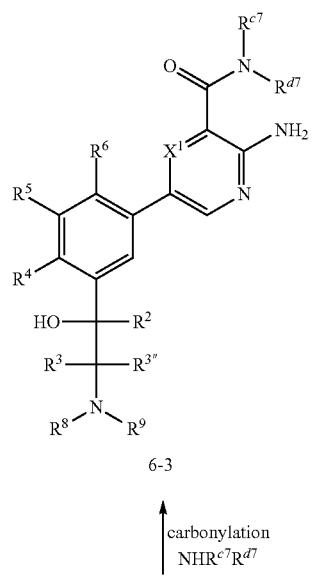

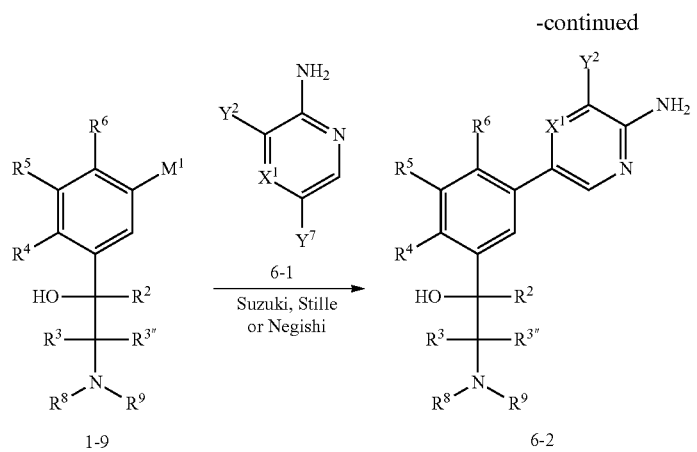
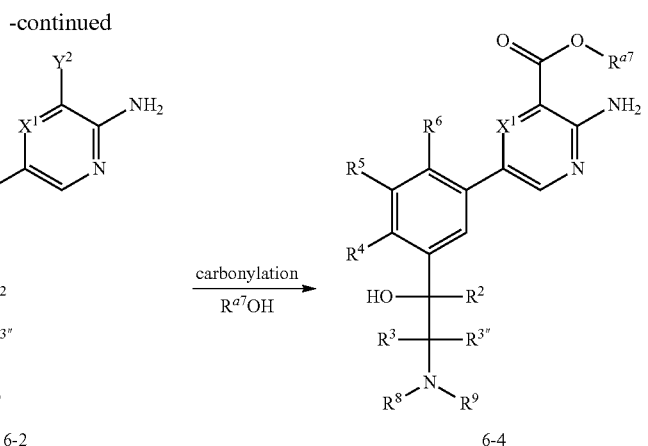
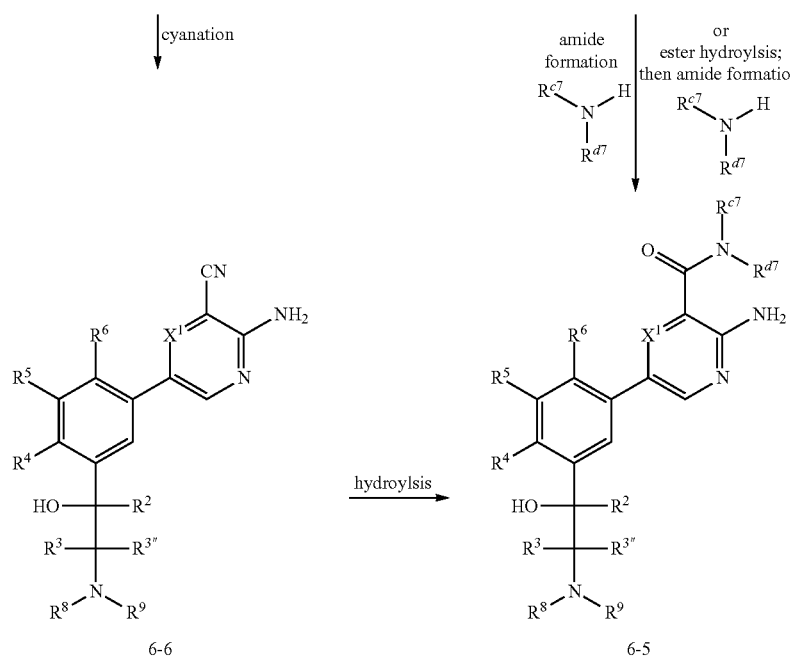

Compounds of Formula (IV) can be prepared as shown in Scheme 7. Intermediate 2-9 (from Scheme 2) can be coupled to 7-1 where $Y^2$ and $Y^7$ are independently a halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium (II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compound 7-2. Compound 7-2 can be reacted with amines (NHR$^{c7}$R$^{d7}$) in the presence of CO gas along with an appropriate catalyst (e.g., [1,1'-bis(diphenylphosphino)ferrocene]dichloropalladium(II) complex with dichloromethane) to give 7-3 (compounds of Formula (IV) where R$^7$ is C(O)NR$^{c7}$R$^{d7}$).

Compound 7-2 can also be reacted with alcohols (R$^{aT}$OH) in the presence of CO gas along with an appropriate catalyst (e.g., [1,1'-bis(diphenylphosphino)ferrocene]dichloropalladium(II) complex with dichloromethane) to give 7-4 (compounds of Formula (IV) where R$^7$ is C(O)OR$^{a7}$).

Compound 7-4 can be converted to amides using standard amidation conditions (e.g., by reacting with amine NHR$^{c7}$R$^{d7}$ in the presence of AlMe$_3$) to give 7-5 (compounds of Formula (IV) where R$^7$ is C(O)NR$^{c7}$R$^{d7}$). Or, compound 7-4 can be converted to amides under standard conditions for hydrolysis (e.g., LiOH), followed by coupling of the resulting acid with amine NHR$^{c7}$R$^{d7}$ using standard amide coupling conditions (e.g., in the presence of a coupling reagent such as HATU) to give 7-5 (compounds of Formula (IV) where R$^7$ is C(O)NR$^{c7}$R$^{d7}$).

Alternatively, the $Y^2$ group of intermediate 7-2 (wherein $Y^2$ is Cl, Br or I) can be converted to a nitrile group via nucleophilic displacement with a cyanide source (e.g., heating in the presence of NaCN) or by coupling with a cyanide source under standard Negishi conditions (e.g., heating with Zn(CN)$_2$ in the presence of a palladium catalyst, such as tetrakis(triphenylphosphine)palladium(0) or [1,1'-bis(diphenylphosphino)ferrocene]dichloropalladium(II)) to afford cyano intermediate 7-6. Nitrile containing intermediate 7-6 can be converted to amides by hydrolysis (e.g., heating in the presence of aqueous acid or KOH in tBuOH) to give 7-5 (compounds of Formula (IV) where $R^7$ is $C(O)NR^{c7}R^{d7}$).
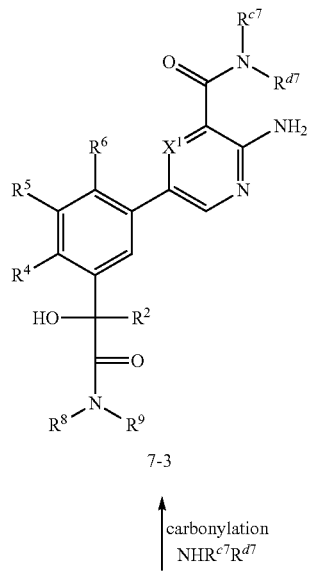
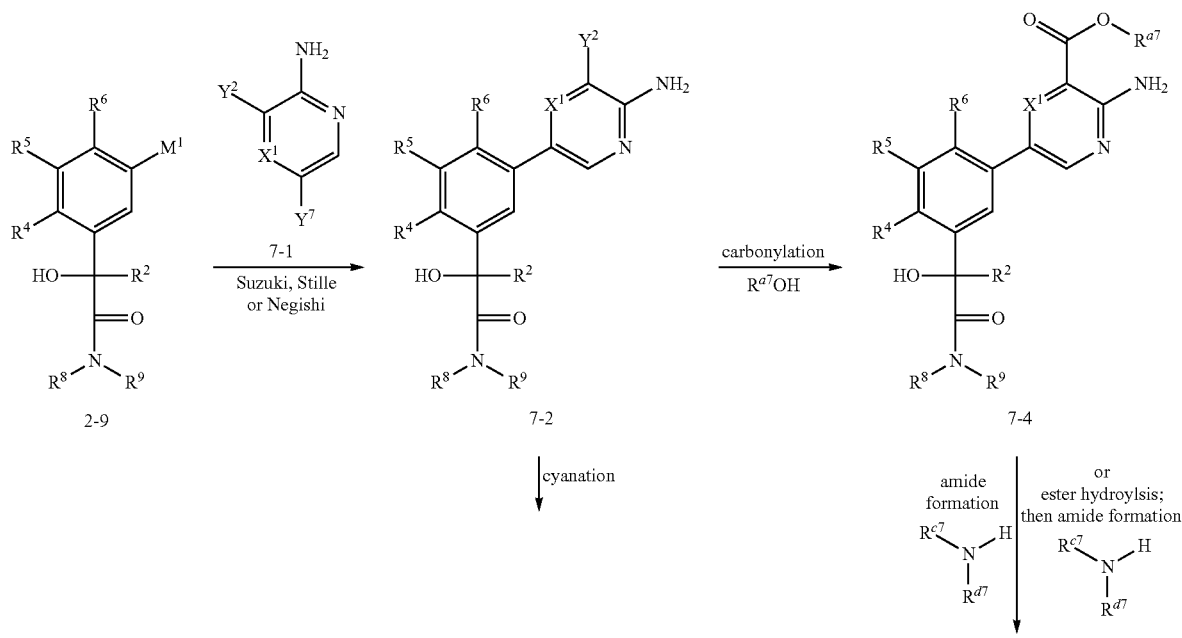

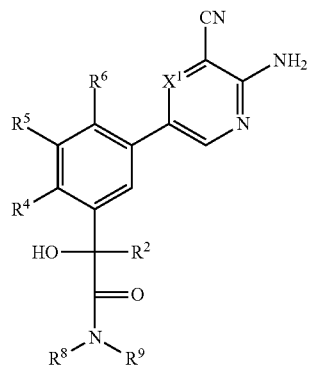

7-6

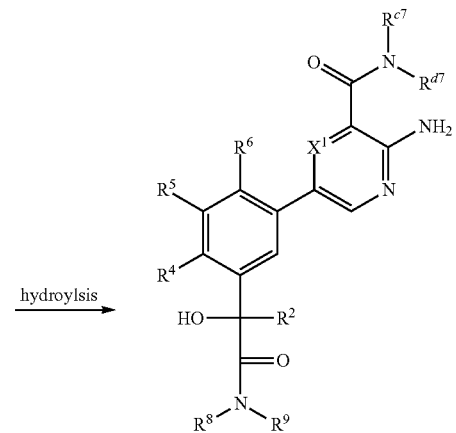

7-5

Compounds of Formula (VII) can be prepared as shown in Scheme 8. Intermediate 3-9 (from Scheme 3) where $R^8$ and/or $R^9$ are hydrogen can be coupled to 8-1 where $Y^2$ and $Y^7$ are independently a halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compound 8-2. Compound 8-2 can be reacted with amines (NHR$^{c7}$R$^{d7}$) in the presence of CO gas along with an appropriate catalyst (e.g., [1,1'-bis(diphenylphosphino)ferrocene]dichloropalladium(II) complex with dichloromethane) to give compound 8-3. Amine 8-3 can be coupled with carboxylic acid 8-4 under standard amide formation conditions (e.g., in the presence of a coupling reagent, such as HATU, and amine, such as diisopropylethylamine) to give 8-5 (compounds of Formula (VII) where $R^7$ is C(O)NR$^{c7}$R$^{d7}$).

Compound 8-2 can also be reacted with alcohols (R$^{a7}$OH) in the presence of CO gas along with an appropriate catalyst (e.g., [1,1'-bis(diphenylphosphino)ferrocene]dichloropalladium(II) complex with dichloromethane) to give compound 8-6. Amine 8-6 can be coupled with carboxylic acid 8-7 under standard amide formation conditions (e.g., in the presence of a coupling reagent, such as HATU, and amine, such as diisopropylethylamine) to give 8-8 (compounds of Formula (VII) where $R^7$ is C(O)OR$^{a7}$).

Compound 8-6 can be converted to amides using standard amidation conditions (e.g., by reacting with amine NHR$^{c7}$R$^{d7}$ in the presence of AlMe$_3$) to give compound 8-9. Or, compound 8-6 can be converted to amides under standard conditions for hydrolysis (e.g., LiOH), followed by coupling of the resulting acid with amine NHR$^{c7}$R$^{d7}$ using standard amide coupling conditions (e.g., in the presence of a coupling reagent such as HATU) to give compound 8-9. Amine 8-9 can be coupled with carboxylic acid 8-7 under standard amide formation conditions (e.g., in the presence of a coupling reagent, such as HATU, and amine, such as diisopropylethylamine) to give 8-10 (compounds of Formula (VII) where $R^7$ is C(O)NR$^{c7}$R$^{d7}$).

Alternatively, the $Y^2$ group of intermediate 8-2 (wherein $Y^2$ is Cl, Br or I) can be converted to a nitrile group via nucleophilic displacement with a cyanide source (e.g., heating in the presence of NaCN) or by coupling with a cyanide source under standard Negishi conditions (e.g., heating with Zn(CN)$_2$ in the presence of a palladium catalyst, such as tetrakis(triphenylphosphine)palladium(0) or [1,1'-bis(diphenylphosphino)ferrocene]dichloropalladium(II)) to afford cyano intermediate 8-11.

Nitrile containing intermediate 8-11 can be converted to amides by hydrolysis (e.g., heating in the presence of aqueous acid or KOH in tBuOH) to give compound 8-9. Amine 8-9 can be coupled with carboxylic acid 8-7 under standard amide formation conditions (e.g., in the presence of a coupling reagent, such as HATU, and amine, such as diisopropylethylamine) to give 8-10 (compounds of Formula (VII) where $R^7$ is C(O)NR$^{c7}$R$^{d7}$).

Scheme 8.

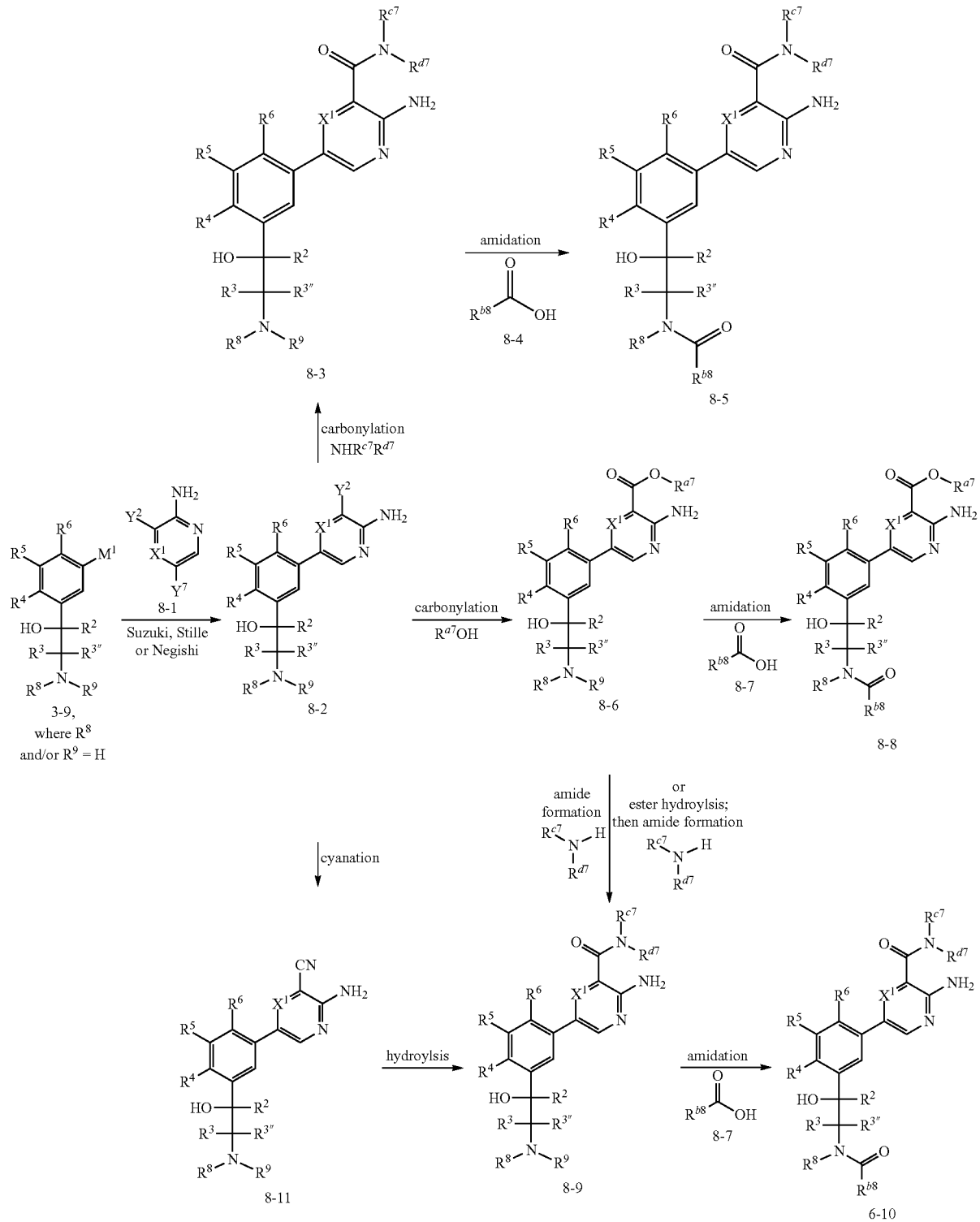

Compounds of Formula (I), (IV), and (VII) can also be prepared as shown in Scheme 9. Suitable starting materials 9-1 can be converted to amide 9-2 using standard amidation conditions (e.g., by reacting with amine $NHR^{c7}R^{d7}$ in the presence of $AlMe_3$). Alternatively, ester 9-1 can be converted to amide 9-2 under standard conditions for hydrolysis (e.g., LiOH), followed by coupling of the resulting acid with amine $NHR^{c7}R^{d7}$ using standard amide coupling conditions (e.g., in the presence of a coupling reagent such as HATU). Nitrile containing starting materials 9-3 can also be converted to amide 9-2 by hydrolysis (e.g., heating in the presence of aqueous acid or KOH in tBuOH). Compound 9-2 where $Y^7$ is a halogen (e.g., Cl, Br, or I) or pseudohalogen (e.g., OTf or OMs) can be coupled with intermediate 1-9 (from Scheme 1) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give 9-4 (compounds of Formula (I) where $R^7$ is C(O)NR$^{c7}$R$^{d7}$).

Compound 9-2 where $Y^7$ is a halogen (e.g., Cl, Br, or I) or pseudohalogen (e.g., OTf or OMs) can also be coupled with intermediate 2-9 (from Scheme 2) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give 9-5 (compounds of Formula (IV) where $R^7$ is C(O)NR$^{c7}$R$^{d7}$).

Compound 9-2 where $Y^7$ is a halogen (e.g., Cl, Br, or I) or pseudohalogen (e.g., OTf or OMs) can also be coupled with intermediate 3-9 (from Scheme 3) where $R^8$ and/or $R^9$ are hydrogen under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compound 9-6. Amine 9-6 can be coupled with carboxylic acid 9-7 under standard amide formation conditions (e.g., in the presence of a coupling reagent, such as HATU, and amine, such as diisopropylethylamine) to give 9-8 (compounds of Formula (VII) where $R^7$ is C(O)NR$^{c7}$R$^{d7}$).

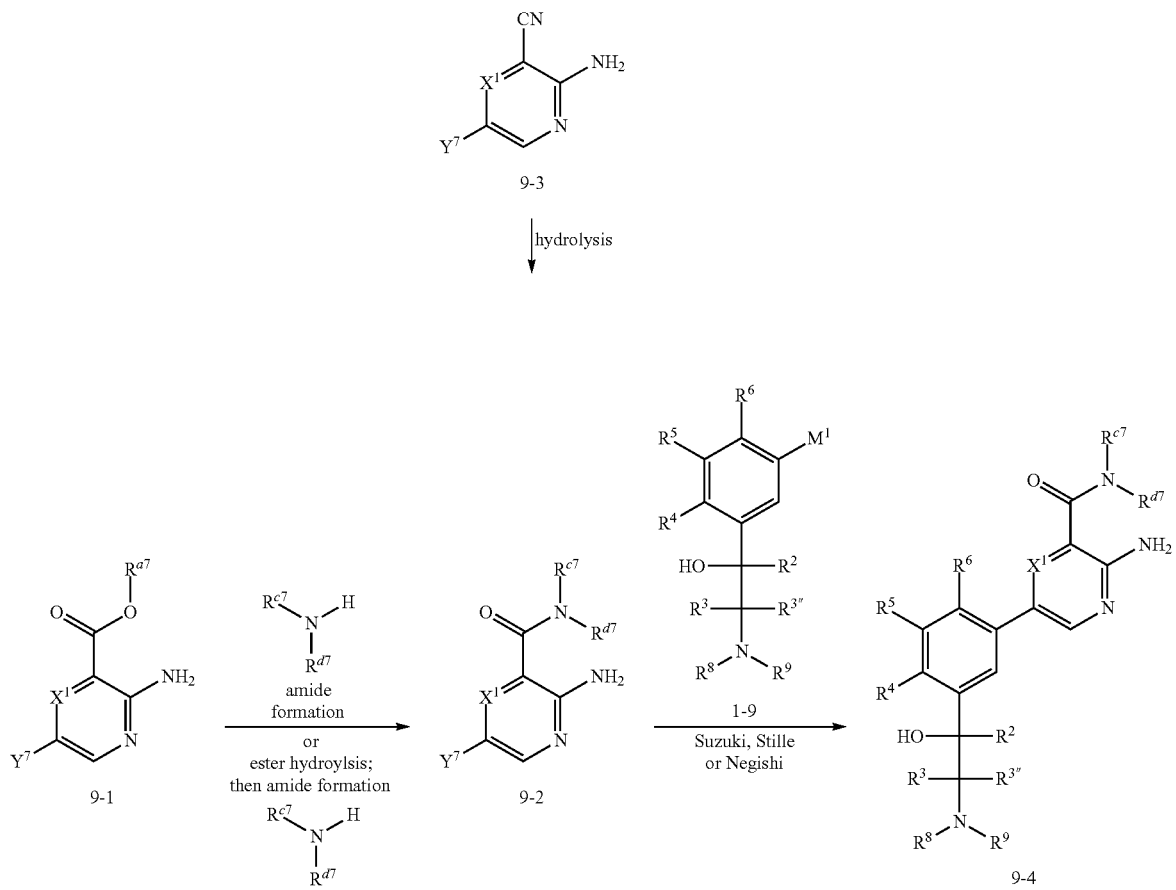

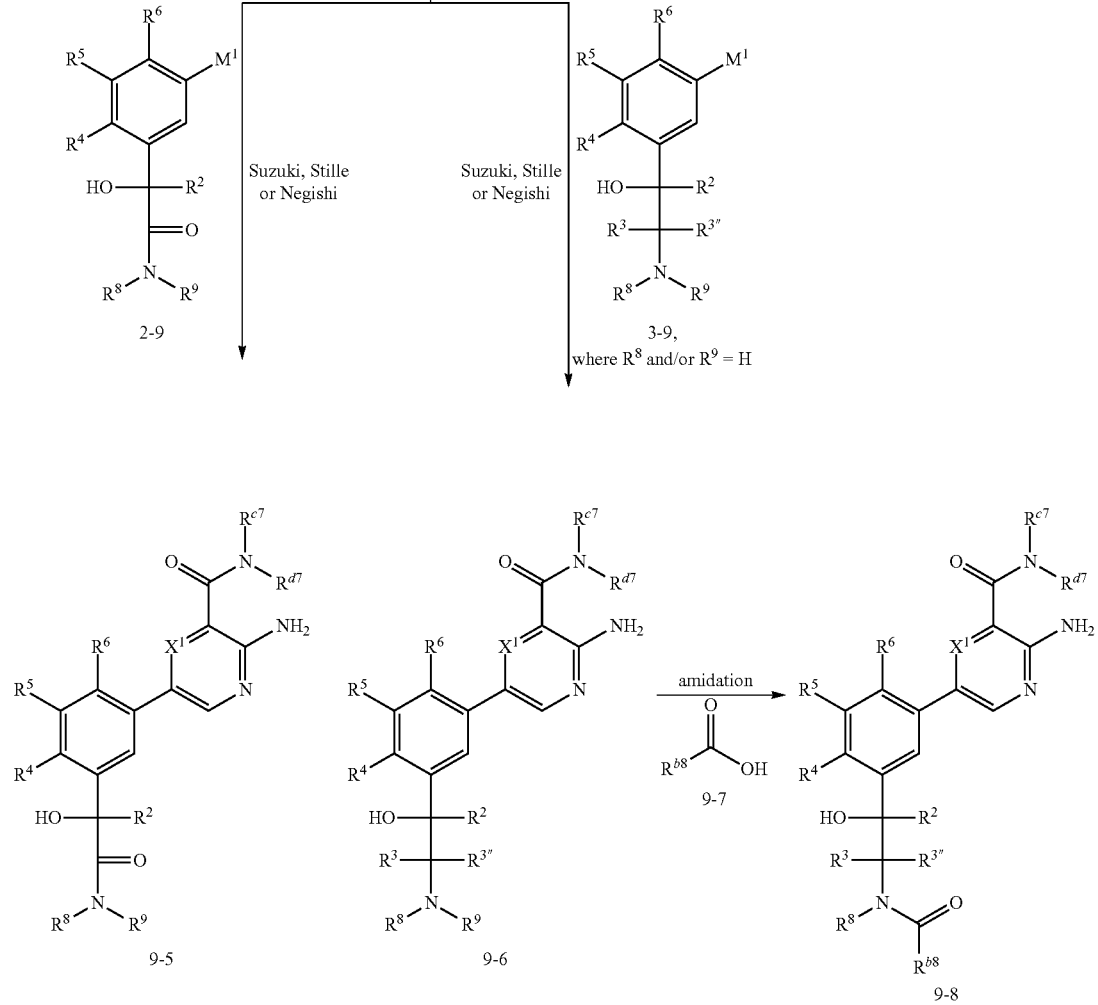

Compounds of Formula (I) can be prepared as shown in Scheme 10. Suitable starting materials 10-1, where $Y^2$ is a halogen (e.g., Cl, Br, or I) or pseudohalogen (e.g., OTf or OMs), can be coupled with an appropriately substituted alkyne using standard cross-coupling reactions, such as Sonogashira conditions (e.g., in the presence of a palladium catalyst, such as tetrakis(triphenylphosphine)palladium(0), dichlorobis(triphenylphosphine)palladium(II), or [1,1'-bis (diphenylphosphino)ferrocene] dichloropalladium(II) complex with dichloromethane, in the presence or absence of a copper (I) catalyst (e.g. CuI) and a base (e.g., triethylamine or potassium carbonate)), iron catalyzed cross coupling of alkynyl Grignard reagents (using procedures such as those outlined in C. W. Cheung, P. Ren, X. Hu, *Org. Lett.*, 2014, 16, 2566-2569), or $Pd_2(dba)_3$-$Ph_3P$-catalyzed Kumada-Corriu coupling (using procedures such as those outlined in L.-M. Yang, L.-F. Huang, T.-Y. Luh, *Org. Lett.*, 2004, 6, 1461-1463) to give 10-4 (compounds of Formula (I) where $R^7$ is alkynyl). Alternatively, 10-1 can be coupled with a silylacetylene to produce compounds of general structure 10-2. The silyl protecting group of 10-2 can be removed under standard conditions (e.g. heating with potassium carbonate in methanol) to afford 10-3. The terminal alkyne of 10-3 can be subsequently coupled with an aryl halide, heteroarylhalide, vinyl halide or pseudohalide (e.g., OTf or OMs) using standard cross coupling procedures, such as those described above (e.g. Sonogashira coupling) to give 10-4 (compounds of Formula (I) where $R^7$ is alkynyl). Alternatively, the terminal alkyne 10-3 can be deprotonated with an appropriate base (e.g. alkyllithium base, sodium amide, LDA) and condensed with a suitable electrophile (e.g. ketone, aldehyde, ester, activated alcohol (e.g. tosylate, mesylate), alkylhalide, epoxide, aziridine, sulfinimine, or Michael acceptor). This latter method may involve protection of the acidic protons present in 10-3 with the appropriate protecting group(s) (e.g. silyl protecting group for the alcohol or Boc protecting group for the heteroaromatic $NH_2$). In the case where the electrophile is a carbonyl, the concomitant alcohol can be eliminated using standard dehydroxylative conditions (e.g. treatment with triethylsilane and trifluoroacetic acid) or converted to an alkyl group using metal catalyzed dehydroxylative coupling procedures (such as those methods described in *J. Am. Chem. Soc.*, 2003, 125 (51), 15760-15761 or *Org. Lett.* 2015, 17, 3000-3003) to give 10-4 (compounds of Formula (I) where $R^7$ is alkynyl).

Scheme 10.

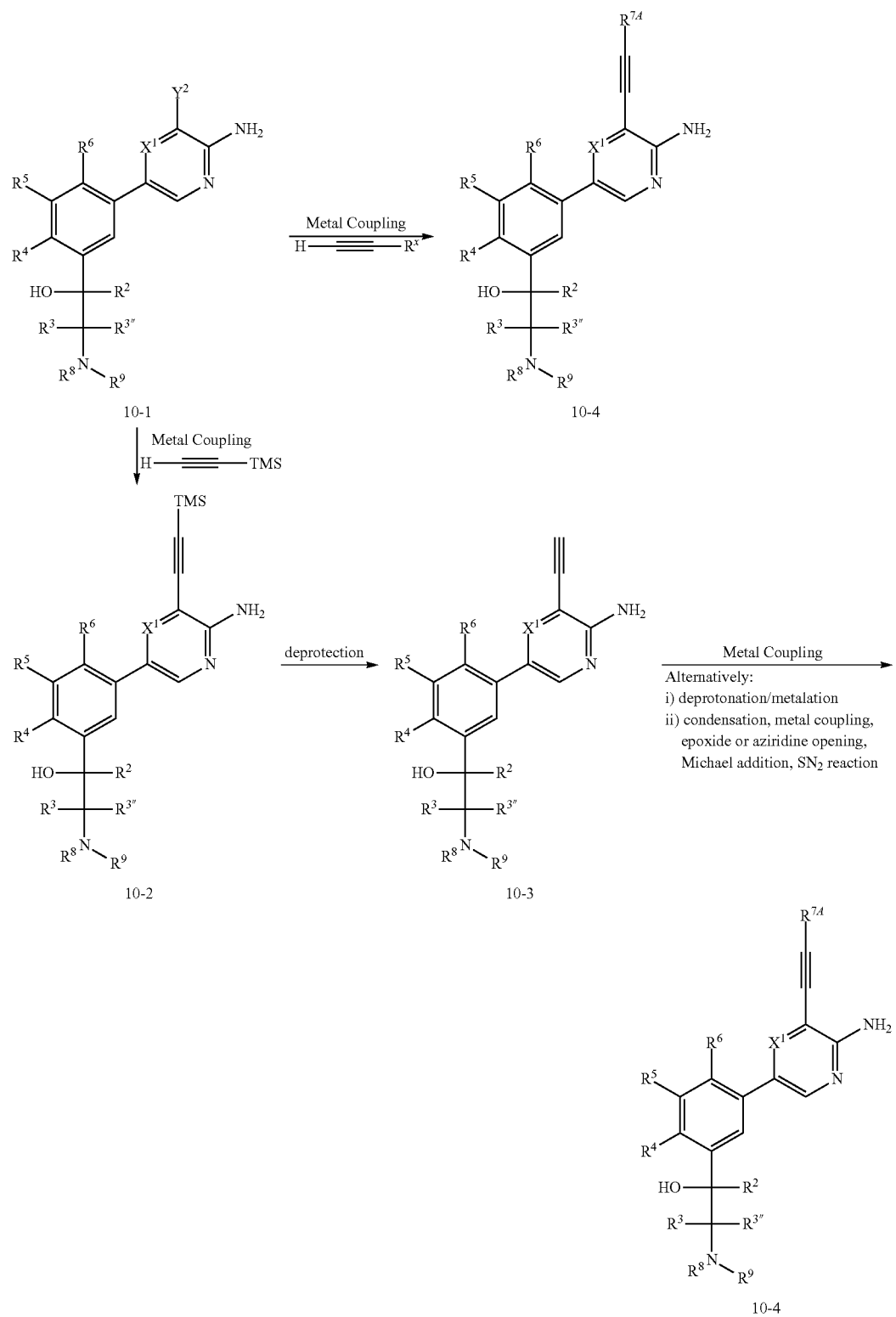

Compounds of Formula (I) can be prepared as shown in Scheme 11. Suitable starting materials 11-1 where X is a halogen (e.g., Cl, Br, or I) or pseudohalogen (e.g., OTf or OMs), can be coupled with an appropriately substituted alkyne using standard cross-coupling reactions, such as Sonogashira conditions (e.g., in the presence of a palladium catalyst, such as tetrakis(triphenylphosphine)palladium(0), dichlorobis(triphenylphosphine)palladium(II), or [1,1′-bis (diphenylphosphino)ferrocene] dichloropalladium(II) complex with dichloromethane, in the presence or absence of a copper (I) catalyst (e.g. CuI) and a base (e.g., triethylamine or potassium carbonate)), iron catalyzed cross coupling of alkynyl Grignard reagents (using procedures such as those outlined in C. W. Cheung, P. Ren, X. Hu, *Org. Lett.*, 2014, 16, 2566-2569), or Pd$_2$(dba)$_3$-Ph$_3$P-catalyzed Kumada-Corriu coupling (using procedures such as those outlined in L.-M. Yang, L.-F. Huang, T.-Y. Luh, *Org. Lett.*, 2004, 6, 1461-1463) to give 11-4. Alternatively, 11-1 can be coupled with a silylacetylene to produce compounds of general structure 11-2. The silyl protecting group of 11-2 can be removed under standard conditions (e.g. heating with potassium carbonate in methanol) to afford 11-3. The terminal alkyne of 11-3 can be subsequently coupled with an aryl halide, heteroarylhalide, vinyl halide or pseudohalide (e.g., OTf or OMs) using standard cross coupling procedures, such as those described above (e.g. Sonogashira coupling) to give 11-4. Alternatively, the terminal alkyne 11-3 can be deprotonated with an appropriate base (e.g. alkyllithium base, sodium amide, LDA) and condensed with a suitable electrophile (e.g. ketone, aldehyde, ester, activated alcohol (e.g. tosylate, mesylate), alkylhalide, epoxide, aziridine, sulfinimine, or Michael acceptor). In the case where the electrophile is a carbonyl, the concomitant alcohol can be eliminated using standard dehydroxylative conditions (e.g. treatment with triethylsilane and trifluoroacetic acid) or converted to an alkyl group using metal catalyzed dehydroxylative coupling procedures (such as those methods described in *J. Am. Chem. Soc.*, 2003, 125 (51), 15760-15761 or *Org. Lett.* 2015, 17, 3000-3003) to give 11-4.

Nucleophilic aromatic substitution of the chloride of 11-4 with an amine (e.g., NH$_3$, methylamine, 4-methoxybenzylamine, ammonium hydroxide, hydroxylamine, or alkoxyamine) can provide amine 11-5 wherein R is selected from hydrogen, alkyl, alkylaryl, hydroxyl, hydroxyl alkyl, or hydroxyl alkylaryl. The R group can be removed using standard conditions (e.g., treatment with acid, such as HCl or TFA for 11-5 wherein R=p-methoxybenzyl or tert-butyl) to liberate the free amino group (11-5, R=H). Compound 11-5 can be halogenated with suitable reagents, such as N-chlorosuccinimide, N-bromosuccinimide, or N-iodosuccinimide, to give halide 11-6 where Y$^7$ is a halo group (e.g., Cl, Br, or I). Intermediate 11-6 can be coupled with an appropriately substituted metal 11-7 (e.g., M$^1$ is B(OH)$_2$, Bpin, BF$_3$K, Sn(Bu)$_3$, or Zn) under standard Suzuki conditions (e.g., in the presence of a palladium catalyst, such as tetrakis(triphenylphosphine)palladium(0) or [1,1'-bis(diphenylphosphino)ferrocene]dichloropalladium (II) complex with dichloromethane and a base (e.g., a carbonate base, such as sodium carbonate or potassium carbonate)) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine) palladium(0) or [1,1'-bis(diphenylphosphino)ferrocene]dichloropalladium(II)) to give 11-8 (compounds of Formula (I) where R$^7$ is alkynyl).

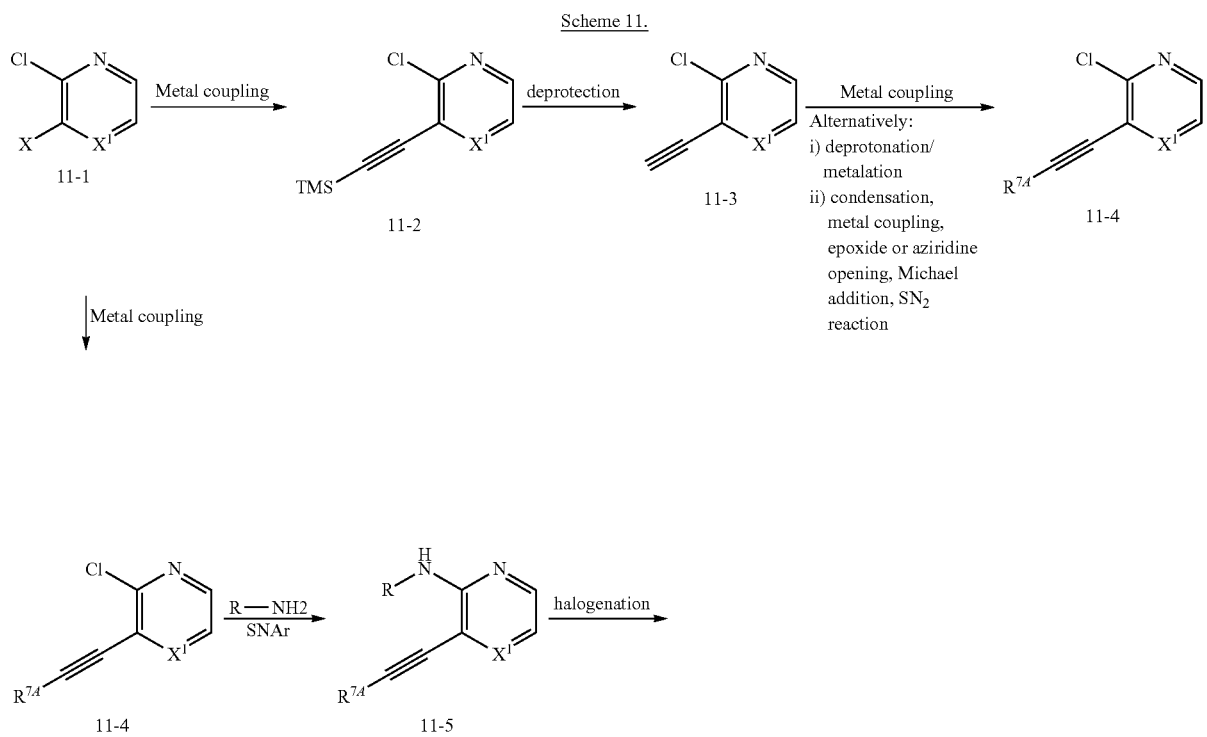

Scheme 11.

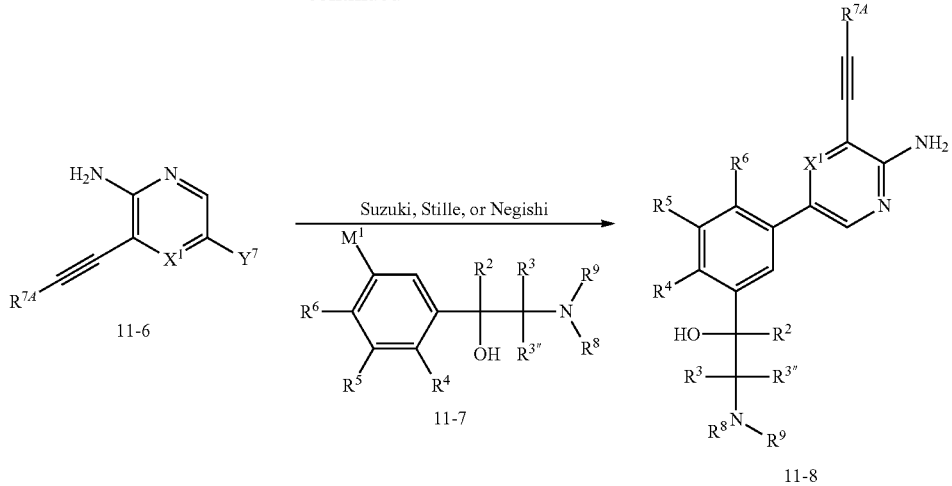

Compounds of Formula (I) can be prepared as shown in Scheme 12. Suitable starting materials 12-1, where $Y^2$ is a halogen (e.g., Cl, Br, or I) or pseudohalogen (e.g., OTf or OMs), can be coupled with a metalated alkene of general structure 12-2 (e.g., $M^1$ is $B(OH)_2$, Bpin, $BF_3K$, $Sn(Bu)_3$, or Zn) under standard Suzuki conditions (e.g., in the presence of a palladium catalyst, such as tetrakis(triphenylphosphine) palladium(0) or [1,1'-bis(diphenylphosphino)ferrocene]dichloropalladium (II) complex with dichloromethane and a base (e.g., a carbonate base, such as sodium carbonate or potassium carbonate)) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compounds of general structure 12-4 (compounds of Formula (I) where $R^7$ is alkenyl). Alternatively, a trisubstituted alkene of general structure 12-3 can be coupled with 12-1 using standard metal catalyzed reactions such as Heck coupling (e.g., in the presence of a palladium catalyst, such as palladium acetate or bis(dibenzylideneacetone)palladium and a base (e.g., a carbonate base, such as sodium carbonate or potassium carbonate in the presence or absence of a ligand (e.g. Dave-Phos, dppp, or TBAB)) to afford 12-4 (compounds of Formula (I) where $R^7$ is alkenyl). The alkene 12-4 can be reduced to afford alkane 12-5 (compounds of Formula (I) where $R^7$ is alkyl) under standard hydrogenation conditions known to one skilled in the art (e.g. hydrogenolysis in the presence of a metal catalyst (e.g. 10% Pd/C or Wilkinson's catalyst) under an atmosphere of hydrogen gas).

Scheme 12.

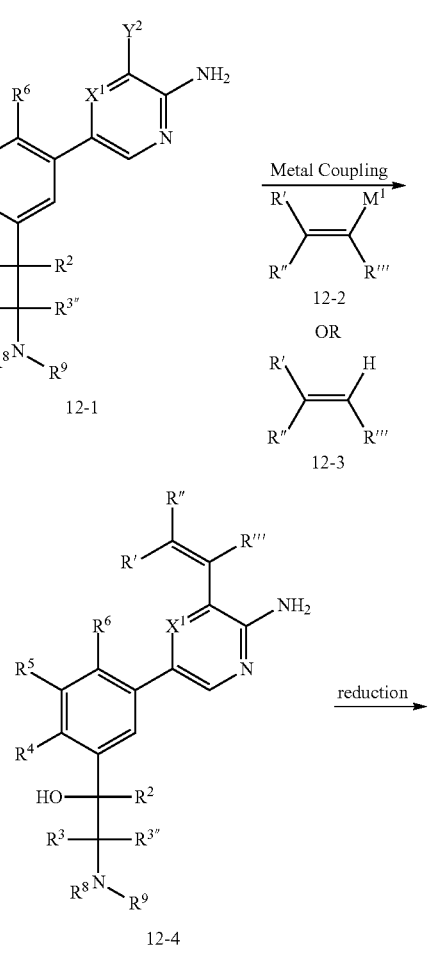

-continued

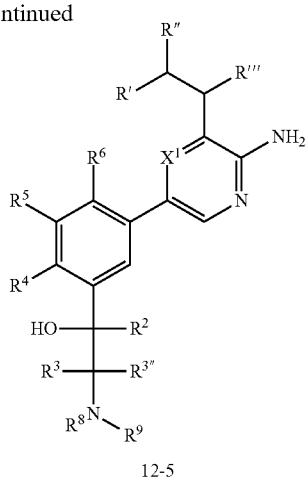

12-5

Compounds of Formula (I), (IV), and (VII) can also be prepared as shown in Scheme 13. Suitable starting materials 13-1 where $Y^2$ and $Y^7$ are independently a halogen (e.g., Cl, Br, or I) or pseudohalogen (e.g., OTf or OMs) can be coupled with intermediate 1-9 (from Scheme 1) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium (II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compound 13-2. Compound 13-2 can be coupled with an appropriate metal $R^7$-M (where M is an appropriately substituted metal, e.g. $B(OH)_2$, Bpin, $BF_3K$, $Sn(Bu)_3$, or Zn) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium (II) complex with dichloromethane, and a base (e.g., a carbonate base such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene] dichloropalladium (II)) to give compounds of Formula (I). Alternatively, compound 13-2 can be reacted with a nucleophile ($R^7$—H) under $S_NAr$ conditions (e.g., by heating in the presence of a carbonate base, such as $Cs_2CO_3$) to give compounds of Formula (I).

Suitable starting materials 13-1 where $Y^2$ and $Y^7$ are independently a halogen (e.g., Cl, Br, or I) or pseudohalogen (e.g., OTf or OMs) can be coupled with intermediate 2-9 (from Scheme 2) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis (triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compound 13-3. Compound 13-3 can be coupled with an appropriate metal $R^7$-M (where M is an appropriately substituted metal, e.g. $B(OH)_2$, Bpin, $BF_3K$, $Sn(Bu)_3$, or Zn) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium (II) complex with dichloromethane, and a base (e.g., a carbonate base such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compounds of Formula (IV). Alternatively, compound 13-3 can be reacted with a nucleophile ($R^7$—H) under $S_NAr$ conditions (e.g., by heating in the presence of a carbonate base, such as $Cs_2CO_3$) to give compounds of Formula (IV).

Suitable starting materials 13-1 where $Y^2$ and $Y^7$ are independently a halogen (e.g., Cl, Br, or I) or pseudohalogen (e.g., OTf or OMs) can be coupled with intermediate 3-9 (from Scheme 3) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis (triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compound 13-4. Compound 13-4 can be coupled with an appropriate metal $R^7$-M (where M is an appropriately substituted metal, e.g. $B(OH)_2$, Bpin, $BF_3K$, $Sn(Bu)_3$, or Zn) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium (II) complex with dichloromethane, and a base (e.g., a carbonate base such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene] dichloropalladium (II)) to give compound 13-5. Alternatively, compound 13-4 can be reacted with a nucleophile ($R^7$—H) under $S_NAr$ conditions (e.g., by heating in the presence of a carbonate base, such as $Cs_2CO_3$) to give compound 13-5. Amine 13-5 can be coupled with carboxylic acid 13-6 under standard amide formation conditions (e.g., in the presence of a coupling reagent, such as HATU, and amine, such as diisopropylethylamine) to give compounds of Formula (VII).

Scheme 13.
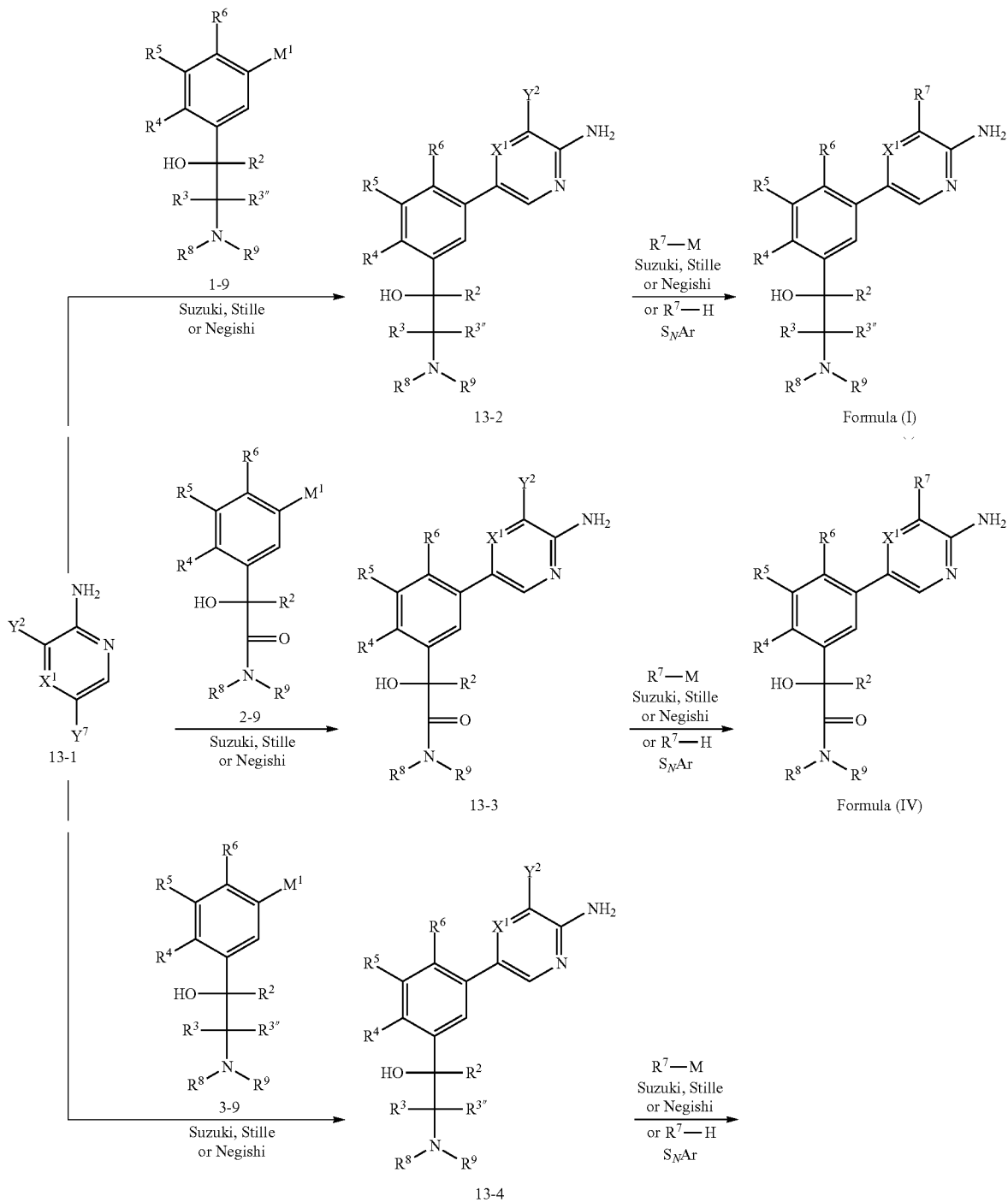

-continued

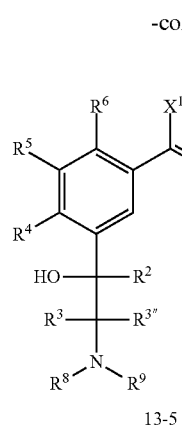 
13-5 amidation
$R^{b8}\text{COOH}$
13-6

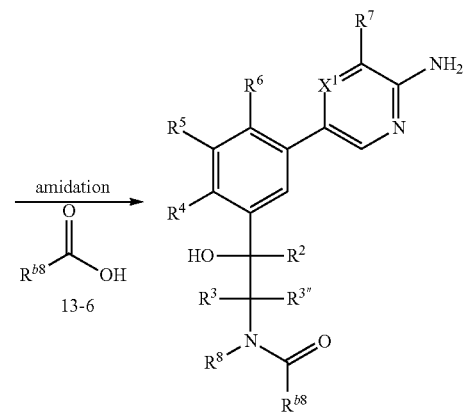
Formula (VII)

Compounds of Formula (I), (IV), and (VII) can also be prepared as shown in Scheme 14. Appropriate starting materials 14-1 can be coupled with an appropriately substituted metal R-M (e.g. M is $B(OH)_2$, Bpin, $BF_3K$, $Sn(Bu)_3$, Zn or ZnX (where X is a halogen such as iodide)) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II), and optionally in the presence of an additive such as copper(I) iodide) to give intermediate 14-2. Nucleophilic aromatic substitution of the chloride of 14-2 with amine 14-3 (e.g., $NH_3$) can provide amine 14-4 or with a substituted amine 14-3 (e.g., where R=p-methoxybenzyl) which after deprotection under standard conditions (e.g., TFA) can provide amine 14-4. Compound 14-4 can be halogenated with suitable reagents, such as N-chlorosuccinimide, N-bromosuccinimide, or N-iodosuccinimide, to give halide 14-5 where $Y^7$ is a halo group (e.g., Cl, Br, or I). Intermediate 14-5 can be coupled with intermediate 1-9 (from Scheme 1) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compounds of Formula (I).

Intermediate 14-5 can be coupled with intermediate 2-9 (from Scheme 2) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compounds of Formula (IV).

Intermediate 14-5 can be coupled with intermediate 3-9 (from Scheme 3) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compound 14-6. Amine 14-6 can be coupled with carboxylic acid 14-7 under standard amide formation conditions (e.g., in the presence of a coupling reagent, such as HATU, and amine, such as diisopropylethylamine) to give compounds of Formula (VII).

Scheme 14.
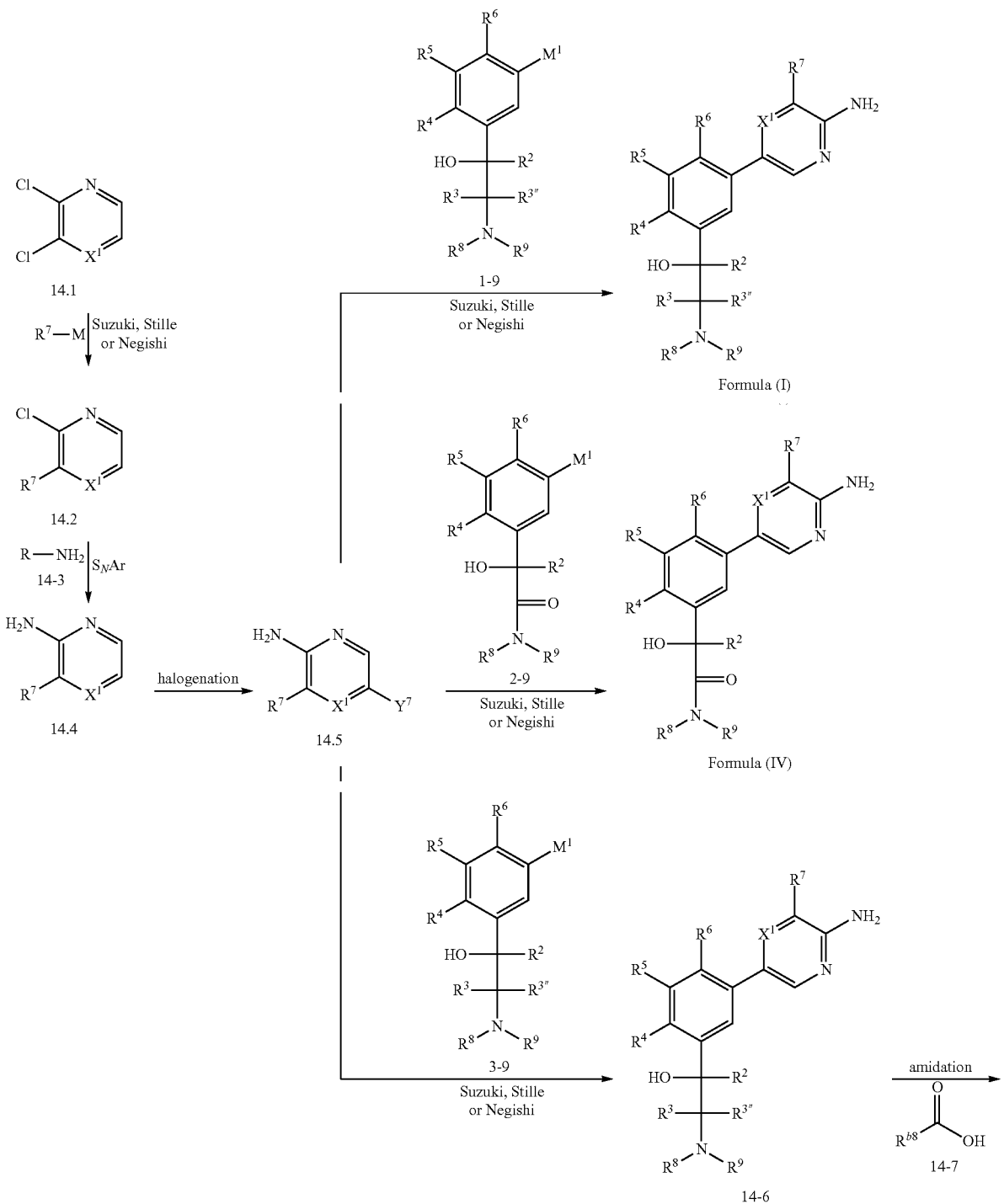

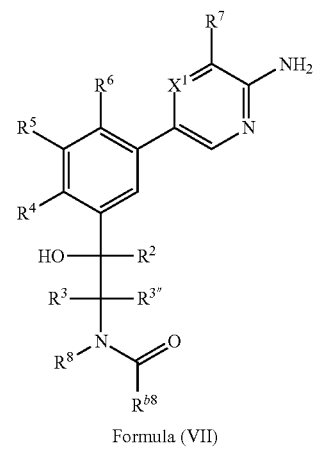

Formula (VII)

Compounds of Formula (I) can be prepared as shown in Scheme 15. Suitable starting materials 15-1, wherein $Y^2$ and $Y^7$ are suitable halogen atoms (e.g., Cl, Br, or I) or pseudohalogens (e.g., OTf or OMs), can be converted to intermediates 15-3 by coupling with an organozinc species formed from a suitable optionally protected halide 15-2 where $Y'''$ is a halogen (e.g., Cl, Br, or I) under standard Negishi conditions (e.g., in the presence of Zn (which can be activated by agents such as 1,2-dibromoethane and TMSCl) and in the presence of a suitable palladium catalyst (e.g., dichloro[1,1'-bis(diphenylphosphino)ferrocene]palladium (II) dichloromethane adduct) and copper (I)iodide. Intermediate 15-3 where $Y^7$ is a halogen (e.g., Cl, Br, or I) or pseudohalogen (e.g., OTf or OMs) can be coupled with an appropriately substituted metal 15-4 (e.g., $M^1$ is $B(OH)_2$, Bpin, $BF_3K$, $Sn(Bu)_3$, or Zn) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane and a base (e.g., a carbonate base, such as sodium carbonate or potassium carbonate)) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give compounds 15-5, which themselves may be compounds of Formula (I), or if protected (with a protecting group P, e.g., Boc), may be deprotected to afford compounds 15-6 using conditions suitable for removal of the protecting group which are also suitable in terms of compatibility with other functional groups that may be present in the molecule. Intermediates 15-6 may be optionally derivatized by reaction with an electrophile $R''$-LG (wherein LG is a leaving group such as halogen (e.g., F, Cl, Br, or I) or pseudohalogen (e.g., OTf or OMs), or a carboxylic acid activated by exposure to a coupling reagent (e.g., DCC, EDC or HATU)) in the presence of a base (e.g., diisopropylethylamine or triethylamine) to furnish compounds of Formula (I).

Scheme 15.

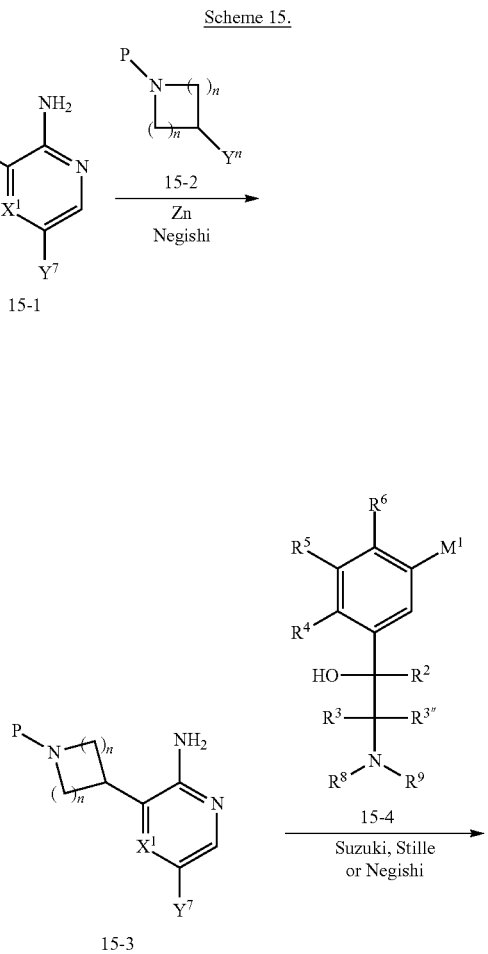

-continued

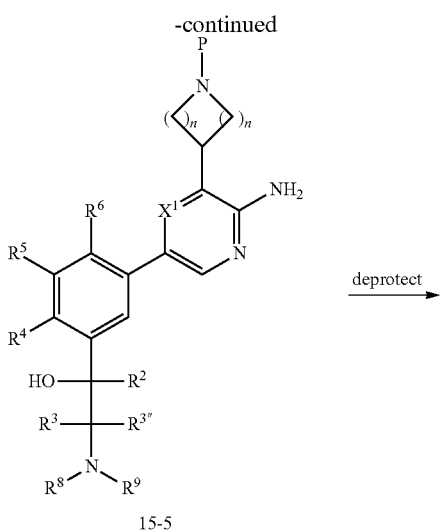

15-5

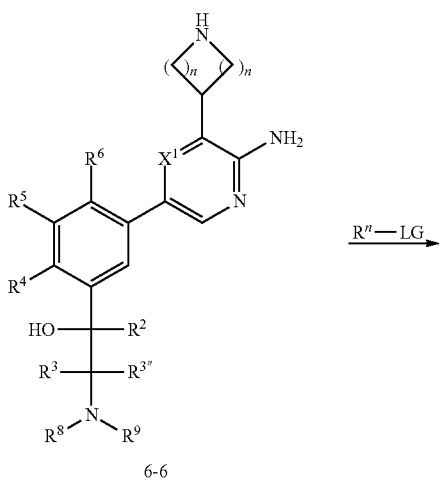

6-6

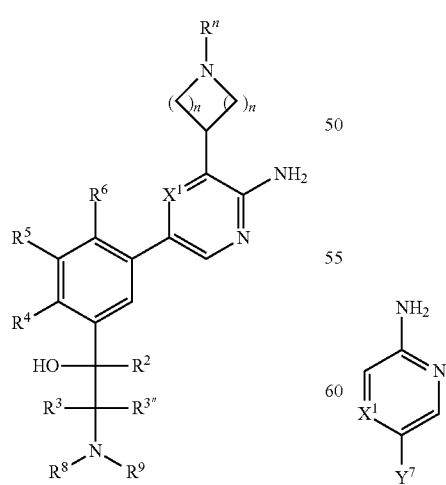

Formula (I)

Compounds of Formula (I) can be prepared as shown in Scheme 16. Suitable starting materials 16-1, wherein $Y^7$ is a halogen (e.g., Cl, Br, or I) or pseudohalogen (e.g., OTf or OMs), can be converted to intermediates 16-3 by coupling with an appropriately substituted metal 16-2 (e.g., $M^1$ is $B(OH)_2$, Bpin, $BF_3K$, $Sn(Bu)_3$, or Zn) under standard Suzuki conditions (e.g., in the presence of a palladium catalyst, such as tetrakis(triphenylphosphine)palladium(O), dichlorobis(triphenylphosphine)palladium(II), or [1,1'-bis(diphenylphosphino)ferrocene]dichloropalladium(II) complex with dichloromethane and a base (e.g., a carbonate base, such as sodium carbonate or potassium carbonate)) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)). Halogen-containing intermediate 16-4 can be prepared by reacting intermediate 16-3 with a reagent suitable for introducing the halogen $Y^2$ (e.g., N-halosuccinimide such as N-iodosuccinimide, N-bromosuccinimide or N-chlorosuccinimide). Intermediate 16-4 bearing a suitable halogen $Y^2$ (e.g., Cl, Br or I) can be coupled with an organozinc derived from a suitable starting material 16-5 wherein $Y^n$ is a suitable halogen (e.g., Br or I) under standard Negishi conditions (e.g., in the presence of Zn (which can be activated by agents such as 1,2-dibromoethane and TMSCl) and in the presence of a suitable palladium catalyst (e.g., [1,3-bis(2,6-diisopropylphenyl)imidazol-2-ylidene](3-chloropyridyl)palladium(II) dichloride)) to furnish compounds of Formula (I).

Scheme 16.

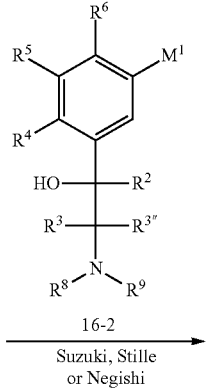

16-1

129

-continued

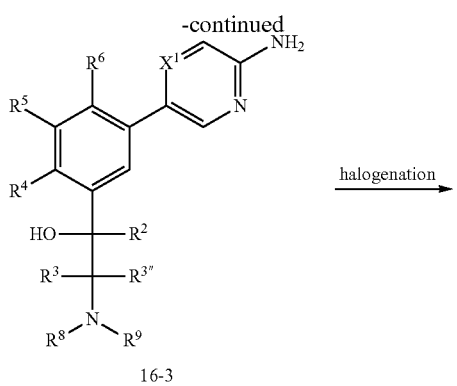

16-3

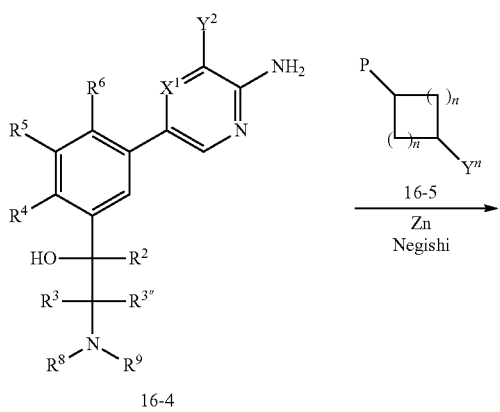

16-4

130

-continued

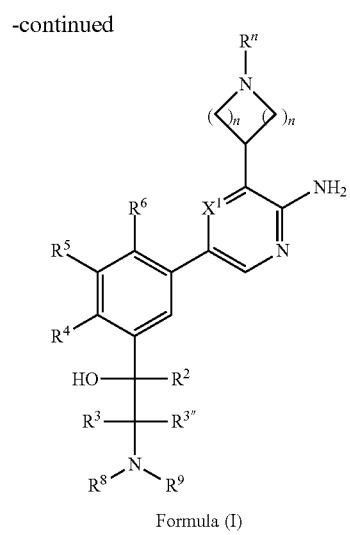

Formula (I)

Compounds of Formula (I) can be prepared as shown in Scheme 17. Intermediates 17-1 which contain an ester (e.g., $R^{n''}$ is methyl or ethyl) can be hydrolyzed by exposure to hydroxide base (e.g., LiOH, NaOH, KOH in water) and a co-solvent (e.g., THF, MeOH or EtOH) to furnish carboxylic acid intermediates 17-2. Carboxylic acid containing intermediates can be coupled with an amine 17-3 in the presence of an amide coupling reagent (e.g., DCC, EDC and HATU) and in the presence of a suitable base (e.g., diisopropylethylamine or triethylamine) to furnish compounds of Formula (I). Alternatively, ester containing intermediates can be converted directly to amide-containing compounds of Formula (I) by reaction at elevated temperature (e.g., 80° C.) with an amine 17-3 in the presence of a Lewis acid catalyst (e.g., AlMe$_3$).

Scheme 17.

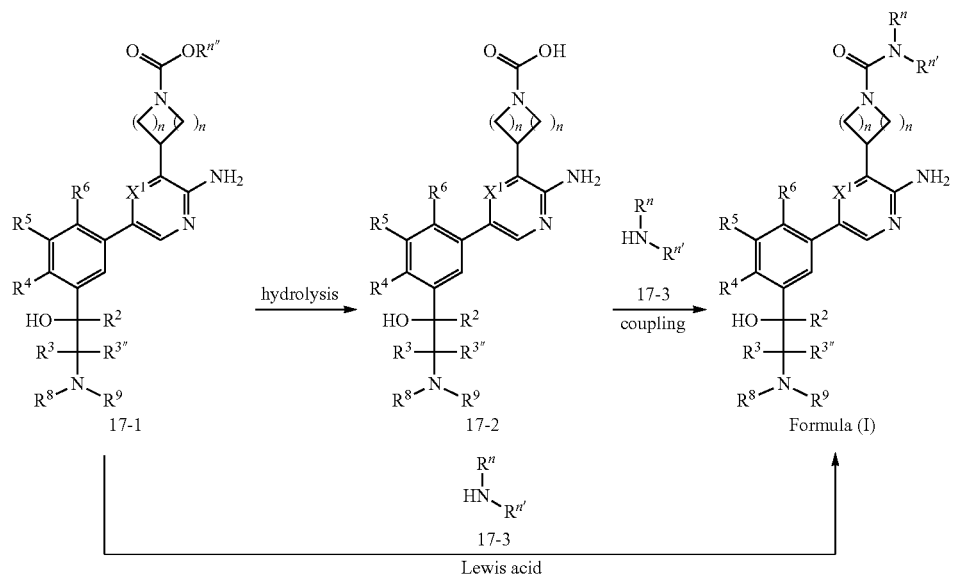

Compounds of Formula (I) can be prepared as shown in Scheme 18. Suitable starting materials 18-1, wherein $Y^2$ and $Y^7$ are suitable halogen atoms (e.g., Cl, Br, or I) or pseudo-halogens (e.g., OTf or OMs), can be converted to intermediates 18-3 via an $S_NAr$ reaction with an amine 18-2 (substituted by R and where X is CR, NR, O, S, or $SO_2$) by heating in an appropriate solvent such as DMF or NMP. Intermediate 18-3 where $Y^7$ is a halogen (e.g., Cl, Br, or I) or pseudohalogen (e.g., OTf or OMs) can be coupled with an appropriately substituted metal 18-4 (e.g., $M^1$ is $B(OH)_2$, Bpin, $BF_3K$, $Sn(Bu)_3$, or Zn) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane and a base (e.g., a carbonate base, such as sodium carbonate or potassium carbonate)) or standard Stille conditions (e.g., in the presence of a palladium(0) catalyst, such as tetrakis(triphenylphosphine)palladium(0)) or standard Negishi conditions (e.g., in the presence of a palladium (0) catalyst, such as tetrakis(triphenylphosphine)palladium (0) or [1,1'-bis(diphenylphosphino)ferrocene] dichloropalladium(II)) to give compounds of Formula (I).

Scheme 18.

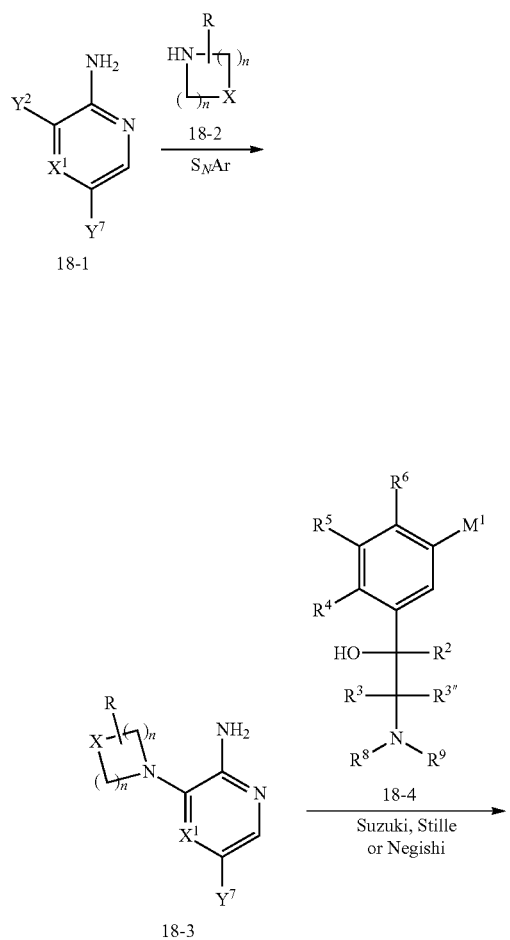

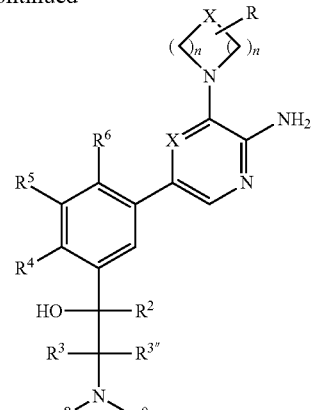

Formula (I)

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds, salts or stereoisomers thereof described herein inhibit activity of PI3Kγ kinase. Accordingly, the compounds, salts or stereoisomers described herein can be used in methods of inhibiting PI3Kγ kinase by contacting the kinase with any one or more of the compounds, salts, or compositions described herein. In some embodiments, the compounds or salts can be used in methods of inhibiting activity of PI3Kγ in an individual/patient in need of the inhibition by administering an effective amount of a compound or salt of described herein. In some embodiments, modulating is inhibiting. In some embodiments, the contacting is in vivo. In some embodiments, the contacting is ex vivo. Advantageously, the compounds as described herein demonstrate better efficacy and favorable safety and toxicity profiles in animal studies.

In some embodiments, the PI3Kγ includes a mutation. A mutation can be a replacement of one amino acid for another, or a deletion of one or more amino acids. In such embodiments, the mutation can be present in the kinase domain of the PI3Kγ.

In some embodiments, the compound or salt further inhibits PI3Kδ.

The compounds or salts described herein can be selective. By "selective" is meant that the compound binds to or inhibits PI3Kγ with greater affinity or potency, respectively, compared to at least one other kinase. In some embodiments, the compounds of the disclosure are selective inhibitors of PI3Kγ over PI3Kδ, PI3Kα, and PI3Kβ. In some embodiments, the compounds of the disclosure are selective inhibitors of PI3Kγ over PI3Kα and PI3Kβ. In some embodiments, selectivity can be at least about 2-fold, 3-fold, 5-fold, 10-fold, at or 20-fold over PI3Kδ as measured by the assays described herein. In some embodiments, selectivity can be tested at the 2 µM ATP concentration of each enzyme. In some embodiments, the selectivity of compounds of the disclosure can be determined by cellular assays associated with particular PI3K kinase activity.

Another aspect of the present disclosure pertains to methods of treating a kinase PI3Kγ-associated disease or disorder in an individual (e.g., patient) by administering to the individual in need of such treatment a therapeutically effective amount or dose of one or more compounds of the present disclosure or a pharmaceutical composition thereof. A PI3Kγ-associated disease or disorder can include any disease, disorder or condition that is directly or indirectly linked to expression or activity of the PI3Kγ, including overexpression and/or abnormal activity levels.

In some embodiments, the disease or disorder is an autoimmune disease or disorder, cancer, cardiovascular disease, or neurodegenerative disease.

In some embodiments, the disease or disorder is lung cancer (e.g., non-small cell lung cancer), melanoma, pancreatic cancer, breast cancer, head and neck squamous cell carcinoma, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is mesothelioma or adrenocarcinoma. In some embodiments, the disease or disorder is mesothelioma. In some embodiments, the disease or disorder is adrenocarcinoma.

In some embodiments, the disease or disorder is adenocarcinoma.

In some embodiments, the disease or disorder is acute myeloid leukemia (e.g., acute monocytic leukemia), small lymphocyctic lymphoma, chronic lymphocytic leukemia (CLL), chronic myelogenous leukemia (CML), multiple myeloma, T-cell acute lymphoblastic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma. In some embodiments, the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, anaplastic large cell lymphoma (T-cell type), enteropathy type T-cell lymphoma, adult T-cell leukemia/lymphoma, or angioimmunoblastic T-cell lymphoma In some embodiments, the anaplastic large cell lymphoma (ALCL) is systemic ALCL or primary cutaneous ALCL.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, xeroderoma pigmentosum, keratoacanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

MDSC (myeloid-derived suppressor cells) are a heterogeneous group of immune cells from the myeloid lineage (a family of cells that originate from bone marrow stem cells). MDSCs strongly expand in pathological situations such as chronic infections and cancer, as a result of an altered haematopoiesis. MDSCs are discriminated from other myeloid cell types in which they possess strong immunosuppressive activities rather than immunostimulatory properties. Similar to other myeloid cells, MDSCs interact with other immune cell types including T cells, dendritic cells, macrophages and natural killer cells to regulate their functions. In some embodiments, the compounds, etc. described herein can be used in methods related to cancer tissue (e.g., tumors) with high infiltration of MDSCs, including Solid tumors with high basal level of macrophage and/or MDSC infiltration.

In some embodiments, the non-Hodgkin's lymphoma (NHL) is relapsed NHL, refractory NHL, recurrent follicular NHL, indolent NHL (iNHL), or aggressive NHL (aNHL).

In some embodiments, the diffuse large B cell lymphoma is activated B-cell like (ABC) diffuse large B cell lymphoma, or germinal center B cell (GCB) diffuse large B cell lymphoma. In some embodiments, the Burkitt's lymphoma is endemic Burkitt's lymphoma, sporadic Burkitt's lymphoma, or Burkitt's-like lymphoma.

In some embodiments, the disease or disorder is rheumatoid arthritis, multiple sclerosis, systemic lupus erythematous, asthma, allergy (e.g., allergic rhinitis), pancreatitis, psoriasis, anaphylaxis, glomerulonephritis, inflammatory bowel disease (e.g., Crohn's disease and ulcerative colitis), thrombosis, meningitis, encephalitis, diabetic retinopathy, benign prostatic hypertrophy, myasthenia gravis, Sjögren's syndrome, osteoarthritis, restenosis, or atherosclerosis.

In some embodiments, the disease or disorder is heart hypertrophy, cardiac myocyte dysfunction, acute coronary syndrome, chronic obstructive pulmonary disease (COPD), chronic bronchitis, elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft-versus-host disease, allogeneic or xenogeneic transplantation, glomerulosclerosis, progressive renal fibrosis, idiopathic thrombocytopenic purpura (ITP), idiopathic pulmonary fibrosis, autoimmune hemolytic anemia, vasculitis, lupus nephritis, pemphigus, or membranous nephropathy.

In some embodiments, disease or disorder is heart hypertrophy, cardiac myocyte dysfunction, chronic obstructive pulmonary disease (COPD), elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft rejection, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

In some embodiments, the disease or disorder is Alzheimer's disease, central nervous system trauma, or stroke.

In some embodiments, the idiopathic thrombocytopenic purpura (ITP) is relapsed ITP or refractory ITP.

In some embodiments, the vasculitis is Behcet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schonlein purpura (HSP), hypersensitivity vasculitis, microscopic polyangiitis, Wegener's granulomatosis, or anti-neutrophil cytoplasm antibody associated (ANCA) systemic vasculitis (AASV).

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "contacting" refers to the bringing together of indicated moieties in an in vitro system or an in vivo system. For example, "contacting" a PI3K with a compound of the disclosure includes the administration of a compound of the present disclosure to an individual or patient, such as a human, having a PI3K, as well as, for example, introducing a compound of the disclosure into a sample containing a cellular or purified preparation containing the PI3K.

It is believed that compounds of provided herein (e.g., compounds of Formula (I), or pharmaceutically acceptable salts thereof) or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" can refer to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

In some embodiments, the PI3Kγ inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Compounds of the present disclosure can be used in combination with one or more immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3K delta, PI3K gamma, TAM, arginase, HPK1, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the PI3Kγ inhibitors provided herein can be used in combination with one or more agonists of immune checkpoint molecules, e.g., OX40, CD27, OX40, GITR, and CD137 (also known as 4-1BB).

In some embodiments, the inhibitor of an immune checkpoint molecule is anti-PD 1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the PI3Kγ inhibitors provided herein can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein. Examples of cancers include solid tumors and liquid tumors, such as blood cancers.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, and FAK kinase inhibitors such as, for example, those described in WO 2006/056399. Other agents such as therapeutic antibodies can be used in combination with the compounds of the present disclosure for treatment of PI3K-associated diseases, disorders or conditions. The one or more additional pharmaceutical agents can be administered to a patient simultaneously or sequentially.

For example, the compounds as disclosed herein can be combined with one or more inhibitors of the following kinases for the treatment of cancer and other diseases or disorders described herein: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf Non-limiting examples of inhibitors that can be combined with the compounds of the present disclosure for treatment of cancer and other diseases and disorders described herein include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a Pim inhibitor, a CSF1R inhibitor, a TAM receptor tyrosine kinases (Tyro-3, Axl, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrozole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumortargeted therapy, adjuvant therapy, immunotherapy, or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, streptozocin, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Additional examples of chemotherapeutics include proteasome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a PI3K inhibitor of the present disclosure with an additional agent.

In some embodiments, the compounds of the disclosure can be used in combination with an inhibitor of JAK or PI3Kδ.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, Leishmania, Staphylococcus aureus, Pseudomonas Aeruginosa.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, Ebola virus, measles virus, herpes virus (e.g., VZV, HSV-1, HAV-6, HSV-II, and CMV, Epstein Barr virus), flaviviruses, echovirus, rhinovirus, coxsackievirus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus Mucorales (*mucor, absidia,* rhizophus), *Sporothrix schenkii, Blastomyces dermatitidis, Paracoccidioides brasiliensis,*

*Coccidioides immitis* and *Histoplasma capsulatum*. Pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerine monostearate, PEG-glycerine monostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Substitution of one or more of the atoms of the compounds of the present disclosure can also be useful in generating differentiated ADME (Adsorption, Distribution, Metabolism and Excretion) Accordingly, the present disclosure includes PI3K assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^8$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups of the disclosed Formulas (e.g., Formula (I), (II), etc.), can be per-deuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1, 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of any alkyl, alkenyl, alkynyl, aryl, phenyl, cycloalkyl, heterocycloalkyl, or heteroaryl substituents, or —$C_{1-6}$ alkyl-, alkylene, alkenylene, and alkynylene linking groups, as described herein, are each optionally replaced by a deuterium atom.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro PI3K labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments the radionuclide is selected from the group consisting of $^3$H, $^{14}$C, $^{125}$, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of PI3K-associated diseases or disorders, such as cancer, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3Kγ inhibitors according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification:

Improved Compound Specific Method Optimization", K. Blom, B. Glass, R. Sparks, A. Combs, *J. Combi. Chem.*, 6, 874-883 (2004)).

The compounds separated were typically subjected to analytical liquid chromatography mass spectrometry (LCMS) for purity analysis under the following conditions: Instrument=Agilent 1100 series, LC/MSD; Column: Waters Sunfire™ $C_{18}$ 5 μm, 2.1×50 mm, Buffers: mobile phase A: 0.025% TFA in water and mobile phase B: acetonitrile; gradient 2% to 80% B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 30×100 mm or Waters XBridge™ $C_{18}$ 5 μm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g., "Preparative LCMS Purification: Improved Compound Specific Method Optimization", K. Blom, B. Glass, R. Sparks, A. Combs, *J. Comb. Chem.*, 6, 874-883 (2004)).

pH=10 purifications: Waters XBridge™ $C_{18}$ 5 μm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g., "Preparative LCMS Purification: Improved Compound Specific Method Optimization", K. Blom, B. Glass, R. Sparks, A. Combs, *J Comb. Chem.*, 6, 874-883 (2004)).

Stereochemical Rationale

The Sharpless asymmetric dihydroxylation of olefins has been studied extensively, and its basis as a model for enantioselectivity is well established (Sharpless, K. B.; Amberg, W.; Bennani, Y. L.; Crispino, G. A.; Hartung, J.; Jeong, K.-S.; Kwong, H.-L.; Morikawa, K.; Wang, Z.-M.; Xu, D.; Zhang, X.-L. *J. Org. Chem.*, 1992, 57, 2768-2771; and Kolb, H. C.; VanNieuwenhze, M. S.; Sharpless, K. B. *Chem. Rev.*, 1994, 94, 2483-2547). Briefly, the application of AD-mix-α (containing $(DHQ)_2$-PHAL) in the dihydroxylation of prop-1-en-2-ylbenzene affords (S)-2-phenylpropane-1,2-diol. Application of AD-mix-β (containing $(DHQD)_2$-PHAL) in the dihydroxylation of prop-1-en-2-ylbenzene affords (R)-2-phenylpropane- 1,2-diol (Sharpless and Kolb, supra). Moreno-Dorado et al. extended the method to the trifluoromethyl case (e.g., (3,3,3-trifluoroprop-1-en-2-yl)benzene affords (S)-3,3,3-trifluoro-2-phenylpropane-1,2-diol when treated with AD-mix-α and affords (R)-3,3,3-trifluoro-2-phenylpropane-1,2-diol when treated with AD-mix-13), and the stereochemical outcome was verified by subsequent conversion to well known compounds whose specific rotations were found to be in agreement with the literature values (Moreno-Dorado, F. J.; Guerra, F. M.; Ortega, M. J.; Zubia, E.; Massanet, G. M. *Tetrahedron: Asymmetry*, 2003, 14, 503-510). While not wishing to be bound by any one theory, in the dihydroxylations performed on vinyl arenes in the examples, we expect to obtain the (S)-configuration with AD-mix-α and the (R)-configuration with AD-mix-β.

Example 1. 3-Amino-6-(5-(3-amino-1,1,1-trifluoro-2-hydroxy-3-oxopropan-2-yl)-2-methylphenyl)-N-(2-hydroxy-2-methylpropyl)pyrazine-2-carboxamide

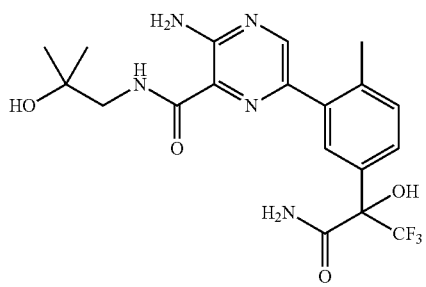 [SMILES: Cc1ccc(C(O)(C(N)=O)C(F)(F)F)cc1-c1cnc(N)c(C(=O)NCC(C)(C)O)n1]

Step 1. 1-(3-Bromo-4-methylphenyl)-2,2,2-trifluoroethan-1-ol

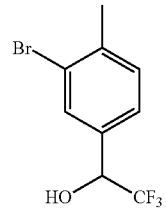

A solution of 3-bromo-4-methylbenzaldehyde (6.51 g, 32.7 mmol) [Combi-Blocks, HC-3454] in dry tetrahydrofuran (65.4 mL) was cooled to 0° C. followed by the addition of trimethyl(trifluoromethyl)silane (6.28 mL, 42.5 mmol). The yellow mixture was treated with 1.0 M tetra-n-butylammonium fluoride in tetrahydrofuran (0.654 mL, 0.654 mmol) at 0° C. and stirred for a few minutes at 0° C. The ice bath was removed and the resulting reaction mixture was stirred for 1.5 h. The reaction mixture was cooled back to 0° C. and treated with water (6.48 mL, 360 mmol) and 1.0 M tetra-n-butylammonium fluoride in tetrahydrofuran (6.54 mL, 6.54 mmol). The ice bath was removed and the reaction mixture was stirred at ambient temperature for 30 min. The yellow reaction mixture was diluted with brine (150 mL) and extracted with ethyl acetate (200 mL). The organic layer was washed with saturated ammonium chloride (100 mL), dried over sodium sulfate, filtered, and concentrated to give a tan oil. Purification by flash column chromatography using methyl tert-butyl ether (MTBE) in hexanes (0% to 50%) gave the desired product (8.42 g, 95.7%) as a yellow oil. LCMS for $C_9H_7BrF_3$ (M−OH)[+]: m/z=251.0, 253.0; Found: 250.9, 252.8.

Step 2. 1-(3-Bromo-4-methylphenyl)-2,2,2-trifluoro-ethan-1-one

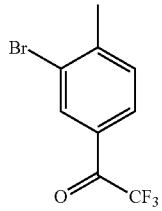

A mixture of 1-(3-bromo-4-methylphenyl)-2,2,2-trifluoroethan-1-ol (8.41 g, 31.3 mmol) in dichloromethane (125 mL) at 0° C. was treated with Dess-Martin periodinane (19.9 g, 46.9 mmol) and stirred at room temperature (rt) for 2.5 h. The reaction mixture was concentrated (by rotary evaporation with the water bath set at 30° C.) to an oily solid that was diluted with diethyl ether (200 mL) which precipitated more solids. This mixture was filtered over Celite® and the Celite® was rinsed with additional diethyl ether (200 mL). The filtrate was washed with saturated sodium bicarbonate solution (3×200 mL) and brine, dried over sodium sulfate, filtered, and concentrated to give an oily solid. The oily solid was partitioned between diethyl ether (150 mL) and water (100 mL). The organic layer was separated and washed with saturated sodium bicarbonate solution (2×75 mL) and brine, dried over sodium sulfate, filtered, and concentrated to give the desired product (7.93 g, 95.0%) as an oil that was used without further purification. LCMS for $C_9H_7BrF_3O$ $(M+H)^+$: m/z=267.0, 269.0; Found: 267.1, 268.9.

Step 3. 2-(3-Bromo-4-methylphenyl)-3,3,3-trifluoro-2-hydroxypropanenitrile

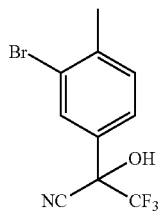

A solution of 1-(3-bromo-4-methylphenyl)-2,2,2-trifluoroethan-1-one (7.92 g, 29.7 mmol) in dichloromethane (29.7 mL) was treated with trimethylsilyl cyanide (8.70 mL, 65.2 mmol), potassium cyanide (0.29 g, 4.45 mmol), and 18-crown-6 (0.29 g, 1.10 mmol) and stirred for 1 h. The reaction can be cooled with an ice bath due to an exotherm after the addition of 18-crown-6. The reaction mixture was concentrated (by rotary evaporation with the water bath set at 28° C.) to give a rust colored solid. The solid was dissolved in THF (29.6 mL), cooled to 0° C., treated with 1.8 M HCl (10.9 mL, 19.6 mmol), and stirred at room temperature (rt) for 1.5 h. The reaction mixture was diluted with water (75 mL) and extracted with diethyl ether (3×75 mL). The combined organic extracts were washed with brine, dried over sodium sulfate, filtered, and concentrated. Reconcetration from hexanes to give the desired product (8.70 g, 99.8%) as an orange solid that was used without further purification. LCMS for $C_9H_7BrF_3O$ $(M-CN)^+$: m/z=267.0, 269.0; Found: 266.9, 269.0.

Step 4. 2-(3-bromo-4-methylphenyl)-3,3,3-trifluoro-2-hydroxypropanamide

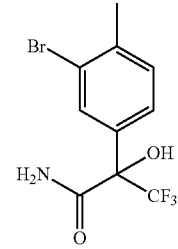 [SMILES: Cc1ccc(C(O)(C(N)=O)C(F)(F)F)cc1Br]

A solution of 2-(3-bromo-4-methylphenyl)-3,3,3-trifluoro-2-hydroxypropanenitrile (Example 1, Step 3, 8.70 g, 29.6 mmol) in dioxane (59.2 mL) at 0° C. was treated with concentrated HCl (9.00 mL, 108 mmol) that had been pre-cooled in an ice bath. While stirring at 0° C., the reaction mixture was bubbled with HCl gas for 45 min. The cooling bath was removed and the reaction mixture was stirred at rt for 61 h. The reaction mixture was bubbled with nitrogen for 10 min to remove some of the HCl, cooled to 0° C., and diluted with brine (200 mL), water (50 mL), and ethyl acetate (200 mL). The organic layer was separated and the aqueous layer was diluted with water (100 mL) to dissolve the remaining solids. The aqueous layer was extracted with ethyl acetate (100 mL). The combined organic extracts were washed with brine, dried over sodium sulfate, filtered, and concentrated to give a brown oil. Purification by flash column chromatography using MTBE in hexanes (0% to 60%) gave the desired product as a yellow oily solid. The racemic mixture was separated via preparative chiral HPLC (Phenomenex Lux Amylose-1 [21.2×250 mm, 5 micron], eluting with 95% ethanol in hexanes, at flow rate of 18 mL/min, loading about 100 mg in 2 mL ethanol) to give the desired second eluting enantiomer (4.50 g, 48.8%) as a viscous yellow oil. The first enantiomer that eluted had a retention time of 4.0 min. The second enantiomer that eluted had a retention time of 5.3 min. Second eluting enantiomer: LCMS for $C_{10}H_{10}BrF_3NO_2$ $(M+H)^+$: m/z=312.0, 314.0; Found: 312.0, 314.0.

Step 5. 3,3,3-Trifluoro-2-hydroxy-2-(4-methyl-3-(4,4,5,5-tetramethyl-1,3,2-dioxaborolan-2-yl)phenyl)propanamide

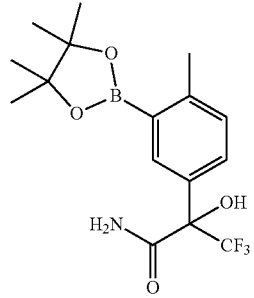 [SMILES: Cc1ccc(C(O)(C(N)=O)C(F)(F)F)cc1B1OC(C)(C)C(C)(C)O1]

A solution of 2-(3-bromo-4-methylphenyl)-3,3,3-trifluoro-2-hydroxypropanamide (3.57 g, 11.5 mmol) (Example 1, Step 4, second eluting enantiomer) in dioxane (57.2 mL) was treated with bis(pinacolato)diboron (3.49 g, 13.7 mmol), and potassium acetate (3.71 g, 37.8 mmol) and degassed with nitrogen for 5 min. The reaction mixture was treated with bis(triphenylphosphine)palladium(II)chloride (0.482 g, 0.687 mmol), degassed for 5 min, and stirred at 100° C. for 2.5 h. The reaction mixture was diluted with ethyl acetate (50 mL), filtered over Celite®, and rinsed with additional ethyl acetate (100 mL). The filtrate was washed with brine, dried over sodium sulfate, filtered, and concentrated to a brown foam. Purification by flash column chromatography using MTBE in hexanes (0% to 100%) gave the desired product (3.35 g, 81.5%) as a thick yellow foam. $^1$H NMR (400 MHz, DMSO-$d_6$) δ 7.96 (d, J=2.2 Hz, 1H), 7.63 (dd, J=7.9, 2.1 Hz, 1H), 7.58 (s, 1H), 7.54 (s, 1H), 7.51-7.40 (m, 1H), 7.21 (d, J=8.2 Hz, 1H), 2.46 (s, 3H), 1.30 (s, 12H). LCMS for $C_{16}H_{22}BF_3NO_4$ (M+H)$^+$: m/z=360.2; Found: 360.1.

Step 6. 2-(3-(5-Amino-6-chloropyrazin-2-yl)-4-methylphenyl)-3,3,3-trifluoro-2-hydroxypropanamide

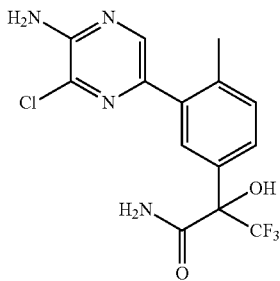 [SMILES: Cc1ccc(C(O)(C(N)=O)C(F)(F)F)cc1-c1cnc(N)c(Cl)n1]

A solution of 5-bromo-3-chloropyrazin-2-amine (0.235 g, 1.13 mmol) [Ark Pharm, AK-25099] and 3,3,3-trifluoro-2-hydroxy-2-(4-methyl-3-(4,4,5,5-tetramethyl-1,3,2-dioxaborolan-2-yl)phenyl)propanamide (0.405 g, 1.13 mmol) (single enantiomer from Example 1, step 5) in dioxane (13.1 mL) was treated with sodium carbonate (0.359 g, 3.38 mmol) in water (2.61 mL) and degassed with nitrogen for 5 min. The reaction mixture was treated with dichloro[1,1'-bis(diphenylphosphino)ferrocene]palladium (II) dichloromethane adduct (0.046 g, 0.056 mmol), degassed with nitrogen for 5 min, and stirred at 100° C. for 15 h. The reaction mixture was diluted with ethyl acetate (50 mL), filtered through a 0.45 micron cartridge, and rinsed with additional ethyl acetate (50 mL). The filtrate was washed with brine (30 mL). The aqueous layers was separated extracted with ethyl acetate (2×50 mL). The combined organic extracts were dried over sodium sulfate, filtered, and concentrated to a brown foam. Purification by flash column chromatography using ethyl acetate (containing 5% MeOH) in hexanes (0% to 100%) gave the desired product (0.180 g, 44.2%) as yellow solid. LCMS for $C_{14}H_{13}ClF_3N_4O_2$ (M+H)$^+$: m/z=361.1; Found: 361.0.

Step 7. 3-Amino-6-(5-(3-amino-1,1,1-trifluoro-2-hydroxy-3-oxopropan-2-yl)-2-methylphenyl)-N-(2-hydroxy-2-methylpropyl)pyrazine-2-carboxamide A solution of 2-(3-(5-amino-6-chloropyrazin-2-yl)-4-methylphenyl)-3,3,3-trifluoro-2-hydroxypropanamide (0.010 g, 0.028 mmol) (single enantiomer from Example 1, step 6) and 1-amino-2-methylpropan-2-ol (0.025 g, 0.277 mmol) in dioxane (0.460 mL) was treated with triethylamine (0.015 mL, 0.111 mmol) and degassed with nitrogen for 5 min. The reaction mixture was treated with dichloro [1,1'-bis(diphenylphosphino)ferrocene]palladium (II) dichloromethane adduct (4.53 mg, 5.54 μmol) and degassed with nitrogen for another 5 min. The reaction mixture was saturated with CO by bubbling the gas through the reaction subsurface for 5 min and the reaction mixture was stirred at 80° C. overnight. The reaction mixture was diluted with methanol and water and filtered through a 0.45 micron cartridge. The filtrate was concentrated and the crude residue was purified via preparative LCMS (XBridge C18 Column, eluting with a gradient of acetonitrile in water with 0.1% trifluoroacetic acid, at flow rate of 60 mL/min) to give the desired product (8.30 mg, 67.8%) as a TFA salt. LCMS for $C_{19}H_{23}F_3N_5O_4$ (M+H)$^+$: m/z=442.1; Found: 442.1.

Examples 2-4, 6, 8-12, and 14-30 were synthesized according to procedures analogous to Example 1 and the data are listed in Table 1.

TABLE 1

| Ex. No. | Name | NR$c^7$R$d^7$ | LCMS [M + H]$^+$ | $^1$H NMR Spectrum |
|---|---|---|---|---|
| 2 | 3-amino-6-(5-(3-amino-1,1,1-trifluoro-2-hydroxy-3-oxopropan-2-yl)-2-methylphenyl)-N-(tetrahydro-2H-pyran-4-yl)pyrazine-2-carboxamide trifluoroacetate | 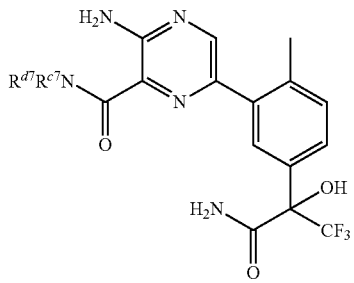 | 454.1 | $^1$H NMR (500 MHz, DMSO-$d_6$) δ 8.34 (s, 1H), 8.30 (d, J = 8.3 Hz, 1H), 7.74 (d, J = 2.0 Hz, 1H), 7.67-7.52 (m, 6H), 7.36 (d, J = 8.2 Hz, 1H), 4.09-3.91 (m, 1H), 3.91-3.77 (m, 2H), 3.47-3.34 (m, 2H), 2.37 (s, 3H), 1.79-1.69 (m, 2H), 1.69-1.55 (m, 2H). |

TABLE 1-continued

| Ex. No. | Name | NR$c^7$R$d^7$ | LCMS [M + H]$^+$ | $^1$H NMR Spectrum |
|---|---|---|---|---|
| 3 | 3-amino-6-(5-(3-amino-1,1,1-trifluoro-2-hydroxy-3-oxopropan-2-yl)-2-methylphenyl)-N-((1r,4r)-4-hydroxycyclohexyl)pyrazine-2-carboxamide trifluoroacetate | | 468.1 | |
| 4 | 3-amino-6-(5-(3-amino-1,1,1-trifluoro-2-hydroxy-3-oxopropan-2-yl)-2-methylphenyl)-N-((1-cyanocyclopropyl)methyl)pyrazine-2-carboxamide trifluoroacetate | | 449.1 | $^1$H NMR (500 MHz, DMSO-d$_6$) δ 8.90 (t, J = 6.5 Hz, 1H), 8.34 (s, 1H), 7.72 (d, J = 2.0 Hz, 1H), 7.67-7.50 (m, 5H), 7.37 (d, J = 8.1 Hz, 1H), 3.50-3.37 (m, 2H), 2.36 (s, 3H), 1.24-1.17 (m, 2H), 1.17-1.08 (m, 2H). |
| 6 | 3-amino-6-(5-(3-amino-1,1,1-trifluoro-2-hydroxy-3-oxopropan-2-yl)-2-methylphenyl)-N-(4,4-difluorocyclohexyl)pyrazine-2-carboxamide trifluoroacetate | | 488.1 | $^1$H NMR (400 MHz, DMSO-d$_6$) δ 8.37 (d, J = 8.3 Hz, 1H), 8.35 (s, 1H), 7.73 (d, J = 2.1 Hz, 1H), 7.68-7.48 (m, 5H), 7.35 (d, J = 8.1 Hz, 1H), 2.36 (s, 3H), 2.09-1.89 (m, 4H), 1.89-1.79 (m, 2H), 1.79-1.61 (m, 2H). |
| 8 | 3-amino-6-(5-(3-amino-1,1,1-trifluoro-2-hydroxy-3-oxopropan-2-yl)-2-methylphenyl)-N-((S)-1-cyanopropan-2-yl)pyrazine-2-carboxamide trifluoroacetate | | 437.1 | $^1$H NMR (500 MHz, DMSO-d$_6$) δ 8.56 (d, J = 8.7 Hz, 1H), 8.33 (s, 1H), 7.71 (d, J = 2.0 Hz, 1H), 7.67-7.50 (m, 3H), 7.37 (d, J = 8.1 Hz, 1H), 4.50-4.16 (m, 1H), 2.97-2.71 (m, 2H), 2.35 (s, 3H), 1.25 (d, J = 6.7 Hz, 3H). |
| 9 | 3-amino-6-(5-(3-amino-1,1,1-trifluoro-2-hydroxy-3-oxopropan-2-yl)-2-methylphenyl)-N-((R)-tetrahydro-2H-pyran-3-yl)pyrazine-2-carboxamide trifluoroacetate | | 454.1 | |
| 10 | 3-amino-6-(5-(3-amino-1,1,1-trifluoro-2-hydroxy-3-oxopropan-2-yl)-2-methylphenyl)-N-((S)-tetrahydro-2H-pyran-3-yl)pyrazine-2-carboxamide trifluoroacetate | | 454.1 | |

TABLE 1-continued

| Ex. No. | Name | NRc⁷Rd⁷ | LCMS [M + H]⁺ | ¹H NMR Spectrum |
|---|---|---|---|---|
| 11 | 3-amino-6-(5-(3-amino-1,1,1-trifluoro-2-hydroxy-3-oxopropan-2-yl)-2-methylphenyl)-N-((S)-tetrahydrofuran-3-yl)pyrazine-2-carboxamide trifluoroacetate | (S)-tetrahydrofuran-3-yl-NH- | 440.1 | ¹H NMR (400 MHz, DMSO-d₆) δ 8.43 (d, J = 7.4 Hz, 1H), 8.35 (s, 1H), 7.73 (d, J = 2.1 Hz, 1H), 7.69-7.47 (m, 5H), 7.36 (d, J = 8.1 Hz, 1H), 4.55-4.40 (m, 1H), 3.83 (dd, J = 8.7, 6.2 Hz, 2H), 3.77-3.65 (m, 1H), 3.59 (dd, J = 8.9, 4.4 Hz, 1H), 2.36 (s, 3H), 2.28-2.08 (m, 1H), 2.03-1.80 (m, 1H). |
| 12 | 3-amino-6-(5-(3-amino-1,1,1-trifluoro-2-hydroxy-3-oxopropan-2-yl)-2-methylphenyl)-N-((S)-1-hydroxypropan-2-yl)pyrazine-2-carboxamide | HO-CH₂-CH(CH₃)-NH- | 428.2 | |
| 14 | 3-amino-6-(5-(3-amino-1,1,1-trifluoro-2-hydroxy-3-oxopropan-2-yl)-2-methylphenyl)-N-(2-cyanoethyl)pyrazine-2-carboxamide trifluoroacetate | NC-CH₂CH₂-NH- | 423.1 | |
| 15 | 3-amino-6-(5-(3-amino-1,1,1-trifluoro-2-hydroxy-3-oxopropan-2-yl)-2-methylphenyl)-N-(2-cyano-2-methylpropyl)pyrazine-2-carboxamide trifluoroacetate | NC-C(CH₃)₂-CH₂-NH- | 451.1 | |
| 16 | 3-amino-6-(5-(3-amino-1,1,1-trifluoro-2-hydroxy-3-oxopropan-2-yl)-2-methylphenyl)-N-((1-cyanocyclobutyl)methyl)pyrazine-2-carboxamide trifluoroacetate | (1-cyanocyclobutyl)methyl-NH- | 463.1 | ¹H NMR (400 MHz, DMSO-d₆) δ 8.86 (t, J = 6.6 Hz, 1H), 8.36 (s, 1H), 7.73 (d, J = 2.0 Hz, 1H), 7.69-7.49 (m, 5H), 7.36 (d, J = 8.1 Hz, 1H), 2.37 (s, 3H), 2.41-2.24 (m, 4H), 2.08-1.92 (m, 2H). |
| 17 | 3-amino-6-(5-(3-amino-1,1,1-trifluoro-2-hydroxy-3-oxopropan-2-yl)-2-methylphenyl)-N-((1r,4r)-4-hydroxy-4-methylcyclohexyl)pyrazine-2-carboxamide trifluoroacetate | (1r,4r)-4-hydroxy-4-methylcyclohexyl-NH- | 482.1 | |
| 18 | 3-amino-6-(5-(3-amino-1,1,1-trifluoro-2-hydroxy-3-oxopropan-2-yl)-2-methylphenyl)-N-((1r,4r)-4-hydroxy-4-(trifluoromethyl)cyclohexyl)pyrazine-2-carboxamide trifluoroacetate | (1r,4r)-4-hydroxy-4-(trifluoromethyl)cyclohexyl-NH- | 536.2 | ¹H NMR (400 MHz, DMSO-d₆) δ 8.39 (s, 1H), 8.23 (d, J = 7.0 Hz, 1H), 7.82-7.74 (m, 1H), 7.69-7.48 (m, 5H), 7.37 (d, J = 8.1 Hz, 1H), 5.82 (br s, 1H), 4.15-3.98 (m, 1H), 2.41 (s, 3H), 1.93-1.83 (m, 2H), 1.82-1.74 (m, 2H), 1.73-1.54 (m, 4H). |

TABLE 1-continued

| Ex. No. | Name | NR$c^7$R$d^7$ | LCMS [M + H]$^+$ | $^1$H NMR Spectrum |
|---|---|---|---|---|
| 19 | 3-amino-6-(5-(3-amino-1,1,1-trifluoro-2-hydroxy-3-oxopropan-2-yl)-2-methylphenyl)-N-((1r,4r)-4-(2-hydroxypropan-2-yl)cyclohexyl)pyrazine-2-carboxamide trifluoroacetate | | 510.1 | |
| 20 | 3-amino-6-(5-(3-amino-1,1,1-trifluoro-2-hydroxy-3-oxopropan-2-yl)-2-methylphenyl)-N-((S)-1-cyanobutan-2-yl)pyrazine-2-carboxamide trifluoroacetate | | 451.1 | |
| 21 | 3-amino-6-(5-(3-amino-1,1,1-trifluoro-2-hydroxy-3-oxopropan-2-yl)-2-methylphenyl)-N-(2-methoxy-2-methylpropyl)pyrazine-2-carboxamide trifluoroacetate | | 456.2 | |
| 22 | 3-amino-6-(5-(3-amino-1,1,1-trifluoro-2-hydroxy-3-oxopropan-2-yl)-2-methylphenyl)-N-((1r,4r)-4-methoxycyclohexyl)pyrazine-2-carboxamide trifluoroacetate | | 482.2 | $^1$H NMR (400 MHz, DMSO-d$_6$) δ 8.34 (s, 1H), 8.16 (d, J = 8.3 Hz, 1H), 7.73 (d, J = 2.1 Hz, 1H), 7.69-7.49 (m, 5H), 7.35 (d, J = 8.1 Hz, 1H), 3.83-3.62 (m, 1H), 3.23 (s, 3H), 3.15-2.98 (m, 1H), 2.36 (s, 3H), 2.06-1.92 (m, 2H), 1.91-1.73 (m, 2H), 1.51-1.32 (m, 2H), 1.32-1.10 (m, 2H). |
| 23 | 3-amino-6-(5-(3-amino-1,1,1-trifluoro-2-hydroxy-3-oxopropan-2-yl)-2-methylphenyl)-N-(3-cyanobicyclo[1.1.1]pentan-1-yl)pyrazine-2-carboxamide trifluoroacetate | | 461.1 | |
| 24 | 3-amino-6-(5-(3-amino-1,1,1-trifluoro-2-hydroxy-3-oxopropan-2-yl)-2-methylphenyl)-N-(4-cyanobicyclo[2.1.1]hexan-1-yl)pyrazine-2-carboxamide trifluoroacetate | | 475.2 | |

TABLE 1-continued

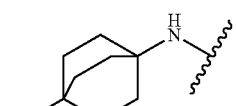

| Ex. No. | Name | NRc⁷Rd⁷ | LCMS [M + H]⁺ | ¹H NMR Spectrum |
|---|---|---|---|---|
| 25 | 3-amino-6-(5-(3-amino-1,1,1-trifluoro-2-hydroxy-3-oxopropan-2-yl)-2-methylphenyl)-N-(4-cyanobicyclo[2.2.2]octan-1-yl)pyrazine-2-carboxamide trifluoroacetate | 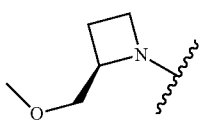 [SMILES: *N1CC[C@@H]1COC] | 503.1 | |
| 26 | 2-(3-(5-amino-6-((R)-2-(methoxymethyl)azetidine-1-carbonyl)pyrazin-2-yl)-4-methylphenyl)-3,3,3-trifluoro-2-hydroxypropanamide | 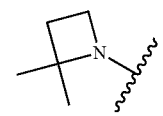 | 454.2 | |
| 27 | 2-(3-(5-amino-6-(2,2-dimethylazetidine-1-carbonyl)pyrazin-2-yl)-4-methylphenyl)-3,3,3-trifluoro-2-hydroxypropanamide | 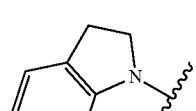 | 438.2 | |
| 28 | 2-(3-(5-amino-6-(2,3-dihydro-1H-pyrrolo[2,3-b]pyridine-1-carbonyl)pyrazin-2-yl)-4-methylphenyl)-3,3,3-trifluoro-2-hydroxypropanamide | 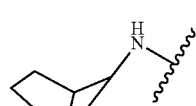 | 473.2 | |
| 29 | 3-amino-6-(5-(3-amino-1,1,1-trifluoro-2-hydroxy-3-oxopropan-2-yl)-2-methylphenyl)-N-(7-oxabicyclo[2.2.1]heptan-2-yl)pyrazine-2-carboxamide (Peak 1) | 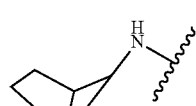 | 466.2 | |
| 30 | 3-amino-6-(5-(3-amino-1,1,1-trifluoro-2-hydroxy-3-oxopropan-2-yl)-2-methylphenyl)-N-(7-oxabicyclo[2.2.1]heptan-2-yl)pyrazine-2-carboxamide (Peak 2) |  | 466.2 | |

Example 5. 3-Amino-6-(5-(3-amino-1,1,1-trifluoro-2-hydroxy-3-oxopropan-2-yl)-2-methylphenyl)-N-isopropylpyrazine-2-carboxamide trifluoroacetate

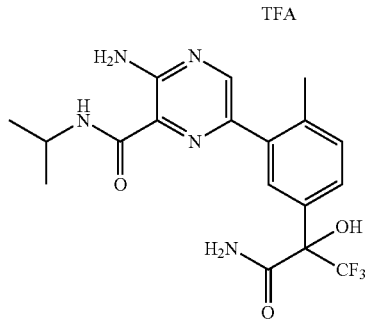 [SMILES: Cc1ccc(C(O)(C(N)=O)C(F)(F)F)cc1-c1cnc(N)c(C(=O)NC(C)C)n1]

The desired compound was prepared according to the procedure of Example 1, Step 7, using isopropylamine as the starting material in place of 1-amino-2-methylpropan-2-ol. $^1$H NMR (500 MHz, DMSO-$d_6$) δ 8.33 (s, 1H), 8.14 (d, J=8.3 Hz, 1H), 7.73 (d, J=2.0 Hz, 1H), 7.68-7.52 (m, 5H), 7.36 (d, J=8.2 Hz, 1H), 4.22-3.95 (m, 1H), 2.36 (s, 3H), 1.17 (d, J=6.6 Hz, 6H). LCMS for $C_{18}H_{21}F_3N_5O_3$ (M+H)$^+$: m/z=412.2; Found: 412.2.

Example 7. 3-Amino-6-(5-(3-amino-1,1,1-trifluoro-2-hydroxy-3-oxopropan-2-yl)-2-methylphenyl)-N-ethylpyrazine-2-carboxamide trifluoroacetate

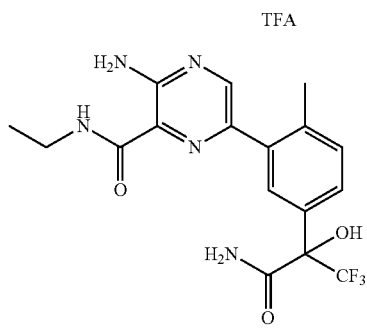 [SMILES: CCNC(=O)c1nc(-c2cc(C(O)(C(N)=O)C(F)(F)F)ccc2C)cnc1N]

The desired compound was prepared according to the procedure of Example 1, Step 7, using ethylamine as the starting material in place of 1-amino-2-methylpropan-2-ol. $^1$H NMR (500 MHz, DMSO-$d_6$) δ 8.53 (t, J=6.0 Hz, 1H), 8.30 (s, 1H), 7.70 (d, J=2.1 Hz, 1H), 7.67-7.46 (m, 3H), 7.35 (d, J=8.1 Hz, 1H), 3.30 (dq, J=7.0, 7.0 Hz, 2H), 2.35 (s, 3H), 1.10 (t, J=7.1 Hz, 3H). LCMS for $C_7H_{19}F_3N_5O_3$(M+H)$^+$: m/z=398.1; Found: 398.1.

Example 13. 3-Amino-6-(5-(3-amino-1,1,1-trifluoro-2-hydroxy-3-oxopropan-2-yl)-2-methylphenyl)-N-(1-hydroxy-2-methylpropan-2-yl)pyrazine-2-carboxamide

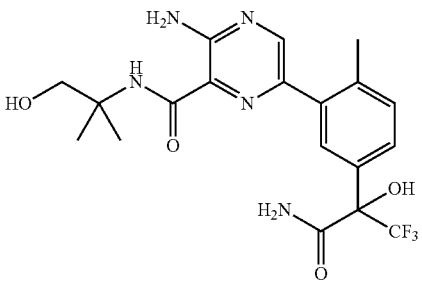 [SMILES: Cc1ccc(C(O)(C(N)=O)C(F)(F)F)cc1-c1cnc(N)c(C(=O)NC(C)(C)CO)n1]

The desired compound was prepared according to the procedure of example 1, step 7, using 2-amino-2-methylpropan-1-ol as the starting material in place of 1-amino-2-methylpropan-2-ol. H NMR (500 MHz, DMSO-$d_6$) δ 8.36 (s, 1H), 8.16 (s, 1H), 7.75 (d, J=2.0 Hz, 1H), 7.68-7.46 (m, 3H), 7.36 (d, J=8.1 Hz, 1H), 3.42 (s, 2H), 2.39 (s, 3H), 1.33 (s, 6H). LCMS for $C_{19}H_{23}F_3N_5O_4$ (M+H)$^+$: m/z=442.2; Found: 442.2.

Example 31. 3-Amino-6-(5-(1-amino-3,3-difluoro-2-hydroxy-1-oxopropan-2-yl)-2-methylphenyl)-N-methylpyrazine-2-carboxamide

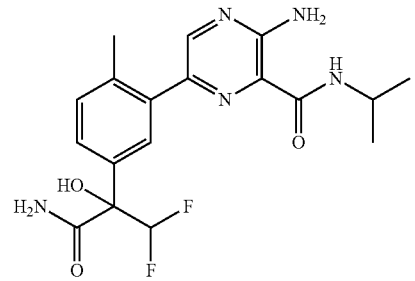 [SMILES: Cc1ccc(C(O)(C(N)=O)C(F)F)cc1-c1cnc(N)c(C(=O)NC(C)C)n1]

Step 1.
1-(3-Bromo-4-methylphenyl)-2,2-difluoroethan-1-ol

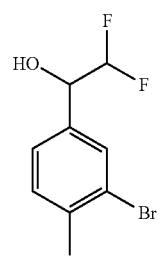
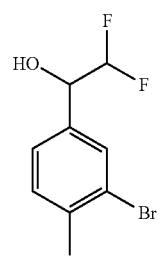

To solution of (difluoromethyl)trimethylsilane (5.1 g, 42 mmol) in dry DMF (20 mL) at 0° C. was added 3-bromo-4-methylbenzaldehyde (4.1 g, 21 mmol) followed by cesium fluoride (0.44 g, 2.9 mmol). The ice bath was removed, and the resulting reaction mixture was stirred for 2 h. The mixture was cooled back to 0° C., water (2.0 mL) and 1.0 M tetra-n-butylammonium fluoride in tetrahydrofuran (4.2 mL, 4.2 mmol) were added. The ice bath was removed and the mixture was stirred for 30 min at rt. The yellow reaction mixture was diluted with water (100 mL), and was extracted with Et$_2$O (150 mL). The organic layer was washed with saturated NH$_4$Cl solution (25 mL), dried over anhydrous sodium sulfate, filtered and concentrated to give a rust colored oil. Purification on silica gel using ethyl acetate/hexane, 0-60% gave the desired compound as a yellow oil, 3.6 g, 69%. LCMS calculated for C$_9$H$_8$BrF$_2$ (M−OH)$^+$: m/z=233.0, 235.0; Found: 232.9, 235.1

Step 2.
1-(3-Bromo-4-methylphenyl)-2,2-difluoroethan-1-one

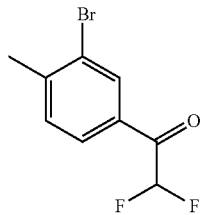

A mixture of 1-(3-bromo-4-methylphenyl)-2,2-difluoroethan-1-ol (3.6 g, 14 mmol) in dichloromethane (57 mL) at 0° C. was treated with Dess-Martin periodinane (9.1 g, 22 mmol). The ice bath was removed and the reaction mixture was stirred at rt for 1.0 h. The reaction mixture was concentrated to an oil. Et$_2$O was added and solid precipitated. The suspended mixture was filtered. The filtrate was washed with saturated NaHCO$_3$ solution and saturated NaCl solution, dried over anhydrous Na$_2$SO$_4$, and filtered. The solution was concentrated to yellow oil, 2.3 g, 64%. LCMS for C$_9$H$_8$BrF$_2$O(M+H)$^+$ calculated for (M+H)$^+$: m/z=249.0, 251.0; Found: 248.9, 251.0

Step 3. 2-(3-Bromo-4-methylphenyl)-3,3-difluoro-2-hydroxypropanenitrile

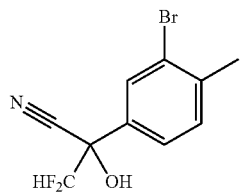

To a solution of 1-(3-bromo-4-methylphenyl)-2,2-difluoroethan-1-one (2.3 g, 9.0 mmol) in dichloromethane (9.0 mL) under N$_2$ was added trimethylsilyl cyanide (2.7 mL, 20 mmol), potassium cyanide (88 mg, 1.4 mmol), and 18-crown-6 (88 mg, 0.33 mmol). The reaction mixture was stirred for 1 h. The reaction mixture was concentrated under nitrogen. The solid was dissolved in THF (9.0 mL) and cooled to 0° C. HCl (1.8M, 0.37 mL, 0.66 mmol), was added with stirring at 0° C. The ice bath was removed, and the reaction mixture was stirred for 1.5 h. Water (75 mL) was added to the reaction mixture. The reaction mixture was extracted with Et$_2$O (3×75 mL). The combined Et$_2$O extracts were washed with saturated NaCl solution, dried over anhydrous Na$_2$SO$_4$, filtered, and concentrated to give orange solid, 2.5 g, 100%.

Step 4. 2-(3-Bromo-4-methylphenyl)-3,3-difluoro-2-hydroxypropanamide

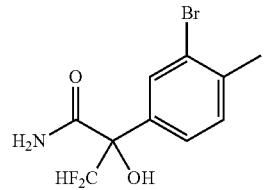

To a solution of 2-(3-bromo-4-methylphenyl)-3,3-difluoro-2-hydroxypropanenitrile (2.0 g, 7.2 mmol) in dioxane (15 mL) under N$_2$ at 0° C. was added HCl (concentrated) (2.2 mL, 26 mmol) (precooled in an ice bath). While cooling at 0° C., the reaction mixture was vigorously bubbled with HCl gas for 10 min. The reaction vial was capped tightly. The cooling bath was removed and the mixture stirred for 16 h. The reaction mixture was cooled at 0° C. and diluted with saturated NH4Cl solution (2 mL), water (10 mL), and of EtOAc (50 mL). The EtOAc layer was separated and washed with water, dried over anhydrous Na$_2$SO$_4$, filtered, and concentrated to brown oil. The oil was dissolved in CH$_2$Cl$_2$ and purified on a silica gel column, EtOAc/hexane, 0-60%. The product fractions were concentrated to yellow oil, 2.1 g, 100%. The racemic mixture was separated via preparative chiral HPLC (Phenomenex Lux Amylose-1 [21.2×250 mm, 5 micron], eluting with 85% ethanol in hexanes, at flow rate of 20 mL/min, loading about 100 mg in 2 mL ethanol) to give the desired second eluting enantiomer (0.9 g, 43%) as a viscous oil. The first enantiomer that eluted had a retention time of 4.2 min. The second enantiomer that eluted had a retention time of 6.4 min. Second eluting enantiomer: LCMS calculated for C$_{10}$H$_{11}$BrF$_2$NO$_2$ (M+H)$^+$: m/z=294.0, 296.0; Found: 294.0, 296.0

Step 5. 3,3-Difluoro-2-hydroxy-2-(4-methyl-3-(4,4,5,5-tetramethyl-1,3,2-dioxaborolan-2-yl)phenyl)propanamide

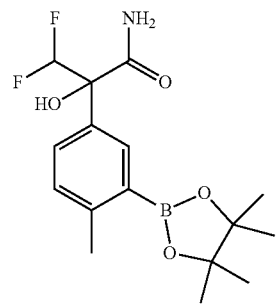 [SMILES: Cc1ccc(C(O)(C(N)=O)C(F)F)cc1B1OC(C)(C)C(C)(C)O1]

A mixture of 2-(3-bromo-4-methylphenyl)-3,3-difluoro-2-hydroxypropanamide (660 mg, 2.2 mmol), (step 4, second eluting isomer), 4,4,4',4',5,5,5',5'-octamethyl-2,2'-bi(1,3,2-dioxaborolane) (680 mg, 2.7 mmol), potassium acetate (720 mg, 7.4 mmol), and dichlorobis(triphenylphosphine)palladium(II) (63 mg, 89 µmol) in THF (5 mL) was degassed for 5 min with $N_2$. The mixture was heated in a microwave at 135° C. for 20 minutes. The reaction mixture was diluted with EtOAc and filtered through Celite®, rinsing with EtOAc. The filtrate was concentrated. Purification via silica gel chromatography (0-100% EtOAc/hexanes) afforded the desired product as clear oil. The yield for the product is: 81%, 620 mg. LCMS calculated for $C_{16}H_{23}BF_2NO_4(M+H)^+$: m/z=342.2; Found 342.2

Step 6. 2-(3-(5-Amino-6-chloropyrazin-2-yl)-4-methylphenyl)-3,3-difluoro-2-hydroxypropanamide

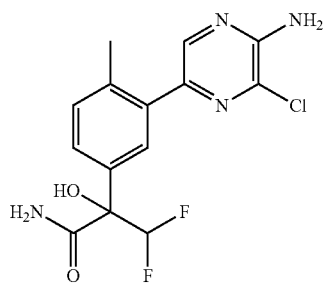 [SMILES: Cc1ccc(C(O)(C(N)=O)C(F)F)cc1-c1cnc(N)c(Cl)n1]

A vial was charged with 5-bromo-3-chloropyrazin-2-amine (35 mg, 0.17 mmol), and 3,3-difluoro-2-hydroxy-2-(4-methyl-3-(4,4,5,5-tetramethyl-1,3,2-dioxaborolan-2-yl)phenyl)propanamide (58 mg, 0.17 mmol) in dioxane. To the mixture was added aqueous sodium carbonate (260 µl, 0.51 mmol) and bubbled with $N_2$ for 5 Min. To the mixture was added [1,1'-bis(diphenylphosphino)ferrocene]dichloropalladium(II) complex with dichloromethane (6.9 mg, 8.5 µmol) and bubbled $N_2$ through the mixture for 5 min. The reaction was heated to 100° C. for 15 h. The reaction mixture was diluted with ethyl acetate and filtered through a 0.5 micrometer cartridge. The filtrate was washed with saturated NaCl solution. The layers were separated and the aqueous layer was back extracted with more EtOAc. The combined EtOAc extracts were dried over anhydrous $Na_2SO_4$, filtered, and concentrated to a brown foam. Purification on silica gel column using 0-100% EtOAc in hexane followed by (0-10% MeOH/DCM) gradient. The yield for the product is 26 mg, 32%, LCMS calculated for $C_{14}H_{14}ClF_2N_4O_2$ $(M+H)^+$: m/z=343.1; Found 343.2.

Step 7. 2-(3-(5-Amino-6-(1-methyl-1H-pyrazol-5-yl)pyrazin-2-yl)-4-methylphenyl)-3,3-difluoro-2-hydroxypropanamide To a microwave vial was added 2-(3-(5-amino-6-chloropyrazin-2-yl)-4-methylphenyl)-3,3-difluoro-2-hydroxypropanamide (10 mg, 0.029 mmol), Pd(dppf)$_2$CH$_2$Cl$_2$ (4.7 mg, 5.8 µmol), dioxane (580 µl), triethylamine (16 µl, 0.12 mmol) and propan-2-amine (50 µl, 0.58 mmol). The vial was capped and degassed with a stream of nitrogen for 5 mins and the solution saturated with CO by bubbling the gas through the reaction subsurface for 30 min. The reactions were heated at 80° C. overnight. The reaction mixture was diluted with methanol and purified on prep LC/MS using pH 10 buffer. The yield for the product is (17%, 2.0 mg). LCMS calculated for $C_{18}H_{22}F_2N_5O_3$ $(M+H)^+$: m/z=394.2. Found 394.2

Examples 32 to 37 were synthesized according to procedures analogous to Example 31 and the data are listed in Table 2.

TABLE 2

![Structure showing pyrazine with H2N, R^{d7}R^{c7}N-C(O)-, methylphenyl with C(OH)(CHF2)C(O)NH2]

| Ex. No. | Name | NR$c^7$R$d^7$ | LCMS [M + H]$^+$ |
|---|---|---|---|
| 32 | 3-amino-6-(5-(1-amino-3,3-difluoro-2-hydroxy-1-oxopropan-2-yl)-2-methylphenyl)-N-ethylpyrazine-2-carboxamide | ethyl-NH- | 380.1 |
| 33 | 3-amino-6-(5-(1-amino-3,3-difluoro-2-hydroxy-1-oxopropan-2-yl)-2-methylphenyl)-N-((1-cyanocyclopropyl)methyl)pyrazine-2-carboxamide | (1-cyanocyclopropyl)methyl-NH- | 431.1 |
| 34 | 3-amino-6-(5-(1-amino-3,3-difluoro-2-hydroxy-1-oxopropan-2-yl)-2-methylphenyl)-N-(4,4-difluorocyclohexyl)pyrazine-2-carboxamide | 4,4-difluorocyclohexyl-NH- | 470.1 |
| 35 | 3-amino-6-(5-(1-amino-3,3-difluoro-2-hydroxy-1-oxopropan-2-yl)-2-methylphenyl)-N-(1-hydroxy-2-methylpropan-2-yl)pyrazine-2-carboxamide | HO-C(CH$_3$)$_2$-CH$_2$-... -NH- | 424.1 |
| 36 | 3-amino-6-(5-(1-amino-3,3-difluoro-2-hydroxy-1-oxopropan-2-yl)-2-methylphenyl)-N-(tetrahydro-2H-pyran-4-yl)pyrazine-2-carboxamide | tetrahydropyran-4-yl-NH- | 436.1 |
| 37 | 3-amino-6-(5-(1-amino-3,3-difluoro-2-hydroxy-1-oxopropan-2-yl)-2-methylphenyl)-N-(2-(tetrahydrofuran-3-yl)ethyl)pyrazine-2-carboxamide | 2-(tetrahydrofuran-3-yl)ethyl-NH- | 450.2 |

Example 38. 3-Amino-6-(5-(3-amino-1,1,1-trifluoro-2-hydroxy-3-oxopropan-2-yl)-2-methylphenyl)-N-(2,2,2-trifluoroethyl)pyrazine-2-carboxamide trifluoroacetate

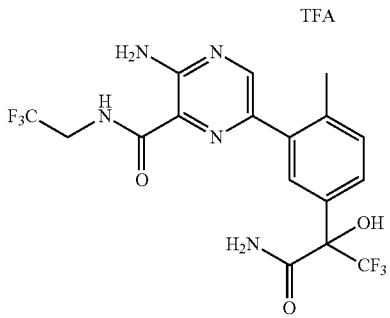 [SMILES: Cc1ccc(C(O)(C(N)=O)C(F)(F)F)cc1-c1cnc(N)c(C(=O)NCC(F)(F)F)n1]

Step 1. Ethyl 3-amino-6-(5-(3-amino-1,1,1-trifluoro-2-hydroxy-3-oxopropan-2-yl)-2-methylphenyl)pyrazine-2-carboxylate

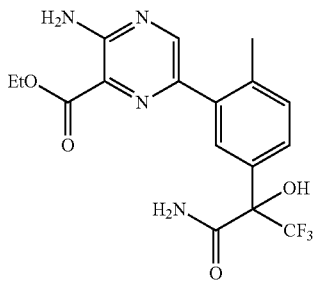 [SMILES: CCOC(=O)c1nc(-c2cc(C(O)(C(N)=O)C(F)(F)F)ccc2C)cnc1N]

A solution of 2-(3-(5-amino-6-chloropyrazin-2-yl)-4-methylphenyl)-3,3,3-trifluoro-2-hydroxypropanamide (single enantiomer from Example 1, step 6, 0.060 g, 0.166 mmol) in ethanol (4.4 mL) was treated with triethylamine (0.093 mL, 0.67 mmol) and degassed with nitrogen for 5 min. The reaction mixture was treated with dichloro[1,1'-bis(diphenylphosphino)ferrocene]palladium (II) dichloromethane adduct (0.027 g, 0.033 mmol) and degassed with nitrogen for another 5 min. The reaction mixture was saturated with CO by bubbling the gas through the reaction subsurface for 5 min and the reaction mixture was stirred at 80° C. overnight. The reaction mixture was diluted with methanol and water and filtered through a 0.45 micron cartridge. The filtrate was concentrated and the crude residue was purified by flash column chromatography using methanol in dichloromethane (0% to 10%) to give the desired product (48.0 mg, 72.1%). LCMS for $C_{17}H_8F_3N_4O_4$ $(M+H)^+$: m/z=399.1; Found: 399.1.

Step 2. 3-Amino-6-(5-(3-amino-1,1,1-trifluoro-2-hydroxy-3-oxopropan-2-yl)-2-methylphenyl)pyrazine-2-carboxylic acid

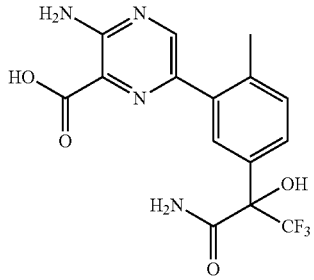 [SMILES: Cc1ccc(C(O)(C(N)=O)C(F)(F)F)cc1-c1cnc(N)c(C(=O)O)n1]

A solution of ethyl 3-amino-6-(5-(3-amino-1,1,1-trifluoro-2-hydroxy-3-oxopropan-2-yl)-2-methylphenyl)pyrazine-2-carboxylate (0.048 g, 0.120 mmol, single enantiomer) in methanol (1.21 mL) was treated with 1.0 N sodium hydroxide (0.602 ml, 0.602 mmol) and stirred at rt for 2.5 h. The reaction mixture was partially concentrated to remove methanol and quenched with 1 N HCl to pH~5 (0.45 mL). The mixture was extracted with ethyl acetate (3×). The combined organic layers were washed with brine (0.5 mL), dried over sodium sulfate, filtered, and concentrated to give the desired product (40.0 g, 88.9%) as a tan solid that was used without further purification. LCMS for $C_{15}H_{14}F_3N_4O_4$ $(M+H)^+$: m/z=371.1; Found: 371.2.

Step 3. 3-Amino-6-(5-(3-amino-1,1,1-trifluoro-2-hydroxy-3-oxopropan-2-yl)-2-methylphenyl)-N-(2,2,2-trifluoroethyl)pyrazine-2-carboxamide trifluoroacetate A solution of 2,2,2-trifluoroethan-1-amine hydrochloride (2.74 mg, 0.020 mmol), HATU (7.70 mg, 0.020 mmol), and 3-amino-6-(5-(3-amino-1,1,1-trifluoro-2-hydroxy-3-oxopropan-2-yl)-2-methylphenyl)pyrazine-2-carboxylic acid (0.005 g, 0.014 mmol) (single enantiomer) in DMF (0.225 mL) was stirred at rt for 5 min, treated with triethylamine (5.65 μL, 0.041 mmol), and stirred at rt for 30 min. The reaction mixture was diluted with methanol and water and purified via preparative LCMS (XBridge C18 Column, eluting with a gradient of acetonitrile in water with 0.1% trifluoroacetic acid, at flow rate of 60 mL/min) to give the desired product (2.50 mg, 32.8%) as a TFA salt. $^1$H NMR (500 MHz, DMSO-$d_6$) δ 9.01 (t, J=6.7 Hz, 1H), 8.36 (s, 1H), 7.70 (d, J=2.0 Hz, 1H), 7.68-7.47 (m, 3H), 7.37 (d, J=8.1 Hz, 1H), 5.09 (br s, 2H), 4.24-3.84 (m, 2H), 2.34 (s, 3H). LCMS for $C_{17}H_{16}F_6N_5O_3(M+H)^+$: m/z=452.1; Found: 452.1.

Example 39. 6-(5-(3-Acetamido-1,1,1-trifluoro-2-hydroxypropan-2-yl)-2-methylphenyl)-3-amino-N-isopropylpyrazine-2-carboxamide trifluoroacetate

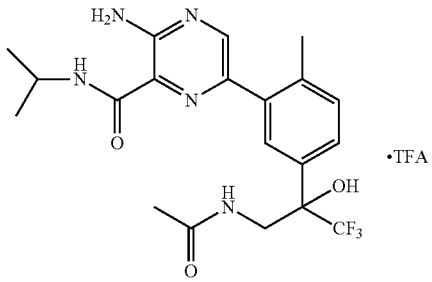 [SMILES: CC(=O)NCC(O)(c1ccc(C)c(-c2cnc(N)c(C(=O)NC(C)C)n2)c1)C(F)(F)F]

Step 1. 3-amino-2-(3-bromo-4-methylphenyl)-1,1,1-trifluoropropan-2-ol

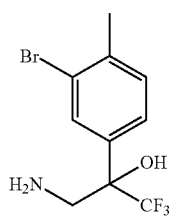

A solution of 2-(3-Bromo-4-methylphenyl)-3,3,3-trifluoro-2-hydroxypropanenitrile (Example 1, Step 3, 600 mg, 1.92 mmol) in Et$_2$O (5 mL) at 0° C., LiAlH$_4$ (100 mg, 2.63 mmol) was added portionwise. The temperature was increased to room temperature and stirred for 3 hours. The resulted mixture was quenched with 2 mL 1N NaOH aqueous at 0° C. slowly with caution, and diluted with 10 mL diethyl ether. The mixture was filtered and concentrated. Purification via SiO$_2$ chromatography (Hexane/EtOAc 3:1 to 1:3) gave the desired product (350 mg, 1.17 mmol, 61%) as a white solid. LCMS for C$_{10}$H$_{12}$BrF$_3$NO (M+H)$^+$: m/z=298.0, 300.0; Found: 298.0, 300.0.

Step 2. 3-amino-1,1,1-trifluoro-2-(4-methyl-3-(4,4,5,5-tetramethyl-1,3,2-dioxaborolan-2-yl)phenyl)propan-2-ol

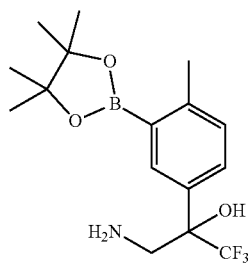 [SMILES: Cc1ccc(C(O)(CN)C(F)(F)F)cc1B1OC(C)(C)C(C)(C)O1]

A solution of 2-(3-bromo-4-methylphenyl)-3,3,3-trifluoro-2-hydroxypropanamide (Example 1, Step 4, racemic mixture, 350 mg, 1.17 mmol) in dioxane (6 mL) was treated with bis(pinacolato)diboron (350 mg, 1.37 mmol), and potassium acetate (370 mg, 3.78 mmol) and degassed with nitrogen for 5 min. The reaction mixture was treated with bis(triphenylphosphine)palladium(II)chloride (0.048 g, 0.069 mmol), degassed for 5 min, and stirred at 100° C. for 2.5 h. The reaction mixture was diluted with ethyl acetate (5 mL), filtered over CELITE®, and rinsed with additional ethyl acetate (10 mL). The filtrate was washed with brine, dried over sodium sulfate, filtered, and concentrated to a brown foam. Purification by flash column chromatography using MTBE in hexanes (30% to 100%) gave the desired product (300 mg, 0.87 mmol, 63%) as a thick yellow foam. LCMS for C$_{16}$H$_{24}$BF$_3$NO$_3$ (M+H)$^+$: m/z=346.2; Found: 346.2.

Step 3. 3-amino-2-(3-(5-amino-6-chloropyrazin-2-yl)-4-methylphenyl)-1,1,1-trifluoropropan-2-ol

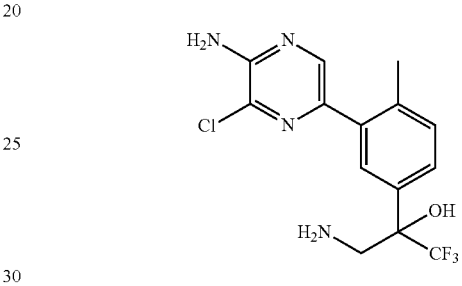

A solution of 5-bromo-3-chloropyrazin-2-amine (200 mg, 0.96 mmol) and 3-amino-1,1,1-trifluoro-2-(4-methyl-3-(4,4,5,5-tetramethyl-1,3,2-dioxaborolan-2-yl)phenyl)propan-2-ol (200 mg, 0.58 mmol, racemic) in dioxane/water (5 mL/1 mL) was treated with sodium carbonate (184 mg, 1.74 mmol) and dichloro[1,1'-bis(diphenylphosphino)ferrocene]palladium (II) dichloromethane adduct (24 mg, 0.029 mmol). The reaction mixture was degassed with nitrogen for 5 min, and stirred at 120° C. for 2.5 h. The resulting mixture was diluted with MeOH and passed through a Celite pad and concentrated. Purification vis flash column chromatography using ethyl acetate (containing 5% MeOH) in hexanes (0% to 100%) gave the desired product (112 mg, 56%) as yellow solid.

Step 4. 3-amino-6-(5-(3-amino-1,1,1-trifluoro-2-hydroxypropan-2-yl)-2-methylphenyl)-N-isopropylpyrazine-2-carboxamide

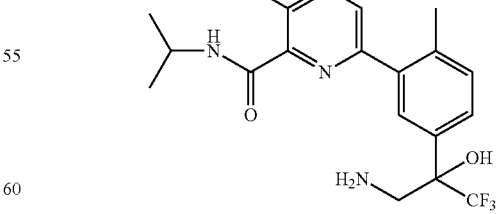

To a microwave vial was added 3-amino-2-(3-(5-amino-6-chloropyrazin-2-yl)-4-methylphenyl)-1,1,1-trifluoropropan-2-ol (100 mg, 0.29 mmol), [1,1'-bis(diphenylphosphino)ferrocene]dichloropalladium (47.1 mg, 0.058 mmol), isopropyl amine (170 mg, 2.88 mmol), sodium carbonate (61.1 mg, 0.58 mmol), dioxane (5 mL) and water (1 mL). The vial was capped and degassed with a stream of nitrogen for 5 min and the solution saturated with CO by bubbling the gas through the reaction mixture for 10 min followed by addition of additional isopropyl amine (170 mg, 2.88 mmol). The reaction was heated at 80° C. overnight. The reaction mixture was diluted with methanol and passed through a Celite® pad. The resulting mixture was concentrated and purified by flash column chromatography using MeOH in $CH_2Cl_2$ (5% to 10%) to give the desired product (68 mg, 59%) as a thick yellow foam. $^1$H NMR (400 MHz, DMSO-$d_6$) δ 8.45 (s, 1H), 8.14 (d, J=7.9 Hz, 1H), 7.96 (brs, 2H), 7.69 (s, 1H), 7.60 (d, J=7.7 Hz, 1H), 7.55 (s, 1H), 7.44 (d, J=8.4 Hz, 1H), 4.09 (m, 1H), 3.75 (m, 2H), 2.42 (s, 3H), 1.18 (d, J=6.2 Hz, 6H); LCMS calculated for $C_{18}H_{23}F_3N_5O_2$ (M+H)$^+$: m/z=398.2. Found 398.2.

Step 5. 6-(5-(3-acetamido-1,1,1-trifluoro-2-hydroxy-propan-2-yl)-2-methylphenyl)-3-amino-N-isopropylpyrazine-2-carboxamide trifluoroacetate A solution of 3-amino-6-(5-(3-amino-1,1,1-trifluoro-2-hydroxypropan-2-yl)-2-methylphenyl)-N-isopropylpyrazine-2-carboxamide (4 mg, 10.07 μmol, racemic) and acetic acid (20 mg, 0.33 mmol) in DMF/Hünig's base (0.5 mL/0.05 mL) was treated with HATU (10 mg, 26.32 μmol). The resulting mixture was stirred for 1 h before it was diluted with MeOH (3 mL). After filtered through a cartridge. The filtrate was purified via preparative LCMS (XBridge C18 Column, eluting with a gradient of acetonitrile in water with 0.1% trifluoroacetic acid, at flow rate of 60 mL/min) to give the desired product (2 mg, 45%) as a white solid. $^1$H NMR (400 MHz, DMSO-$d_6$) δ 8.40 (s, 1H), 8.40 (d, J=7.9 Hz, 1H), 7.96 (m, 1H), 7.58 (s, 1H), 7.53 (d, J=8.5 Hz, 1H), 7.34 (d, J=8.5 Hz, 1H), 4.15 (m, 1H), 3.62 (m, 2H), 2.39 (s, 3H), 1.77 (s, 3H), 1.19 (dd, J=6.0 Hz, 1.2 Hz, 6H); LCMS for $C_{20}H_{25}F_3N_5O_3$ (M+H)$^+$: m/z=440.2; Found: 440.2.

Example 40. 3-Amino-N-isopropyl-6-(2-methyl-5-(1,1,1,-trifluoro-3-(2-fluoroacetamido)-2-hydroxy-propan-2-yl)phenyl)pyrazine-2-carboxamide trifluoroacetate

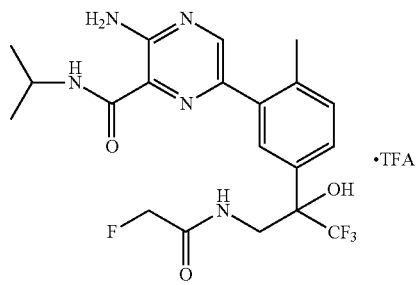 [SMILES: Cc1ccc(C(O)(CNC(=O)CF)C(F)(F)F)cc1-c1cnc(N)c(C(=O)NC(C)C)n1]

Example 31 was synthesized according to the procedure of Example 38, using 2-fluoroacetic acid as the starting material in place of acetic acid in Step 2. LCMS for $C_{20}H_{24}F_4N_5O_3$(M+H)$^+$: m/z=458.2; Found: 458.2

Example 41. 3-Amino-N-isopropyl-6-(2-methyl-5-(1,1,1-trifluoro-2-hydroxy-3-(2-hydroxy-2-methyl-propanamido)propan-2-yl)phenyl)pyrazine-2-carboxamide trifluoroacetate

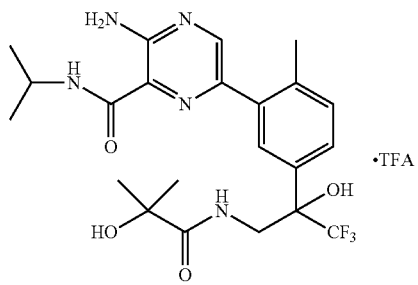 [SMILES: Cc1ccc(C(O)(CNC(=O)C(C)(C)O)C(F)(F)F)cc1-c1cnc(N)c(C(=O)NC(C)C)n1]

Example 32 was synthesized according to the procedure of Example 38, using 2-hydroxy-2-methylpropanoic acid as the starting material in place of acetic acid in Step 2. LCMS for $C_{22}H_{29}F_3N_5O_4$(M+H)$^+$: m/z=484.2; Found: 484.2.

Example 42. 3-Amino-6-(5-(3-(2-cyanoacetamido)-1,1,1-trifluoro-2-hydroxypropan-2-yl)-2-methylphenyl)-N-isopropylpyrazine-2-carboxamide trifluoroacetate

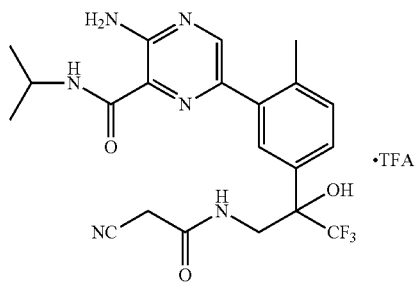 [SMILES: Cc1ccc(C(O)(CNC(=O)CC#N)C(F)(F)F)cc1-c1cnc(N)c(C(=O)NC(C)C)n1]

Example 33 was synthesized according to the procedure of Example 38, using 2-cyanoacetic acid as the starting material in place of acetic acid in Step 2. LCMS for $C_{21}H_{24}F_3N_6O_3$ (M+H)$^+$: m/z=465.2; Found: 465.2.

Examples 43A and 43B. Diastereoisomers of 3-amino-6-(5-(3-amino-1,1,1-trifluoro-2-hydroxy-3-oxopropan-2-yl)-2-methylphenyl)-N-(3,3,3-trifluoro-2-hydroxypropyl)pyrazine-2-carboxamide

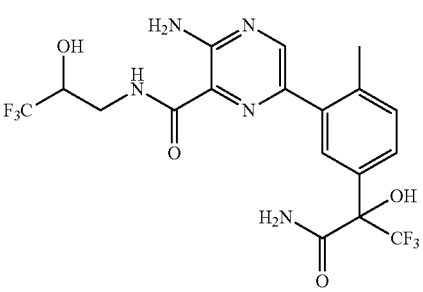 [SMILES: Cc1ccc(C(O)(C(N)=O)C(F)(F)F)cc1-c1cnc(N)c(C(=O)NCC(O)C(F)(F)F)n1]

A solution of 3-amino-1,1,1-trifluoropropan-2-ol (0.016 g, 0.122 mmol), HATU (0.046 mg, 0.122 mmol), and 3-amino-6-(5-(3-amino-1,1,1-trifluoro-2-hydroxy-3-oxo-propan-2-yl)-2-methylphenyl)pyrazine-2-carboxylic acid (0.030 g, 0.081 mmol) (single enantiomer, synthesized according to procedure in Example 38) in DMF (0.810 mL) was stirred at rt for 5 min, treated with triethylamine (0.034 mL, 0.243 mmol), and stirred at rt for 30 min. The reaction mixture was concentrated and purified by flash column chromatography using methanol in dichloromethane (0% to 20%) to give the desired product that still contained some impurities. This material was repurified by flash column chromatography using ethyl acetate in hexanes (0% to 100%) to give the desired product as a mixture of diastereomers. The mixture of diastereomers was separated via preparative chiral HPLC (Chiral Technologies ChiralPak IA [20×250 mm, 5 micron], eluting with 15% ethanol in hexanes, at flow rate of 20 mL/min, loading about 8 mg in 1.8 mL ethanol) to give the first eluting diastereomer (3.20 mg, 8.21%) as 43A and the second eluting diastereomer (3.00 mg, 7.69%) as 43B. The first diastereomer that eluted had a retention time of 12.2 min. The second diastereomer that eluted had a retention time of 16.6 min. 43A: LCMS for $C_{18}H_{18}F_6N_5O_4(M+H)^+$: m/z=482.1; Found: 482.1. 43B: LCMS for $C_{18}H_{18}F_6N_5O_4 {}_{(M+H)}{}^+$: m/z=482.1; Found: 482.1.

Example 44. (Z)-2-(3-(5-amino-6-(prop-1-en-1-yl)pyrazin-2-yl)-4-methylphenyl)-3,3,3-trifluoro-2-hydroxypropanamide

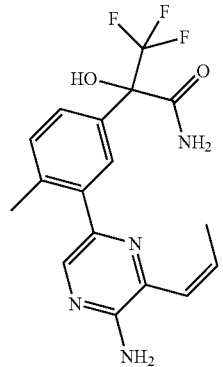 [SMILES: C/C=C\c1nc(-c2cc(C(O)(C(N)=O)C(F)(F)F)ccc2C)cnc1N]

Step 1. 1-(3-Bromo-4-methylphenyl)-2,2,2-trifluoro-ethan-1-ol

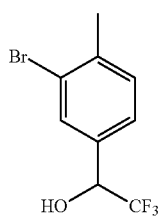

A solution of 3-bromo-4-methylbenzaldehyde (6.51 g, 32.7 mmol) [Combi-Blocks, HC-3454] in dry tetrahydrofuran (65.4 mL) was cooled to 0° C., followed by the addition of trimethyl(trifluoromethyl)silane (6.28 mL, 42.5 mmol). The yellow mixture was treated with 1.0 M tetra-n-butylammonium fluoride in tetrahydrofuran (0.654 mL, 0.654 mmol) at 0° C. and stirred for a few minutes at 0° C. The ice bath was removed and the resulting reaction mixture was stirred for 1.5 h. The reaction mixture was cooled back to 0° C. and treated with water (6.48 mL, 360 mmol) and 1.0 M tetra-n-butylammonium fluoride in tetrahydrofuran (6.54 mL, 6.54 mmol). The ice bath was removed and the reaction mixture was stirred at ambient temperature for 30 min. The yellow reaction mixture was diluted with brine (150 mL) and extracted with ethyl acetate (200 mL). The organic layer was washed with saturated ammonium chloride (100 mL), dried over sodium sulfate, filtered, and concentrated to give a tan oil. Purification by flash column chromatography using methyl tert-butyl ether (MTBE) in hexanes (0% to 50%) gave the desired product (8.42 g, 95.7%) as a yellow oil. LCMS for $C_9H_7BrF_3$ (M–OH)$^+$: m/z=251.0, 253.0; Found: 250.9, 252.8.

Step 2. 1-(3-Bromo-4-methylphenyl)-2,2,2-trifluoro-ethan-1-one

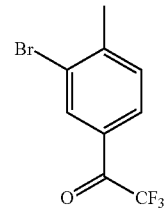

A mixture of 1-(3-bromo-4-methylphenyl)-2,2,2-trifluoroethan-1-ol (8.41 g, 31.3 mmol) in dichloromethane (125 mL) at 0° C. was treated with Dess-Martin periodinane (19.9 g, 46.9 mmol) and stirred at room temperature (rt) for 2.5 h. The reaction mixture was concentrated by rotary evaporation with the water bath set at 30° C., to afford an oily solid that was subsequently diluted with diethyl ether (200 mL), which precipitated more solids. This mixture was filtered over Celite® and the Celite® was rinsed with additional diethyl ether (200 mL). The filtrate was washed with saturated sodium bicarbonate solution (3×200 mL) and brine, dried over sodium sulfate, filtered, and concentrated to give an oily solid. The oily solid was partitioned between diethyl ether (150 mL) and water (100 mL). The organic layer was separated and washed with saturated sodium bicarbonate solution (2×75 mL) and brine, dried over sodium sulfate, filtered, and concentrated to give the desired product (7.93 g, 95.0%) as an oil that was used without further purification. LCMS for $C_9H_7BrF_3O$ (M+H)$^+$: m/z=267.0, 269.0; Found: 267.1, 268.9.

Step 3. 2-(3-Bromo-4-methylphenyl)-3,3,3-trifluoro-2-hydroxypropanenitrile

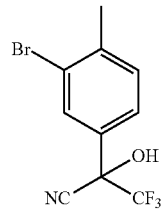

A solution of 1-(3-bromo-4-methylphenyl)-2,2,2-trifluoroethan-1-one (7.92 g, 29.7 mmol) in dichloromethane (29.7 mL) was treated with trimethylsilyl cyanide (8.70 mL, 65.2 mmol), potassium cyanide (0.29 g, 4.45 mmol), and 18-crown-6 (0.29 g, 1.10 mmol) and stirred for 1 h. The reaction can be cooled with an ice bath due to an exotherm after the addition of 18-crown-6. The reaction mixture was concentrated by rotary evaporation with the water bath set at 28° C. to give a rust colored solid. The solid was dissolved in THF (29.6 mL), cooled to 0° C., treated with 1.8 M HCl (10.9 mL, 19.6 mmol), and stirred at rt for 1.5 h. The reaction mixture was diluted with water (75 mL) and extracted with diethyl ether (3×75 mL). The combined organic extracts were washed with brine, dried over sodium sulfate, filtered, and concentrated. Reconcetration from hexanes to give the desired product (8.70 g, 99.8%) as an orange solid that was used without further purification. LCMS for $C_9H_7BrF_3O$ $(M-CN)^+$: m/z=267.0, 269.0; Found: 266.9, 269.0.

Step 4. 2-(3-bromo-4-methylphenyl)-3,3,3-trifluoro-2-hydroxypropanamide

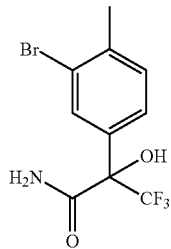 [SMILES: Cc1ccc(C(O)(C(N)=O)C(F)(F)F)cc1Br]

A solution of 2-(3-bromo-4-methylphenyl)-3,3,3-trifluoro-2-hydroxypropanenitrile (8.70 g, 29.6 mmol) in dioxane (59.2 mL) at 0° C. was treated with concentrated HCl (9.00 mL, 108 mmol) that had been pre-cooled in an ice bath. While stirring at 0° C., the reaction mixture was bubbled with HCl gas for 45 min. The cooling bath was removed and the reaction mixture was stirred at rt for 61 h. The reaction mixture was bubbled with nitrogen for 10 min to remove some of the HCl, cooled to 0° C., and diluted with brine (200 mL), water (50 mL), and ethyl acetate (200 mL). The organic layer was separated and the aqueous layer was diluted with water (100 mL) to dissolve the remaining solids. The aqueous layer was extracted with ethyl acetate (100 mL). The combined organic extracts were washed with brine, dried over sodium sulfate, filtered, and concentrated to give a brown oil. Purification by flash column chromatography using MTBE in hexanes (0% to 60%) gave the desired product as a yellow oily solid. The racemic mixture was separated via preparative chiral HPLC (Phenomenex Lux Amylose-1 [21.2×250 mm, 5 micron], eluting with 95% ethanol in hexanes, at flow rate of 18 mL/min, loading about 100 mg in 2 mL ethanol) to give the desired second eluting enantiomer (4.50 g, 48.8%) as a viscous yellow oil. The first enantiomer that eluted had a retention time of 4.0 min. The second enantiomer that eluted had a retention time of 5.3 min. Second eluting enantiomer: LCMS for $C_{10}H_{10}BrF_3NO_2$ $(M+H)^+$: m/z=312.0, 314.0; Found: 312.0, 314.0.

Step 5. 3,3,3-Trifluoro-2-hydroxy-2-(4-methyl-3-(4,4,5,5-tetramethyl-1,3,2-dioxaborolan-2-yl)phenyl)propanamide

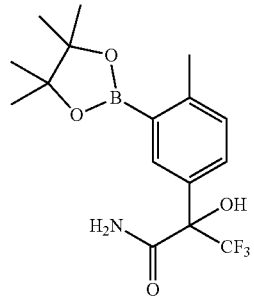 [SMILES: Cc1ccc(C(O)(C(N)=O)C(F)(F)F)cc1B1OC(C)(C)C(C)(C)O1]

A solution of 2-(3-bromo-4-methylphenyl)-3,3,3-trifluoro-2-hydroxypropanamide (3.57 g, 11.5 mmol) (Example 1, step 4, second eluting enantiomer) in dioxane (57.2 mL) was treated with bis(pinacolato)diboron (3.49 g, 13.7 mmol), and potassium acetate (3.71 g, 37.8 mmol) and degassed with nitrogen for 5 min. The reaction mixture was treated with bis(triphenylphosphine)palladium(II)chloride (0.482 g, 0.687 mmol), degassed for 5 min, and stirred at 100° C. for 2.5 h. The reaction mixture was diluted with ethyl acetate (50 mL), filtered over Celite®, and rinsed with additional ethyl acetate (100 mL). The filtrate was washed with brine, dried over sodium sulfate, filtered, and concentrated to a brown foam. Purification by flash column chromatography using MTBE in hexanes (0% to 100%) gave the desired product (3.35 g, 81.5%) as a thick yellow foam. $^1$H NMR (400 MHz, DMSO-$d_6$) δ 7.96 (d, J=2.2 Hz, 1H), 7.63 (dd, J=7.9, 2.1 Hz, 1H), 7.58 (s, 1H), 7.54 (s, 1H), 7.51-7.40 (m, 1H), 7.21 (d, J=8.2 Hz, 1H), 2.46 (s, 3H), 1.30 (s, 12H). LCMS for $C_{16}H_{22}BF_3NO_4$ $(M+H)^+$: m/z=360.2; Found: 360.1.

Step 6. 2-(3-(5-Amino-6-chloropyrazin-2-yl)-4-methylphenyl)-3,3,3-trifluoro-2-hydroxypropanamide

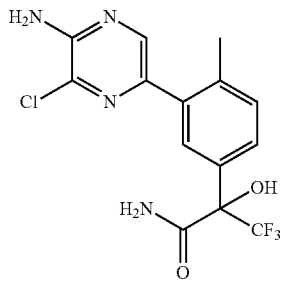 [SMILES: Cc1ccc(C(O)(C(N)=O)C(F)(F)F)cc1-c1cnc(N)c(Cl)n1]

A solution of 5-bromo-3-chloropyrazin-1-amine (0.235 g, 1.13 mmol) [Ark Pharm, AK-25099] and 3,3,3-trifluoro-2-hydroxy-2-(4-methyl-3-(4,4,5,5-tetramethyl-1,3,2-dioxaborolan-2-yl)phenyl)propanamide (0.405 g, 1.13 mmol) (single enantiomer from Example 1, step 5) in dioxane (13.1 mL) was treated with sodium carbonate (0.359 g, 3.38 mmol) in water (2.61 mL) and degassed with nitrogen for 5 min. The reaction mixture was treated with dichloro[1,1'-bis(diphenylphosphino)ferrocene]palladium (II) dichloromethane adduct (0.046 g, 0.056 mmol), degassed with nitrogen for 5 min, and stirred at 100° C. for 15 h. The reaction mixture was diluted with ethyl acetate (50 mL), filtered through a 0.45 micron cartridge, and rinsed with additional ethyl acetate (50 mL). The filtrate was washed with brine (30 mL). The aqueous layers was separated extracted with ethyl acetate (2×50 mL). The combined organic extracts were dried over sodium sulfate, filtered, and concentrated to a brown foam. Purification by flash column chromatography using ethyl acetate (containing 5% MeOH) in hexanes (0% to 100%) gave the desired product (0.180 g, 44.2%) as yellow solid. LCMS for $C_{14}H_{13}ClF_3N_4O_2$ $(M+H)^+$: m/z=361.1; Found: 361.0.

Step 7. (Z)-2-(3-(5-amino-6-(prop-1-en-1-yl) pyrazin-2-yl)-4-methylphenyl)-3,3,3-trifluoro-2-hydroxypropanamide A mixture of (Z)-prop-1-en-1-ylboronic acid (9.5 mg, 0.111 mmol), 2-(3-(5-amino-6-chloropyrazin-2-yl)-4-methylphenyl)-3,3,3-trifluoro-2-hydroxypropanamide (20 mg, 0.055 mmol), Pd(Ph₃P)₄ (9.6 mg, 8.3 µmol), and 1M K₂CO₃ (aq) (0.166 ml, 0.166 mmol) in 1,4-dioxane (0.8 ml) was de-gassed and purged with nitrogen several times prior to heating at 110° C. in a sealed vial overnight. The crude reaction mixture was diluted with EtOAc (20 mL) and filtered through a pad of celite. The inorganics were washed thoroughly with EtOAc. The volatiles were removed in-vacuo and the crude product was purified by CombiFlash chromatography (12 g silica gel column, eluting with 0-15% MeOH/DCM) to afford the desired product (18 mg, 100% yld). LCMS for $C_{17}H_{17}F_3N_4O_2(M+H)^+$: m/z=367.3; Found: 367.1.

Example 45. 2-(3-(5-amino-6-propylpyrazin-2-yl)-4-methylphenyl)-3,3,3-trifluoro-2-hydroxypropanamide

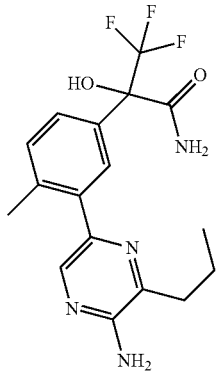 [SMILES: CCCc1nc(-c2cc(C(O)(C(N)=O)C(F)(F)F)ccc2C)cnc1N]

A mixture of (Z)-2-(3-(5-amino-6-(prop-1-en-1-yl) pyrazin-2-yl)-4-methylphenyl)-3,3,3-trifluoro-2-hydroxypropanamide (Example 1, 15 mg, 0.041 mmol) and 10% palladium on carbon (3.6 mg, 3.4 µmol) in methanol (3 mL) was purged with hydrogen and stirred overnight under an atmosphere of hydrogen via a balloon. The crude reaction mixture was filtered through a pad of Celite® and washed with methanol. The filtrate was concentrated in vacuo and purified via preparative LCMS (XBridge C18 Column, eluting with a gradient of acetonitrile in water with 0.1% trifluoroacetic acid, at flow rate of 60 mL/min) to give the desired product as a trifluoroacetic acid (TFA) salt. LCMS for $C_{17}H_{19}F_3N_4O_2(M+H)^+$: m/z=369.4; Found: 369.2.

Example 46. 2-(3-(5-Amino-6-(trifluoromethyl) pyrazin-2-yl)-4-methylphenyl)-3,3,3-trifluoro-2-hydroxypropanamide trifluoroacetate

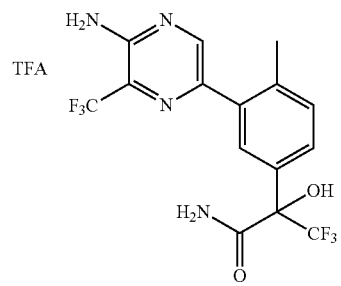 [SMILES: Cc1ccc(C(O)(C(N)=O)C(F)(F)F)cc1-c1cnc(N)c(C(F)(F)F)n1]

Step 1. 5-Bromo-3-(trifluoromethyl)pyrazin-2-amine

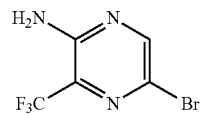

A solution of 3-(trifluoromethyl)pyrazin-2-amine (0.075 g, 0.460 mmol) [Oakwood, 500509] in dichloromethane (1.88 mL) was treated with N-bromosuccinimide (0.082 g, 0.460 mmol) and stirred at rt for 15 h. The reaction mixture was treated with additional N-bromosuccinimide (0.041 g, 0.230 mmol) and stirred for 21 h. The reaction mixture was diluted with water (10 mL) and extracted with dichloromethane (2×20 mL). The combined organic extracts were dried over sodium sulfate, filtered, and concentrated to brown, oily-solid. Purification by flash column chromatography using EtOAc in hexanes (0% to 30%) gave the desired product (64.5 mg, 58.1%) as a white solid. LCMS for $C_5H_4BrF_3N_3(M+H)^+$: m/z=242.0, 243.9; Found: 241.9, 243.9.

Step 2. 2-(3-(5-Amino-6-(trifluoromethyl)pyrazin-2-yl)-4-methylphenyl)-3,3,3-trifluoro-2-hydroxypropanamide trifluoroacetate The desired compound was prepared according to the procedure of Example 1, step 6, using 5-bromo-3-(trifluoromethyl)pyrazin-2-amine as the starting material in place of 5-bromo-3-chloropyrazin-2-amine. ¹H NMR (400 MHz, DMSO-d₆) δ 8.43 (s, 1H), 7.71 (d, J=2.1 Hz, 1H), 7.67-7.47 (m, 4H), 7.35 (d, J=8.1 Hz, 1H), 6.99 (s, 2H), 2.34 (s, 3H). LCMS for $C_{15}H_{13}F_6N_4O_2$ $(M+H)^+$: m/z=395.1; Found: 395.1.

Example 47. 2-(3-(5-amino-6-(3-methoxyprop-1-ynyl)pyrazin-2-yl)-4-methylphenyl)-3,3,3-trifluoro-2-hydroxypropanamide trifluoroacetate

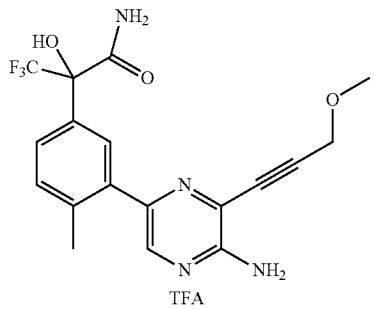 [SMILES: COCC#Cc1nc(-c2cc(C(O)(C(N)=O)C(F)(F)F)ccc2C)cnc1N]

A solution of 2-(3-(5-amino-6-chloropyrazin-2-yl)-4-methylphenyl)-3,3,3-trifluoro-2-hydroxypropanamide (45 mg, 0.125 mmol), which was prepared by methods described in Example 1, steps 1-6, 3-methoxyprop-1-yne (0.105 mL, 1.248 mmol), Pd(Ph$_3$P)$_4$ (21.62 mg, 0.019 mmol), copper(I) iodide (7.13 mg, 0.037 mmol), and triethylamine (0.174 mL, 1.248 mmol) in DMF (0.5 mL) was de-gassed and purged with nitrogen several times prior to heating in a sealed vial at 90° C. for 6 h. The crude reaction mixture was purified by flash column chromatography eluting with EtOAc in hexanes (0% to 100%) to afford the desired product (48 mg, 98%) as a yellow solid. A second purification was conducted via preparative LCMS (XBridge C18 Column, eluting with a gradient of acetonitrile in water with 0.1% trifluoroacetic acid, at flow rate of 60 mL/min). $^1$H NMR (600 MHz, DMSO-d$_6$) δ 8.17-8.06 (s, 1H), 7.69-7.66 (d, J=2.1 Hz, 1H), 7.65-7.62 (s, 1H), 7.61-7.57 (dd, J=8.2, 2.0 Hz, 1H), 7.57-7.53 (s, 1H), 7.38-7.29 (d, J=8.1 Hz, 1H), 6.99-6.44 (bs, 2H), 4.49-4.36 (s, 2H), 3.45-3.22 (s, 3H), 2.38-2.29 (s, 3H). LCMS for C$_{18}$H$_{17}$F$_3$N$_4$O$_3$(M+H)$^+$: m/z=395.1; Found: 395.1.

Examples 48-68 were synthesized according to procedures analogous to Example 47 and the data are listed in Table 3.

TABLE 3

| Ex. No. | Name | R$^7$ | LCMS [M + H]$^+$ |
|---|---|---|---|
| 48 | 2-(3-(5-amino-6-(cyclopropylethynyl)pyrazin-2-yl)-4-methylphenyl)-3,3,3-trifluoro-2-hydroxypropanamide | | 391.3 |
| 49 | 2-(3-(5-amino-6-(3-methylbut-1-ynyl)pyrazin-2-yl)-4-methylphenyl)-3,3,3-trifluoro-2-hydroxypropanamide | | 393.2 |
| 50 | 2-(3-(5-amino-6-(3-hydroxy-3-methylbut-1-ynyl)pyrazin-2-yl)-4-methylphenyl)-3,3,3-trifluoro-2-hydroxypropanamide | | 409.2 |
| 51 | 2-(3-(5-amino-6-(4-hydroxypent-1-ynyl)pyrazin-2-yl)-4-methylphenyl)-3,3,3-trifluoro-2-hydroxypropanamide | | 409.2 |

TABLE 3-continued

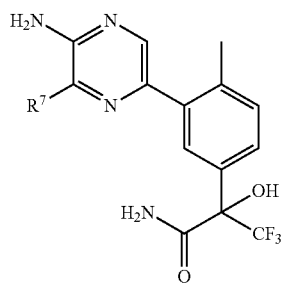

| Ex. No. | Name | R⁷ | LCMS [M + H]⁺ |
|---|---|---|---|
| 52 | 2-(3-(6-((1H-pyrazol-5-yl)ethynyl)-5-aminopyrazin-2-yl)-4-methylphenyl)-3,3,3-trifluoro-2-hydroxypropanamide | 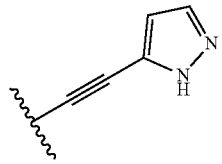 [SMILES: *C#Cc1ccn[nH]1] | 417.2 |
| 53 | 2-(3-(5-amino-6-((1-methyl-1H-imidazol-5-yl)ethynyl)pyrazin-2-yl)-4-methylphenyl)-3,3,3-trifluoro-2-hydroxypropanamide | 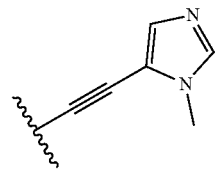 [SMILES: *C#Cc1cncn1C] | 431.2 |
| 54 | 2-(3-(5-amino-6-((1-methyl-1H-pyrazol-4-yl)ethynyl)pyrazin-2-yl)-4-methylphenyl)-3,3,3-trifluoro-2-hydroxypropanamide | 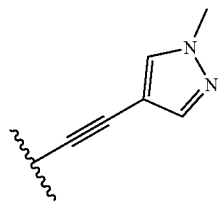 [SMILES: *C#Cc1cnn(C)c1] | 431.2 |
| 55 | 2-(3-(5-amino-6-(pyridin-2-ylethynyl)pyrazin-2-yl)-4-methylphenyl)-3,3,3-trifluoro-2-hydroxypropanamide | 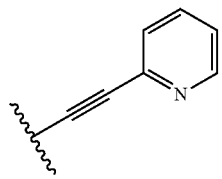 [SMILES: *C#Cc1ccccn1] | 428.2 |
| 56 | 2-(3-(5-amino-6-(pyrimidin-5-ylethynyl)pyrazin-2-yl)-4-methylphenyl)-3,3,3-trifluoro-2-hydroxypropanamide | 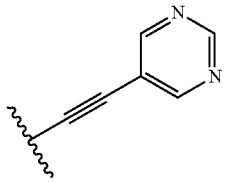 [SMILES: *C#Cc1cncnc1] | 429.2 |
| 57 | 2-(3-(5-amino-6-(pyrazin-2-ylethynyl)pyrazin-2-yl)-4-methylphenyl)-3,3,3-trifluoro-2-hydroxypropanamide | 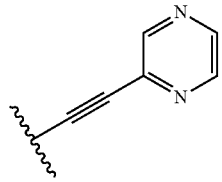 [SMILES: *C#Cc1cnccn1] | 429.2 |

TABLE 3-continued

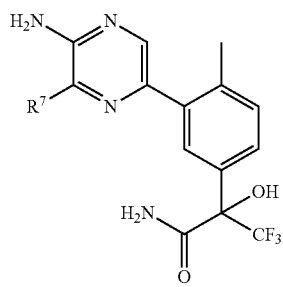

| Ex. No. | Name | R⁷ | LCMS [M + H]⁺ |
|---|---|---|---|
| 58 | 2-(3-(5-amino-6-((4-cyanophenyl)ethynyl)pyrazin-2-yl)-4-methylphenyl)-3,3,3-trifluoro-2-hydroxypropanamide | 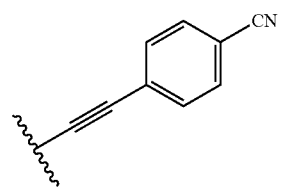 [SMILES: *C#Cc1ccc(C#N)cc1] | 452.1 |
| 59 | 2-(3-(5-amino-6-((4-(cyanomethyl)phenyl)ethynyl)pyrazin-2-yl)-4-methylphenyl)-3,3,3-trifluoro-2-hydroxypropanamide | 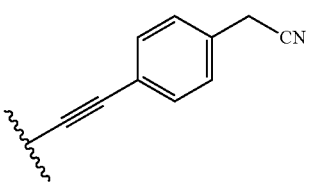 [SMILES: *C#Cc1ccc(CC#N)cc1] | 466.2 |
| 60 | 2-(3-(5-amino-6-((3,5-dimethoxyphenyl)ethynyl)pyrazin-2-yl)-4-methylphenyl)-3,3,3-trifluoro-2-hydroxypropanamide | 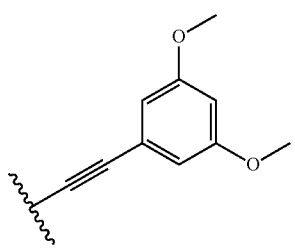 [SMILES: *C#Cc1cc(OC)cc(OC)c1] | 487.1 |
| 61 | 2-(3-(5-amino-6-((3-fluorophenyl)ethynyl)pyrazin-2-yl)-4-methylphenyl)-3,3,3-trifluoro-2-hydroxypropanamide | 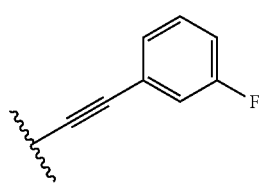 [SMILES: *C#Cc1cccc(F)c1] | 445.1 |
| 62 | 2-(3-(5-amino-6-(3-hydroxy-3,4-dimethylpent-1-ynyl)pyrazin-2-yl)-4-methylphenyl)-3,3,3-trifluoro-2-hydroxypropanamide | 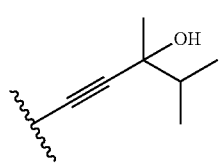 [SMILES: *C#CC(C)(O)C(C)C] | 437.2 |
| 63 | 2-(3-(5-amino-6-((tetrahydro-2H-pyran-4-yl)ethynyl)pyrazin-2-yl)-4-methylphenyl)-3,3,3-trifluoro-2-hydroxypropanamide | 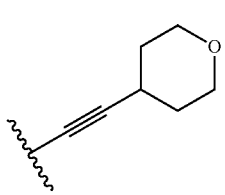 [SMILES: *C#CC1CCOCC1] | 435.2 |

TABLE 3-continued

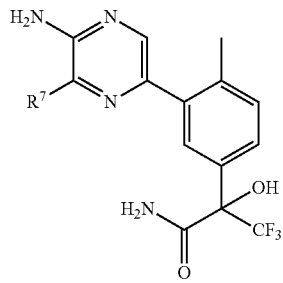

| Ex. No. | Name | R⁷ | LCMS [M + H]⁺ |
|---|---|---|---|
| 64 | 2-(3-(5-amino-6-((4-methyltetrahydro-2H-pyran-4-yl)ethynyl)pyrazin-2-yl)-4-methylphenyl)-3,3,3-trifluoro-2-hydroxypropanamide | | 449.2 |
| 65 | 2-(3-(5-amino-6-((3-hydroxy-1-methyl-2-oxopyrrolidin-3-yl)ethynyl)pyrazin-2-yl)-4-methylphenyl)-3,3,3-trifluoro-2- | | 464.2 |
| 66 | 2-(3-(5-amino-6-((5-methylpyrazin-2-yl)ethynyl)pyrazin-2-yl)-4-methylphenyl)-3,3,3-trifluoro-2-hydroxypropanamide | | 443.2 |
| 67 | 2-(3-(5-amino-6-((5-methoxypyrazin-2-yl)ethynyl)pyrazin-2-yl)-4-methylphenyl)-3,3,3-trifluoro-2-hydroxypropanamide | | 459.2 |
| 68 | 2-(3-(5-amino-6-(imidazo[1,2-a]pyrazin-6-ylethynyl)pyrazin-2-yl)-4-methylphenyl)-3,3,3-trifluoro-2-hydroxypropanamide | | 468.1 |

Example 69. 2-(3-(5-Amino-6-(1-methyl-1H-pyrazol-5-yl)pyrazin-2-yl)-4-methylphenyl)-3,3,3-trifluoro-2-hydroxypropanamide trifluoroacetate

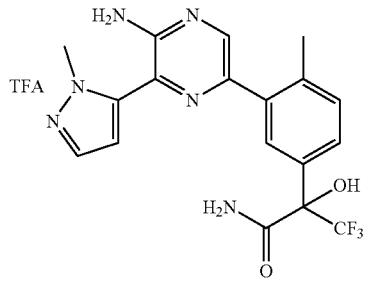 [SMILES: Cc1ccc(C(O)(C(N)=O)C(F)(F)F)cc1-c1cnc(N)c(-c2ccnn2C)n1]

Step 1. 1-(3-Bromo-4-methylphenyl)-2,2,2-trifluoroethan-1-ol

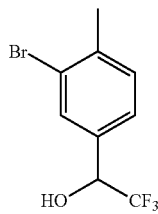

A solution of 3-bromo-4-methylbenzaldehyde (6.51 g, 32.7 mmol) [Combi-Blocks, HC-3454] in dry tetrahydrofuran (65.4 mL) was cooled to 0° C. followed by the addition of trimethyl(trifluoromethyl)silane (6.28 mL, 42.5 mmol). The yellow mixture was treated with 1.0 M tetra-n-butylammonium fluoride in tetrahydrofuran (0.654 mL, 0.654 mmol) at 0° C. and stirred for a few minutes at 0° C. The ice bath was removed and the resulting reaction mixture was stirred for 1.5 h. The reaction mixture was cooled back to 0° C. and treated with water (6.48 mL, 360 mmol) and 1.0 M tetra-n-butylammonium fluoride in tetrahydrofuran (6.54 mL, 6.54 mmol). The ice bath was removed and the reaction mixture was stirred at ambient temperature for 30 min. The yellow reaction mixture was diluted with brine (150 mL) and extracted with ethyl acetate (200 mL). The organic layer was washed with saturated ammonium chloride (100 mL), dried over sodium sulfate, filtered, and concentrated to give a tan oil. Purification by flash column chromatography using methyl tert-butyl ether (MTBE) in hexanes (0% to 50%) gave the desired product (8.42 g, 95.7%) as a yellow oil. LCMS for $C_9H_7BrF_3$ (M−OH)$^+$: m/z=251.0, 253.0; Found: 250.9, 252.8.

Step 2. 1-(3-Bromo-4-methylphenyl)-2,2,2-trifluoroethan-1-one

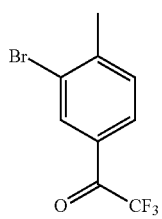

A mixture of 1-(3-bromo-4-methylphenyl)-2,2,2-trifluoroethan-1-ol (8.41 g, 31.3 mmol) in dichloromethane (125 mL) at 0° C. was treated with Dess-Martin periodinane (19.9 g, 46.9 mmol) and stirred at room temperature (rt) for 2.5 h. The reaction mixture was concentrated (by rotary evaporation with the water bath set at 30° C.) to an oily solid that was diluted with diethyl ether (200 mL) which precipitated more solids. This mixture was filtered over CELITE® and the CELITE® was rinsed with additional diethyl ether (200 mL). The filtrate was washed with saturated sodium bicarbonate solution (3×200 mL) and brine, dried over sodium sulfate, filtered, and concentrated to give an oily solid. The oily solid was partitioned between diethyl ether (150 mL) and water (100 mL). The organic layer was separated and washed with saturated sodium bicarbonate solution (2×75 mL) and brine, dried over sodium sulfate, filtered, and concentrated to give the desired product (7.93 g, 95.0%) as an oil that was used without further purification. LCMS for $C_9H_7BrF_3O$ (M+H)$^+$: m/z=267.0, 269.0; Found: 267.1, 268.9.

Step 3. 2-(3-Bromo-4-methylphenyl)-3,3,3-trifluoro-2-hydroxypropanenitrile

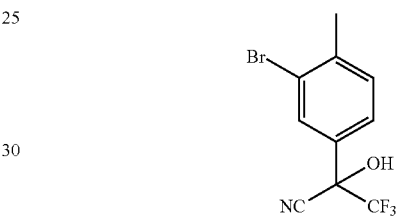

A solution of 1-(3-bromo-4-methylphenyl)-2,2,2-trifluoroethan-1-one (7.92 g, 29.7 mmol) in dichloromethane (29.7 mL) was treated with trimethylsilyl cyanide (8.70 mL, 65.2 mmol), potassium cyanide (0.29 g, 4.45 mmol), and 18-crown-6 (0.29 g, 1.10 mmol) and stirred for 1 h. The reaction mixture was concentrated by rotary evaporation with a water bath set at 28° C. to give a rust colored solid. The solid was dissolved in THF (29.6 mL), cooled to 0° C., treated with 1.8 M HCl (10.9 mL, 19.6 mmol), and stirred at rt for 1.5 h. The reaction mixture was diluted with water (75 mL) and extracted with diethyl ether (3×75 mL). The combined organic extracts were washed with brine, dried over sodium sulfate, filtered, and concentrated. Reconcetration from hexanes to give the desired product (8.70 g, 99.8%) as an orange solid that was used without further purification. LCMS for $C_9H_7BrF_3O$ (M−CN)$^+$: m/z=267.0, 269.0; Found: 266.9, 269.0.

Step 4. 2-(3-bromo-4-methylphenyl)-3,3,3-trifluoro-2-hydroxypropanamide

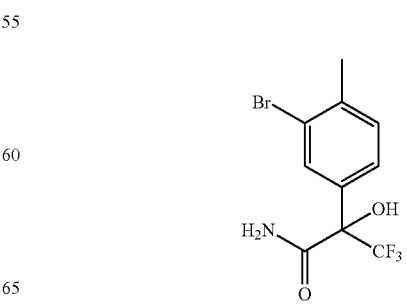

A solution of 2-(3-bromo-4-methylphenyl)-3,3,3-trifluoro-2-hydroxypropanenitrile (8.70 g, 29.6 mmol) in dioxane (59.2 mL) at 0° C. was treated with concentrated HCl (9.00 mL, 108 mmol) that had been pre-cooled in an ice bath. While stirring at 0° C., the reaction mixture was bubbled with HCl gas for 45 min. The cooling bath was removed and the reaction mixture was stirred at rt for 61 h. The reaction mixture was bubbled with nitrogen for 10 min to remove some of the HCl, cooled to 0° C., and diluted with brine (200 mL), water (50 mL), and ethyl acetate (200 mL). The organic layer was separated and the aqueous layer was diluted with water (100 mL) to dissolve the remaining solids. The aqueous layer was extracted with ethyl acetate (100 mL). The combined organic extracts were washed with brine, dried over sodium sulfate, filtered, and concentrated to give a brown oil. Purification by flash column chromatography using MTBE in hexanes (0% to 60%) gave the desired product as a yellow oily solid. The racemic mixture was separated via preparative chiral HPLC (Phenomenex Lux Amylose-1 [21.2×250 mm, 5 micron], eluting with 95% ethanol in hexanes, at flow rate of 18 mL/min, loading about 100 mg in 2 mL ethanol) to give the desired second eluting enantiomer (4.50 g, 48.8%) as a viscous yellow oil.

The first enantiomer that eluted had a retention time of 4.0 min. The second enantiomer that eluted had a retention time of 5.3 min. Second eluting enantiomer: LCMS for $C_{10}H_{10}BrF_3NO_2$ (M+H)$^+$: m/z=312.0, 314.0; Found: 312.0, 314.0.

Step 5. 3,3,3-Trifluoro-2-hydroxy-2-(4-methyl-3-(4, 4,5,5-tetramethyl-1,3,2-dioxaborolan-2-yl)phenyl) propanamide

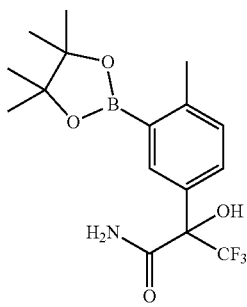 [SMILES: Cc1ccc(C(O)(C(N)=O)C(F)(F)F)cc1B1OC(C)(C)C(C)(C)O1]

A solution of 2-(3-bromo-4-methylphenyl)-3,3,3-trifluoro-2-hydroxypropanamide (3.57 g, 11.5 mmol) (step 4, second eluting enantiomer) in dioxane (57.2 mL) was treated with bis(pinacolato)diboron (3.49 g, 13.7 mmol), and potassium acetate (3.71 g, 37.8 mmol) and degassed with nitrogen for 5 min. The reaction mixture was treated with bis(triphenylphosphine)palladium(II)chloride (0.482 g, 0.687 mmol), degassed for 5 min, and stirred at 100° C. for 2.5 h. The reaction mixture was diluted with ethyl acetate (50 mL), filtered over CELITER, and rinsed with additional ethyl acetate (100 mL). The filtrate was washed with brine, dried over sodium sulfate, filtered, and concentrated to a brown foam. Purification by flash column chromatography using MTBE in hexanes (0% to 100%) gave the desired product (3.35 g, 81.5%) as a thick yellow foam. $^1$H NMR (400 MHz, DMSO-$d_6$) δ 7.96 (d, J=2.2 Hz, 1H), 7.63 (dd, J=7.9, 2.1 Hz, 1H), 7.58 (s, 1H), 7.54 (s, 1H), 7.51-7.40 (m, 1H), 7.21 (d, J=8.2 Hz, 1H), 2.46 (s, 3H), 1.30 (s, 12H). LCMS for $C_{16}H_{22}BF_3NO_4$ (M+H)$^+$: m/z=360.2; Found: 360.1.

Step 6. 2-(3-(5-Amino-6-chloropyrazin-2-yl)-4-methylphenyl)-3,3,3-trifluoro-2-hydroxypropanamide

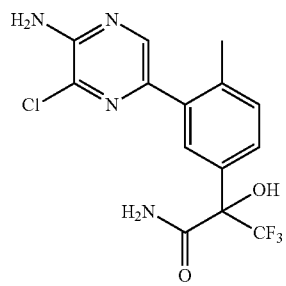 [SMILES: Cc1ccc(C(O)(C(N)=O)C(F)(F)F)cc1-c1cnc(N)c(Cl)n1]

A solution of 5-bromo-3-chloropyrazin-2-amine (0.235 g, 1.13 mmol) [Ark Pharm, AK-25099] and 3,3,3-trifluoro-2-hydroxy-2-(4-methyl-3-(4,4,5,5-tetramethyl-1,3,2-dioxaborolan-2-yl)phenyl)propanamide (0.405 g, 1.13 mmol) (single enantiomer from step 5) in dioxane (13.1 mL) was treated with sodium carbonate (0.359 g, 3.38 mmol) in water (2.61 mL) and degassed with nitrogen for 5 min. The reaction mixture was treated with dichloro[1,1'-bis(diphenylphosphino)ferrocene]palladium (II) dichloromethane adduct (0.046 g, 0.056 mmol), degassed with nitrogen for 5 min, and stirred at 100° C. for 15 h. The reaction mixture was diluted with ethyl acetate (50 mL), filtered through a 0.45 micron cartridge, and rinsed with additional ethyl acetate (50 mL). The filtrate was washed with brine (30 mL). The aqueous layers was separated extracted with ethyl acetate (2×50 mL). The combined organic extracts were dried over sodium sulfate, filtered, and concentrated to a brown foam. Purification by flash column chromatography using ethyl acetate (containing 5% MeOH) in hexanes (0% to 100%) gave the desired product (0.180 g, 44.2%) as yellow solid. LCMS for $C_{14}H_{13}ClF_3N_4O_2$ (M+H)$^+$: m/z=361.1; Found: 361.0.

Step 7. 2-(3-(5-Amino-6-(1-methyl-1H-pyrazol-5-yl)pyrazin-2-yl)-4-methylphenyl)-3,3,3-trifluoro-2-hydroxypropanamide trifluoroacetate A solution of 1-methyl-5-(4,4,5,5-tetramethyl-1,3,2-dioxaborolan-2-yl)-1H-pyrazole (0.026 g, 0.125 mmol) and 2-(3-(5-amino-6-chloropyrazin-2-yl)-4-methylphenyl)-3,3, 3-trifluoro-2-hydroxypropanamide (0.015 g, 0.042 mmol) (single enantiomer from step 6) in dioxane (0.832 mL) was treated with sodium carbonate (1.0 M in water) (0.166 mL, 0.166 mmol) and degassed with nitrogen for 5 min. The reaction mixture was treated with dichloro[1,1'-bis(diphenylphosphino)ferrocene]palladium (II) dichloromethane adduct (5.09 mg, 6.24 µmol), degassed with nitrogen for 5 min, and stirred at 120° C. for 2.5 h. The reaction mixture was diluted with THF and filtered through a 0.45 micron cartridge. The cartridge was rinsed with THF and ethyl acetate. The filtrate was concentrated and the crude residue was purified via preparative LCMS (XBridge C18 Column, eluting with a gradient of acetonitrile in water with 0.1% trifluoroacetic acid, at flow rate of 60 mL/min) to give the desired product (14.6 mg, 66.4%) as a yellow tinted solid. $^1$H NMR (400 MHz, DMSO-$d_6$) δ 8.18 (s, 1H), 7.77 (d, J=2.1 Hz, 1H), 7.68-7.49 (m, 5H), 7.34 (d, J=8.2 Hz, 1H), 6.71 (d, J=2.0 Hz, 1H), 3.92 (s, 3H), 2.39 (s, 3H). LCMS for $C_{18}H_{18}F_3N_6O_2$ (M+H)$^+$: m/z=407.1; Found: 407.1.

Examples 70-92 were synthesized according to procedures analogous to Example 69 and the data are listed in Table 4.

TABLE 4

| Ex. No. | Name | R$^7$ | LCMS [M + H]$^+$ | $^1$H NMR Spectrum |
|---|---|---|---|---|
| 70 | 2-(3-(5-amino-6-(2-methyloxazol-5-yl)pyrazin-2-yl)-4-methylphenyl)-3,3,3-trifluoro-2-hydroxypropanamide trifluoroacetate | | 408.1 | $^1$H NMR (400 MHz, DMSO-d$_6$) δ 8.12 (s, 1H), 7.71 (d, J = 2.1 Hz, 1H), 7.68-7.50 (m, 5H), 7.34 (d, J = 8.1 Hz, 1H), 6.59 (br s, 2H), 2.53 (s, 3H), 2.36 (s, 3H). |
| 71 | 2-(3-(5-amino-6-(1-methyl-1H-pyrazol-4-yl)pyrazin-2-yl)-4-methylphenyl)-3,3,3-trifluoro-2-hydroxypropanamide trifluoroacetate | | 407.1 | $^1$H NMR (400 MHz, DMSO-d$_6$) δ 8.30 (s, 1H), 7.97 (d, J = 2.2 Hz, 2H), 7.73 (d, J = 2.1 Hz, 1H), 7.68-7.46 (m, 4H), 7.33 (d, J = 8.1 Hz, 1H), 3.91 (s, 3H), 2.39 (s, 3H). |
| 72 | 2-(3-(5-amino-6-(2-methylthiazol-5-yl)pyrazin-2-yl)-4-methylphenyl)-3,3,3-trifluoro-2-hydroxypropanamide trifluoroacetate | | 423.1 | $^1$H NMR (400 MHz, DMSO-d$_6$) δ 8.27 (s, 1H), 8.11 (s, 1H), 7.74 (d, J = 2.0 Hz, 1H), 7.68-7.47 (m, 4H), 7.35 (d, J = 8.1 Hz, 1H), 2.68 (s, 3H), 2.40 (s, 3H). |
| 73 | 2-(3-(5-amino-6-(2-methyl-2H-1,2,3-triazol-4-yl)pyrazin-2-yl)-4-methylphenyl)-3,3,3-trifluoro-2-hydroxypropanamide trifluoroacetate | | 408.1 | $^1$H NMR (400 MHz, DMSO-d$_6$) δ 8.28 (s, 1H), 8.18 (s, 1H), 7.77 (d, J = 2.1 Hz, 1H), 7.71-7.47 (m, 4H), 7.36 (d, J = 8.1 Hz, 1H), 7.22 (br s, 2H), 4.30 (s, 3H), 2.41 (s, 3H). |
| 74 | 2-(3-(5-amino-6-(1-methyl-1H-1,2,3-triazol-5-yl)pyrazin-2-yl)-4-methylphenyl)-3,3,3-trifluoro-2-hydroxypropanamide trifluoroacetate | | 408.1 | $^1$H NMR (400 MHz, DMSO-d$_6$) δ 8.24 (s, 1H), 8.17 (s, 1H), 7.78 (d, J = 2.1 Hz, 1H), 7.72-7.45 (m, 4H), 7.35 (d, J = 8.1 Hz, 1H), 6.59 (br s, 2H), 4.14 (s, 3H), 2.39 (s, 3H). |
| 75 | 2-(3-(5-amino-6-(1-(2,2,2-trifluoroethyl)-1H-pyrazol-4-yl)pyrazin-2-yl)-4-methylphenyl)-3,3,3-trifluoro-2-hydroxypropanamide trifluoroacetate | | 475.1 | $^1$H NMR (400 MHz, DMSO-d$_6$) δ 8.47 (s, 1H), 8.15 (s, 1H), 8.02 (s, 1H), 7.74 (d, J = 2.1 Hz, 1H), 7.70-7.44 (m, 4H), 7.34 (d, J = 8.1 Hz, 1H), 6.30 (br s, 2H), 5.20 (q, J = 9.1 Hz, 2H), 2.39 (s, 3H). |

TABLE 4-continued

| Ex. No. | Name | R⁷ | LCMS [M + H]⁺ | ¹H NMR Spectrum |
|---|---|---|---|---|
| 76 | 2-(3-(5-amino-6-(1-(2-cyanopropan-2-yl)-1H-pyrazol-4-yl)pyrazin-2-yl)-4-methylphenyl)-3,3,3-trifluoro-2-hydroxypropanamide trifluoroacetate | | 460.2 | ¹H NMR (400 MHz, DMSO-d₆) δ 8.48 (s, 1H), 8.15 (s, 1H), 8.03 (s, 1H), 7.74 (d, J = 2.2 Hz, 1H), 7.69-7.51 (m, 4H), 7.34 (d, J = 8.2 Hz, 1H), 2.39 (s, 3H), 2.04 (s, 6H). |
| 77 | 2-(3-(5-amino-6-(1-(tetrahydro-2H-pyran-4-yl)-1H-pyrazol-4-yl)pyrazin-2-yl)-4-methylphenyl)-3,3,3-trifluoro-2-hydroxypropanamide trifluoroacetate | | 477.2 | ¹H NMR (400 MHz, DMSO-d₆) δ 8.37 (s, 1H), 8.03 (s, 1H), 7.98 (s, 1H), 7.74 (d, J = 2.1 Hz, 1H), 7.69-7.46 (m, 4H), 7.33 (d, J = 8.1 Hz, 1H), 6.24 (br s, 2H), 4.56-4.31 (m, 1H), 4.10-3.85 (m, 2H), 3.64-3.32 (m, 2H), 2.39 (s, 3H), 2.12-1.98 (m, 4H). |
| 78 | 2-(3-(5-amino-6-(1-((1-cyanocyclopropyl)methyl)-1H-pyrazol-4-yl)pyrazin-2-yl)-4-methylphenyl)-3,3,3-trifluoro-2-hydroxypropanamide trifluoroacetate | | 472.2 | ¹H NMR (400 MHz, DMSO-d₆) δ 8.44 (s, 1H), 8.11 (s, 1H), 8.01 (s, 1H), 7.75 (d, J = 2.1 Hz, 1H), 7.69-7.49 (m, 4H), 7.35 (d, J = 8.2 Hz, 1H), 4.35 (s, 2H), 2.40 (s, 3H), 1.46-1.20 (m, 4H). |
| 79 | 2-(3-(5-amino-6-(1-(2-methoxyethyl)-1H-pyrazol-4-yl)pyrazin-2-yl)-4-methylphenyl)-3,3,3-trifluoro-2-hydroxypropanamide trifluoroacetate | | 451.1 | ¹H NMR (400 MHz, DMSO-d₆) δ 8.32 (s, 1H), 8.02 (s, 1H), 7.98 (s, 1H), 7.74 (d, J = 2.1 Hz, 1H), 7.66-7.46 (m, 4H), 7.33 (d, J = 8.1 Hz, 1H), 6.21 (br s, 2H), 4.32 (t, J = 5.4 Hz, 2H), 3.74 (t, J = 5.3 Hz, 2H), 3.25 (s, 3H), 2.39 (s, 3H). |
| 80 | 5-(3-amino-6-(5-(3-amino-1,1,1-trifluoro-2-hydroxy-3-oxopropan-2-yl)-2-methylphenyl)pyrazin-2-yl)-N-methylpicolinamide bistrifluoroacetate | | 461.1 | ¹H NMR (400 MHz, DMSO-d₆) δ 8.96 (d, J = 2.1 Hz, 1H), 8.86 (dd, J = 4.7, 4.7 Hz, 1H), 8.33 (dd, J = 8.1, 2.2 Hz, 1H), 8.17 (s, 1H), 8.12 (d, J = 8.1 Hz, 1H), 7.76 (d, J = 2.1 Hz, 1H), 7.69-7.44 (m, 4H), 7.34 (d, J = 8.1 Hz, 1H), 6.60 (br s, 2H), 2.85 (d, J = 4.8 Hz, 3H), 2.40 (s, 3H). |
| 81 | 2-(3-(5-amino-6-(pyrimidin-5-yl)pyrazin-2-yl)-4-methylphenyl)-3,3,3-trifluoro-2-hydroxypropanamide trifluoroacetate | | 405.1 | ¹H NMR (400 MHz, DMSO-d₆) δ 9.24 (s, 1H), 9.12 (s, 2H), 8.18 (s, 1H), 7.76 (d, J = 2.1 Hz, 1H), 7.69-7.48 (m, 4H), 7.34 (d, J = 8.1 Hz, 1H), 6.67 (s, 2H), 2.39 (s, 3H). |

TABLE 4-continued

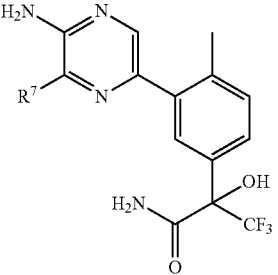

| Ex. No. | Name | R⁷ | LCMS [M + H]⁺ | ¹H NMR Spectrum |
|---|---|---|---|---|
| 82 | 2-(3-(5-amino-6-(6-methylpyridin-3-yl)pyrazin-2-yl)-4-methylphenyl)-3,3,3-trifluoro-2-hydroxypropanamide bistrifluoroacetate | | 418.1 | ¹H NMR (400 MHz, DMSO-d₆) δ 8.98 (d, J = 2.3 Hz, 1H), 8.43 (d, J = 8.2 Hz, 1H), 8.18 (s, 1H), 7.85-7.68 (m, 2H), 7.68-7.47 (m, 4H), 7.34 (d, J = 8.1 Hz, 1H), 6.63 (br s, 2H), 2.68 (s, 3H), 2.38 (s, 3H). |
| 83 | 2-(3-(5-amino-6-(6-(trifluoromethyl)pyridin-3-yl)pyrazin-2-yl)-4-methylphenyl)-3,3,3-trifluoro-2-hydroxypropanamide bistrifluoroacetate | | 472.1 | ¹H NMR (400 MHz, DMSO-d₆) δ 9.09 (d, J = 2.2 Hz, 1H), 8.42 (dd, J = 8.2, 2.1 Hz, 1H), 8.20 (s, 1H), 8.02 (d, J = 8.1 Hz, 1H), 7.76 (d, J = 2.1 Hz, 1H), 7.71-7.48 (m, 4H), 7.34 (d, J = 8.1 Hz, 1H), 6.66 (br s, 2H), 2.39 (s, 3H). |
| 84 | 2-(3-(5-amino-6-(2-cyclopropylthiazol-5-yl)pyrazin-2-yl)-4-methylphenyl)-3,3,3-trifluoro-2-hydroxypropanamide trifluoroacetate | | 450.1 | ¹H NMR (400 MHz, DMSO-d₆) δ 8.22 (s, 1H), 8.08 (s, 1H), 7.72 (d, J = 2.1 Hz, 1H), 7.68-7.45 (m, 4H), 7.35 (d, J = 8.1 Hz, 1H), 6.62 (br s, 2H), 2.46-2.40 (m, 1H), 2.39 (s, 3H), 1.22-1.09 (m, 2H), 1.07-0.97 (m, 2H). |
| 85 | 2-(3-(5-amino-6-(2-(hydroxymethyl)pyridin-4-yl)pyrazin-2-yl)-4-methylphenyl)-3,3,3-trifluoro-2-hydroxypropanamide bistrifluoroacetate | | 434.1 | ¹H NMR (400 MHz, DMSO-d₆) δ 8.72 (d, J = 5.7 Hz, 1H), 8.25 (s, 1H), 8.11 (s, 1H), 8.03-7.90 (m, 1H), 7.74 (d, J = 2.1 Hz, 1H), 7.70-7.47 (m, 4H), 7.36 (d, J = 8.1 Hz, 1H), 6.80 (br s, 2H), 4.81 (s, 2H), 2.38 (s, 3H). |
| 86 | 2-(3-(5-amino-6-(1-(cyclopropylmethyl)-1H-pyrazol-4-yl)pyrazin-2-yl)-4-methylphenyl)-3,3,3-trifluoro-2-hydroxypropanamide trifluoroacetate | | 447.1 | ¹H NMR (400 MHz, DMSO-d₆) δ 8.36 (s, 1H), 8.01 (s, 1H), 7.98 (s, 1H), 7.74 (d, J = 2.1 Hz, 1H), 7.68-7.49 (m, 4H), 7.34 (d, J = 8.1 Hz, 1H), 4.03 (d, J = 7.1 Hz, 2H), 2.39 (s, 3H), 1.37-1.22 (m, 1H), 0.60-0.47 (m, 2H), 0.45-0.32 (m, 2H). |

TABLE 4-continued

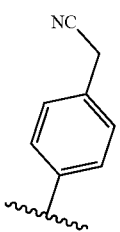

| Ex. No. | Name | R⁷ | LCMS [M + H]⁺ | ¹H NMR Spectrum |
|---|---|---|---|---|
| 87 | 2-(3-(5-amino-6-(4-(cyanomethyl)phenyl)pyrazin-2-yl)-4-methylphenyl)-3,3,3-trifluoro-2-hydroxypropanamide trifluoroacetate | 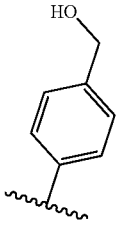 [SMILES: *c1ccc(CO)cc1] | 442.1 | ¹H NMR (400 MHz, DMSO-d₆) δ 8.08 (s, 1H), 7.84-7.76 (m, 2H), 7.73 (d, J = 2.1 Hz, 1H), 7.66-7.51 (m, 4H), 7.48 (d, J = 8.0 Hz, 2H), 7.33 (d, J = 8.1 Hz, 1H), 6.33 (br s, 2H), 4.12 (s, 2H), 2.39 (s, 3H). |
| 88 | 2-(3-(5-amino-6-(4-(hydroxymethyl)phenyl)pyrazin-2-yl)-4-methylphenyl)-3,3,3-trifluoro-2-hydroxypropanamide trifluoroacetate | 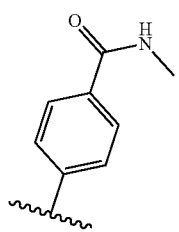 [SMILES: *c1ccc(C(=O)NC)cc1] | 433.1 | ¹H NMR (400 MHz, DMSO-d₆) δ 8.06 (s, 1H), 7.77-7.69 (m, 3H), 7.65-7.50 (m, 4H), 7.44 (d, J = 7.9 Hz, 2H), 7.33 (d, J = 8.1 Hz, 1H), 4.57 (s, 2H), 2.39 (s, 3H). |
| 89 | 4-(3-amino-6-(5-(3-amino-1,1,1-trifluoro-2-hydroxy-3-oxopropan-2-yl)-2-methylphenyl)pyrazin-2-yl)-N-methylbenzamide trifluoroacetate | 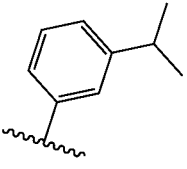 [SMILES: *c1cccc(C(C)C)c1] | 460.1 | ¹H NMR (400 MHz, DMSO-d₆) δ 8.51 (q, J = 4.4 Hz, 1H), 8.11 (s, 1H), 7.99-7.92 (m, 2H), 7.86-7.80 (m, 2H), 7.74 (d, J = 2.1 Hz, 1H), 7.64-7.49 (m, 4H), 7.34 (d, J = 8.2 Hz, 1H), 6.37 (br s, 2H), 2.81 (d, J = 4.5 Hz, 3H), 2.39 (s, 3H). |
| 90 | 2-(3-(5-amino-6-(3-isopropylphenyl)pyrazin-2-yl)-4-methylphenyl)-3,3,3-trifluoro-2-hydroxypropanamide trifluoroacetate | 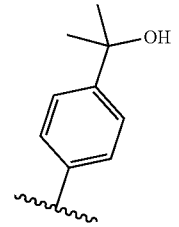 [SMILES: *c1ccc(C(C)(C)O)cc1] | 445.2 | ¹H NMR (400 MHz, DMSO-d₆) δ 8.07 (s, 1H), 7.75 (d, J = 2.1 Hz, 1H), 7.69-7.47 (m, 6H), 7.42 (dd, J = 7.6, 7.6 Hz, 1H), 7.33 (d, J = 8.0 Hz, 2H), 6.31 (br s, 2H), 3.04-2.89 (m, 1H), 2.40 (s, 3H), 1.25 (d, J = 6.9 Hz, 6H). |
| 91 | 2-(3-(5-amino-6-(4-(2-hydroxypropan-2-yl)phenyl)pyrazin-2-yl)-4-methylphenyl)-3,3,3-trifluoro-2-hydroxypropanamide trifluoroacetate | | 461.1 | ¹H NMR (400 MHz, DMSO-d₆) δ 8.06 (s, 1H), 7.78-7.66 (m, 3H), 7.66-7.44 (m, 6H), 7.33 (d, J = 8.1 Hz, 1H), 2.39 (s, 3H), 1.47 (s, 6H). |

TABLE 4-continued

| Ex. No. | Name | R[7] | LCMS [M + H]+ | $^1$H NMR Spectrum |
|---|---|---|---|---|
| 92 | 2-(3-(5-amino-6-(4-cyclopropylphenyl)pyrazin-2-yl)-4-methylphenyl)-3,3,3-trifluoro-2-hydroxypropanamide trifluoroacetate | | 443.1 | $^1$H NMR (400 MHz, DMSO-$d_6$) δ 8.04 (s, 1H), 7.73 (d, J = 2.1 Hz, 1H), 7.69-7.46 (m, 6H), 7.33 (d. J = 8.2 Hz, 1H), 7.25-7.12 (m, 2H), 6.23 (br s, 2H), 2.38 (s, 3H), 2.09-1.89 (m, 1H), 1.05-0.94 (m, 2H), 0.81-0.64 (m, 2H). |

Example 93. 2-(3-(5-Amino-6-(1H-pyrazol-1-yl)pyrazin-2-yl)-4-methylphenyl)-3,3,3-trifluoro-2-hydroxypropanamide

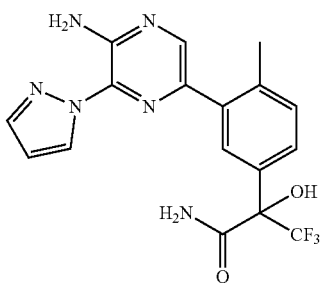 [SMILES: Cc1ccc(C(O)(C(N)=O)C(F)(F)F)cc1-c1cnc(N)c(-n2cccn2)n1]

Step 1.
5-Bromo-3-(1H-pyrazol-1-yl)pyrazin-2-amine

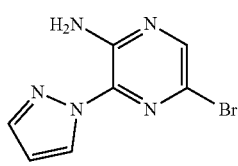 [SMILES: Nc1ncc(Br)nc1-n1cccn1]

A mixture of 5-bromo-3-chloropyrazin-2-amine (200 mg, 0.959 mmol) [Ark Pharm, AK-25099], 1H-pyrazole (65.3 mg, 0.959 mmol) [Aldrich, P56607], and cesium carbonate (469 mg, 1.44 mmol) in N-methyl-2-pyrrolidinone (4.00 mL) was stirred at 130° C. for 3 h. The reaction mixture was diluted with water (50 mL) and EtOAc (50 mL). The aqueous layer was separated and extracted with additional EtOAc (50 mL). The combined organic extracts were washed with brine, dried over sodium sulfate, filtered, and concentrated to give an orange oil. Purification by flash column chromatography using EtOAc in hexanes (0% to 50%) gave the desired product (0.178 g, 77.4%) as a yellow solid. LCMS for $C_7H_7BrN_5$ (M+H)+: m/z=240.0, 242.0; Found: 240.0, 242.0.

Step 2. 2-(3-(5-Amino-6-(1H-pyrazol-1-yl)pyrazin-2-yl)-4-methylphenyl)-3,3,3-trifluoro-2-hydroxypropanamide The desired compound was prepared according to the procedure of Example 1, step 6, using 5-bromo-3-(1H-pyrazol-1-yl)pyrazin-2-amine as the starting material in place of 5-bromo-3-chloropyrazin-2-amine. $^1$H NMR (400 MHz, DMSO-$d_6$) δ 8.63 (d, J=2.6 Hz, 1H), 8.17 (s, 1H), 7.94 (d, J=1.7 Hz, 1H), 7.82 (d, J=2.1 Hz, 1H), 7.74-7.47 (m, 6H), 7.37 (d, J=8.1 Hz, 1H), 6.67 (dd, J=2.2, 2.2 Hz, 1H), 2.44 (s, 3H). LCMS for $C_{17}H_{16}F_3N_6O_2$ (M+H)+: m/z=393.1; Found: 393.1.

Example 94. 2-(3-(5-Amino-6-(1H-1,2,4-triazol-1-yl)pyrazin-2-yl)-4-methylphenyl)-3,3,3-trifluoro-2-hydroxy-N-methylpropanamide trifluoroacetate

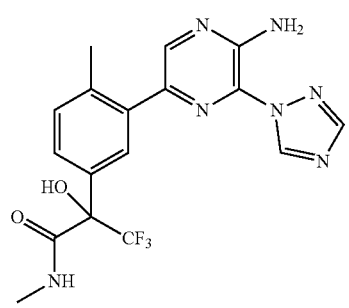 [SMILES: CNC(=O)C(O)(c1ccc(C)c(-c2cnc(N)c(-n3cncn3)n2)c1)C(F)(F)F]

Step 1. 5-Bromo-3-(1H-1,2,4-triazol-1-yl)pyrazin-2-amine

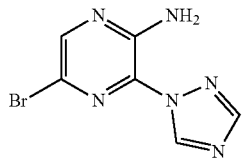 [SMILES: Nc1ncc(Br)nc1-n1cncn1]

To a solution of 5-bromo-3-chloropyrazin-2-amine (150 mg, 0.720 mmol) and 1,2,4-triazole (74.6 mg, 1.08 mmol) in DMF (4.00 mL) was added $Cs_2CO_3$ (352 mg, 1.08 mmol). The reaction mixture was heated at 70° C. for 15.5 h. Water (40 mL) and EtOAc (40 mL) were added, and the layers were separated. The aqueous layer was extracted with EtOAc (40 mL). The combined organic layers were washed with brine, dried over $Na_2SO_4$, filtered, and concentrated. Purification via silica gel chromatography (0-100% EtOAc/hexanes) afforded the title compound as a white solid (150 mg, 86.7%). $^1$H NMR (500 MHz, DMSO-$d_6$) δ 9.24 (s, 1H), 8.39 (s, 1H), 8.29 (s, 1H), 7.33 (br s, 2H). $^{13}$C NMR (126 MHz, DMSO-$d_6$) δ 152.24, 146.59, 144.13, 144.12, 129.09, 119.35. LCMS for $C_6H_6BrN_6$ (M+H)$^+$: calculated m/z=241.0, 243.0; found 241.0, 243.0.

Step 2. 2-(3-Chloro-4-methylphenyl)-4,4,5,5-tetramethyl-1,3,2-dioxaborolane

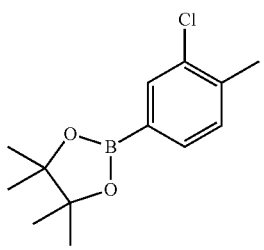

A degassed mixture of 4-bromo-2-chloro-1-methylbenzene (12.0 g, 58.4 mmol, Aldrich), potassium acetate (17.2 g, 175 mmol), bis(pinacolato)diboron (16.3 g, 64.2 mmol), and $PdCl_2$(dppf)-$CH_2Cl_2$ adduct (1.91 g, 2.34 mmol) in dioxane (120 mL) was heated at 75° C. overnight. After cooling to room temperature, the reaction mixture was diluted with EtOAc, filtered, and the solvent was removed in vacuo. Purification via flash chromatography, eluting with a gradient of 0-5% EtOAc in hexanes, afforded product as a white solid (11.7 g, 79.6%). LCMS for $C_{13}H_{19}BClO_2$ (M+H)$^+$: calculated m/z=253.1; found 253.0.

Step 3. 2-Chloro-1-methyl-4-(3,3,3-trifluoroprop-1-en-2-yl)benzene

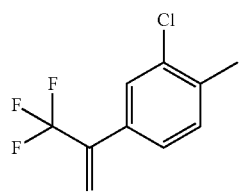

A degassed mixture of 2-(3-chloro-4-methylphenyl)-4,4,5,5-tetramethyl-1,3,2-dioxaborolane (11.7 g, 46.6 mmol), 2-bromo-3,3,3-trifluoroprop-1-ene (11.4 g, 65.2 mmol, Aldrich), $K_2CO_3$ (1.0 M in water, 140 mL, 140 mmol), and $Pd(PPh_3)_2Cl_2$ (1.63 g, 2.33 mmol) in THF (300 mL) was heated at 65° C. under $N_2$ for 3 hours. Upon cooling to room temperature, the reaction mixture was diluted with water and extracted with EtOAc. The organic layer was washed with water, followed by brine, dried over $Na_2SO_4$, filtered, and solvent was removed in vacuo. Purification via flash chromatography, eluting with hexanes, afforded product as a yellow oil (8.56 g, 83.2%). $^1$H NMR (400 MHz, CDCl$_3$) δ 7.47 (s, 1H), 7.27 (s, 2H), 6.00-5.96 (m, 1H), 5.81-5.76 (m, 1H), 2.42 (s, 3H). $^{19}$F NMR (376 MHz, CDCl$_3$) δ −64.93 (s).

Step 4. 2-(3-Chloro-4-methylphenyl)-3,3,3-trifluoropropane-1,2-diol

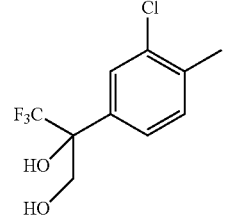 [SMILES: Cc1ccc(C(O)(CO)C(F)(F)F)cc1Cl]

To a suspension of AD-mix-α (54 g, 120 mmol) in water (100 mL) at 0° C. was added a solution of 2-chloro-1-methyl-4-(3,3,3-trifluoroprop-1-en-2-yl)benzene (8.6 g, 39 mmol) in t-BuOH (100 mL). The mixture was then stirred at 6° C. for 46 hours. The reaction was cooled in an ice bath to 0° C., and sodium sulfite (18 g) was added. The reaction mixture was warmed to room temperature and stirred for 30 minutes. tert-Butanol was removed in vacuo and the aqueous mixture was extracted twice with EtOAc. The combined organic extracts were dried over $Na_2SO_4$, filtered, and the solvent was removed in vacuo. Purification via flash chromatography, eluting with a gradient of 0-40% EtOAc in hexanes afforded the scalemic product as a colorless oil (8.7 g, 88%). Subsequent purification via chiral preparatory HPLC on a Phenomenx Lux Amylose-1 column (5% EtOH/hexanes, 20 mL/min) afforded the title compound, which was further enriched (>98:2 er) in the first eluting enantiomer ($t_R$=19.3 min). Due to use of AD-mix-a, and without being bound by theory, it is believed that the title compound was predominantly the (S)-enantiomer. $^1$H NMR (400 MHz, CDCl$_3$) δ 7.59 (s, 1H), 7.36 (d, J=8.0 Hz, 1H), 7.30 (d, J=8.0 Hz, 1H), 4.31 (dd, J=11.9, 6.1 Hz, 1H), 3.91-3.84 (m, 1H), 3.70 (s, 1H), 2.41 (s, 3H), 1.88-1.79 (dd, J=7.1, 6.3 Hz, 1H). $^{19}$F NMR (376 MHz, CDCl$_3$) δ −77.25 (s).

Step 5. 2-(3-Chloro-4-methylphenyl)-3,3,3-trifluoro-2-hydroxypropanoic acid

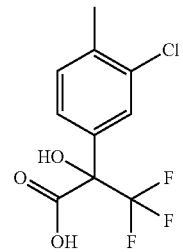 [SMILES: Cc1ccc(C(O)(C(=O)O)C(F)(F)F)cc1Cl]

To a mixture of 2-(3-chloro-4-methylphenyl)-3,3,3-trifluoropropane-1,2-diol (0.40 g, 1.6 mmol) (from Step 4), sodium bicarbonate (0.14 g, 1.6 mmol), and 5% platinum on carbon (0.31 g, 0.079 mmol) in water (11.2 mL) was added one drop of antifoam A concentrate (Aldrich A5633). The mixture was then heated at 75° C. for 2.5 days while air was bubbled through the reaction mixture. After cooling to room temperature (rt), the reaction mixture was diluted with water and filtered through CELITE®. The CELITE® was rinsed with water (3×), and the combined filtrate was acidified to pH 2 via slow addition of 1 N $H_2SO_4$. The aqueous mixture was extracted with EtOAc (3×). The combined organic layers were dried over $MgSO_4$, filtered, and concentrated to afford the title compound as an off-white solid (0.36 g, 79%). $^1$H NMR (500 MHz, DMSO-$d_6$) δ 7.63 (d, J=1.9 Hz, 1H), 7.49 (dd, J=8.1, 1.9 Hz, 1H), 7.42 (d, J=8.1 Hz, 1H), 2.34 (s, 3H). $^{19}$F NMR (471 MHz, DMSO-$d_6$) δ −75.31. LCMS for $C_{10}H_7ClF_3O_3$(M−H)$^-$: calculated m/z=267.0; found 267.0.

Step 6. 2-(3-Chloro-4-methylphenyl)-3,3,3-trifluoro-2-hydroxy-N-methylpropanamide

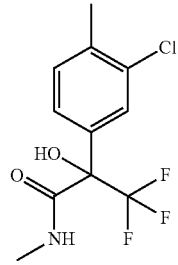 [SMILES: CNC(=O)C(O)(c1ccc(C)c(Cl)c1)C(F)(F)F]

To a suspension of 2-(3-chloro-4-methylphenyl)-3,3,3-trifluoro-2-hydroxypropanoic acid (0.11 g, 0.398 mmol) (from Step 5) in DCM (3.6 mL) at 0° C. was added oxalyl chloride (0.070 mL, 0.80 mmol) and one drop of DMF. The reaction mixture was stirred 2 h during which it slowly warmed to rt. Methylamine (1.0 mL, 12 mmol, 40 wt % in water) was added dropwise, and the biphasic reaction mixture was stirred for 3 h at rt. The reaction mixture was diluted with water (10 mL), and extracted with EtOAc (3×). The combined organic layers were washed with brine (20 mL), dried over $MgSO_4$, and concentrated. Purification via silica gel chromatography (1-20% MTBE/DCM) afforded the title compound as a light yellow solid (94 mg, 84%). $^1$H NMR (400 MHz, CDCl$_3$) δ 7.62 (s, 1H), 7.43 (d, J=7.7 Hz, 1H), 7.27 (d, J=8.0 Hz, 1H), 6.12 (br s, 1H), 4.85 (s, 1H), 2.90 (d, J=4.9 Hz, 3H), 2.38 (s, 3H). $^{19}$F NMR (376 MHz, CDCl$_3$) δ −74.48. LCMS for $C_{11}H_{12}ClF_3NO_2$ (M+H)$^+$: calculated m/z=282.0; found 282.0.

Step 7. 3,3,3-Trifluoro-2-hydroxy-N-methyl-2-(4-methyl-3-(4,4,5,5-tetramethyl-1,3,2-dioxaborolan-2-yl)phenyl)propanamide

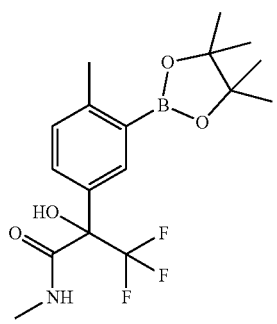 [SMILES: CNC(=O)C(O)(c1ccc(C)c(B2OC(C)(C)C(C)(C)O2)c1)C(F)(F)F]

A mixture of 2-(3-chloro-4-methylphenyl)-3,3,3-trifluoro-2-hydroxy-N-methylpropanamide (42 mg, 0.15 mmol) (from Step 6), bis(pinacolato)diboron (110 mg, 0.45 mmol), potassium acetate (88 mg, 0.90 mmol), tris(dibenzylideneacetone)dipalladium(0) (11 mg, 0.012 mmol), and 2-dicyclohexylphosphino-2',4',6'-triisopropylbiphenyl (23 mg, 0.048 mmol) (Aldrich 638064) in 1,4-dioxane (1.2 mL) was degassed with $N_2$ for 3 min and then heated at 120° C. for 1 h. The reaction mixture was diluted with EtOAc and filtered through CELITE®. The filtrate was concentrated. Purification via silica gel chromatography (1-100% MTBE in hexanes) afforded a red-brown residue (39 mg). This material was carried forward without further purification. LCMS for $C_{17}H_{24}BF_3NO_4$ (M+H)$^+$: calculated m/z=374.2; found 374.1.

Step 8. 2-(3-(5-Amino-6-(1H-1,2,4-triazol-1-yl)pyrazin-2-yl)-4-methylphenyl)-3,3,3-trifluoro-2-hydroxy-N-methylpropanamide trifluoroacetate A mixture of 3,3,3-trifluoro-2-hydroxy-N-methyl-2-(4-methyl-3-(4,4,5,5-tetramethyl-1,3,2-dioxaborolan-2-yl)phenyl)propanamide (19 mg) (from Step 7) in 1,4-dioxane (1.1 mL), 5-bromo-3-(1H-1,2,4-triazol-1-yl)pyrazin-2-amine (12 mg, 0.051 mmol) (from Step 1), 2.0 M $Na_2CO_3$ (76 μL, 0.15 mmol), and water (0.36 mL) in a microwave vial was sparged with $N_2$. [1,1'-Bis(diphenylphosphino)ferrocene]dichloropalladium(II) complex with dichloromethane (4 mg, 5 μmol) was added. The mixture was sparged with $N_2$ for 3 min, sealed, and heated at 120° C. for 3 h in an oil bath. The reaction mixture was cooled to rt and diluted with MeOH/water. Purification via preparative HPLC on a C-18 column (pH=2, 28-40% MeCN/0.1% TFA (aq) over 5 min, 60 mL/min) afforded the title compound as a light yellow solid (7.2 mg, 27%). Due to use of AD-mix-α in Step 4, and without being bound by theory, it is believed that the title compound was enriched (>98:2 er) in the (S)-enantiomer, (S)-2-(3-(5-amino-6-(1H-1,2,4-triazol-1-yl)pyrazin-2-yl)-4-methylphenyl)-3,3,3-trifluoro-2-hydroxy-N-methylpropanamide trifluoroacetate. $^1$H NMR (500 MHz, DMSO-$d_6$) δ 9.29 (s, 1H), 8.41 (s, 1H), 8.29 (s, 1H), 8.19 (q, J=4.7 Hz, 1H), 7.78 (d, J=2.1 Hz, 1H), 7.74 (s, 1H), 7.61 (dd, J=8.1, 2.1 Hz, 1H), 7.36 (d, J=8.2 Hz, 1H), 7.30 (s, 2H), 2.61 (d, J=4.7 Hz, 3H), 2.42 (s, 3H). $^{19}$F NMR (470 MHz, DMSO-$d_6$) δ −73.43, −73.88. LCMS for $C_{17}H_{17}F_3N_7O_2$ (M+H)$^+$: calculated m/z=408.1; found 408.1.

Example 95. 2-(3-(5-Amino-6-(1H-1,2,4-triazol-1-yl)pyrazin-2-yl)-4-methylphenyl)-3,3,3-trifluoro-2-hydroxy-N,N-dimethylpropanamide trifluoroacetate

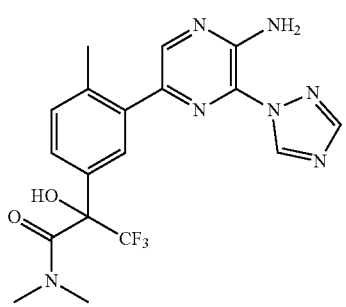 [SMILES: Cc1ccc(C(O)(C(=O)N(C)C)C(F)(F)F)cc1-c1cnc(N)c(-n2cncn2)n1]

The title compound was synthesized according to an experimental procedure analogous to Example 27, substituting dimethylamine (40 wt % in water) for methylamine (40 wt % in water) in Step 6. Due to use of AD-mix-α in Example 27, Step 4, and without being bound by theory, it is believed that the title compound was enriched (>98:2 er) in the (S)-enantiomer, (S)-2-(3-(5-amino-6-(1H-1,2,4-triazol-1-yl)pyrazin-2-yl)-4-methylphenyl)-3,3,3-trifluoro-2-hydroxy-N,N-dimethylpropanamide trifluoroacetate. $^1$H NMR (500 MHz, DMSO-$d_6$) δ 9.27 (s, 1H), 8.41 (s, 1H), 8.28 (s, 1H), 7.96 (s, 1H), 7.56 (s, 1H), 7.44-7.34 (m, 2H), 7.31 (br s, 2H), 2.85 (s, 3H), 2.71 (s, 3H), 2.44 (s, 3H). $^{19}$F NMR (470 MHz, DMSO-$d_6$) δ−74.26, −74.97. LCMS for $C_{18}H_{19}F_3N_7O_2$(M+H)$^+$: calculated m/z=422.2; found 422.1.

Example 96. 2-(3-(5-Amino-6-(1-methyl-1H-pyrazol-4-yl)pyrazin-2-yl)-4-methylphenyl)-3,3,3-trifluoro-2-hydroxy-N-methylpropanamide

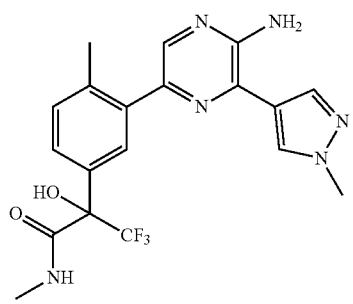 [SMILES: CNC(=O)C(O)(c1ccc(C)c(-c2cnc(N)c(-c3cnn(C)c3)n2)c1)C(F)(F)F]

Step 1. 2-(3-(5-Amino-6-chloropyrazin-2-yl)-4-methylphenyl)-3,3,3-trifluoro-2-hydroxy-N-methylpropanamide

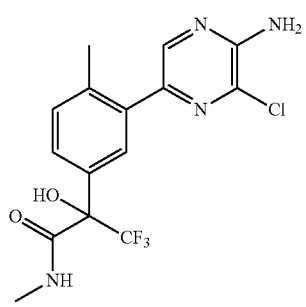 [SMILES: CNC(=O)C(O)(c1ccc(C)c(-c2cnc(N)c(Cl)n2)c1)C(F)(F)F]

A mixture of 5-bromo-3-chloropyrazin-2-amine (18 mg, 0.088 mmol) and 3,3,3-trifluoro-2-hydroxy-N-methyl-2-(4-methyl-3-(4,4,5,5-tetramethyl-1,3,2-dioxaborolan-2-yl)phenyl)propanamide (45 mg) (see Example 27, Step 7) in 1,4-dioxane (0.33 mL) was sparged with N$_2$. Sodium carbonate monohydrate (36 mg, 0.29 mmol), water (81 μL), and [1,1'-bis(diphenylphosphino)ferrocene]dichloropalladium (II) complex with dichloromethane (4 mg, 5 μmol) were added, and the mixture was sparged with N$_2$ for 2 min. The reaction was heated at 100° C. for 3 h. Upon cooling to rt, the reaction mixture was partitioned between water and EtOAc, and the layers were separated. The aqueous layer was extracted with EtOAc (2×). The combined organic layers were washed with brine, dried over Na$_2$SO$_4$, filtered, and concentrated. Purification by silica gel chromatography (15-60% EtOAc/Hexanes) afforded the title compound as a yellow oil (14 mg, 33% yield, 85% purity). LCMS for $C_{15}H_{15}ClF_3N_4O_2$ (M+H)$^+$: calculated m/z=375.1; found 375.1.

Step 2. 2-(3-(5-Amino-6-(1-methyl-1H-pyrazol-4-yl)pyrazin-2-yl)-4-methylphenyl)-3,3,3-trifluoro-2-hydroxy-N-methylpropanamide A mixture of 2-(3-(5-amino-6-chloropyrazin-2-yl)-4-methylphenyl)-3,3,3-trifluoro-2-hydroxy-N-methylpropanamide (14 mg, 0.032 mmol, 85% purity) (from Step 1), [1,1'-bis(diphenylphosphino)ferrocene]dichloropalladium (II) complex with dichloromethane (5 mg, 6 mol), 1-methyl-4-(4,4,5,5-tetramethyl-1,3,2-dioxaborolan-2-yl)-1H-pyrazole (20 mg, 0.095 mmol), THF (0.75 mL), and 1.0 M K$_2$CO$_3$ (79 μL, 0.079 mmol) was degassed with N$_2$ for 3 min and then heated at 130° C. for 20 min in a microwave. Upon cooling to rt, the reaction mixture was diluted with MeOH/water and filtered through a syringe filter. Purification via preparative HPLC on a C-18 column (pH=2, 23-35% MeCN/0.1% TFA (aq) over 5 min, 60 mL/min) afforded a yellow residue (6.5 mg).

A portion of this material (4.8 mg) was partitioned between EtOAc and sat. NaHCO$_3$. The organic layer was removed, and the aqueous layer extracted with EtOAc (2×). The organic layers were filtered through Na$_2$SO$_4$, combined, and concentrated to afford the title compound as a white solid (1.8 mg). Due to use of AD-mix-α in Example 27, Step 4, and without being bound by theory, it is believed that the title compound was enriched (>98:2 er) in the (S)-enantiomer, (S)-2-(3-(5-amino-6-(1-methyl-1H-pyrazol-4-yl)pyrazin-2-yl)-4-methylphenyl)-3,3,3-trifluoro-2-hydroxy-N-methylpropanamide. LCMS for $C_{19}H_{20}F_3N_6O_2$ (M+H)$^+$: calculated m/z=421.2; found 421.1.

Example 97. (4-(3-Amino-6-(5-(3-amino-1,1,1-trifluoro-2-hydroxy-3-oxopropan-2-yl)-2-methylphenyl)pyrazin-2-yl)phenyl)boronic acid

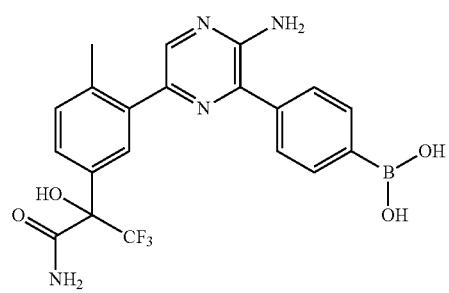 [SMILES: Cc1ccc(C(O)(C(N)=O)C(F)(F)F)cc1-c1cnc(N)c(-c2ccc(B(O)O)cc2)n1]

The title compound was synthesized according to an experimental procedure analogous to Example 1, substituting 1,4-phenylenediboronic acid for 1-methyl-5-(4,4,5,5-tetramethyl-1,3,2-dioxaborolan-2-yl)-1H-pyrazole in Step 7. $^1$H NMR (600 MHz, 4:1 DMSO-$d_6$/D$_2$O) δ 8.04 (s, 1H), 7.87 (d, J=6.6 Hz, 2H), 7.72-7.64 (m, 3H), 7.55 (br d, J=7.8 Hz, 1H), 7.33 (d, J=8.2 Hz, 1H), 2.34 (s, 3H). $^{19}$F NMR (565 MHz, 4:1 DMSO-$d_6$/D$_2$O) δ−73.80. LCMS for $C_{20}H_{19}BF_3N_4O_4$ (M+H)$^+$: calculated m/z=447.1; found 447.1.

Example 98. 2-(3-(5-Amino-6-(1-methyl-1H-pyrazol-5-yl)pyrazin-2-yl)-4-methylphenyl)-3,3-difluoro-2-hydroxypropanamide

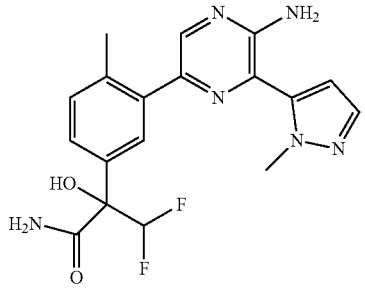 [SMILES: Cc1ccc(C(O)(C(N)=O)C(F)F)cc1-c1cnc(N)c(-c2ccnn2C)n1]

Step 1.
1-(3-Bromo-4-methylphenyl)-2,2-difluoroethan-1-ol

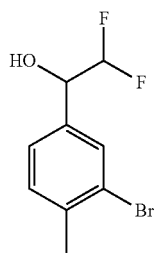

To solution of (difluoromethyl)trimethylsilane (5.1 g, 42 mmol) in dry DMF (20 mL) at 0° C. was added 3-bromo-4-methylbenzaldehyde (4.1 g, 21 mmol) followed by cesium fluoride (0.44 g, 2.9 mmol). The ice bath was removed, and the resulting reaction mixture was stirred for 2 h. The mixture was cooled back to 0° C., water (2.0 mL) and 1.0 M tetra-n-butylammonium fluoride in tetrahydrofuran (4.2 mL, 4.2 mmol) were added. The ice bath was removed and the mixture was stirred for 30 min at rt. The yellow reaction mixture was diluted with water (100 mL), and was extracted with Et$_2$O (150 mL). The organic layer was washed with saturated NH$_4$Cl solution (25 mL), dried over anhydrous sodium sulfate, filtered, and concentrated to give a rust colored oil. Purification on silica gel using ethyl acetate/hexane, 0-60% gave the desired compound as a yellow oil, 3.6 g, 69%. LCMS calculated for C$_9$H$_8$BrF$_2$ (M–OH)$^+$: m/z=233.0, 235.0; Found: 232.9, 235.1

Step 2. 1-(3-Bromo-4-methylphenyl)-2,2-difluoroethan-1-one

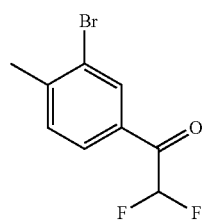

A mixture of 1-(3-bromo-4-methylphenyl)-2,2-difluoroethan-1-ol (3.6 g, 14 mmol) in dichloromethane (57 mL) at 0° C. was treated with Dess-Martin periodinane (9.1 g, 22 mmol). The ice bath was removed and the reaction mixture was stirred at rt for 1.0 h. The reaction mixture was concentrated to an oil. Et$_2$O was added and solid precipitated. The suspended mixture was filtered, the filtrate was washed with saturated NaHCO$_3$ solution and saturated NaCl solution, dried over anhydrous Na$_2$SO$_4$, and filtered. The solution was concentrated to yellow oil, 2.3 g, 64%. LCMS for C$_9$H$_8$BrF$_2$O (M+H)$^+$ calculated for (M+H)$^+$: m/z=249.0, 251.0; Found: 248.9, 251.0

Step 3. 2-(3-Bromo-4-methylphenyl)-3,3-difluoro-2-hydroxypropanenitrile

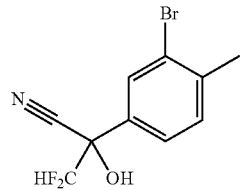

To a solution of 1-(3-bromo-4-methylphenyl)-2,2-difluoroethan-1-one (2.3 g, 9.0 mmol) in dichloromethane (9.0 mL) under N$_2$ was added trimethylsilyl cyanide (2.7 mL, 20 mmol), potassium cyanide (88 mg, 1.4 mmol), and 18-crown-6 (88 mg, 0.33 mmol). The reaction mixture was stirred for 1 h. The reaction mixture was concentrated under nitrogen. The solid was dissolved in THF (9.0 mL) and cooled to 0° C. HCl (1.8M) (0.37 mL, 0.66 mmol), was added with stirring at 0° C. The ice bath was removed, and the reaction mixture was stirred for 1.5 h. Water (75 mL) was added to the reaction mixture. The reaction mixture was extracted with Et$_2$O (3×75 mL). The combined Et$_2$O extracts were washed with saturated NaCl solution, dried over anhydrous Na$_2$SO$_4$, filtered, and concentrated to give orange solid, 2.5 g, 100%.

Step 4. 2-(3-Bromo-4-methylphenyl)-3,3-difluoro-2-hydroxypropanamide

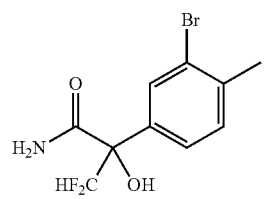

To a solution of 2-(3-bromo-4-methylphenyl)-3,3-difluoro-2-hydroxypropanenitrile (2.0 g, 7.2 mmol) in dioxane (15 mL) under N$_2$ at 0° C. was added HCl (concentrated) (2.2 mL, 26 mmol) (precooled in an ice bath). While cooling at 0° C., the reaction mixture was vigorously bubbled with HCl gas for 10 min. The reaction vial was capped tightly. The cooling bath was removed and the mixture stirred for 16 h. The reaction mixture was cooled at 0° C. and diluted with saturated NH$_4$Cl solution (2 mL), water (10 mL), and of EtOAc (50 mL). The EtOAc layer was separated and washed with water, dried over anhydrous Na$_2$SO$_4$, filtered, and concentrated to brown oil. The oil was dissolved in CH$_2$Cl$_2$ and purified on a silica gel column, EtOAc/hexane, 0-60%. The product fractions were concentrated to yellow oil, 2.1 g (100%). The racemic mixture was separated via preparative chiral HPLC (Phenomenex Lux Amylose-1 [21.2×250 mm, 5 micron], eluting with 85% ethanol in hexanes, at flow rate of 20 mL/min, loading about 100 mg in 2 mL ethanol) to give the desired second eluting enantiomer (0.9 g, 43%) as a viscous oil. The first enantiomer that eluted had a retention time of 4.2 min. The second enantiomer that eluted had a retention time of 6.4 min. Second eluting enantiomer: LCMS calculated for C$_{10}$H$_{11}$BrF$_2$NO$_2$ (M+H)$^+$: m/z=294.0, 296.0; Found: 294.0, 296.0

Step 5. 3, 3-Difluoro-2-hydroxy-2-(4-methyl-3-(4,4, 5,5-tetramethyl-1,3,2-dioxaborolan-2-yl)phenyl) propanamide

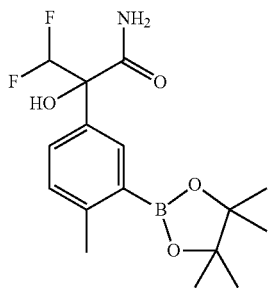 [SMILES: Cc1ccc(C(O)(C(N)=O)C(F)F)cc1B1OC(C)(C)C(C)(C)O1]

A mixture of 2-(3-bromo-4-methylphenyl)-3,3-difluoro-2-hydroxypropanamide (660 mg, 2.2 mmol; step 4, second eluting isomer), 4,4,4',4',5,5,5',5'-octamethyl-2,2'-bi(1,3,2-dioxaborolane) (680 mg, 2.7 mmol), potassium acetate (720 mg, 7.4 mmol), and dichlorobis(triphenylphosphine)palladium(II) (63 mg, 89 μmol) in THF (5 mL) was degassed for 5 min with N$_2$. The mixture was heated in a microwave at 135° C. for 20 minutes. The reaction mixture was diluted with EtOAc and filtered through CELITE®, rinsing with EtOAc. The filtrate was concentrated. Purification via silica gel chromatography (0-100% EtOAc/hexanes) afforded the desired product as clear oil. The yield for the product is: 81%, 620 mg. LCMS calculated for C$_{16}$H$_{23}$BF$_2$NO$_4$ (M+H)$^+$: m/z=342.2; Found 342.2

Step 6. 2-(3-(5-Amino-6-chloropyrazin-2-yl)-4-methylphenyl)-3, 3-difluoro-2-hydroxypropanamide

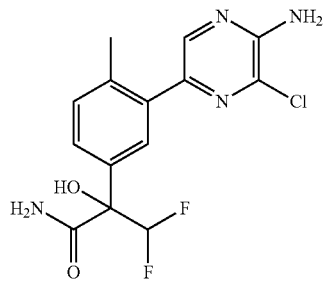 [SMILES: Cc1ccc(C(O)(C(N)=O)C(F)F)cc1-c1cnc(N)c(Cl)n1]

A vial was charged with 5-bromo-3-chloropyrazin-2-amine (35 mg, 0.17 mmol), and 3,3-difluoro-2-hydroxy-2-(4-methyl-3-(4,4,5,5-tetramethyl-1,3,2-dioxaborolan-2-yl)phenyl)propanamide (58 mg, 0.17 mmol) in dioxane. To the mixture was added aqueous sodium carbonate (260 μl, 0.51 mmol) and bubbled with N$_2$ for 5 min. To the mixture was added [1,1'-bis(diphenylphosphino)ferrocene]dichloropalladium(II) complex with dichloromethane (6.9 mg, 8.5 μmol) and bubbled N$_2$ through the mixture for 5 min. The reaction was heated at 100° C. for 15 h. The reaction mixture was diluted with ethyl acetate and filtered through a 0.5 micrometer cartridge. The filtrate was washed with saturated NaCl solution. The layers were separated and the aqueous layer was back extracted with more EtOAc. The combined EtOAc extracts were dried over anhydrous Na$_2$SO$_4$, filtered, and concentrated to a brown foam. Purification on silica gel column using 0-100% EtOAc in hexane followed by (0-10% MeOH/DCM) gradient (26 mg, 32%). LCMS calculated for C$_{14}$H$_{14}$ClF$_2$N$_4$O$_2$ (M+H)$^+$: m/z=343.1; Found 343.2.

Step 7. 2-(3-(5-Amino-6-(1-methyl-1H-pyrazol-5-yl)pyrazin-2-yl)-4-methylphenyl)-3, 3-difluoro-2-hydroxypropanamide Into a microwave vial was added 1-methyl-5-(4,4,5,5-tetramethyl-1,3,2-dioxaborolan-2-yl)- 1H-pyrazole (0.015 g, 0.070 mmol), 2-(3-(5-amino-6-chloropyrazin-2-yl)-4-methylphenyl)-3,3-difluoro-2-hydroxypropanamide (8 mg, 0.023 mmol) and dioxane (0.47 mL). An aqueous solution of sodium carbonate (1.0M, 0.093 mL) and dichloro[1,1'-bis(diphenylphosphino)ferrocene]palladium (II) dichloromethane adduct (2.9 mg, 3.50 μmol) were added. The mixture was degassed with nitrogen for 5 min. and heated at 140° C. for 20 minutes in a microwave. The mixture was diluted with MeOH and purified on preparative LC/MS using pH 10 buffer. The yield for the product is 58%, 5.8 mg. LCMS calculated for C$_{18}$H$_{19}$F$_2$N$_6$O$_2$ (M+H)$^+$: m/z=389.2: Found=389.2.

Examples 99-101 were synthesized according to procedures analogous to Example 98 and the data are listed in Table 5.

TABLE 5

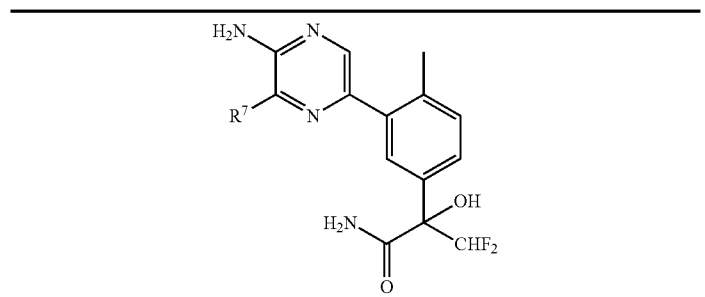

| Ex. No. | Name | R⁷ | LCMS [M + H]⁺ | ¹H NMR Spectrum |
|---|---|---|---|---|
| 99 | 2-(3-(5-amino-6-(1-methyl-1H-pyrazol-5-yl)pyrazin-2-yl)-4-methylphenyl)-3,3-difluoro-2-hydroxypropanamide | | 389.1 | ¹H NMR (DMSO) δ: 8.20 (s, 1H), 7.71 (d, J = 1.9 Hz, 1H), 7.57 (d, J = 1.9 Hz, 1H), 7.53 (dd, J = 8.0, 1.9 Hz, 1H), 7.46 (d, J = 23.7 Hz, 2H), 7.31 (d, J = 8.1 Hz, 1H), 6.81 (s, 1H), 6.81 (s, 1H), 6.71 (d, J = 1.9 Hz, 1H), 6.39 (s, 2H), 3.92 (s, 3H), 2.38 (s, 3H) |
| 100 | 2-(3-(5-amino-6-(2-methyloxazol-5-yl)pyrazin-2-yl)-4-methylphenyl)-3,3-difluoro-2-hydroxypropanamide | | 390.1 | |
| 101 | 2-(3-(5-amino-6-(2-methyl-2H-1,2,3-triazol-4-yl)pyrazin-2-yl)-4-methylphenyl)-3,3-difluoro-2-hydroxypropanamide | | 390.1 | |

Example 102. N-(2-(3-(5-amino-6-(2-cyclopropylthiazol-5-yl)pyrazin-2-yl)-4-methylphenyl)-3,3,3-trifluoro-2-hydroxypropyl)formamide trifluoroacetate

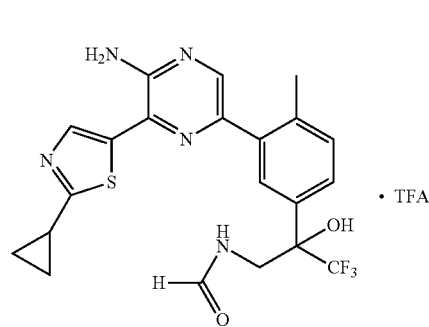 [SMILES: Cc1ccc(C(O)(CNC=O)C(F)(F)F)cc1-c1cnc(N)c(-c2cnc(C3CC3)s2)n1]

Step 1. 3-amino-2-(3-bromo-4-methylphenyl)-1,1,1-trifluoropropan-2-ol

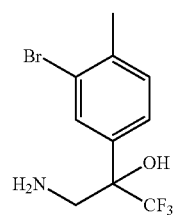 [SMILES: Cc1ccc(C(O)(CN)C(F)(F)F)cc1Br]

A solution of 2-(3-bromo-4-methylphenyl)-3,3,3-trifluoro-2-hydroxypropanenitrile (Example 1, step 3, 600 mg, 1.92 mmol) in Et₂O (5 mL) at 0° C., LiAlH₄ (100 mg, 2.63 mmol) was added portionwise. The temperature was increased to room temperature and stirred for 3 hours. The resulted mixture was quenched with 2 mL 1N NaOH aqueous at 0° C., and diluted with 10 mL diethyl ether. The mixture was filtered and concentrated. Purification via SiO₂ chromatography (Hexane/EtOAc 3:1 to 1:3) gave the desired product (350 mg, 1.17 mmol, 61%) as a white solid. LCMS for C₁₀H₁₂BrF₃NO (M+H)⁺: m/z=298.0, 300.0; Found: 298.0, 300.0.

Step 2. 3-amino-1,1,1-trifluoro-2-(4-methyl-3-(4,4,5,5-tetramethyl-1,3,2-dioxaborolan-2-yl)phenyl)propan-2-ol

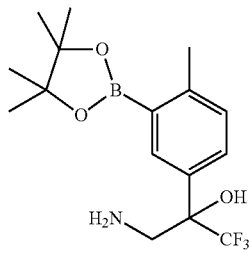 [SMILES: Cc1ccc(C(O)(CN)C(F)(F)F)cc1B1OC(C)(C)C(C)(C)O1]

A solution of 2-(3-bromo-4-methylphenyl)-3,3,3-trifluoro-2-hydroxypropanamide (Example 1, Step 4, racemic mixture, 350 mg, 1.17 mmol) in dioxane (6 mL) was treated with bis(pinacolato)diboron (350 mg, 1.37 mmol), and potassium acetate (370 mg, 3.78 mmol) and degassed with nitrogen for 5 min. The reaction mixture was treated with bis(triphenylphosphine)palladium(II)chloride (0.048 g, 0.069 mmol), degassed for 5 min, and stirred at 100° C. for 2.5 h. The reaction mixture was diluted with ethyl acetate (5 mL), filtered over CELITER, and rinsed with additional ethyl acetate (10 mL). The filtrate was washed with brine, dried over sodium sulfate, filtered, and concentrated to a brown foam. Purification by flash column chromatography using MTBE in hexanes (30% to 100%) gave the desired product (300 mg, 0.87 mmol, 63%) as a thick yellow foam. LCMS for C₁₆H₂₄BF₃NO₃ (M+H)⁺: m/z=346.2; Found: 346.2.

Step 3. 3-amino-2-(3-(5-amino-6-chloropyrazin-2-yl)-4-methylphenyl)-1,1,1-trifluoropropan-2-ol, bis(trifluoroacetate)

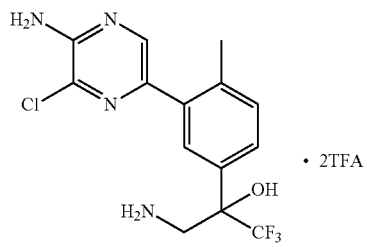 [SMILES: Cc1ccc(C(O)(CN)C(F)(F)F)cc1-c1cnc(N)c(Cl)n1]

A solution of 5-bromo-3-chloropyrazin-2-amine (200 mg, 0.96 mmol) and 3-amino-1,1,1-trifluoro-2-(4-methyl-3-(4,4,5,5-tetramethyl-1,3,2-dioxaborolan-2-yl)phenyl)propan-2-ol (200 mg, 0.58 mmol, racemic) in dioxane/water (5 mL/1 mL) was treated with sodium carbonate (184 mg, 1.74 mmol) and dichloro[1,1'-bis(diphenylphosphino)ferrocene]palladium (II) dichloromethane adduct (24 mg, 0.029 mmol). The reaction mixture was degassed with nitrogen for 5 min, and stirred at 120° C. for 2.5 h. The resulting mixture was diluted with MeOH and passed through a Celite pad and concentrated. Purification vis flash column chromatography using ethyl acetate (containing 5% MeOH) in hexanes (0% to 100%) gave the desired product (112 mg, 56%) as yellow solid.

The same product which was submitted to biological assay was repurified via preparative LCMS (XBridge C18 Column, eluting with a gradient of acetonitrile in water with 0.1% trifluoroacetic acid, at flow rate of 60 mL/min) to give the desired product as a white solid. LCMS for C₁₄H₁₅ClF₃N₄O (M+H)⁺: m/z=347.1; Found: 347.1.

Step 4. 3-amino-2-(3-(5-amino-6-(2-cyclopropylthiazol-5-yl)pyrazin-2-yl)-4-methylphenyl)-1,1,1-trifluoropropan-2-ol, bis(trifluoroacetate)

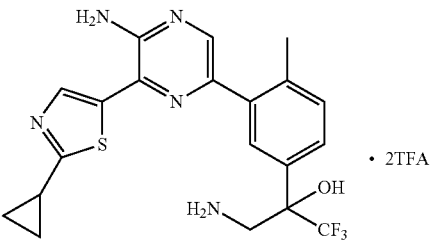 [SMILES: Cc1ccc(C(O)(CN)C(F)(F)F)cc1-c1cnc(N)c(-c2cnc(C3CC3)s2)n1]

A solution of 2-cyclopropyl-5-(4,4,5,5-tetramethyl-1,3,2-dioxaborolan-2-yl)thiazole (36 mg, 0.144 mmol) and 3-amino-2-(3-(5-amino-6-chloropyrazin-2-yl)-4-methylphenyl)-1,1,1-trifluoropropan-2-ol (25 mg, 0.072 mmol, racemic) in dioxane/water (0.8 mL/0.2 mL) was treated with sodium carbonate (15 mg, 0.144 mmol) and dichloro[1,1'-bis(diphenylphosphino)ferrocene]palladium (II) dichloromethane adduct (12 mg, 0.014 mmol). The resulting mixture was degassed with nitrogen for 5 min, and stirred at 120° C. for 2.5 h. The reaction mixture was diluted with THF, filtered through a 0.45 micron cartridge, and rinsed with THF and ethyl acetate. The filtrate was concentrated and the crude residue was purified via preparative LCMS (XBridge C18 Column, eluting with a gradient of acetonitrile in water with 0.1% trifluoroacetic acid, at flow rate of 60 mL/min) to give the desired product (16 mg, 51%) as a white solid. ¹H NMR (400 MHz, DMSO-d₆) δ 8.23 (s, 1H), 8.18 (s, 1H), 8.00 (brs, 2H), 7.69 (s, 1H), 7.57 (s, 1H), 7.42 (d, J=8.4 Hz, 1H), 6.62 (brs, 2H), 3.71 (m, 2H), 2.44 (s, 3H), 1.16 (m, 3H), 1.02 (m, 2H). LCMS for C₂₀H₂₁F₃N₅O₂S (M+H)⁺: m/z=436.1; Found: 436.2.

Step 5. N-(2-(3-(5-amino-6-(2-cyclopropylthiazol-5-yl)pyrazin-2-yl)-4-methylphenyl)-3,3,3-trifluoro-2-hydroxypropyl)formamide, trifluoroacetate A solution of 3-amino-2-(3-(5-amino-6-(2-cyclopropylthiazol-5-yl)pyrazin-2-yl)-4-methylphenyl)-1,1,1-trifluoropropan-2-ol (4 mg, 9.19 µmol, racemic) and formic acid (20 mg, 0.43 mmol) in DMF/Hünig base (0.5 mL/0.05 mL) was treated with HATU (10 mg, 26.32 mol). The resulting mixture was stirred for 1 h before it was diluted with MeOH (3 mL). After filtered through a 0.45 micron cartridge, the filtrate was purified via preparative LCMS (XBridge C18 Column, eluting with a gradient of acetonitrile in water with 0.1% trifluoroacetic acid, at flow rate of 60 mL/min) to give the desired product (2 mg, 4.32 µmol, 47%) as a white solid. ¹H NMR (400 MHz, DMSO-d₆). δ 8.23 (s, 1H), 8.14 (s, 1H), 8.00 (brs, 2H), 7.95 (s, 1H), 0.59 (s, 1H), 7.48 (d, J=8.4 Hz, 1H), 7.34 (d, J=8.4 Hz, 1H), 6.95 (brs, 1H), 4.13 (m, 2H), 2.41 (s, 3H), 1.77 (m, 1H), 1.14 (m, 2H), 1.02 (m, 2H) LCMS for C$_{21}$H$_{21}$F$_3$N$_5$O$_2$S (M+H)$^+$: m/z=464.1; Found: 464.2.

Example 103. N-(2-(3-(5-amino-6-(1H-pyrazol-4-yl)pyrazin-2-yl)-4-methylphenyl)-3,3,3-trifluoro-2-hydroxypropyl)formamide trifluoroacetate

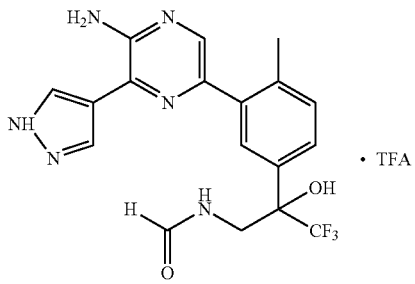 [SMILES: Cc1ccc(C(O)(CNC=O)C(F)(F)F)cc1-c1cnc(N)c(-c2cn[nH]c2)n1]

Example 103 was synthesized according to procedures of Example 102, using 4-(4,4,5,5-tetramethyl-1,3,2-dioxaborolan-2-yl)-1H-pyrazole as the starting material in place of 2-cyclopropyl-5-(4,4,5,5-tetramethyl-1,3,2-dioxaborolan-2-yl)thiazole in Step 4. LCMS for C$_{18}$H$_{18}$F$_3$N$_6$O$_2$ (M+H)$^+$: m/z=407.1; Found: 407.2.

Example 104. N-(2-(3-(5-amino-6-(1-(2,2,2-trifluoroethyl)-1H-pyrazol-4-yl)pyrazin-2-yl)-4-methylphenyl)-3,3,3-trifluoro-2-hydroxypropyl)acetamide trifluoroacetate

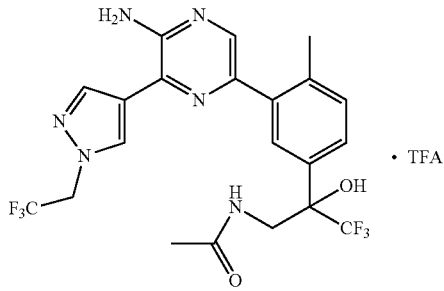 [SMILES: CC(=O)NCC(O)(c1ccc(C)c(-c2cnc(N)c(-c3cnn(CC(F)(F)F)c3)n2)c1)C(F)(F)F]

Example 104 was synthesized according to procedures of Example 102, using 1-(2,2,2-trifluoroethyl)-1H-pyrazol-4-yl boronic acid as the starting material in place of 2-cyclopropyl-5-(4,4,5,5-tetramethyl-1,3,2-dioxaborolan-2-yl)thiazole in Step 4, and using acetic acid in place of formic acid in Step 5. H NMR (400 MHz, DMSO-d$_6$) δ 8.49 (s, 1H), 8.16 (s, 1H), 8.08 (s, 1H), 7.97 (t, J=6.5 Hz, 1H), 7.58 (s, 1H), 7.47 (d, J=8.3 Hz, 1H), 7.34 (d, J=11.5 Hz, 1H), 6.95 (s, 1H), 5.21 (q, J=7.5 Hz, 2H), 3.99 (m, 1H), 3.70 (m, 1H), 2.40 (s, 3H), 1.77 (s, 3H). LCMS for C$_{21}$H$_{21}$F$_6$N$_6$O$_2$ (M+H)$^+$: m/z=503.2; Found: 503.2.

Example 105. N-(2-(3-(5-amino-6-(1H-pyrazol-4-yl)pyrazin-2-yl)-4-methylphenyl)-3,3,3-trifluoro-2-hydroxypropyl)acetamide trifluoroacetate

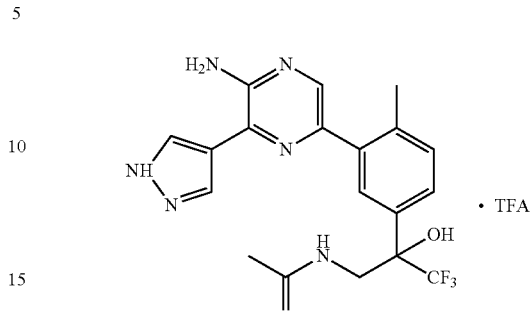

Example 105 was synthesized according to procedures of Example 102, using 4-(4,4,5,5-tetramethyl-1,3,2-dioxaborolan-2-yl)-1H-pyrazole as the starting material in place of 2-cyclopropyl-5-(4,4,5,5-tetramethyl-1,3,2-dioxaborolan-2-yl)thiazole in Step 4, and using acetic acid in place of formic acid in Step 5. LCMS for C$_{19}$H$_{20}$F$_3$N$_6$O$_2$ (M+H)$^+$: m/z=421.2; Found: 421.2.

Example 106. 3-amino-6-(5-(3-amino-1,1,1-trifluoro-2-hydroxy-3-oxopropan-2-yl)-2-methylphenyl)-N-(1-methyl-1H-pyrazol-5-yl)pyrazine-2-carboxamide trifluoroacetate

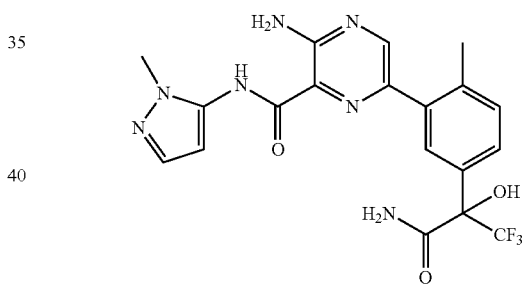

Step 1. Ethyl 3-amino-6-(5-(3-amino-1,1,1-trifluoro-2-hydroxy-3-oxopropan-2-yl)-2-methylphenyl)pyrazine-2-carboxylate

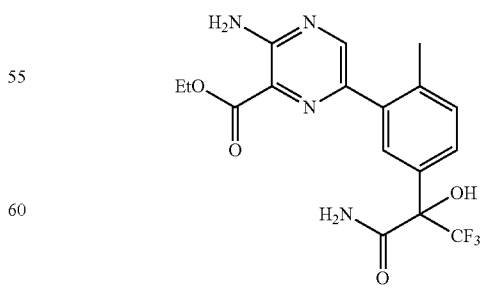

A solution of 2-(3-(5-amino-6-chloropyrazin-2-yl)-4-methylphenyl)-3,3,3-trifluoro-2-hydroxypropanamide (0.060 g, 0.166 mmol) (single enantiomer from Example 1, step 6) in ethanol (4.4 mL) was treated with triethylamine (0.093 mL, 0.67 mmol) and degassed with nitrogen for 5 min. The reaction mixture was treated with dichloro[1,1'-bis(diphenylphosphino)ferrocene]palladium (II) dichloromethane adduct (0.027 g, 0.033 mmol) and degassed with nitrogen for another 5 min. The reaction mixture was saturated with CO by bubbling the gas through the reaction subsurface for 5 min and the reaction mixture was stirred at 80° C. overnight. The reaction mixture was diluted with methanol and water and filtered through a 0.45 micron cartridge. The filtrate was concentrated and the crude residue was purified by flash column chromatography using methanol in dichloromethane (0% to 10%) to give the desired product (48.0 mg, 72.1%). LCMS for $C_{17}H_{18}F_3N_4O_4$ (M+H)$^+$: m/z=399.1; Found: 399.1.

Step 2. 3-Amino-6-(5-(3-amino-1,1,1-trifluoro-2-hydroxy-3-oxopropan-2-yl)-2-methylphenyl)pyrazine-2-carboxylic acid

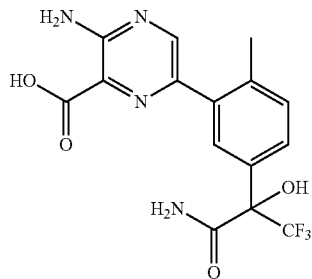 [SMILES: Cc1ccc(C(O)(C(N)=O)C(F)(F)F)cc1-c1cnc(N)c(C(=O)O)n1]

A solution of ethyl 3-amino-6-(5-(3-amino-1,1,1-trifluoro-2-hydroxy-3-oxopropan-2-yl)-2-methylphenyl)pyrazine-2-carboxylate (0.048 g, 0.120 mmol) (single enantiomer) in methanol (1.21 mL) was treated with 1.0 N sodium hydroxide (0.602 ml, 0.602 mmol) and stirred at rt for 2.5 h. The reaction mixture was partially concentrated to remove methanol and quenched with 1 N HCl to pH-5 (0.45 mL). The mixture was extracted with ethyl acetate (3×). The combined organic layers were washed with brine (0.5 mL), dried over sodium sulfate, filtered, and concentrated to give the desired product (40.0 g, 88.9%) as a tan solid that was used without further purification. LCMS for $C_{15}H_{14}F_3N_4O_4$ (M+H)$^+$: m/z=371.1; Found: 371.2.

Step 3. 3-Amino-6-(5-(3-amino-1,1,1-trifluoro-2-hydroxy-3-oxopropan-2-yl)-2-methylphenyl)-N-(1-methyl-1H-pyrazol-5-yl)pyrazine-2-carboxamide trifluoroacetate A solution of 1-methyl-1H-pyrazol-5-amine (3.93 mg, 0.041 mmol), HATU (7.70 mg, 0.020 mmol), and 3-amino-6-(5-(3-amino-1,1,1-trifluoro-2-hydroxy-3-oxopropan-2-yl)-2-methylphenyl)pyrazine-2-carboxylic acid (0.005 g, 0.014 mmol) (single enantiomer) in DMF (0.270 mL) was stirred at rt for 5 min, treated with triethylamine (5.65 µL, 0.041 mmol), and stirred at rt for 30 min. The reaction mixture was diluted with methanol and water and purified via preparative LCMS (XBridge C18 Column, eluting with a gradient of acetonitrile in water with 0.1% trifluoroacetic acid, at flow rate of 60 mL/min) to give the desired product (3.60 mg, 47.3%) as a TFA salt. $^1$H NMR (500 MHz, DMSO-d$_6$) δ 10.31 (s, 1H), 8.46 (s, 1H), 7.81 (d, J=2.0 Hz, 1H), 7.74-7.50 (m, 5H), 7.44-7.32 (m, 2H), 6.29 (d, J=1.9 Hz, 1H), 3.70 (s, 3H), 2.44 (s, 3H). LCMS for $C_{19}H_{19}F_3N_7O_3$ (M+H)$^+$: m/z=450.1; Found: 450.1.

Example 107. 2-(3-(5-Amino-6-(1-((1-methyl-1H-pyrazol-4-yl)sulfonyl)azetidin-3-yl)pyrazin-2-yl)-4-methylphenyl)-3,3,3-trifluoro-2-hydroxypropanamide, trifluoroacetate salt (Single Enantiomer Prepared)

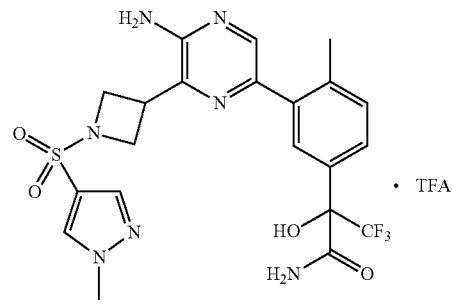 [SMILES: Cc1ccc(C(O)(C(N)=O)C(F)(F)F)cc1-c1cnc(N)c(C2CN(S(=O)(=O)c3cnn(C)c3)C2)n1]

Step 1. 1-(3-Bromo-4-methylphenyl)-2,2,2-trifluoroethan-1-ol

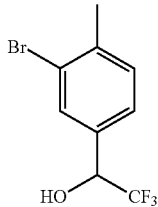

A solution of 3-bromo-4-methylbenzaldehyde (6.51 g, 32.7 mmol) [Combi-Blocks, HC-3454] in dry tetrahydrofuran (65.4 mL) was cooled to 0° C. followed by the addition of trimethyl(trifluoromethyl)silane (6.28 mL, 42.5 mmol). The yellow mixture was treated with 1.0 M tetra-n-butylammonium fluoride in tetrahydrofuran (0.654 mL, 0.654 mmol) at 0° C. and stirred for a few minutes at 0° C. The ice bath was removed and the resulting reaction mixture was stirred for 1.5 h. The reaction mixture was cooled back to 0° C. and treated with water (6.48 mL, 360 mmol) and 1.0 M tetra-n-butylammonium fluoride in tetrahydrofuran (6.54 mL, 6.54 mmol). The ice bath was removed and the reaction mixture was stirred at ambient temperature for 30 min. The yellow reaction mixture was diluted with brine (150 mL) and extracted with ethyl acetate (200 mL). The organic layer was washed with saturated ammonium chloride (100 mL), dried over sodium sulfate, filtered, and concentrated to give a tan oil. Purification by flash column chromatography using methyl tert-butyl ether (MTBE) in hexanes (0% to 50%) gave the desired product (8.42 g, 95.7%) as a yellow oil. LCMS for $C_9H_7BrF_3$ (M−OH)$^+$: m/z=251.0, 253.0; Found: 250.9, 252.8.

Step 2. 1-(3-Bromo-4-methylphenyl)-2,2,2-trifluoro-ethan-1-one

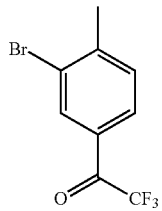

A mixture of 1-(3-bromo-4-methylphenyl)-2,2,2-trifluoroethan-1-ol (8.41 g, 31.3 mmol) in dichloromethane (125 mL) at 0° C. was treated with Dess-Martin periodinane (19.9 g, 46.9 mmol) and stirred at rt for 2.5 h. The reaction mixture was concentrated by rotary evaporation with a water bath set at 30° C. to an oily solid that was diluted with diethyl ether (200 mL), which precipitated more solids. This mixture was filtered over Celite® and the Celite® was rinsed with additional diethyl ether (200 mL). The filtrate was washed with saturated sodium bicarbonate solution (3×200 mL) and brine, dried over sodium sulfate, filtered, and concentrated to give an oily solid. The oily solid was partitioned between diethyl ether (150 mL) and water (100 mL). The organic layer was separated and washed with saturated sodium bicarbonate solution (2×75 mL) and brine, dried over sodium sulfate, filtered, and concentrated to give the desired product (7.93 g, 95.0%) as an oil that was used without further purification. LCMS for $C_9H_7BrF_3O$ $(M+H)^+$: m/z=267.0, 269.0; Found: 267.1, 268.9.

Step 3. 2-(3-Bromo-4-methylphenyl)-3,3,3-trifluoro-2-hydroxypropanenitrile

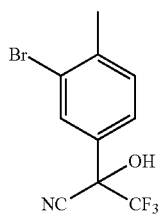

A solution of 1-(3-bromo-4-methylphenyl)-2,2,2-trifluoroethan-1-one (7.92 g, 29.7 mmol) in dichloromethane (29.7 mL) was treated with trimethylsilyl cyanide (8.70 mL, 65.2 mmol) and potassium cyanide (0.29 g, 4.45 mmol), and 18-crown-6 (0.29 g, 1.10 mmol) and stirred for 1 h. The reaction mixture was concentrated by rotary evaporation with a water bath set at 28° C. to give a rust colored solid. The solid was dissolved in THF (29.6 mL), cooled to 0° C., treated with 1.8 M HCl (10.9 mL, 19.6 mmol), and stirred at room temperature (rt) for 1.5 h. The reaction mixture was diluted with water (75 mL) and extracted with diethyl ether (3×75 mL). The combined organic extracts were washed with brine, dried over sodium sulfate, filtered, and concentrated. Reconcentration from hexanes afforded the desired product (8.70 g, 99.8%) as an orange solid that was used without further purification. LCMS for $C_9H_7BrF_3O$ $(M-CN)^+$: m/z=267.0, 269.0; Found: 266.9, 269.0.

Step 4. 2-(3-bromo-4-methylphenyl)-3,3,3-trifluoro-2-hydroxypropanamide

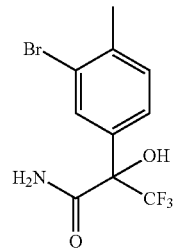 [SMILES: Cc1ccc(C(O)(C(N)=O)C(F)(F)F)cc1Br]

A solution of 2-(3-bromo-4-methylphenyl)-3,3,3-trifluoro-2-hydroxypropanenitrile (8.70 g, 29.6 mmol) in dioxane (59.2 mL) at 0° C. was treated with concentrated HCl (9.00 mL, 108 mmol) that had been pre-cooled in an ice bath. While stirring at 0° C., the reaction mixture was bubbled with HCl gas for 45 min. The cooling bath was removed and the reaction mixture was stirred at rt for 61 h. The reaction mixture was bubbled with nitrogen for 10 min to remove some of the HCl, cooled to 0° C., and diluted with brine (200 mL), water (50 mL), and ethyl acetate (200 mL). The organic layer was separated and the aqueous layer was diluted with water (100 mL) to dissolve the remaining solids. The aqueous layer was extracted with ethyl acetate (100 mL). The combined organic extracts were washed with brine, dried over sodium sulfate, filtered, and concentrated to give a brown oil. Purification by flash column chromatography using MTBE in hexanes (0% to 60%) gave the desired product as a yellow oily solid. The racemic mixture was separated via preparative chiral HPLC (Phenomenex Lux Amylose-1 [21.2×250 mm, 5 micron], eluting with 95% ethanol in hexanes, at flow rate of 18 mL/min, loading about 100 mg in 2 mL ethanol) to give the desired second eluting enantiomer (4.50 g, 48.8%) as a viscous yellow oil. The first enantiomer that eluted had a retention time of 4.0 min. The second enantiomer that eluted had a retention time of 5.3 min. Second eluting enantiomer: LCMS for $C_{10}H_{10}BrF_3NO_2$ $(M+H)^+$: m/z=312.0, 314.0; Found: 312.0, 314.0.

Step 5. 3,3,3-Trifluoro-2-hydroxy-2-(4-methyl-3-(4,4,5,5-tetramethyl-1,3,2-dioxaborolan-2-yl)phenyl)propanamide

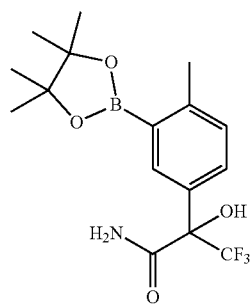 [SMILES: Cc1ccc(C(O)(C(N)=O)C(F)(F)F)cc1B1OC(C)(C)C(C)(C)O1]

A solution of 2-(3-bromo-4-methylphenyl)-3,3,3-trifluoro-2-hydroxypropanamide (3.57 g, 11.5 mmol) (Example 1, step 4, second eluting enantiomer) in dioxane (57.2 mL)

was treated with bis(pinacolato)diboron (3.49 g, 13.7 mmol), and potassium acetate (3.71 g, 37.8 mmol) and degassed with nitrogen for 5 min. The reaction mixture was treated with bis(triphenylphosphine)palladium(II)chloride (0.482 g, 0.687 mmol), degassed for 5 min, and stirred at 100° C. for 2.5 h. The reaction mixture was diluted with ethyl acetate (50 mL), filtered over Celite®, and rinsed with additional ethyl acetate (100 mL). The filtrate was washed with brine, dried over sodium sulfate, filtered, and concentrated to a brown foam. Purification by flash column chromatography using MTBE in hexanes (0% to 100%) gave the desired product (3.35 g, 81.5%) as a thick yellow foam. $^1$H NMR (400 MHz, DMSO-$d_6$) δ 7.96 (d, J=2.2 Hz, 1H), 7.63 (dd, J=7.9, 2.1 Hz, 1H), 7.58 (s, 1H), 7.54 (s, 1H), 7.51-7.40 (m, 1H), 7.21 (d, J=8.2 Hz, 1H), 2.46 (s, 3H), 1.30 (s, 12H). LCMS for $C_{16}H_{22}BF_3NO_4$ (M+H)$^+$: m/z=360.2; Found: 360.1.

Step 6. tert-Butyl 3-(3-amino-6-chloropyrazin-2-yl)azetidine-1-carboxylate

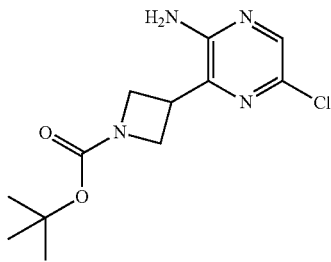 [SMILES: CC(C)(C)OC(=O)N1CC(c2nc(Cl)cnc2N)C1]

Zinc dust (0.627 g, 9.59 mmol) (activated by the procedure described in WO2011/143365, the disclosure of which is incorporated herein by reference in its entirety) was charged to a dry flask and suspended in DMA (2.5 mL). 1,2-Dibromoethane (0.031 mL, 0.36 mmol) and TMSCl (0.092 mL, 0.72 mmol) were added and the reaction was stirred for 25 min. tert-Butyl 3-iodoazetidine-1-carboxylate (2.04 g, 7.20 mmol) (Oakwood) in DMA (6.0 mL) was added slowly to the mixture which was immersed in a water bath to keep the temperature below 65° C. The mixture was stirred for 1 hour and was degassed by bubbling a stream of nitrogen subsurface for 5 minutes.

A separate flask was charged with 3-bromo-5-chloropyrazin-2-amine (0.50 g, 2.4 mmol, D-L Chiral Chemicals), dichloro[1,1'-bis(diphenylphosphino)ferrocene]palladium(II) dichloromethane adduct (0.118 g, 0.144 mmol) and copper(I) iodide (0.057 g, 0.30 mmol). DMA (6.0 mL) was added, and the mixture was degassed by bubbling a stream of nitrogen subsurface for 5 minutes. The solution containing the organozinc in DMA generated above was added, excluding any remaining zinc solids. The reaction was then heated to 80° C. for 30 min. Upon cooling to room temperature, the reaction mixture was partitioned between water and EtOAc. The aqueous layer was extracted with two additional portions of EtOAc. The combined organic extracts were washed with water and brine, dried over sodium sulfate, filtered and concentrated. The product was purified by flash chromatography, eluting with a gradient from 0-100% EtOAc in hexanes to afford product (0.62 g, 90%). LCMS calculated for $C_{12}H_{18}ClN_4O_2$ (M+H)$^+$: m/z=285.1, found: 285.1. H NMR (400 MHz, CDCl$_3$) δ 7.91 (s, 1H), 4.67 (s, 2H), 4.35-4.22 (m, 4H), 3.71 (p, J=7.4 Hz, 1H), 1.43 (s, 9H).

Step 7. 2-(3-(5-Amino-6-(azetidin-3-yl)pyrazin-2-yl)-4-methylphenyl)-3, 3,3-trifluoro-2-hydroxypropanamide, HCl salt (Single Enantiomer Prepared)

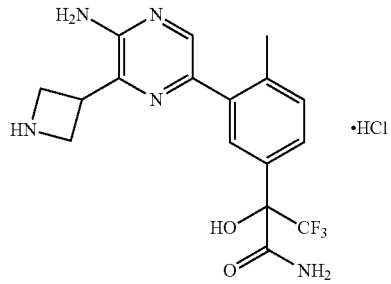 [SMILES: Cc1ccc(C(O)(C(N)=O)C(F)(F)F)cc1-c1cnc(N)c(C2CNC2)n1 ; Cl]

In a sealed vial, a degassed mixture of tert-butyl 3-(3-amino-6-chloropyrazin-2-yl)azetidine-1-carboxylate (0.25 g, 0.88 mmol), 3,3,3-trifluoro-2-hydroxy-2-(4-methyl-3-(4,4,5,5-tetramethyl-1,3,2-dioxaborolan-2-yl)phenyl)propanamide (0.315 g, 0.878 mmol, single enantiomer, step 5), and PdCl$_2$(dppf)-CH$_2$Cl$_2$ adduct (0.036 g, 0.044 mmol) in dioxane (4.4 mL) and sodium carbonate (1.0 M in water, 2.6 mL, 2.6 mmol) was heated in an oil bath held at 120° C. for 3 hours. Upon cooling to room temperature, the reaction mixture was diluted with EtOAc and water. The layers were separated and the aqueous layer was extracted with two further portions of EtOAc. The combined organic extracts were dried over sodium sulfate, filtered and concentrated. To recover material remaining in the aqueous layer, water was evaporated and the solids were washed with MeOH and insolubles were removed by filtration. The product so obtained was combined with that obtained from the extracts, and the product was used without further purification (0.30 g, 71%). LCMS calculated for $C_{22}H_{26}F_3N_5NaO_4$ (M+Na)$^+$: m/z=504.2, found: 504.1.

The above product was deprotected by stirring in a solution of HCl (1.25 N in MeOH, prepared by diluting concentrated HCl with MeOH, 6.1 mL, 7.6 mmol) for 2 days. After removal of solvent and trituration of the resulting solid with ether, the product was obtained by filtration as a tan solid (0.25 g, 68%). LCMS calculated for $C_{17}H_{19}F_3N_5O_2$ (M+H)$^+$: m/z=382.1, found: 382.1.

Step 8. 2-(3-(5-Amino-6-(1-((1-methyl-1H-pyrazol-4-yl)sulfonyl)azetidin-3-yl)pyrazin-2-yl)-4-methylphenyl)-3,3,3-trifluoro-2-hydroxypropanamide, trifluoroacetate salt (Single Enantiomer Prepared)

To a mixture of 2-(3-(5-amino-6-(azetidin-3-yl)pyrazin-2-yl)-4-methylphenyl)-3,3,3-trifluoro-2-hydroxypropanamide, HCl salt (4.0 mg, 9.6 μmol) in DCM (0.5 mL) at 0° C. was added DIPEA (2 μl, 10 μmol), followed by 1-methyl-1H-pyrazole-4-sulfonyl chloride (1.9 mg, 10 μmol). After stirring for 1 hour, the reaction was diluted with MeOH, filtered and purified via preparative HPLC-MS (pH=2) to afford product as the trifluoroacetate salt (2 mg, 30%). LCMS calculated for $C_{21}H_{23}F_3N_7O_4S$ (M+H)$^+$: m/z=526.1, found: 526.1. 1H NMR (400 MHz, CD$_3$OD) δ 8.10 (s, 1H), 7.89 (s, 1H), 7.75 (s, 1H), 7.72 (d, J=1.7 Hz, 1H), 7.66 (dd, J=8.1, 1.7 Hz, 1H), 7.34 (d, J=8.1 Hz, 1H), 4.22-4.16 (m, 2H), 4.09-3.96 (m, 3H), 3.51 (s, 3H), 2.29 (s, 3H).

Examples 108 & 109. Ethyl 3-(3-amino-6-(5-(3-amino-1,1,1-trifluoro-2-hydroxy-3-oxopropan-2-yl)-2-methylphenyl)pyrazin-2-yl)cyclobutane-1-carboxylate (two diastereomers isolated: cis- and trans-cyclobutanes)

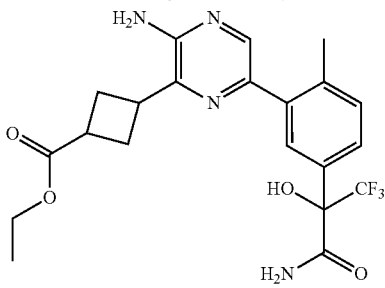 [SMILES: CCOC(=O)C1CC(c2nc(-c3cc(C(O)(C(N)=O)C(F)(F)F)ccc3C)cnc2N)C1]

Step 1. 2-(3-(5-Aminopyrazin-2-yl)-4-methylphenyl)-3,3,3-trifluoro-2-hydroxypropanamide

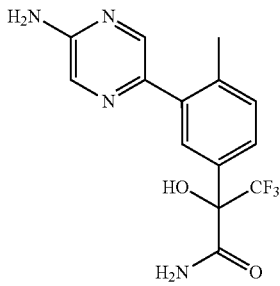 [SMILES: Cc1ccc(C(O)(C(N)=O)C(F)(F)F)cc1-c1cnc(N)cn1]

In a sealed vial, a degassed mixture of 5-bromopyrazin-2-amine (0.050 g, 0.287 mmol, Ark Pharm), 3,3,3-trifluoro-2-hydroxy-2-(4-methyl-3-(4,4,5,5-tetramethyl-1,3,2-dioxaborolan-2-yl)phenyl)propanamide (0.103 g, 0.287 mmol, single enantiomer, Example 1, step 5) and PdCl$_2$(dppf)-CH$_2$Cl$_2$ adduct (0.012 g, 0.014 mmol) in dioxane (3.0 mL) and sodium carbonate (1.0 M in water, 0.86 mL, 0.86 mmol) was heated in an oil bath held at 120° C. for 3 h. Upon cooling to room temperature, the reaction mixture was partitioned between water and EtOAc. The aqueous portion was extracted with three additional portions of EtOAc. The combined organic extracts were dried over sodium sulfate, filtered and concentrated to afford product which was used without further purification. LCMS calculated for C$_{14}$H$_{14}$F$_3$N$_4$O$_2$ (M+H)$^+$: m/z=327.1, found: 327.1.

Step 2. 2-(3-(5-Amino-6-bromopyrazin-2-yl)-4-methylphenyl)-3,3-trifluoro-2-hydroxypropanamide

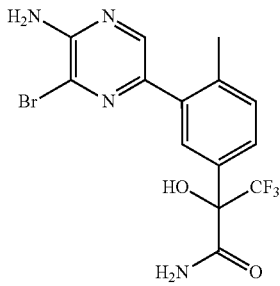 [SMILES: Cc1ccc(C(O)(C(N)=O)C(F)(F)F)cc1-c1cnc(N)c(Br)n1]

To 2-(3-(5-aminopyrazin-2-yl)-4-methylphenyl)-3,3,3-trifluoro-2-hydroxypropanamide (0.070 g, 0.21 mmol, crude from Step 1) in DMF (2.0 mL) was added NBS (0.038 g, 0.21 mmol). The reaction was stirred for 30 min. Purification of the crude reaction mixture via flash chromatography, eluting with a gradient from 0-100% EtOAc in hexanes, afforded product (0.042 g, 48%). LCMS calculated for C$_{14}$H$_{13}$BrF$_3$N$_4$O$_2$ (M+H)$^+$: m/z=405.0, found: 405.0. $^1$H NMR (400 MHz, CDCl$_3$) δ 8.05 (s, 1H), 7.68 (d, J=2.1 Hz, 1H), 7.63 (dd, J=8.3, 2.0 Hz, 1H), 7.30 (d, J=8.1 Hz, 1H), 6.56 (br s, 1H), 6.12 (br s, 1H), 5.90 (br s, 1H), 5.23 (br s, 2H), 2.38 (s, 3H).

Step 3. Ethyl 3-(3-amino-6-(5-(3-amino-, 1,1,1-trifluoro-2-hydroxy-3-oxopropan-2-yl)-2-methylphenyl)pyrazin-2-yl)cyclobutane-1-carboxylate (two diastereomers isolated: cis- and trans-cyclobutanes)

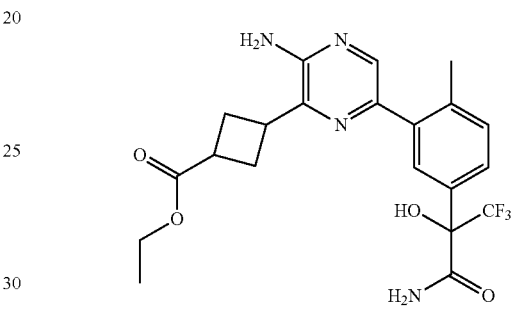

A vial was charged with 2-(3-(5-amino-6-bromopyrazin-2-yl)-4-methylphenyl)-3,3,3-trifluoro-2-hydroxypropanamide (42.0 mg, 0.104 mmol) and [1,3-bis(2,6-diisopropylphenyl)imidazol-2-ylidene](3-chloropyridyl)palladium(II) dichloride (7.0 mg, 10. mol). DMA (1.4 mL) was added and the solution was degassed by bubbling nitrogen subsurface for 5 min. Separately, a vial was charged with zinc (0.118 g, 1.80 mmol) (freshly activated and dried according to the procedures found in WO2011/143365) and the vial was flushed with N$_2$ and heated with a heat gun and cooled. Dry THF (1.6 mL) was added. 1,2-Dibromoethane (0.016 mL, 0.19 mmol) was added and the mixture was heated with a heat gun to reflux, and then cooled to room temperature. This heating and cooling cycle was performed three times. TMSCl (0.048 mL, 0.37 mmol) was added. The mixture was heated to 50° C. in an oil bath, and ethyl 3-iodocyclobutane-1-carboxylate (0.158 g, 0.622 mmol; see e.g., WO 2014/200882, the disclosure of which is incorporated herein by reference in its entirety) in THF (0.8 mL) was added dropwise. The mixture was maintained at 50° C. for about 1 hour, then was cooled to room temperature and degassed by bubbling a stream of nitrogen subsurface for 5 min. One-half of this mixture (excluding the zinc solids) was removed via syringe and added to the degassed solution containing 2-(3-(5-amino-6-bromopyrazin-2-yl)-4-methylphenyl)-3,3,3-trifluoro-2-hydroxypropanamide and [1,3-bis(2,6-diisopropylphenyl)imidazol-2-ylidene](3-chloropyridyl)palladium(II) dichloride in DMA. The reaction was heated to 50° C. for 1 hour. The second half of the organozinc solution in THF prepared above was added, and heating at 50° C. was continued for 1 hour. Upon cooling, the reaction mixture was partitioned between EtOAc and water. The aqueous portion was extracted with an additional portion of EtOAc. The combined organic extracts were washed with brine, dried over sodium sulfate, filtered and concentrated. The product was purified via preparative HPLC-MS (pH=10; Waters XBridge™ C$_{18}$ 5 μm, 30×100 mm column, eluting with mobile phase A: 0.1% NH$_4$OH in water and mobile phase B: acetonitrile; the flow rate was 60 mL/minute, the gradient was 22.3-40.3% B in 12 minutes) and each of the two diastereomers eluted separately.

Peak 1 (Example 2, retention time: 8.5 min) Example 2 (10 mg, 20%) LCMS calculated for C$_{21}$H$_{24}$F$_3$N$_4$O$_4$ (M+H)$^+$: m/z=453.2, found: 453.2.

Peak 2 (Example 3, retention time: 9.8 min) Example 3 (10 mg, 20%) LCMS calculated for C$_{21}$H$_{24}$F$_3$N$_4$O$_4$ (M+H)$^+$: m/z=453.2, found: 453.2.

Example 110. 3-(3-Amino-6-(5-(3-amino-1,1,1-trifluoro-2-hydroxy-3-oxopropan-2-yl)-2-methylphenyl)pyrazin-2-yl)-N-isopropylcyclobutane-1-carboxamide (Single Isomer Prepared)

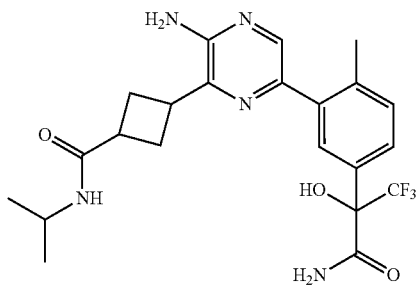 [SMILES: Cc1ccc(C(O)(C(N)=O)C(F)(F)F)cc1-c1cnc(N)c(C2CC(C(=O)NC(C)C)C2)n1]

A solution of ethyl 3-(3-amino-6-(5-(3-amino-1,1,1-trifluoro-2-hydroxy-3-oxopropan-2-yl)-2-methylphenyl)pyrazin-2-yl)cyclobutane-1-carboxylate (0.005 g, 0.011 mmol, Example 2) in DCM (0.5 mL) and DCE (2.0 mL) at reflux was treated with isopropylamine (20 μL, 0.23 mmol) and AlMe$_3$ (2.0 M in toluene, 0.12 mL, 0.23 mmol) three times at 1 hour intervals while being heated in an oil bath at 80° C. After the third addition, the reaction mixture was heated at 80° C. overnight. Upon cooling to room temperature, saturated NH$_4$Cl solution was added. The layers were separated and the organic layer was dried over sodium sulfate, filtered and concentrated. The residue was reconstituted in MeOH and water and was purified via preparative HPLC-MS (pH=10) to afford product (0.7 mg, 14%). LCMS calculated for C$_{22}$H$_{27}$F$_3$N$_5$O$_3$ (M+H)$^+$: m/z=466.2, found: 466.1.

Example 111. 3-(3-Amino-6-(5-(3-amino-1,1,1-trifluoro-2-hydroxy-3-oxopropan-2-yl)-2-methylphenyl)pyrazin-2-yl)-N-isopropylcyclobutane-1-carboxamide (Single Isomer Prepared)

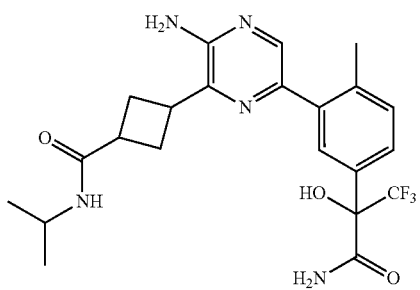 [SMILES: Cc1ccc(C(O)(C(N)=O)C(F)(F)F)cc1-c1cnc(N)c(C2CC(C(=O)NC(C)C)C2)n1]

The title compound was prepared by the method of Example 110, using Example 109 as starting material (0.5 mg, 10%). LCMS calculated for C$_{22}$H$_{27}$F$_3$N$_5$O$_3$ (M+H)$^+$: m/z=466.2, found: 466.1.

Example 112. 2-(3-(5-amino-6-(4-cyclopropyl-3-oxopiperazin-1-yl)pyrazin-2-yl)-4-methylphenyl)-3,3,3-trifluoro-2-hydroxypropanamide trifluoroacetate

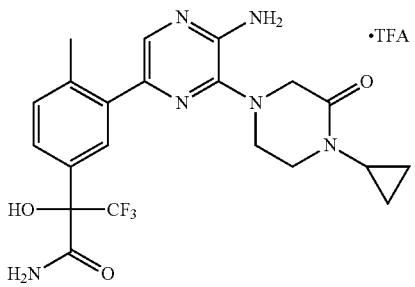 [SMILES: Cc1ccc(C(O)(C(N)=O)C(F)(F)F)cc1-c1cnc(N)c(N2CCN(C3CC3)C(=O)C2)n1]

Step 1. 4-(3-amino-6-bromopyrazin-2-yl)-1-cyclopropylpiperazin-2-one

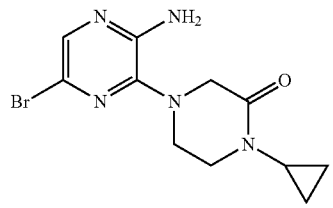 [SMILES: Nc1ncc(Br)nc1N1CCN(C2CC2)C(=O)C1]

To a solution of 5-bromo-3-chloropyrazin-2-amine (30 mg, 0.14 mmol) and 1-cyclopropylpiperazin-2-one (30.3 mg, 0.22 mmol) in NMP (2 mL) was added triethylamine (0.040 mL, 0.29 mmol), and the reaction mixture was heated at 150° C. for 6 h. The reaction mixture was cooled to room temperature, partitioned between water and EtOAc, and the layers were separated. The aqueous layer was extracted with EtOAc and the combined organic layers were washed with brine, dried over MgSO$_4$, filtered, and concentrated. The residue was purified by flash chromatography (0-100% EtOAc/hexanes) to afford the title compound (25 mg, 56%). LCMS for C$_{11}$H$_{15}$BrN$_5$O (M+H)$^+$: m/z=312.0; Found: 312.0.

Step 2. 2-(3-(5-amino-6-(4-cyclopropyl-3-oxopiperazin-1-yl)pyrazin-2-yl)-4-methylphenyl)-3,3,3-trifluoro-2-hydroxypropanamide trifluoroacetate A mixture of 4-(3-amino-6-bromopyrazin-2-yl)-1-cyclopropylpiperazin-2-one (25 mg, 0.08 mmol), 3,3,3-trifluoro-2-hydroxy-2-(4-methyl-3-(4,4,5,5-tetramethyl-1,3,2-dioxaborolan-2-yl)phenyl)propanamide (Example 1, step 5, 34.5 mg, 0.096 mmol), (1,1'-Bis(diphenylphosphino)ferrocene)-dichloropalladium(II) (2.93 mg, 4.00 μmol), and sodium carbonate (25.5 mg, 0.240 mmol) in dioxane (2 mL) and water (0.5 mL) was sparged with N$_2$ and heated to 100° C. for 2 h. The reaction mixture was cooled to room temperature and concentrated. The residue was dissolved in MeOH, filtered, and purified by prep HPLC (pH 2). Due to use of AD-mix-α, and without being bound by theory, it is believed that the product was enriched in the (S)-enantiomer (see stereochemical rationale supra). LCMS for $C_{21}H_{24}F_3N_6O_3$ (M+H)$^+$: m/z=465.2; Found: 465.2.

Examples 113-129 of Table 6 were prepared according to the procedure described for Example 112, utilizing the appropriate amines in Step 1.

TABLE 6

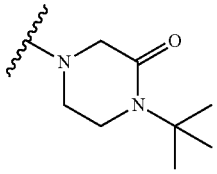 [SMILES: *N1CCN(C(C)(C)C)C(=O)C1]

| Ex. No. | Name | R | LCMS |
|---|---|---|---|
| 113 | 2-(3-(5-amino-6-(4-tert-butyl-3-oxopiperazin-1-yl)pyrazin-2-yl)-4-methylphenyl)-3,3,3-trifluoro-2-hydroxypropanamide trifluoroacetate | 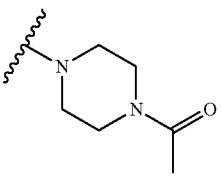 [SMILES: *N1CCN(C(C)=O)CC1] | Calculated for $C_{22}H_{28}F_3N_6O_3$ (M + H)$^+$: m/z = 481.2; Found: 481.3. |
| 114 | 2-(3-(6-(4-acetylpiperazin-1-yl)-5-aminopyrazin-2-yl)-4-methylphenyl)-3,3,3-trifluoro-2-hydroxypropanamide trifluoroacetate | 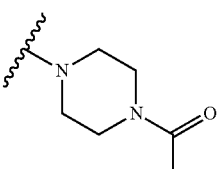 | Calculated for $C_{20}H_{24}F_3N_6O_3$ (M + H)$^+$: m/z = 453.2; Found: 453.2. |
| 115 | (R)-2-(3-(5-amino-6-(4-(cyclopropanecarbonyl)piperazin-1-yl)pyrazin-2-yl)-4-methylphenyl)-3,3,3-trifluoro-2-hydroxypropanamide trifluoroacetate | 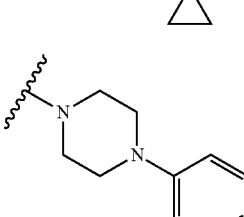 | Calculated for $C_{22}H_{26}F_3N_6O_3$ (M + H)$^+$: m/z = 479.2; Found: 479.1. |
| 116 | 2-(3-(5-amino-6-(4-phenylpiperazin-1-yl)pyrazin-2-yl)-4-methylphenyl)-3,3,3-trifluoro-2-hydroxypropanamide trifluoroacetate | 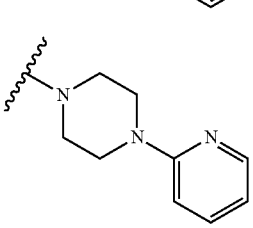 | Calculated for $C_{24}H_{26}F_3N_6O_3$ (M + H)$^+$: m/z = 487.2; Found: 487.1. |
| 117 | 2-(3-(5-amino-6-(4-(pyridin-2-yl)piperazin-1-yl)pyrazin-2-yl)-4-methylphenyl)-3,3,3-trifluoro-2-hydroxypropanamide trifluoroacetate | 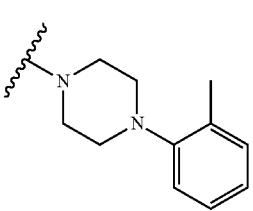 [SMILES: *N1CCN(c2ccccc2C)CC1] | Calculated for $C_{24}H_{26}F_3N_6O_3$ (M + H)$^+$: m/z = 488.2; Found: 488.2. |
| 118 | 2-(3-(5-amino-6-(4-o-tolylpiperazin-1-yl)pyrazin-2-yl)-4-methylphenyl)-3,3,3-trifluoro-2-hydroxypropanamide trifluoroacetate | | Calculated for $C_{25}H_{28}F_3N_6O_2$ (M + H)$^+$: m/z = 501.2; Found: 501.2 |

TABLE 6-continued

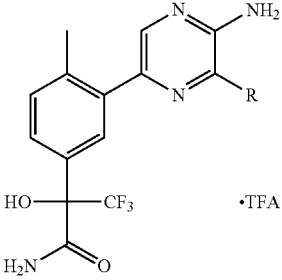

·TFA

| Ex. No. | Name | R | LCMS |
|---|---|---|---|
| 119 | 2-(3-(5-amino-6-(4-(2,5-dimethylphenyl)piperazin-1-yl)pyrazin-2-yl)-4-methylphenyl)-3,3,3-trifluoro-2-hydroxypropanamide trifluoroacetate | 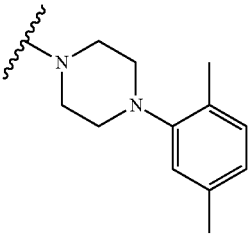 [SMILES: *N1CCN(c2cc(C)ccc2C)CC1] | Calculated for $C_{26}H_{30}F_3N_6O_2$ $(M + H)^+$: m/z = 515.2; Found: 515.2. |
| 120 | 2-(3-(5-amino-6-(4-(thiazol-5-yl)piperazin-1-yl)pyrazin-2-yl)-4-methylphenyl)-3,3,3-trifluoro-2-hydroxypropanamide trifluoroacetate | 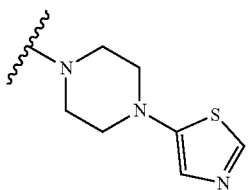 [SMILES: *N1CCN(c2cncs2)CC1] | Calculated for $C_{21}H_{23}F_3N_7O_2S$ $(M + H)^+$: m/z = 494.2; Found: 494.1. |
| 121 | 2-(3-(5-amino-6-(4-(3-(trifluoromethyl)phenyl)piperazin-1-yl)pyrazin-2-yl)-4-methylphenyl)-3,3,3-trifluoro-2-hydroxypropanamide trifluoroacetate | 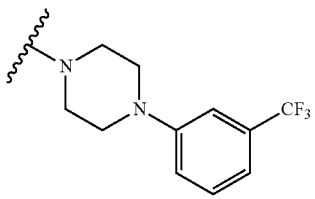 [SMILES: *N1CCN(c2cccc(C(F)(F)F)c2)CC1] | Calculated for $C_{25}H_{25}F_6N_6O_2$ $(M + H)^+$: m/z = 555.2; Found: 555.2 |
| 122 | 2-(3-(5-amino-6-(4-(2-cyanophenyl)piperazin-1-yl)pyrazin-2-yl)-4-methylphenyl)-3,3,3-trifluoro-2-hydroxypropanamide trifluoroacetate | 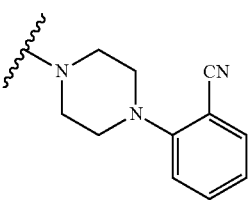 [SMILES: *N1CCN(c2ccccc2C#N)CC1] | Calculated for $C_{25}H_{25}F_3N_7O_2$ $(M + H)^+$: m/z = 512.2; Found: 512.1. |
| 123 | 2-(3-(5-amino-6-(4-(4-cyanophenyl)piperazin-1-yl)pyrazin-2-yl)-4-methylphenyl)-3,3,3-trifluoro-2-hydroxypropanamide trifluoroacetate | 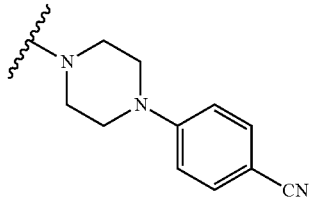 [SMILES: *N1CCN(c2ccc(C#N)cc2)CC1] | Calculated for $C_{25}H_{25}F_3N_7O_2$ $(M + H)^+$: m/z = 512.2; Found: 512.1. |

TABLE 6-continued

| Ex. No. | Name | R | LCMS |
|---|---|---|---|
| 124 | 2-(3-(5-amino-6-((R)-3-(hydroxymethyl)-4-(4-hydroxyphenyl)-5-oxopiperazin-1-yl)pyrazin-2-yl)-4-methylphenyl)-3,3,3-trifluoro-2-hydroxypropanamide trifluoroacetate | *(piperazinone with hydroxymethyl and 4-hydroxyphenyl substituents)* | Calculated for $C_{25}H_{26}F_3N_6O_5$ (M + H)$^+$: m/z = 547.2; Found: 547.2. |
| 125 | 2-(3-(5-amino-6-(4-(2-cyanoethyl)piperazin-1-yl)pyrazin-2-yl)-4-methylphenyl)-3,3,3-trifluoro-2-hydroxypropanamide trifluoroacetate | *(4-(2-cyanoethyl)piperazin-1-yl)* | Calculated for $C_{21}H_{25}F_3N_7O_2$ (M + H)$^+$: m/z = 464.2; Found: 464.2. |
| 126 | 2-(3-(5-amino-6-(6-oxohexahydropyrrolo[1,2-a]pyrazin-2(1H)-yl)pyrazin-2-yl)-4-methylphenyl)-3,3,3-trifluoro-2-hydroxypropanamide trifluoroacetate | *(6-oxohexahydropyrrolo[1,2-a]pyrazin-2(1H)-yl)* | Calculated for $C_{21}H_{24}F_3N_6O_3$ (M + H)$^+$: m/z = 465.2; Found: 465.2. |
| 127 | 2-(3-(5-amino-6-(4-(furan-2-carbonyl)piperazin-1-yl)pyrazin-2-yl)-4-methylphenyl)-3,3,3-trifluoro-2-hydroxypropanamide trifluoroacetate | *(4-(furan-2-carbonyl)piperazin-1-yl)* | Calculated for $C_{23}H_{24}F_3N_6O_4$ (M + H)$^+$: m/z = 505.2; Found: 505.2. |
| 128 | 2-(3-(5-amino-6-(4-(3-cyanopyrazin-2-yl)piperazin-1-yl)pyrazin-2-yl)-4-methylphenyl)-3,3,3-trifluoro-2-hydroxypropanamide trifluoroacetate | *(4-(3-cyanopyrazin-2-yl)piperazin-1-yl)* | Calculated for $C_{23}H_{23}F_3N_9O_2$ (M + H)$^+$: m/z = 514.2; Found: 514.2. |
| 129 | 2-(3-(5-amino-6-(4-(2-ethoxyphenyl)piperazin-1-yl)pyrazin-2-yl)-4-methylphenyl)-3,3,3-trifluoro-2-hydroxypropanamide trifluoroacetate | *(4-(2-ethoxyphenyl)piperazin-1-yl)* | Calculated for $C_{26}H_{30}F_3N_6O_3$ (M + H)$^+$: m/z = 531.2; Found: 531.2. |

Example A. THP-1 RPS6 ELISA Assay

To measure the Phosphorylated Ribosomal Protein S6 (RPS6) in cell lysates, THP-1 cells (Human Acute Monocytic Leukemia) are purchased from ATCC (Manassas, Va.) and maintained in RPMI with 10% FBS (Gibco/Life Technologies, Carlsbad, Calif.). For the assay, THP-1 cells are serum starved overnight in RPMI, then plated in RPMI ($2 \times 10^5$ cells/well in 90 µL) into 96-well flat-bottom tissue culture treated plates (Corning, Corning, N.Y.), in the presence or absence of a concentration range of test compounds. Covered plates are incubated for 2 hours at 37° C., 5% $CO_2$ then treated with or without 10 nM MCP-1(MYBioSource, San Diego, Calif.) for 15 minutes at 37° C., 5% $CO_2$. Plates are centrifuged at 1600 RPM and supernatants are removed. Cells are lysed in Lysis Buffer (Cell Signaling, Danvers, Mass.) with Protease Inhibitor (Calbiochem/EMD, Germany), PMSF (Sigma, St Louis Mo.), HALTS (Thermo Fisher, Rockford, Ill.) for 30 min on wet ice. Cell lysates are frozen at −80 OC before testing. The lysates are tested in the Human/Mouse/Rat Phospho-RPS6 ELISA (R&D Systems, Inc. Minn, Minn.). The plate is measured using a microplate reader (SpectraMax M5—Molecular Devices, LLC Sunnyvale, Calif.) set to 450 nm with a wavelength correction of 540. $IC_{50}$ determination is performed by fitting the curve of inhibitor percent inhibition versus the log of the inhibitor concentration using the GraphPad Prism 5.0 software.

Example B. PI3K-γ Scintillation Proximity Assay

Materials: [γ-$^{33}$P]ATP (10 mCi/mL) and Wheat Germ Agglutinin (WGA) YSi SPA Scintillation Beads was purchased from Perkin Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kγ (p110γ) Recombinant Human Protein was purchased from Life technology (Grand Island, N.Y.). ATP, $MgCl_2$, DTT, EDTA, MOPS and CHAPS were purchased from Sigma Aldrich (St. Louis, Mo.).

The kinase reaction was conducted in polystyrene 384-well Greiner Bio-one white plate from Thermo Fisher Scientific in a final volume of 25 µL. Inhibitors were first diluted serially in DMSO and added to the plate wells before the addition of other reaction components. The final concentration of DMSO in the assay was 2%. The PI3Kγ assay was carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 µM PIP2, 2 µM ATP, 0.5 µCi [γ-$^{33}$P] ATP, 13 nM PI3Kγ. Reactions were incubated for 120 min and terminated by the addition of 40 µL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). $IC_{50}$ determination was performed by fitting the curve of percent of the solvent control activity versus the log of the inhibitor concentration using the GraphPad Prism 6.0 software.

Example C. PI3Kδ Scintillation Proximity Assay

Materials: [γ-$^{33}$P]ATP (10 mCi/mL) and Wheat Germ Agglutinin (WGA) YSi SPA Scintillation Beads was purchased from Perkin Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) Recombinant Human Protein was purchased from Eurofins (St Charles, Mo.). ATP, $MgCl_2$, DTT, EDTA, MOPS and CHAPS were purchased from Sigma Aldrich (St. Louis, Mo.).

The kinase reaction was conducted in polystyrene 384-well Greiner Bio-one white plate from Thermo Fisher Scientific in a final volume of 25 µL. Inhibitors were first diluted serially in DMSO and added to the plate wells before the addition of other reaction components. The final concentration of DMSO in the assay was 2%. The PI3Kδ assay was carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 µM PIP2, 2 µM ATP, 0.5 µCi [γ-$^{33}$P] ATP, 3.4 nM PI3Kδ. Reactions were incubated for 120 min and terminated by the addition of 40 µL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (PerkinElmer). $IC_{50}$ determination was performed by fitting the curve of percent of the solvent control activity versus the log of the inhibitor concentration using the GraphPad Prism 6.0 software.

The compounds of the Examples were tested in the assays described in Examples A, B and C and found to have the $IC_{50}$s are shown in Tables A1, A2, A3 and A4.

TABLE A1

| Ex. No. | PI3Kγ $IC_{50}$ (nM) | PI3Kδ $IC_{50}$ (nM) | PI3Kγ_THP1_RPS6_ELISA $IC_{50}$ (nM) |
|---|---|---|---|
| 1 | + | + | # |
| 2 | + | + | # |
| 3 | + | + | # |
| 4 | + | + | # |
| 5 | + | + | # |
| 6 | + | + | # |
| 7 | + | + | # |
| 8 | + | + | # |
| 9 | + | + | # |
| 10 | + | + | # |
| 11 | + | + | # |
| 12 | + | + | # |
| 13 | + | + | # |
| 14 | + | + | # |
| 15 | + | + | # |
| 16 | + | + | # |
| 17 | + | + | # |
| 18 | + | + | # |
| 19 | + | + | # |
| 20 | + | + | # |
| 21 | + | + | # |
| 22 | + | + | # |
| 23 | + | + | # |
| 24 | + | + | # |
| 25 | + | + | # |
| 26 | + | + | ## |
| 27 | + | + | # |
| 28 | + | ++ | # |
| 29 | + | + | # |
| 30 | + | + | # |
| 31 | + | + | # |
| 32 | + | + | # |
| 33 | + | + | # |

TABLE A1-continued

| Ex. No. | PI3Kγ IC$_{50}$ (nM) | PI3Kδ IC$_{50}$ (nM) | PI3Kγ_THP1_RPS6_ELISA IC$_{50}$ (nM) |
|---|---|---|---|
| 34 | + | + | # |
| 35 | + | + | # |
| 36 | + | + | # |
| 37 | + | + | # |
| 38 | + | + | # |
| 39 | + | + | ## |
| 40 | + | + | ## |
| 41 | + | ++ | #### |
| 42 | + | + | ## |
| 43A | + | + | # |
| 43B | + | + | # |

+ refers to IC$_{50}$ of ≤100 nM;
++ refers to IC$_{50}$ of ≤500 nM;
+++ refers to an IC$_{50}$ of <2000 nM;
++++ refers to an IC$_{50}$ of ≥2000 nM.
# refers to IC$_{50}$ of ≤100 nM;
## refers to IC$_{50}$ of ≤500 nM;
### refers to IC$_{50}$ of <1000 nM;
#### refers to an IC$_{50}$ of ≥1000 nM.

TABLE A2

| Ex. No. | PI3Kγ IC$_{50}$ (nM) | PI3Kδ IC$_{50}$ (nM) | PI3Kγ_THP1_RPS6_ELISA IC$_{50}$ (nM) |
|---|---|---|---|
| 44 | + | ++ | NT |
| 45 | + | ++ | ## |
| 46 | + | ++ | NT |
| 47 | + | + | # |
| 48 | + | + | #### |
| 49 | + | + | ## |
| 50 | + | + | # |
| 51 | + | + | # |
| 52 | + | + | ## |
| 53 | + | + | ## |
| 54 | + | + | # |
| 55 | + | + | # |
| 56 | + | + | # |
| 57 | + | + | # |
| 58 | + | + | # |
| 59 | + | + | # |
| 60 | + | + | # |
| 61 | + | + | # |
| 62 | + | + | # |
| 63 | + | + | # |
| 64 | + | + | # |
| 65 | + | + | # |
| 66 | + | + | NT |
| 67 | + | + | NT |
| 68 | + | + | NT |

+ refers to IC$_{50}$ of ≤100 nM;
++ refers to IC$_{50}$ of ≤500 nM;
+++ refers to an IC$_{50}$ of <2000 nM;
++++ refers to an IC$_{50}$ of ≥2000 nM.
# refers to IC$_{50}$ of ≤100 nM;
## refers to IC$_{50}$ of ≤500 nM;
### refers to IC$_{50}$ of <1000 nM;
#### refers to an IC$_{50}$ of ≥1000 nM.
NT refers to data not available.

TABLE A3

| Ex. No. | PI3Kγ IC$_{50}$ (nM) | PI3Kδ IC$_{50}$ (nM) | PI3Kγ_THP1_RPS6_ELISA IC$_{50}$ (nM) |
|---|---|---|---|
| 69 | + | + | # |
| 70 | + | + | # |
| 71 | + | + | # |
| 72 | + | + | # |
| 73 | + | + | # |
| 74 | + | + | # |
| 75 | + | + | # |
| 76 | + | + | # |
| 77 | + | + | # |
| 78 | + | + | # |
| 79 | + | + | # |
| 80 | + | ++ | ### |
| 81 | + | ++ | ## |
| 82 | + | + | ## |
| 83 | + | + | ## |
| 84 | + | + | ## |
| 85 | + | + | ## |
| 86 | + | + | # |
| 87 | + | + | ## |
| 88 | + | + | ## |
| 89 | + | + | ## |
| 90 | + | ++ | ## |
| 91 | + | + | # |
| 92 | + | ++ | ## |
| 93 | + | + | # |
| 94 | + | + | # |
| 95 | ++ | ++ | NT |
| 96 | + | ++ | # |
| 97 | + | + | ## |
| 98 | + | + | # |
| 99 | + | + | # |
| 100 | + | + | # |
| 101 | + | + | # |
| 102 | + | + | # |
| 103 | + | ++ | ## |
| 104 | + | + | # |
| 105 | + | + | # |
| 106 | + | + | # |

+ refers to IC$_{50}$ of ≤100 nM;
++ refers to IC$_{50}$ of ≤500 nM;
+++ refers to an IC$_{50}$ of <2000 nM;
++++ refers to an IC$_{50}$ of ≥2000 nM.
# refers to IC$_{50}$ of ≤100 nM;
## refers to IC$_{50}$ of ≤500 nM;
### refers to IC$_{50}$ of <1000 nM;
#### refers to an IC$_{50}$ of ≥1000 nM.
NT refers to data not available.

TABLE A4

| Ex. No. | PI3Kγ IC$_{50}$ (nM) | PI3Kδ IC$_{50}$ (nM) | PI3Kγ_THP1_RPS6_ELISA IC$_{50}$ (nM) |
|---|---|---|---|
| 107 | + | +++ | ### |
| 108 | ++ | +++ | #### |
| 109 | + | ++ | #### |
| 110 | ++ | ++ | NT |
| 111 | + | ++ | NT |
| 112 | + | ++ | ## |
| 113 | + | ++ | ## |
| 114 | + | + | + |
| 115 | + | + | + |
| 116 | + | ++ | + |
| 117 | + | + | + |
| 118 | + | ++ | ### |
| 119 | + | ++ | #### |
| 120 | + | + | + |
| 121 | + | ++ | #### |
| 122 | + | + | + |
| 123 | + | + | ## |
| 124 | + | ++ | ### |

TABLE A4-continued

| Ex. No. | PI3Kγ IC$_{50}$ (nM) | PI3Kδ IC$_{50}$ (nM) | PI3Kγ_THP1_RPS6_ELISA IC$_{50}$ (nM) |
|---|---|---|---|
| 125 | + | + | ## |
| 126 | + | + | + |
| 127 | + | + | + |
| 128 | + | + | + |
| 129 | + | ++ | ### |

+ refers to IC$_{50}$ of ≤100 nM;
++ refers to IC$_{50}$ of ≤500 nM;
+++ refers to an IC$_{50}$ of <2000 nM;
++++ refers to an IC$_{50}$ of ≥2000 nM.
# refers to IC$_{50}$ of ≤100 nM;
## refers to IC$_{50}$ of ≤500 nM;
### refers to IC$_{50}$ of <1000 nM;
#### refers to an IC$_{50}$ of ≥1000 nM.
NT refers to data not available.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (II):

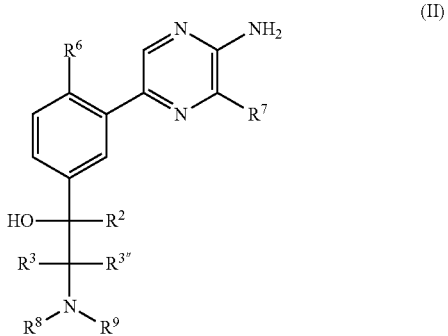

or a pharmaceutically acceptable salt thereof; wherein:
  $R^2$ is a $C_{1-6}$ haloalkyl, wherein each halogen is independently selected from F and Cl;
  $R^3$ is selected from H, D, $C_{1-6}$alkyl, $C_{2-6}$alkenyl, $C_{2-6}$alkynyl, and $C_{1-6}$haloalkyl;
  $R^{3''}$ is selected from H, D, $C_{1-6}$ alkyl, $C_{2-6}$ alkenyl, $C_{2-6}$ alkynyl, and $C_{1-6}$ haloalkyl;
  or, alternatively, $R^3$ and $R^{3''}$ together form an oxo group;
  $R^6$ is selected from H, D, halo, CN, OH, NH$_2$, and $C_{1-6}$ alkyl;
  $R^7$ is C(O)NR$^{c7}$R$^{d7}$;
  $R^7$ is selected from H, $C_{1-6}$ alkyl, $C_{2-6}$ alkenyl, and $C_{2-6}$ alkynyl;
  $R^{d7}$ is selected from H, $C_{1-6}$ alkyl, $C_{3-10}$ cycloalkyl, and 4-8 membered heterocycloalkyl, wherein the $C_{1-6}$ alkyl, $C_{3-10}$ cycloalkyl and 4-8 membered heterocycloalkyl of $R^{d7}$ are each optionally substituted with 1 or 2 independently selected $R^{74}$ substituents;
  or, $R^{c7}$ and $R^{d7}$, together with the N atom to which they are attached, form a 5-10 membered heteroaryl or a 4-12-membered heterocycloalkyl group, wherein the 5-10 membered heteroaryl or 4-12 membered heterocycloalkyl group is optionally substituted with 1, 2, 3 or 4 independently selected $R^{74}$ substituents;
  $R^8$ is selected from H, $C_{1-6}$ alkyl, $C_{2-6}$ alkenyl, $C_{2-6}$ alkynyl, $C_{1-6}$ haloalkyl, C(O)R$^{b8}$;
  $R^9$ is selected from H, $C_{1-6}$ alkyl, $C_{2-6}$ alkenyl, $C_{2-6}$ alkynyl, and $C_{1-6}$ haloalkyl;
  provided that either: (a) $R^3$ and $R^{3''}$ together form an oxo group; or (b) $R^8$ is C(O)R$^{b8}$;
  each $R^{74}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, NO$_2$, OR$^{a71}$, and SR$^{a71}$;
  each $R^{a71}$ is independently selected from H, $C_{1-6}$ alkyl, $C_{1-6}$ haloalkyl, $C_{2-6}$ alkenyl, and $C_{2-6}$ alkynyl;
  $R^{b8}$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl is optionally substituted with 1, 2, 3 or 4 independently selected $R^{84}$ substituents; and
  each $R^{84}$ is independently selected from D, halo, CN, NO$_2$, OH, and SH.

2. The compound of claim 1, or a pharmaceutically acceptable salt thereof, wherein $R^2$ is CF$_3$ or CHF$_2$.

3. The compound of claim 1, or a pharmaceutically acceptable salt thereof, wherein $R^3$ is H.

4. The compound of claim 1, or a pharmaceutically acceptable salt thereof, wherein $R^{3''}$ is H.

5. The compound of claim 1, or a pharmaceutically acceptable salt thereof, wherein $R^6$ is methyl.

6. The compound of claim 1, or a pharmaceutically acceptable salt thereof, wherein $R^9$ is H.

7. The compound of claim 1, or a pharmaceutically acceptable salt thereof, wherein $R^3$ and $R^{3''}$ together form an oxo group.

8. The compound of claim 1, or a pharmaceutically acceptable salt thereof, wherein $R^8$ is H or C(O)R$^{b8}$.

9. The compound of claim 1, or a pharmaceutically acceptable salt thereof, wherein $R^{b8}$ is selected from methyl, fluoromethyl, cyanomethyl, and hydroxypropyl.

10. The compound of claim 1, or a pharmaceutically acceptable salt thereof, wherein R$^{c7}$ is H.

11. The compound of claim 1, or a pharmaceutically acceptable salt thereof, wherein each $R^{74}$ is independently selected from halo, $C_{1-6}$ alkyl, $C_{1-6}$ haloalkyl, $C_{3-8}$ cycloalkyl, CN, and OR$^{a71}$, wherein each R$^{a71}$ is independently selected from H and $C_{1-6}$ alkyl.

12. The compound of claim 1, or a pharmaceutically acceptable salt thereof, wherein $R^{d7}$ is selected from $C_{1-6}$ alkyl, hydroxyl-$C_{1-6}$ alkyl, cyano-$C_{1-6}$ alkyl, monocyclic $C_{3-6}$ cycloalkyl, bicyclic $C_{5-8}$ cycloalkyl, and 4-6 membered heterocycloalkyl, wherein the $C_{1-6}$ alkyl, hydroxyl-$C_{1-6}$ alkyl, cyano-$C_{1-6}$ alkyl, monocyclic $C_{3-6}$ cycloalkyl, bicyclic $C_{5-8}$ cycloalkyl, and 4-6 membered heterocycloalkyl are each optionally substituted by 1 or 2 substituents $R^{74}$ independently selected from halo, OH, CN, $C_{1-3}$ alkoxy, and $C_{3-10}$ cycloalkyl.

13. The compound of claim 1, or a pharmaceutically acceptable salt thereof, wherein $R^{d7}$ is selected from ethyl, 2-cyanoethyl, 2,2,2-trifluoroethyl, 2-propyl, 1-(cyanomethyl)propyl, 2-methoxy-2-methylpropyl, 2-cyano-2,2-dimethylethyl, 2-hydroxy-2-methylprop-1-yl, 2-cyano-1-methylethyl, 2-hydroxy-1-methylethyl, 2-hydroxy-1,1-dimethylethyl, 1-cyanocycloprop-1-ylethyl, 1-cyanocyclobut-1-ylethyl, 4-hydroxycyclohexyl, 4-methoxycyclohexyl, 4-hydroxy-4-methylcyclohexyl, 4-hydroxy-4-(trifluoromethyl)cyclohexyl, 4-(1-hydroxy-1- methylethyl)cyclohexyl, 4,4-difluorocyclohexyl, 3-cyanobicyclo[1.1.1]pentan-1-yl, 4-cyanobicyclo[2.1.1]hexan-1-yl, 4-cyanobicyclo[2.2.2]octan-1-yl, tetrahydrofuran-3-yl, tetrahydropyran-3-yl, and tetrahydropyran-4-yl.

14. The compound of claim 1, or a pharmaceutically acceptable salt, wherein:
$R^2$ is a $C_{1-6}$ haloalkyl, wherein each halogen of the $C_{1-6}$ haloalkyl is independently selected from F and Cl;
$R^3$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and $NH_2$;
$R^{3''}$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and $NH_2$;
or, alternatively, $R^3$ and $R^{3''}$ together form an oxo group;
$R^6$ is selected from H, D, halo, CN, OH, $NH_2$, and $C_{1-6}$ alkyl;
$R^{c7}$ and $R^{d7}$ are each independently selected H, $C_{1-6}$ alkyl, $C_{2-6}$ alkenyl, $C_{2-6}$ alkynyl, $C_{3-10}$ cycloalkyl, and 4-8 membered heterocycloalkyl, wherein the $C_{1-6}$ alkyl, $C_{2-6}$ alkenyl, $C_{2-6}$ alkynyl, $C_{3-10}$ cycloalkyl, and 4-8 membered heterocycloalkyl of $R^{c7}$ and $R^{d7}$ are each optionally substituted with 1 or 2 independently selected $R^{7A}$ substituents;
$R^8$ is selected from H, $C_{1-6}$ alkyl, $C_{2-6}$ alkenyl, $C_{2-6}$ alkynyl, $C_{1-6}$ haloalkyl, and $C(O)R^{b8}$; provided that either: (a) $R^3$ and $R^{3''}$ together form an oxo group; or (b) $R^8$ is $C(O)R^{b8}$;
$R^9$ is selected from H, $C_{1-6}$ alkyl, $C_{2-6}$ alkenyl, $C_{2-6}$ alkynyl, and $C_{1-6}$ haloalkyl; each $R^{7A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-8}$ cycloalkyl, 5-10 membered heteroaryl, 4-10 membered heterocycloalkyl, CN, $NO_2$, $OR^{a71}$, and $SR^{a71}$;
each $R^{a71}$ is independently selected from H, $C_{1-6}$ alkyl, $C_{1-6}$ haloalkyl, $C_{2-6}$ alkenyl, and $C_{2-6}$ alkynyl;
$R^{b8}$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{b8}$ are each optionally substituted with 1, 2, 3 or 4 independently selected $R^{8A}$ substituents; and
each $R^{8A}$ is independently selected from D, halo, CN, $NO_2$, OH, and SH.

15. The compound of claim 1, selected from:
3-amino-6-(5-(3-amino-1,1,1-trifluoro-2-hydroxy-3-oxopropan-2-yl)-2-methylphenyl)-N-(2-hydroxy-2-methylpropyl)pyrazine-2-carboxamide;
3-amino-6-(5-(3-amino-1,1,1-trifluoro-2-hydroxy-3-oxopropan-2-yl)-2-methylphenyl)-N-(tetrahydro-2H-pyran-4-yl)pyrazine-2-carboxamide;
3-amino-6-(5-(3-amino-1,1,1-trifluoro-2-hydroxy-3-oxopropan-2-yl)-2-methylphenyl)-N-((1r,4r)-4-hydroxycyclohexyl)pyrazine-2-carboxamide;
3-amino-6-(5-(3-amino-1,1,1-trifluoro-2-hydroxy-3-oxopropan-2-yl)-2-methylphenyl)-N-((1-cyanocyclopropyl)methyl)pyrazine-2-carboxamide;
3-amino-6-(5-(3-amino-1,1,1-trifluoro-2-hydroxy-3-oxopropan-2-yl)-2-methylphenyl)-N-isopropylpyrazine-2-carboxamide;
3-amino-6-(5-(3-amino-1,1,1-trifluoro-2-hydroxy-3-oxopropan-2-yl)-2-methylphenyl)-N-(4,4-difluorocyclohexyl)pyrazine-2-carboxamide;
3-amino-6-(5-(3-amino-1,1,1-trifluoro-2-hydroxy-3-oxopropan-2-yl)-2-methylphenyl)-N-ethylpyrazine-2-carboxamide;
3-amino-6-(5-(3-amino-1,1,1-trifluoro-2-hydroxy-3-oxopropan-2-yl)-2-methylphenyl)-N-((S)-1-cyanopropan-2-yl)pyrazine-2-carboxamide;
3-amino-6-(5-(3-amino-1,1,1-trifluoro-2-hydroxy-3-oxopropan-2-yl)-2-methylphenyl)-N-((R)-tetrahydro-2H-pyran-3-yl)pyrazine-2-carboxamide;
3-amino-6-(5-(3-amino-1,1,1-trifluoro-2-hydroxy-3-oxopropan-2-yl)-2-methylphenyl)-N-((S)-tetrahydro-2H-pyran-3-yl)pyrazine-2-carboxamide;
3-amino-6-(5-(3-amino-1,1,1-trifluoro-2-hydroxy-3-oxopropan-2-yl)-2-methylphenyl)-N-((S)-tetrahydrofuran-3-yl)pyrazine-2-carboxamide;
3-amino-6-(5-(3-amino-1,1,1-trifluoro-2-hydroxy-3-oxopropan-2-yl)-2-methylphenyl)-N-((S)-1-hydroxypropan-2-yl)pyrazine-2-carboxamide;
3-amino-6-(5-(3-amino-1,1,1-trifluoro-2-hydroxy-3-oxopropan-2-yl)-2-methylphenyl)-N-(1-hydroxy-2-methylpropan-2-yl)pyrazine-2-carboxamide;
3-amino-6-(5-(3-amino-1,1,1-trifluoro-2-hydroxy-3-oxopropan-2-yl)-2-methylphenyl)-N-(2-cyanoethyl)pyrazine-2-carboxamide;
3-amino-6-(5-(3-amino-1,1,1-trifluoro-2-hydroxy-3-oxopropan-2-yl)-2-methylphenyl)-N-(2-cyano-2-methylpropyl)pyrazine-2-carboxamide;
3-amino-6-(5-(3-amino-1,1,1-trifluoro-2-hydroxy-3-oxopropan-2-yl)-2-methylphenyl)-N-((1-cyanocyclobutyl)methyl)pyrazine-2-carboxamide;
3-amino-6-(5-(3-amino-1,1,1-trifluoro-2-hydroxy-3-oxopropan-2-yl)-2-methylphenyl)-N-((1r,4r)-4-hydroxy-4-methylcyclohexyl)pyrazine-2-carboxamide;
3-amino-6-(5-(3-amino-1,1,1-trifluoro-2-hydroxy-3-oxopropan-2-yl)-2-methylphenyl)-N-((1r,4r)-4-hydroxy-4-(trifluoromethyl)cyclohexyl)pyrazine-2-carboxamide;
3-amino-6-(5-(3-amino-1,1,1-trifluoro-2-hydroxy-3-oxopropan-2-yl)-2-methylphenyl)-N-((1r,4r)-4-(2-hydroxypropan-2-yl)cyclohexyl)pyrazine-2-carboxamide;
3-amino-6-(5-(3-amino-1,1,1-trifluoro-2-hydroxy-3-oxopropan-2-yl)-2-methylphenyl)-N-((S)-1-cyanobutan-2-yl)pyrazine-2-carboxamide;
3-amino-6-(5-(3-amino-1,1,1-trifluoro-2-hydroxy-3-oxopropan-2-yl)-2-methylphenyl)-N-(2-methoxy-2-methylpropyl)pyrazine-2-carboxamide;
3-amino-6-(5-(3-amino-1,1,1-trifluoro-2-hydroxy-3-oxopropan-2-yl)-2-methylphenyl)-N-((1r,4r)-4-methoxycyclohexyl)pyrazine-2-carboxamide;
3-amino-6-(5-(3-amino-1,1,1-trifluoro-2-hydroxy-3-oxopropan-2-yl)-2-methylphenyl)-N-(3-cyanobicyclo[1.1.1]pentan-1-yl)pyrazine-2-carboxamide;
3-amino-6-(5-(3-amino-1,1,1-trifluoro-2-hydroxy-3-oxopropan-2-yl)-2-methylphenyl)-N-(4-cyanobicyclo[2.1.1]hexan-1-yl)pyrazine-2-carboxamide;
3-amino-6-(5-(3-amino-1,1,1-trifluoro-2-hydroxy-3-oxopropan-2-yl)-2-methylphenyl)-N-(4-cyanobicyclo[2.2.2]octan-1-yl)pyrazine-2-carboxamide;
3-amino-6-(5-(1-amino-3,3-difluoro-2-hydroxy-1-oxopropan-2-yl)-2-methylphenyl)-N-methylpyrazine-2-carboxamide;
3-amino-6-(5-(1-amino-3,3-difluoro-2-hydroxy-1-oxopropan-2-yl)-2-methylphenyl)-N-ethylpyrazine-2-carboxamide;
3-amino-6-(5-(1-amino-3,3-difluoro-2-hydroxy-1-oxopropan-2-yl)-2-methylphenyl)-N-((1-cyanocyclopropyl)methyl)pyrazine-2-carboxamide;
3-amino-6-(5-(1-amino-3,3-difluoro-2-hydroxy-1-oxopropan-2-yl)-2-methylphenyl)-N-(4,4-difluorocyclohexyl)pyrazine-2-carboxamide;

3-amino-6-(5-(1-amino-3,3-difluoro-2-hydroxy-1-oxo-propan-2-yl)-2-methylphenyl)-N-(2,2,2-trifluoroethyl)pyrazine-2-carboxamide;

3-amino-6-(5-(1-amino-3,3-difluoro-2-hydroxy-1-oxo-propan-2-yl)-2-methylphenyl)-N-(1-hydroxy-2-methylpropan-2-yl)pyrazine-2-carboxamide;

3-amino-6-(5-(1-amino-3,3-difluoro-2-hydroxy-1-oxo-propan-2-yl)-2-methylphenyl)-N-(tetrahydro-2H-pyran-4-yl)pyrazine-2-carboxamide;

6-(5-(3-acetamido-1,1,1-trifluoro-2-hydroxypropan-2-yl)-2-methylphenyl)-3-amino-N-isopropylpyrazine-2-carboxamide;

3-amino-N-isopropyl-6-(2-methyl-5-(1,1,1-trifluoro-3-(2-fluoroacetamido)-2-hydroxypropan-2-yl)phenyl)pyrazine-2-carboxamide;

3-amino-N-isopropyl-6-(2-methyl-5-(1,1,1-trifluoro-2-hydroxy-3-(2-hydroxy-2-methylpropanamido)propan-2-yl)phenyl)pyrazine-2-carboxamide; and 3-amino-6-(5-(3-(2-cyanoacetamido)-1,1,1-trifluoro-2-hydroxypropan-2-yl)-2-methylphenyl)-N-isopropylpyrazine-2-carboxamide;

or a pharmaceutically acceptable salt thereof.

16. The compound of claim 1, selected from:

2-(3-(5-amino-6-((R)-2-(methoxymethyl)azetidine-1-carbonyl)pyrazin-2-yl)-4-methylphenyl)-3,3,3-trifluoro-2-hydroxypropanamide;

2-(3-(5-amino-6-(2,2-dimethylazetidine-1-carbonyl)pyrazin-2-yl)-4-methylphenyl)-3,3,3-trifluoro-2-hydroxypropanamide;

2-(3-(5-amino-6-(2,3-dihydro-1H-pyrrolo[2,3-b]pyridine-1-carbonyl)pyrazin-2-yl)-4-methylphenyl)-3,3,3-trifluoro-2-hydroxypropanamide;

3-amino-6-(5-(3-amino-1,1,1-trifluoro-2-hydroxy-3-oxopropan-2-yl)-2-methylphenyl)-N-(7-oxabicyclo[2.2.1]heptan-2-yl)pyrazine-2-carboxamide;

3-amino-6-(5-(1-amino-3,3-difluoro-2-hydroxy-1-oxo-propan-2-yl)-2-methylphenyl)-N-(2-(tetrahydrofuran-3-yl)ethyl)pyrazine-2-carboxamide; and 3-amino-6-(5-(3-amino-1,1,1-trifluoro-2-hydroxy-3-oxopropan-2-yl)-2-methylphenyl)-N-(3,3,3-trifluoro-2-hydroxypropyl)pyrazine-2-carboxamide;

or a pharmaceutically acceptable salt thereof.

17. A pharmaceutical composition comprising a compound of claim 1, or a pharmaceutically acceptable salt thereof, and a pharmaceutically acceptable excipient or carrier.

18. A method of inhibiting an activity of PI3Kγ kinase, comprising contacting the kinase with a compound of claim 1, or a pharmaceutically acceptable salt thereof.

19. The method of claim 18, wherein said compound, or a pharmaceutically acceptable salt thereof, is a selective inhibitor for PI3Kγ over one or more of PI3Kα, PI3Kβ, and PI3Kδ.

20. A method of treating a disease or disorder in a patient, wherein said disease or disorder is associated with abnormal expression or activity of PI3Kγ kinase, comprising administering to said patient a therapeutically effective amount of a compound of claim 1, or a pharmaceutically acceptable salt thereof, wherein the disease or disorder is Burkitt's lymphoma, acute myeloblastic leukemia, chronic myeloid leukemia, non-Hodgkin's lymphoma (NHL), Hodgkin's lymphoma, hairy cell leukemia, Mantle cell lymphoma, small lymphocytic lymphoma, follicular lymphoma, xeroderoma pigmentosum, keratoacanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

21. The method of claim 20, wherein the diffuse large B cell lymphoma is activated B-cell like (ABC) diffuse large B cell lymphoma, or germinal center B cell (GCB) diffuse large B cell lymphoma.

22. A method of treating a disease or disorder in a patient, wherein said disease or disorder is associated with abnormal expression or activity of PI3Kγ kinase, comprising administering to said patient a therapeutically effective amount of a compound of claim 1, or a pharmaceutically acceptable salt thereof, wherein the disease or disorder is rheumatoid arthritis, multiple sclerosis, systemic lupus erythematous, asthma, allergy, allergic rhinitis, pancreatitis, psoriasis, anaphylaxis, glomerulonephritis, inflammatory bowel disease, thrombosis, meningitis, encephalitis, diabetic retinopathy, benign prostatic hypertrophy, myasthenia gravis, Sjögren's syndrome, osteoarthritis, restenosis, or atherosclerosis.

23. A method of treating a disease or disorder in a patient, wherein said disease or disorder is associated with abnormal expression or activity of PI3Kγ kinase, comprising administering to said patient a therapeutically effective amount of a compound of claim 1, or a pharmaceutically acceptable salt thereof, wherein the disease or disorder is heart hypertrophy, cardiac myocyte dysfunction, acute coronary syndrome, chronic obstructive pulmonary disease (COPD), chronic bronchitis, elevated blood pressure, ischemia, ischemia-reperfusion, vasoconstriction, anemia, bacterial infection, viral infection, graft rejection, kidney disease, anaphylactic shock fibrosis, skeletal muscle atrophy, skeletal muscle hypertrophy, angiogenesis, sepsis, graft-versus-host disease, allogeneic or xenogeneic transplantation, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

* * * * *

UNITED STATES PATENT AND TRADEMARK OFFICE
CERTIFICATE OF CORRECTION

PATENT NO. : 11,046,658 B2  
APPLICATION NO. : 16/458530  
DATED : June 29, 2021  
INVENTOR(S) : Brent Douty et al.

Page 1 of 1

It is certified that error appears in the above-identified patent and that said Letters Patent is hereby corrected as shown below:

In the Claims

Column 239, Line 48, Claim 1, delete "$C_{1-6}$alkyl," and insert -- $C_{1-6}$ alkyl, --;

Column 239, Line 48, Claim 1, delete "$C_{2-6}$alkenyl," and insert -- $C_{2-6}$ alkenyl, --;

Column 239, Line 49, Claim 1, delete "$C_{2-6}$alkynyl," and insert -- $C_{2-6}$ alkynyl, --;

Column 239, Line 49, Claim 1, delete "$C_{1-6}$haloalkyl;" and insert -- $C_{1-6}$ haloalkyl; --;

Column 239, Line 57, Claim 1, delete "$R^7$" and insert -- $R^{c7}$ --;

Column 239, Line 66, Claim 1, delete "4-12-membered" and insert -- 4-12 membered --;

Column 240, Line 4, Claim 1, after "haloalkyl," insert -- and --;

Column 241, Line 19, Claim 14, after "selected" insert -- from --; and

Column 244, Lines 8-9, Claim 20, delete "xeroderoma" and insert -- xeroderma --.

Signed and Sealed this  
Fifth Day of October, 2021

Drew Hirshfeld  
*Performing the Functions and Duties of the  
Under Secretary of Commerce for Intellectual Property and  
Director of the United States Patent and Trademark Office*